US007344723B2

(12) United States Patent
Kukolj et al.

(10) Patent No.: US 7,344,723 B2
(45) Date of Patent: *Mar. 18, 2008

(54) SELF-REPLICATING RNA MOLECULE FROM HEPATITIS C VIRUS

(75) Inventors: George Kukolj, Laval (CA); Arnim Pause, Laval (CA)

(73) Assignee: Boehringer Ingelheim (Canada) Ltd., Laval (CA)

(*) Notice: Subject to any disclaimer, the term of this patent is extended or adjusted under 35 U.S.C. 154(b) by 277 days.

This patent is subject to a terminal disclaimer.

(21) Appl. No.: 10/789,355

(22) Filed: Feb. 27, 2004

(65) Prior Publication Data

US 2004/0180333 A1 Sep. 16, 2004

Related U.S. Application Data

(62) Division of application No. 10/309,561, filed on Dec. 4, 2004, now Pat. No. 6,956,117, which is a division of application No. 10/029,907, filed on Dec. 21, 2001, now Pat. No. 6,706,874.

(60) Provisional application No. 60/257,857, filed on Dec. 22, 2000.

(51) Int. Cl.
*C12N 7/00* (2006.01)
*C12N 15/85* (2006.01)

(52) U.S. Cl. ............................... 424/228.1; 435/235.1; 435/236; 435/237; 435/239; 435/325; 435/370; 435/320.1

(58) Field of Classification Search ............. 424/205.1, 424/228.1; 435/235.1, 325; 536/23.72
See application file for complete search history.

(56) References Cited

U.S. PATENT DOCUMENTS 6,630,343 B1 10/2003 Bartenschlager (Continued)

FOREIGN PATENT DOCUMENTS

CA 2303526 3/2000

(Continued)

OTHER PUBLICATIONS

Fournier, Sureau et al.; In vitro infection of adult normal human hepatocytes in primary culture by hepatitis C virus; J. Virol.; 1998, V. 79; 2367-2374.

(Continued)

*Primary Examiner*—Bruce R. Campell
*Assistant Examiner*—Bao Qun Li
(74) *Attorney, Agent, or Firm*—Michael P. Morris; Mary-Ellen M. Devlin

(57) ABSTRACT

A unique HCV RNA molecule is provided having an enhanced efficiency of establishing cell culture replication. Novel adaptive mutations have been identified within the HCV non-structural region that improves the efficiency of establishing persistently replicating HCV RNA in cell culture. This self-replicating polynucleotide molecule contains, contrary to all previous reports, a 5'-NTR that can be either an A as an alternative to the G already disclosed and therefore provides an alternative to existing systems comprising a self-replicating HCV RNA molecule. The G-->A mutation gives rise to HCV RNA molecules that, in conjunction with mutations in the HCV non-structural region, such as the G(2042)C/R mutations, possess greater efficiency of transduction and/or replication. These RNA molecules when transfected in a cell line are useful for evaluating potential inhibitors of HCV replication.

6 Claims, 9 Drawing Sheets

APGK12 (SEQ ID NO 1) Replicon RNA compared to I377/NS2-3' Replicon RNA

U.S. PATENT DOCUMENTS

Figure 1:
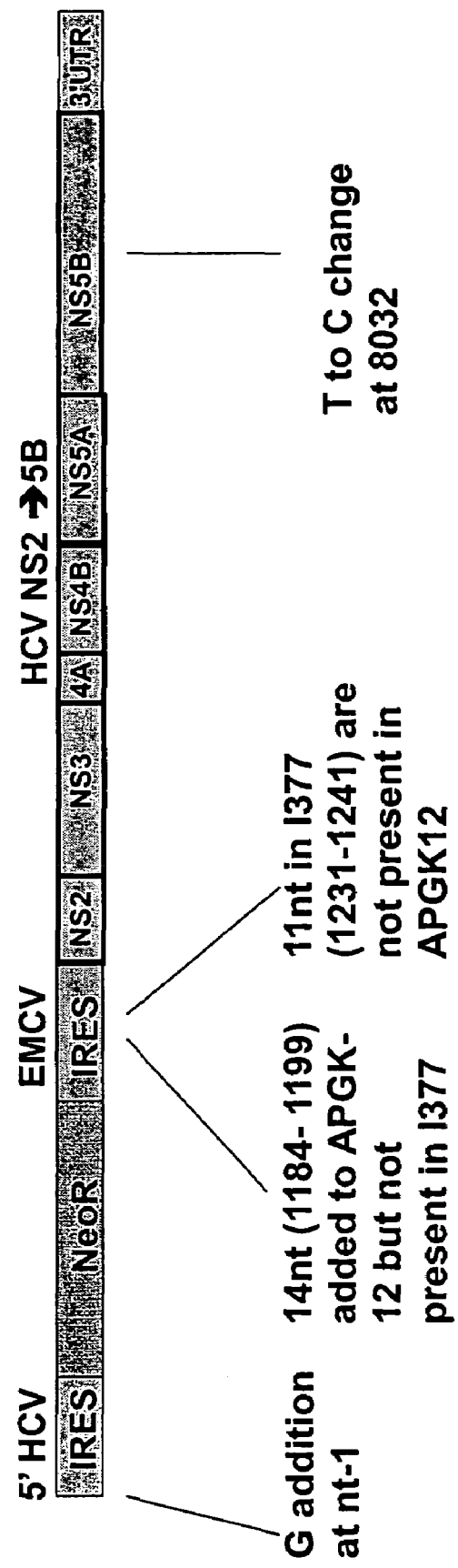

| | | | |
|---|---|---|---|
| 6,689,559 B2 * | 2/2004 | Wimmer et al. | 435/5 |
| 2002/0142350 A1 | 10/2002 | Kukolj | |
| 2003/0148348 A1 | 8/2003 | Kukolj | |

FOREIGN PATENT DOCUMENTS

| | | |
|---|---|---|
| EP | 1043399 | 10/2000 |
| WO | WO 98/04008 | 1/1998 |
| WO | WO 98/39031 | 9/1998 |
| WO | WO 00/66623 | 9/2000 |
| WO | WO 01/89364 A2 | 11/2001 |

OTHER PUBLICATIONS

Grakoui, Wychowski et al.; Expression and Identification of Hepatitis C Virus Polyprotein Cleavage Products; J. Virol.; 1993, V. 67, No. 3; 1385-1395.

Hijikata, Mizushima et al.; Two Distinct Proteinase Activities Required for the Processing of a Putative Nonstructural Precursor Protein of Hepatitis C Virus; J. Virol.; 1993, V. 67, No. 8; 4665-4675.

Bartenschlager, Ahlborn-Laake et al.; Nonstructural Protein 3 of the Hepatitis C Virus Encodes a Serine-Type Proteinase Required for Cleavage at the NS3/4 and NS4/5 Junctions; J. Virol.; 1993, V. 67, No. 7; 3835-3844.

Reed, Xu et al.; Phosphorylation of the Hepatitis C Virus NS5A Protein In Vitro and In Vivo: Properties of the NS5A-Associated Kinase; J. Virol.; 1997, V. 71, No. 10; 7187-7197.

Khromykh, Westaway; Subgenomic Replicons of the Flavivirus Kunjin: Construction and Applications; J. Virol.; 1997, V. 71, No. 2; 1497-1505.

Behrens, Grassmann et al.; Characterization of an Autonomous Subgenomic Pestivirus RNA Replicon; J. Virol.; 1998, V. 72, No. 3; 2364-2372.

Mizutani, Kato et al.; Characterization of Hepatitis C Virus Replication in Cloned Cells Obtained from a Human T-Cell Leukemia Virus Type 1-Infected Cell Line, MT-2; J. Virol.; 1996, V. 70, No. 10; 7219-7223.

Moser, Tratschin et al.; A Recombinant Classical Swine Fever Virus Stably Expresses a Marker Gene; J. Virol.; 1998, V. 72, No. 6; 5318-5322.

Ikeda, Sugiyama et al.; Human hepatocyte clonal cell lines that support persistent replication of hepatitis C virus; Virus Research; 1998, V. 56; 157-167.

Dash, Halim et al.; Transfection of HepG2 Cells with Infectious Hepatitis C Virus Genome; Amer. J. Pathology; 1997, V. 151; 363-373.

Kim, Morgenstern et al.; Hepatitis C virus NS3 RNA helicase domain with a bound oligonucleotide: the crystal structure provides insights into the mode of unwinding; Structure; 1998, V. 6; 89-100.

Yan, Li et al.; Complex of NS3 protease and NS4A peptide of BK strain hepatitis C virus; A 2.2 A resolution structure in a hexagonal crystal form; Protein Science; 1998, V. 7; 837-847.

Yao, Hesson et al.; Structure of the hepatitis C virus RNA helicase domain; Nature Structural Biology; 1997, V. 4, No. 6; 463-467.

Ito, Mukaigawa et al.; Cultivation of hepatitis C virus in primary hepacyte culture from patients with chronic hepatitis C results in release of high titre infectious virus; J. Gen. Virol.; 1996, V. 77; 1043-1054.

Yoo, Selby et al.; Transfection of a Differentiated Human Hepatoma Cell Line (Huh7) with In Vitro-Transcribed Hepatitis C Virus (HCV) RNA and Establishment of a Long-Term Culture Persistently Infected with HCV: J. Virol.: 1992, V. 69, No. 1: 32-38.

Ago, Adachi et al.; Crystal structure of the RNA-dependent RNA polymerase of hepatitis C virus; Structure; 1999, V. 7; 1417-1426.

Blight, Kolykhalov et al.; Efficient Initiation of HCV RNA Replication in Call Culture; Science; 2000, V. 290; 1972-1974.

Bressanelli, Tomei et al.; Crystal structure of the RNA-dependent RNA polymerase of hepatitis C virus; PNAS; 1999, V. 96, No. 23; 13034-13039.

Cho, Ha et al.; Crystal Structure of RNA Helicase from Genotype 1b Hepatitis C Virus; J. Biol. Chemistry; 1998, V. 273, No. 24; 15054-15052.

Gale Jr., Korth et al.; Evidence that Hepatitis C Virus Resistance to Interferon is Mediated through Repression of the PKR Protein Kinase by the Nonstractural 5A Protein; Virology; 1997, V. 230; 217-227.

Grakoui, McCourt et al.; A second hepatitis C virus-encoded proteinase; Proc. Natl. Acad. Sci. USA; 1993, V. 90; 10583-10587.

Kwong, Kim et al.; Hepatitis C virus NS3/4A protease; Antiviral Research; 1998, V. 40; 1-18.

Lanford, Sureau et al.; Demonstration of in Vitro Infection of Chimpanzee Hepatocytes with hepatitis C Virus Using Strand-Specific RT/PCR; Virology; 1994, V. 202; 606-614.

Lesburg, Cable et al.; Crystal structure of the RNA-dependent RNA polymerase from hepatitis C virus reveals a fully encircled active site; Nat. Struc. Biolo.; 1999, V. 6, No. 10; 937-943.

Lohmann, Korner et al.; Replication of Subgenomic Hepatitis C Virus RNAs in a Hepatoma Cell Line; Science; 1999, V. 285; 110-113.

Lohmann, Korner et al.; Mutations in Hepatitis C Virus RNAs Conferring Cell Culture Adaptation; J. Virology; 2001, V. 75, No. 3; 1437-1449.

Love, Parge et al.; The Crystal Structure of Hepatitis C Virus NS3 Proteinase Reveals a Trypsin-like Fold and a Structural Zinc Binding Site; Cell; 1996, V. 87, 331-342.

Shimizu, Purcell et al.; Correlation between the infectivity of hepatitis C virus in vivo and its infectivty in vitro; Proc. Natl. Acad. Sci. USA; 1993, V. 90, 6037-6041.

Yanagi, St. Claire et al.; In vivo analysis of the 3' untranslated region of the hepatitis C virus after in vitro mutagenesis of an infectious cDNA clone; Proc. Natl. Acad. Sci. USA; 1999, V. 96, 2291-2295.

Gou, Ju-Tao et al.; Effect of Alpha Interferon on the Hepatitis C virus Replicon; J. Virol.; 2001, 75(18):8516-8523.

Hijikata, Makoto et al.; Gene mapping of the putative structural region of the hepatitis C virus genome by in vitro processing analysis; Proc. Natl. Acad. Sci.; 1991, 88:5547-5551.

Kim, Dong Wook et al.; C-Terminal Domain of the Hepatitis C Virus NS3 Protein Contains an RNA Helicase Activity; 1995, 215(1):160-166.

Kim, J.-E. et al; Subcellular localization of hepatitis C viral proteins in mammalian cells; Arch Virol.; 1999, 144:329-343.

Kim, J.L. et al; Crystal Structure of the Hepatitis C Virus NS3 Protease Domain Complexed with a Synthetic NS4A Cofactor Peptide; Cell; 1996, 87:343-355.

Krieger, Nicole, et al; Enhancement of Hepatitis C Virus RNA Replication by Cell Culture-Adaptive Mutations; J. of Virol.; 2001, 75(10:4614-4624.

Bartenschlager, Lohmann; Replication of hepatitis C virus; Journal of General Virology (2000), vol. 81, pp. 1631-1648.

Ali, Pellerin, et al; Hepatitis C Virus Subgenomic Replicons in the Human Embryonic Kidney 293 Cell Line; Journal of Virology; Jan. 2004; vol. 78, No. 1; pp. 491-501.

* cited by examiner

B.

Anti-HCV NS4A
Immunofluoresence

DIC Microscopy

A.

C. Anti-HCV NS5B

B. Anti-HCV NS3

A. Anti-Neomycin Phosphotransferase

FIGURE 5A

| | S 22-3 SEQ ID NO 2 | R3 SEQ ID NO. 4 | R3-rep SEQ ID NO. 7 | R7 SEQ ID NO. 5 | R16 SEQ ID NO 6 |
|---|---|---|---|---|---|
| 5'end - FIRST nt (HCV IRES) | *G (nt 1) A | G (nt 1) A | - | - | G (nt 1) A |
| Neo | | A (nt 461) G | | | |
| EMCV IRES | | | | | |
| NS 2 | | A (nt 1739) G | | | |
| NS 3 | | G (nt 2778) A<br>A (nt 2840) C<br>A (nt 4052) G | T (nt 2509) C<br>G (nt 2778) A<br>A (nt 2840) C<br>T (nt 3574) C<br>A (nt 4052) G | A (nt 2935) G<br>A (nt 2978) G | A (nt 2816) G<br>A (nt 2978) G |
| NS 4A | A (nt 4446) R | A (nt 4446) G | C (nt 4387) T<br>A (nt 4446) G<br>C (nt 4507) T | | C (nt 4475) T |
| NS 4B | | T (nt 4855) C | T (nt 4855) C | | |
| NS 5A | G (nt 5498) T<br>A (nt 6268) R | A (nt 5351) G<br>G (nt 5498) T<br>G (nt 5659) A<br>C (nt 5871) T<br>A (nt 6268) G | A (nt 5351) G<br>G (nt 5498) T<br>G (nt 5659) A<br>G (nt 5838) C<br>C (nt 5871) T<br>A (nt 6115) G | A (nt 5324) C<br>G (nt 5498) T<br>T (nt 6001) C | G (nt 5498) C<br>T (nt 6320) C<br>T (nt 6684) C |
| NS 5B | | A (nt 6652) G | | C (nt 7252) T<br>T (nt 8349) C | |
| 3'end = last 98 nt | | | | | |

*first nt = G from HCV ires

FIGURE 5B

| | S 22-3 SEQ ID NO. 2 | R3 SEQ ID NO. 4 | R3 Rep SEQ ID NO. 7 | R7 SEQ ID NO. 5 | R16 SEQ ID NO. 6 |
|---|---|---|---|---|---|
| 5'end - FIRST nt (HCV IRES) | G (nt 1) A | G (nt 1) A | - | - | G (nt 1) A |
| NS 2 | | | | | |
| NS 3 | - | R (1135) K<br>S (1560) G | R (1135) K<br>S (1560) G | E (1202) G | S (1148) G<br>E (1202) G |
| NS 4A | K (1691) mix K/R | K (1691) R | K (1691) R | - | L (1701) F |
| NS 4B | - | - | - | - | - |
| NS 5A | G (2042) C | T (1993) A<br>G (2042) C<br>P (2166) L | T (1993) A<br>G (2042) C<br>L (2155) P<br>P (2166) L | I (1984) V<br>G (2042) C | G (2042) R<br>S (2404) P |
| NS 5B | - | - | - | M (2992) T | - |
| 3'end - last 98 nt | | | | | | first a.a. of NS2 = 810

FIGURE 6

AMINO ACID SUBSTITUTIONS

| CLONE APGK-12 | 5' HCV IRES | NeoR | EMCV IRES | HCV NS2→5B | | | | | | 3'HCV UTR | |
|---|---|---|---|---|---|---|---|---|---|---|---|
| | | | | NS2 | NS3 | 4A | NS4B | NS5A | NS5B | | |
| G (nt1) SEQ ID NO 1 | | | | | | | | | | | 77 cfu/µg |
| A (nt1) SEQ ID NO 24 | | | | - | - | - | - | - | - | | 86 cfu/µg |
| R3 rep A(nt1) SEQ ID NO 25 | | | | | R(1135)K S(1560)G | K(1691)R | - | T(1993)A G(2042)C L(2155)P P(2166)L | | | 1100000 cfu/µg |
| G(nt1) SEQ ID NO 7 | | | | | R(1135)K S(1560)G | K(1691)R | - | T(1993)A G(2042)C L(2155)P P(2166)L | | | 2000000 cfu/µg |

HCV-Replicon: RNA Quantification

Ct = Threshold cycle α Starting RNA Quantity

SELF-REPLICATING RNA MOLECULE FROM HEPATITIS C VIRUS

RELATED APPLICATIONS

This application is a divisional of U.S. application Ser. No. 10/309,561, filed Dec. 4, 2004 now U.S. Pat. No. 6,956,117 which is a divisional of U.S. application Ser. No. 10/029,907, filed Dec. 21, 2001, both of which claim, as does the present application priority to U.S. Provisional Application Ser. No. 60/257,857 filed on Dec. 22, 2000, now U.S. Pat. No. 6,706,874 the disclosures of all of which are incorporated by reference in their entirety.

FIELD OF THE INVENTION

The present invention relates generally to a HCV RNA molecule that self-replicates in appropriate cell lines, particularly to a self-replicating HCV RNA construct having an enhanced efficiency of establishing cell culture replication.

BACKGROUND OF THE INVENTION

Hepatitis C virus (HCV) is the major etiological agent of post-transfusion and community-acquired non-A non-B hepatitis worldwide. It is estimated that over 200 million people worldwide are infected by the virus. A high percentage of carriers become chronically infected and many progress to chronic liver disease, so called chronic hepatitis C. This group is in turn at high risk for serious liver disease such as liver cirrhosis, hepatocellular carcinoma and terminal liver disease leading to death. The mechanism by which HCV establishes viral persistence and causes a high rate of chronic liver disease has not been thoroughly elucidated. It is not known how HCV interacts with and evades the host immune system. In addition, the roles of cellular and humoral immune responses in protection against HCV infection and disease have yet to be established.

Various clinical studies have been conducted with the goal of identifying pharmaceutical compounds capable of effectively treating HCV infection in patients afflicted with chronic hepatitis C. These studies have involved the use of interferon-alpha, alone and in combination with other antiviral agents such as ribavirin. Such studies have shown that a substantial number of the participants do not respond to these therapies, and of those that do respond favorably, a large proportion were found to relapse after termination of treatment. To date there are no broadly effective antiviral compounds for treatment of HCV infection.

HCV is an enveloped positive strand RNA virus in the Flaviviridae family. The single strand HCV RNA genome is of positive polarity and comprises one open reading frame (ORF) of approximately 9600 nucleotides in length, which encodes a linear polyprotein of approx. 3010 amino acids. In infected cells, this polyprotein is cleaved at multiple sites by cellular and viral proteases to produce structural and non-structural (NS) proteins. The structural proteins (C, E1, E2 and E2-p7) comprise polypeptides that constitute the virus particle (Hijikata, M. et al., 1991, Proc. Natl. Acad. Sci. USA. 88, 5547-5551; Grakoui et al., 1993(a), J. Virol. 67, 1385-1395). The non-structural proteins (NS2, NS3, NS4A, NS4B, NS5A, NS5B) encode for enzymes or accessory factors that catalyze and regulate the replication of the HCV RNA genome. Processing of the structural proteins is catalyzed by host cell proteases (Hijikata, M. et al., 1991, Proc. Natl. Acad. Sci. USA. 88, 5547-5551). The generation of the mature non-structural proteins is catalyzed by two virally encoded proteases. The first is the NS2/3 zinc-dependent metalloprotease which auto-catalyses the release of the NS3 protein from the polyprotein. The released NS3 contains a N-terminal serine protease domain (Grakoui et al., 1993(b), Proc Natl Acad Sci USA, 90,10583-7; Hijikata, M. et al., 1993, J. Virol. 67, 4665-4675) and catalyzes the remaining cleavages from the polyprotein. The released NS4A protein has at least two roles. First, forming a stable complex with NS3 protein and assisting in the membrane localization of the NS3/NS4A complex (Kim et al., Arch Virol. 1999, 144, 329-343) and second, acting as a cofactor for NS3 protease activity. This membrane-associated complex, in turn catalyzes the cleavage of the remaining sites on the polyprotein, thus effecting the release of NS4B, NS5A and NS5B (Bartenschlager, R. et al., 1993, J. Virol., 67, 3835-3844; Grakoui et al., 1993(a), J. Virol. 67, 1385-1395; Hijikata, M. et al., 1993, J. Virol. 67, 4665-4675; Love, R. A. et al., 1996, Cell, 87, 331-342; reviewed in Kwong et al., 1998 Antiviral Res., 40,1-18). The C-terminal segment of the NS3 protein also harbors nucleoside triphosphatase and RNA helicase activity (Kim et al., 1995, Biochem. Biophys. Res. Comm., 215, 160-166.). The function of the protein NS4B is unknown. NS5A, a highly phosphorylated protein, seems to be responsible for the Interferon resistance of various HCV genotypes (Gale Jr. et al. 1997 Virology 230, 217; Reed et al., 1997 J. Virol. 71, 7187. NS5B is an RNA-dependent RNA polymerase (RdRp) that is involved in the replication of HCV.

The open reading frame of the HCV RNA genome is flanked on its 5' end by a non-translated region (NTR) of approx. 340 nucleotides that functions as the internal ribosome entry site (IRES), and on its 3' end by a NTR of approximately 230 nucleotides. Both the 5' and 3' NTRs are important for RNA genome replication. The genomic sequence variance is not evenly distributed over the genome and the 5' NTR and parts of the 3' NTR are the most highly conserved portions. The authentic, highly conserved 3' NTR is the object of U.S. Pat. No. 5,874,565 granted to Rice et al. The cloned and characterized partial and complete sequences of the HCV genome have also been analyzed with regard to appropriate targets for a prospective antiviral therapy. Four viral enzyme activities provide possible targets such as (1) the NS2/3 protease; (2) the NS3/4A protease complex, (3) the NS3 Helicase and (4) the NS5B RNA-dependent RNA polymerase. The NS3/4A protease complex and the NS3 helicase have already been crystallized and their three-dimensional structure determined (Kim et al., 1996, Cell, 87, 343; Yem et al. Protein Science, 7, 837,1998; Love, R. A. et al., 1996, Cell, 87, 331-342 ; Kim et al., 1998, Structure, 6, 89; Yao et al., 1997 Nature Structural Biology, 4, 463; Cho et al., 1998, J. Biol. Chem., 273, 15045). The NS5B RNA dependent RNA polymerase has also been crystallized to reveal a structure reminiscent of other nucleic acid polymerases (Bressanelli et al. 1999, Proc. Natl. Acad. Sci, USA 96,13034-13039; Ago et al. 1999, Structure 7, 1417-1426; Lesburg et al. 1999, Nat. Struct. Biol. 6, 937-943).

Even though important targets for the development of a therapy for chronic HCV infection have been defined with these enzymes and even though a worldwide intensive search for suitable inhibitors is ongoing with the aid of rational drug design and HTS, the development of therapy has one major deficiency, namely the lack of cell culture systems or simple animal models, which allow direct and reliable propagation of HCV viruses. The lack of an efficient cell culture system is still the main reason to date that an understanding of HCV replication remains elusive.

Although flavi- and pestivirus self-replicating RNAs have been described and used for the replication in different cell lines with a relatively high yield, similar experiments with HCV have not been successful to date (Khromykh et al., 1997, J. Virol. 71, 1497; Behrens et al., 1998, J. Virol. 72, 2364; Moser et al., 1998 J. Virol. 72, 5318). It is known from different publications that cell lines or primary cell cultures can be infected with high-titer patient serum containing HCV (Lanford et al. 1994 Virology 202, 606; Shimizu et al. 1993 PNAS, USA 90, 6037-6041; Mizutani et al. 1996 J. Virol. 70, 7219-7223; Ikda, et al. 1998, Virus Res. 56, 157; Fourner et al. 1998, J. Gen. Virol. 79, 2376; Ito et al. 1996, J. Gen. Virol. 77,1043-1054). However, these virus-infected cell lines or cell cultures do not allow the direct detection of HCV-RNA or HCV antigens.

It is also known from the publications of Yoo et al. 1995 J. Virol., 69, 32-38; and of Dash et al., 1997, Am. J. Pathol., 151, 363-373; that hepatoma cell lines can be transfected with synthetic HCV-RNA obtained through in vitro transcription of the cloned HCV genome. In both publications the authors started from the basic idea that the viral HCV genome is a plus-strand RNA functioning directly as mRNA after being transfected into the cell, permitting the synthesis of viral proteins in the course of the translation process, and so new HCV particles could form HCV viruses and their RNA detected through RT-PCR. However the published results of the RT-PCR experiments indicate that the HCV replication in the described HCV transfected hepatoma cells is not particularly efficient and not sufficient to measure the quality of replication, let alone measure the modulations in replication after exposure to potential antiviral drugs. Furthermore it is now known that the highly conserved 3' NTR is essential for the virus replication (Yanagi et al., 1999 Proc. Natl. Acad. Sci. USA, 96, 2291-95). This knowledge strictly contradicts the statements of Yoo et al. J. Virol., 69, 32-38 (supra) and Dash et al., 1997, Am. J. Pathol., 151, 363-373. (supra), who used for their experiments only HCV genomes with shorter 3' NTRs and not the authentic 3' end of the HCV genome.

In WO 98/39031, Rice et al. disclosed authentic HCV genome RNA sequences, in particular containing: a) the highly conserved 5'-terminal sequence "GCCAGCC" (SEQ ID NO. 26); b) the HCV polyprotein coding region; and c) 3'-NTR authentic sequences.

In WO 99/04008, Purcell et al. disclosed an HCV infectious clone that also contained only the highly conserved 5'-terminal sequence "GCCAGC" (SEQ ID NO. 27).

Recently Lohman et al. 1999 (Science 285, 110-113) and Bartenschlager, R. et al., 1993, J. Virol., 67, 3835-3844(in CA 2,303,526, laid-open on Oct. 3, 2000) disclosed a HCV cell culture system where the viral RNA (1377/N52-3') self-replicates in the transfected cells with such efficiency that the quality of replication can be measured with accuracy and reproducibility. The Lohman and Bartenschlager, R. et al., 1993, J. Virol., 67, 3835-3844 disclosures were the first demonstration of HCV RNA replication in cell culture that was substantiated through direct measurement by Northern blots. This replicon system and sequences disclosed therein highlight once again the conserved 5' sequence "GCCAGC" (SEQ ID NO. 27). A similar observation highlighting the conservation of the 5'NTR was made by Blight et al. 2000 (Science 290,1972-1974) and WO 01/89364 published on Nov. 29, 2001.

In addition to the conservation of the 5' and 3' untranslated regions in cell culture replicating RNAs, three other publications by Lohman et al. 2001, J. Virol. 1437-1449 Krieger et al. 2001 J. Virol. 4614-4624 and Guo et al., (2001) J. Virol. 8516-8523 have recently disclosed distinct adaptive mutants within the HCV non-structural protein coding region. Specific nucleotide changes that alter the amino acids of the HCV non-structural proteins are shown to enhance the efficiency of establishing stable replicating HCV subgenomic replicons in culture cells.

Applicant has now found that, contrary to all previous reports, the highly conserved 5'-NTR can be mutated by adaptation to give rise to a HCV RNA sequence that, in conjunction with mutations in the HCV non-structural region, provides for a greater efficiency of transduction and/or replication.

Applicant has also identified novel adaptive mutations within the HCV non-structural region that improves the efficiency of establishing persistently replicating HCV RNA in cell culture.

One advantage of the present invention is to provide an alternative to these existing systems comprising a HCV RNA molecule that self-replicates. Moreover, the present invention demonstrates that the initiating nucleotide of the plus-strand genome can be either an A as an alternative to the G already disclosed.

A further advantage of the present invention is to provide a unique HCV RNA molecule that transduces and/or replicates with higher efficiency. The Applicant demonstrates the utility of this specific RNA molecule in a cell line and its use in evaluating a specific inhibitor of HCV replication.

SUMMARY OF THE INVENTION

In a first embodiment, the present invention provides a 5'-non translated region of the hepatitis C virus wherein its highly conserved guanine at position 1 is substituted for adenine.

Particularly, the present invention provides a hepatitis C virus polynucleotide comprising adenine at position 1 as numbered according to the 1377/NS2-3' construct (Lohmann et al. 1999, Science 285,110-113, Accession # AJ242651).

Particularly, the invention provides a HCV self-replicating polynucleotide comprising a 5'-terminus consisting of ACCAGC (SEQ ID NO.8).

In a second embodiment, the present invention is directed to a HCV self-replicating polynucleotide encoding a polyprotein comprising one or more amino acid substitution selected from the group consisting of: R(1135)K; S(1148)G; S(1560)G; K(1691)R; L(1701)F; I(1984)V; T(1993)A; G(2042)C; G(2042)R; S(2404)P; L(2155)P; P(2166)L and M(2992)T.

Particularly, the invention is directed to a HCV self-replicating polynucleotide encoding a polyprotein comprising the any one of the amino acid substitutions as described above, further comprising the amino acid substitution E(1202)G.

More particularly, the invention provides a HCV self-replicating polynucleotide encoding a polyprotein comprising a G2042C or a G2042R mutation.

Most particularly, the invention provides for HCV self-replicating polynucleotide comprising a nucleotide substitution G-->A at position 1, and said polynucleotide encodes a polyprotein further comprising a G2042C or a G2042R mutation.

Particularly, the polynucleotide of the present invention can be in the form of RNA or DNA that can be transcribed to RNA.

In a third embodiment, the invention also provides for an expression vector comprising a DNA form of the above polynucleotide, operably linked with a promoter.

According to a fourth embodiment, there is provided a host cell transfected with the self-replicating polynucleotide or the vector as described above.

In a fifth embodiment, the present invention provides a RNA replication assay comprising the steps of:
  incubating the host cell as described above in the absence or presence of a potential hepatitis C virus inhibitor;
  isolating the total cellular RNA from the cells;
  analyzing the RNA so as to measure the amount of HCV RNA replicated;
  comparing the levels of HCV RNA in cells in the absence and presence of the inhibitor.

In a sixth embodiment, the invention is directed to a method for testing a compound for inhibiting HCV replication, including the steps of:
  a) treating the above described host cell with the compound;
  b) evaluating the treated host cell for reduced replication, wherein reduced replication indicates the ability of the compound to inhibit replication.

DETAILED DESCRIPTION OF THE DRAWINGS

FIG. 1 is a schematic view of the bi-cistronic replicon RNA. The sequence deviations between the 1377/NS2-3' replicon from Lohman et al., 1999 Science 285:110-113 and the APGK12 replicon are indicated below the replicon. In place of a G nucleotide at the +1 position in the 1377/NS2-3' replicon, the APGK12 contains an additional G resulting in GG at the 5' terminus (the first G being counted as position 1). In the linker region between the neo gene and the EMCV IRES sequence two areas deviate from 1377/NS2-3': 14 nucleotides (CGCGCCCAGATGTT) (SEQ ID NO. 28) which are not present in 1377/NS2/3 are inserted at position 1184 in APGK12; 11 nucleotides (1231-1241) present in 1377/NS2-3' are deleted to generate APGK-12. In the NS5B coding region, a T at position 8032 was mutated to C to eliminate a NcoI restriction site.

Figure 2:
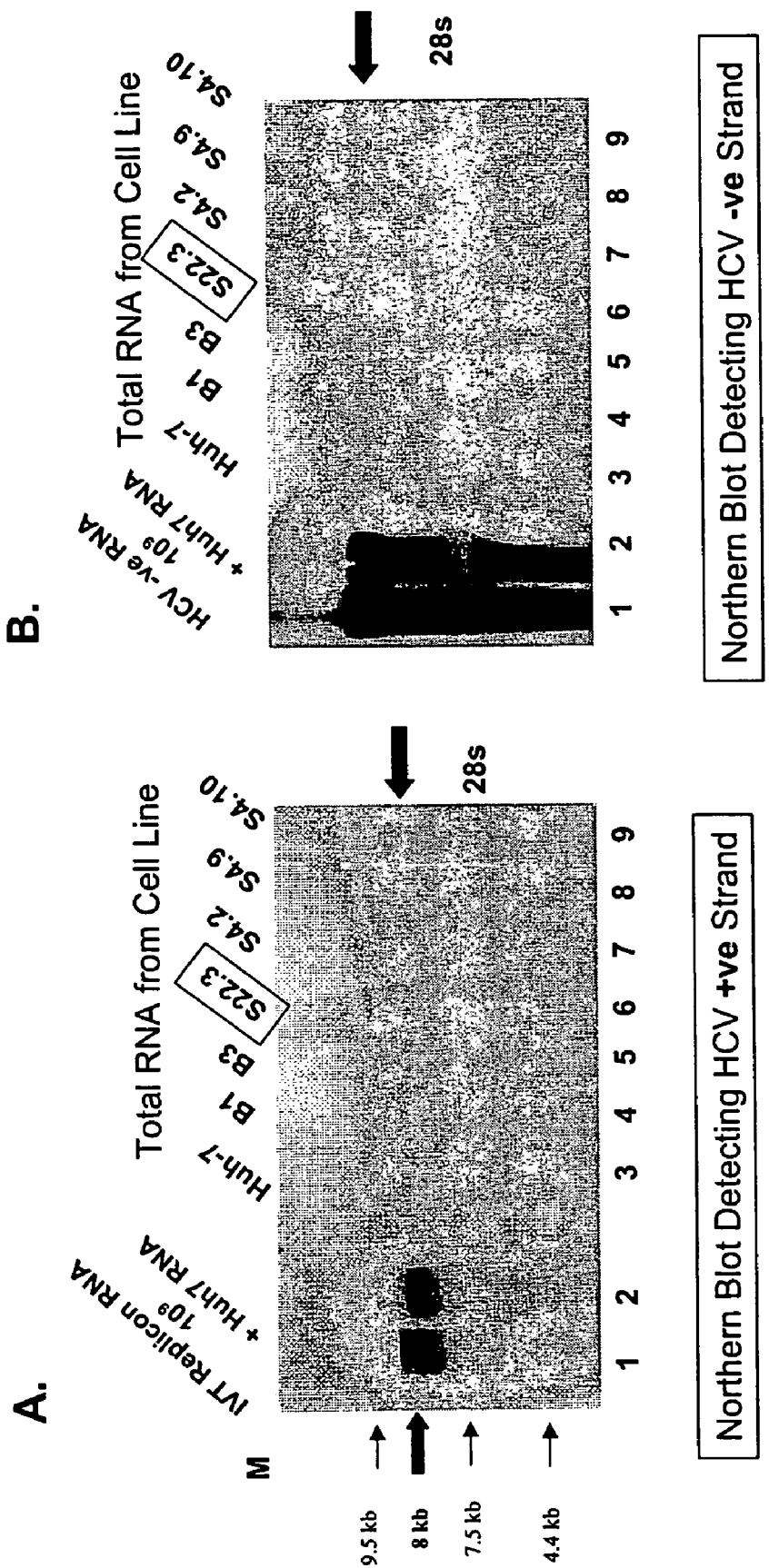

FIG. 2 shows Northern blots of RNA-transfected Huh-7 cell lines. 12 µg of total cellular RNA or control RNA was separated on 0.5% agarose-formaldehyde gels and transferred to Hybond N+ paper, fixed and (FIG. 2A) radioactively probed with HCV specific minus-strand RNA that detects the presence of plus-strand replicon RNA. Lanes 1 and 2: positive controls that contain $10^9$ copies of in vitro transcribed APGK12 RNA. Lane 3: negative control of total cellular RNA from untransfected Huh-7 cells. Lanes 4 and 5: cellular RNA from B1 and B3 cell lines that have integrated DNA copies of the neomycin phosphotransferase gene. Lane 6: total cellular RNA from a Huh-7 cell line, designated S22.3, that harbors high copy number HCV sub-genomic replicon RNA as highlighted by the arrow. Other cell lines have no detectable replicon RNA. FIG. 2B is identical to FIG. 2A with the exception that the blot was radioactively probed with HCV specific plus-strand RNA to detect the presence of HCV minus-strand RNA. Lanes 1 and 2 are positive control lanes that contain $10^9$ copies of full length HCV minus strand RNA. Lane 6, which contains 12 µg of total cellular RNA from cell line S22.3, harbors detectable minus-strand replicon RNA at the expected size of 8-9 kilobases. M represent the migration of non-radioactive molecular size markers on the agarose gel. 28s represents the migration of 28s ribosomal RNA and accounts for the detection of this species in a samples of total cellular RNA.

Figure 3:
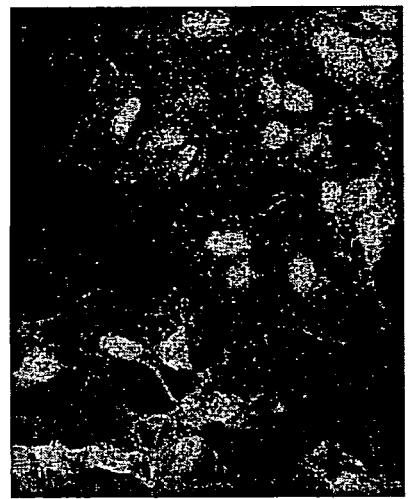
Figure 3:
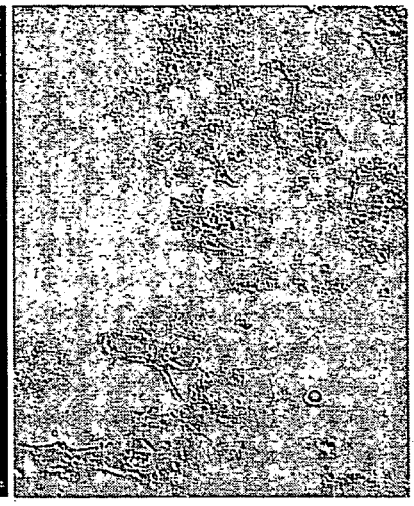
Figure 3:
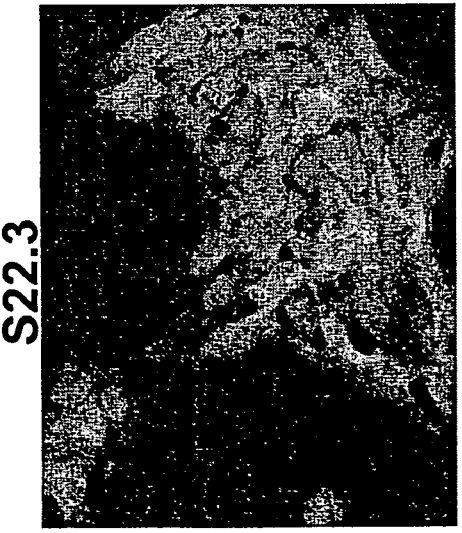
Figure 3:
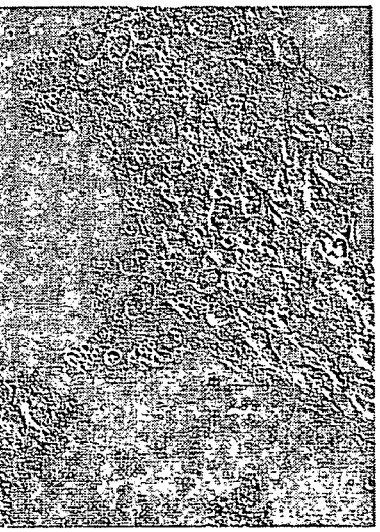

FIG. 3 shows indirect immunofluorescence of a HCV non-structural protein in the S22.3 cell line. Indirect immunofluorescence was performed on cells that were cultured and fixed, permeabilized and exposed to a rabbit polyclonal antibody specific for a segment of the HCV NS4A protein. Secondary goat anti-rabbit antibody conjugated with red-fluor Alexa 594 (Molecular Probes) was used for detection. Top panels shows the results of immunofluorescence (40X objective) and the specific staining of the S22.3 cells. The bottom panels represent the identical field of cells viewed by diffractive interference contrast (DIC) microscopy. The majority of S22.3 (FIG. 3A) cells within the field stain positively for HCV NS4A protein that localizes in the cytoplasm, whereas the B1 cells (FIG. 3B) that fail to express any HCV proteins, only have background level of staining.

Figure 4:
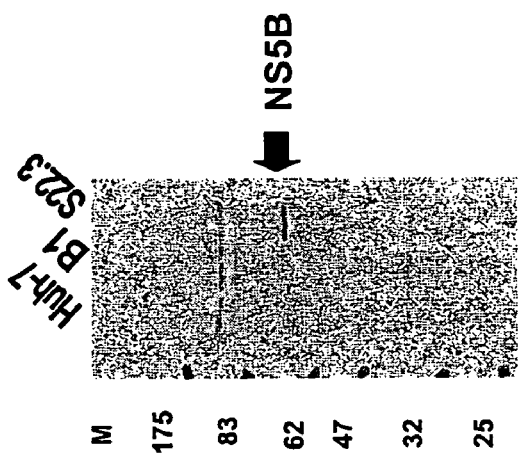
Figure 4:
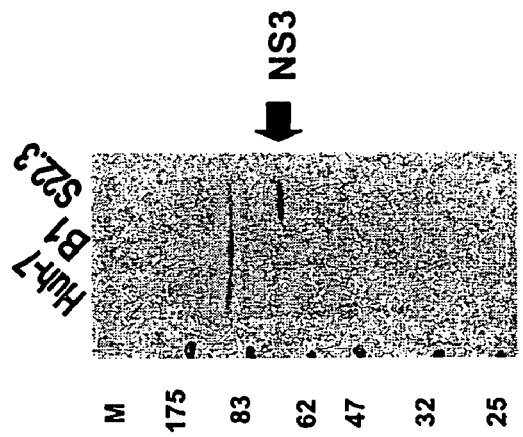
Figure 4:
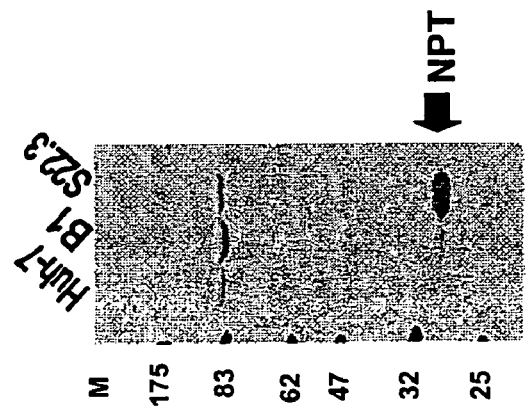

FIG. 4 shows Western-blots following SDS-PAGE separation of total proteins extracted from three cell lines: (i) naïve Huh-7 cell line, (ii) neomycin resistant Huh-7 cell line B1, and (iii) the S22.3 cell line. Panels A, B, and C, demonstrate the results of western blots probed with rabbit polyclonal antisera specific for neomycin phosphotransferase (NPT), HCV NS3, and HCV NS5B, respectively. Visualization was achieved through autoradiographic detection of a chemiluminescent reactive secondary\goat anti-rabbit antibody. Panel A shows that the S22.3 RNA replicon cell line, expresses the NPT protein at levels higher than control B1 cells and that the naive Huh-7 cell line does not produce the NPT protein. Panels B and C show that only the S22.3 cell line produces the mature HCV NS3 and NS5B proteins, respectively. M represents molecular weight (in kilodaltons) of pre-stained polypeptide markers.

FIGS. 5A and 5B identify the nucleotide and amino acid sequences respectively that differ from the APGK12 sequence in the different HCV bi-cistronic replicons. The S22.3 adapted replicon is a first generation replicon selected following the transfection of RNA transcribed from the APGK12 template. R3, R7, R16 are second generation replicons that were selected following the transfection of RNA isolated from the S22.3 first generation replicon cell line. FIG. 5A: Nucleotide mutations that were characterized in each of the adapted replicons are indicated adjacent to the respective segment of the replicon (IRES, NS3, NS4A, NS5A, and NS5B). FIG. 5B: Amino acid numbers are numbered according to the full length HCV poly-protein with the first amino acid in the second cistron corresponding to amino acid 810 in NS2 of 1377/NS2-3' construct.

FIG. 6 depicts the colony formation efficiency of four in vitro transcribed HCV sub-genomic bi-cistronic replicon RNAs. The APGK12 serves as the reference sequence; highlighted are the initiating nucleotides of the HCV IRES in each of the constructs and the amino acid differences (from the APGK12 reference sequence) in the HCV non-structural region for the two R3-rep. Note that the in vitro transcribed APGK-12 RNAs that harbor either a 5'G or 5'A form colonies with the same efficiency (ca. 80 cfu/µg in panels A and B) following selection with 0.25 mg/ml G418. RNA isolated from the second generation R3 cell line was reverse transcribed into DNA and cloned into the pAPGK12 vector backbone to generate the R3-rep, which was sequenced and found to encode additional changes that included the L(2155)P substitution in the NS5A segment of the HCV polyprotein (compare R3-rep sequence with the R3 sequence in tables 2 and 3). Various quantities of in vitro transcribed R3-rep-5'A RNA, were transfected into naive Huh-7 cells to determine a colony formation efficiency of $1.2 \times 10^6$ cfu/µg of RNA (panel C). Various quantities of R3-rep-5'G were also transfected resulting in a colony formation efficiency of $2 \times 10^6$ cfu/µg of RNA (panel D).

Figure 7:
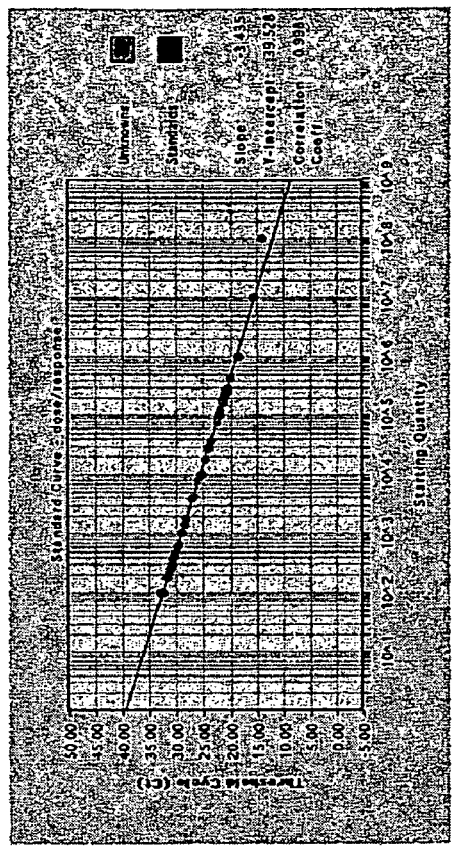
Figure 7:
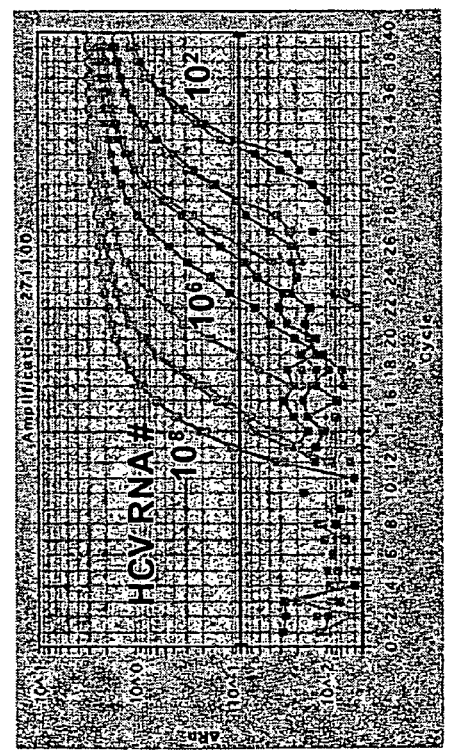

FIG. 7 displays a typical RT-PCR amplification plot (left panel) and the graphical representation of Ct values versus known HCV RNA quantity in a standard curve (right panel). Each of the plotted curves in the left panel, graph the increment of fluorescence reporter signal (delta-Rn) versus PCR cycle number for a predetermined quantity of HCV replicon RNA. The Ct value is obtained by determining the point at which the fluorescence exceeds an arbitrary value (horizontal line). The right panel demonstrates the linear relationship between starting RNA copy number of the predetermined standards (large black dots) and the Ct value. Smaller dots are the Ct values of RNA samples (containing unknown quantity of HCV replicon RNA) from S22.3 cells treated with various concentrations of a specific inhibitor of HCV replication.

Figure 8:
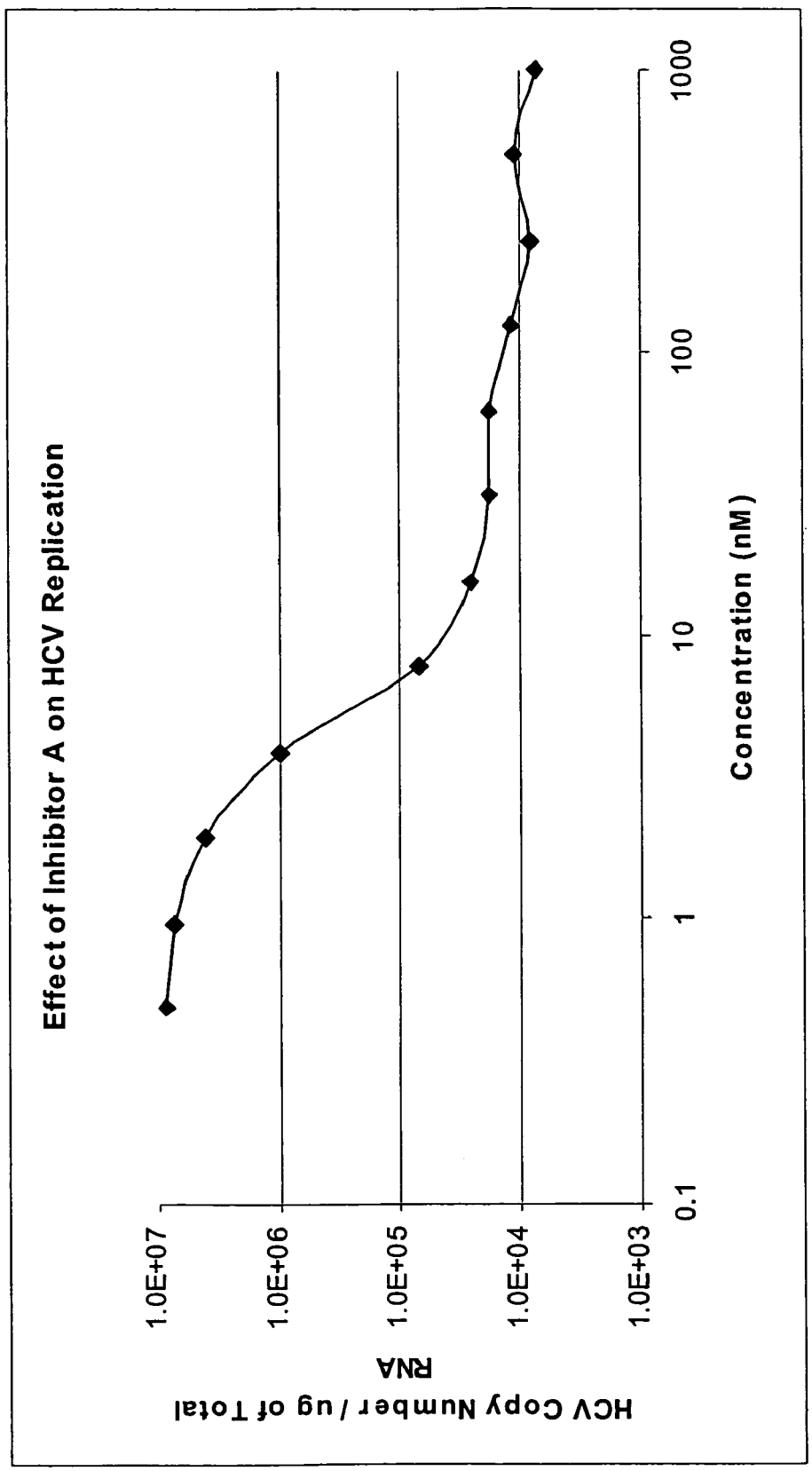

FIG. 8 shows the effect of increasing concentration of inhibitor A on HCV RNA replicon levels in Huh7 cells. S22.3 cells were grown in the presence of increasing concentrations of inhibitor A starting at 0.5 nM and ranging to 1024 nM. The inhibitor dose-response curve is the result of 11 concentrations from serial two-fold dilutions (1:1). One control well, without any inhibitor, was also included during the course of the experiment. The cells were incubated for 4 days in a 5% $CO_2$ incubator at 37° C. Total cellular RNA was extracted, quantified by optical density. HCV replicon RNA was evaluated by real time RT-PCR and plotted as genome equivalents/µg total RNA as a function of inhibitor concentration

DEFINITIONS

Unless defined otherwise, the scientific and technological terms and nomenclature used herein have the same meaning as commonly understood by a person of ordinary skill to which this invention pertains. Generally, the procedures for cell culture, infection, molecular biology methods and the like are common methods used in the art. Such standard techniques can be found in reference manuals such as for example Sambrook et al. (1989) Molecular Cloning—A Laboratory Manual, Cold Spring Harbor Labs and Ausubel et al. (1994).

Nucleotide sequences are presented herein by single strand, in the 5' to 3' direction, from left to right, using the one letter nucleotide symbols as commonly used in the art and in accordance with the recommendations of the IUPAC-IUB Biochemical Nomenclature Commission (1972) Biochemistry, 11, 1726-1732.

The present description refers to a number of routinely used recombinant DNA (rDNA) technology terms. Nevertheless, definitions of selected examples of such rDNA terms are provided for clarity and consistency.

The term "DNA segment or molecule or sequence", is used herein, to refer to molecules comprised of the deoxyribonucleotides adenine (A), guanine (G), thymine (T) and/or cytosine (C). These segments, molecules or sequences can be found in nature or synthetically derived. When read in accordance with the genetic code, these sequences can encode a linear stretch or sequence of amino acids which can be referred to as a polypeptide, protein, protein fragment and the like.

As used herein, the term "gene" is well known in the art and relates to a nucleic acid sequence defining a single protein or polypeptide. The polypeptide can be encoded by a full-length sequence or any portion of the coding sequence, so long as the functional activity of the protein is retained.

A "structural gene" defines a DNA sequence which is transcribed into RNA and translated into a protein having a specific structural function that constitute the viral particles. "Structural proteins" defines the HCV proteins incorporated into the virus particles namely, core "C", E1, E2, and E2-p7.

"Non-structural proteins", defines the HCV proteins that are not comprised in viral particles namely, NS2, NS3, NS4A, NS5A and NS5B.

"Restriction endonuclease or restriction enzyme" is an enzyme that has the capacity to recognize a specific base sequence (usually 4, 5 or 6 base pairs in length) in a DNA molecule, and to cleave the DNA molecule at every place where this sequence appears. An example of such an enzyme is EcoRl, which recognizes the base sequence G↓AATTC (SEQ ID NO. 29) and cleaves a DNA molecule at this recognition site.

"Restriction fragments" are DNA molecules produced by the digestion of DNA with a restriction endonuclease. Any given genome or DNA segment can be digested by a particular restriction endonuclease into at least two discrete molecules of restriction fragments.

"Agarose gel electrophoresis" is an analytical method for fractionating polynucleotide molecules based on their size. The method is based on the fact that nucleic acid molecules migrate through a gel as through a sieve, whereby the smallest molecule has the greatest mobility and travels the farthest through the gel. The sieving characteristics of the gel retards the largest molecules such that, these have the least mobility. The fractionated polynucleotides can be visualized by staining the gel using methods well known in the art, nucleic acid hybridization or by tagging the fractionated molecules with a detectable label. All these methods are well known in the art, specific methods can be found in Ausubel et al. (supra).

"Oligonucleotide or oligomer" is a molecule comprised of two or more deoxyribonucleotides or ribonucleotides, preferably more than three. The exact size of the molecule will depend on many factors, which in turn depend on the ultimate function or use of the oligonucleotide. An oligonucleotide can be derived synthetically, by cloning or by amplification.

"Sequence amplification" is a method for generating large amounts of a target sequence. In general, one or more amplification primers are annealed to a nucleic acid sequence. Using appropriate enzymes, sequences found adjacent to, or in between the primers are amplified. An amplification method used herein is the polymerase chain reaction (PCR) and can be used in conjunction with the reverse-transcriptase (RT) to produce amplified DNA copies of specific RNA sequences.

"Amplification primer" refers to an oligonucleotide, capable of annealing to a RNA or DNA region adjacent to a target sequence and serving as the initiation primer for DNA synthesis under suitable conditions well known in the art. The synthesized primer extension product is complementary to the target sequence.

The term "domain" or "region" refers to a specific amino acid sequence that defines either a specific function or structure within a protein. As an example herein, is the NS3 protease domain comprised within the HCV non-structural polyprotein.

The terms "plasmid" "vector" or "DNA construct" are commonly known in the art and refer to any genetic element, including, but not limited to, plasmid DNA, phage DNA, viral DNA and the like which can incorporate the oligonucleotide sequences, or sequences of the present invention and serve as DNA vehicle into which DNA of the present invention can be cloned. Numerous types of vectors exist and are well known in the art.

The terminology "expression vector" defines a vector as described above but designed to enable the expression of an inserted sequence following transformation or transfection into a host. The cloned gene (inserted sequence) is usually placed under the control of control element sequences such as promoter sequences. Such expression control sequences will vary depending on whether the vector is designed to express the operably linked gene in vitro or in vivo in a prokaryotic or eukaryotic host or both (shuttle vectors) and can additionally contain transcriptional elements such as enhancer elements, termination sequences, tissue-specificity elements, and/or translational initiation and termination sites.

A host cell or indicator cell has been "transfected" by exogenous or heterologous DNA (e.g. a DNA construct) or RNA, when such nucleic acid has been introduced inside the cell. The transfecting DNA may or may not be integrated (covalently linked) into chromosomal DNA making up the genome of the cell. In prokaryotes, yeast, and mammalian cells for example, the transfecting/transforming DNA may be maintained on an episomal element such as a plasmid. With respect to eukaryotic cells, an example of a stably transfected cell is one in which the transfecting DNA has become integrated into a chromosome and is inherited by daughter cells through chromosome replication. A host cell or indicator cell can be transfected with RNA. A cell can be stably transfected with RNA if the RNA replicates and copies of the RNA segregate to daughter cells upon cell division. This stability is demonstrated by the ability of the eukaryotic cell to establish cell lines or clones comprised of a population of daughter cells containing the transfecting DNA or RNA. Transfection methods are well known in the art (Sambrook et al., 1989, Molecular Cloning—A Laboratory Manual, Cold Spring Harbor Labs; Ausubel et al., 1994, Current Protocols in Molecular Biology, Wiley, N.Y.). If the RNA encodes for a genetic marker that imparts an observable phenotype, such as antibiotic resistance, then the stable transfection of replicating RNA can be monitored by the acquisition of such phenotype by the host cell.

As used herein the term "transduction" refers to the transfer of a genetic marker to host cells by the stable transfection of a replicating RNA.

The nucleotide sequences and polypeptides useful to practice the invention include without being limited thereto, mutants, homologs, subtypes, quasi-species, alleles, and the like. It is understood that generally, the sequences of the present invention encode a polyprotein. It will be clear to a person skilled in the art that the polyprotein of the present invention and any variant, derivative or fragment thereof, is auto-processed to an active protease.

As used herein, the designation "variant" denotes in the context of this invention a sequence whether a nucleic acid or amino acid, a molecule that retains a biological activity (either functional or structural) that is substantially similar to that of the original sequence. This variant may be from the same or different species and may be a natural variant or be prepared synthetically. Such variants include amino acid sequences having substitutions, deletions, or additions of one or more amino acids, provided the biological activity of the protein is conserved. The same applies to variants of nucleic acid sequences which can have substitutions, deletions, or additions of one or more nucleotides, provided that the biological activity of the sequence is generally maintained.

The term "derivative" is intended to include any of the above described variants when comprising additional chemical moiety not normally a part of these molecules. These chemical moieties can have varying purposes including, improving a molecule's solubility, absorption, biological half life, decreasing toxicity and eliminating or decreasing undesirable side effects. Furthermore, these moieties can be used for the purpose of labeling, binding, or they may be comprised in fusion product(s). Different moieties capable of mediating the above described effects can be found in Remington's The Science and Practice of Pharmacy (1995).

Methodologies for coupling such moieties to a molecule are well known in the art. The term "fragment" refers to any segment of an identified DNA, RNA or amino acid sequence and/or any segment of any of the variants or derivatives described herein above that substantially retains its biological activity (functional or structural) as required by the present invention.

The terms "variant", "derivative", and "fragment" of the present invention refer herein to proteins or nucleic acid molecules which can be isolated/purified, synthesized chemically or produced through recombinant DNA technology. All these methods are well known in the art. As exemplified herein below, the nucleotide sequences and polypeptides used in the present invention can be modified, for example by in vitro mutagenesis.

As used herein, the term "HCV polyprotein coding region" means the portion of a hepatitis C virus that codes for the polyprotein open reading frame (ORF). This ORF may encode proteins that are the same or different than wild-type HCV proteins. The ORF may also encode only some of the functional protein encoded by wild-type polyprotein coding region. The protein encoded therein may also be from different isolates of HCV, and non-HCV protein may also be encoded therein.

As used herein, the abbreviation "NTR" used in the context of a polynucleotide molecule means a non-translated region. The term "UTR" means untranslated region. Both are used interchangeably.

Preferred embodiments

Particularly, the invention provides a HCV self-replicating polynucleotide molecule comprising a 5'-terminus consisting of ACCAGC (SEQ ID NO.8).

According to the first embodiment of this invention, there is particularly provided a HCV polynucleotide construct comprising:
 a 5'-non translated region (NTR) comprising the sequence ACCAGC (SEQ ID NO. 8) at, or proximal to, its 5'-terminus;
 a HCV polyprotein coding region; and
 a 3'-NTR region.

In a second embodiment, the present invention is directed to a HCV self-replicating polynucleotide encoding a polyprotein comprising one or more amino acid substitution selected from the group consisting of: R(1135)K; S(1148)G; S(1560)G; K(1691)R; L(1701)F; l(1984)V; T(1993)A; G(2042)C; G(2042)R; S(2404)P; L(2155)P; P(2166)L and M(2992)T.

Particularly, the invention is directed to a HCV self-replicating polynucleotide encoding a polyprotein comprising the any one of the amino acid substitutions as described above, further comprising the amino acid substitution E(1202)G.

Alternatively, the first embodiment of the present invention is directed to HCV self-replicating polynucleotide molecule comprising a G2042C/R mutation.

According to the second embodiment, the present invention particularly provides a HCV polynucleotide construct comprising:
- a 5'-NTR region comprising the sequence ACCAGO (SEQ ID NO. 8) at, or proximal to, its 5'-terminus;
- a HCV polyprotein region coding for a HCV polyprotein comprising a G(2042)C or a G(2042)R mutation; and
- a 3'-NTR region.

Preferably, the polynucleotide construct of the present invention is a DNA or RNA molecule. More preferably, the construct is a RNA molecule. Most preferably, the construct is a DNA molecule.

More particularly, the first embodiment of this invention is directed to a RNA molecule encoded by the DNA molecule selected from the group consisting of: SEQ ID NO.2, 4, 5, 6, 7, 24 and 25.

Most particularly, the invention provides a DNA molecule selected from the group consisting of: SEQ ID NO.2, 4, 5, 6, 7, 24 and 25.

In a third embodiment, the invention also is directed to an expression vector comprising DNA forms of the above polynucleotide, operably linked with a promoter.

Preferably, the promoter is selected from the group consisting of: T3, T7 and SP6.

According to a fourth embodiment, there is provided a host cell transfected with the self-replicating polynucleotide or vector as described above. Particularly, the host cell is a eukaryotic cell line. More particularly, the eukaryotic cell line is a hepatic cell line. Most particularly, the hepatic cell line is Huh-7.

In a fifth embodiment, the present invention provides a RNA replication assay comprising the steps of:
a) incubating the host cell as described above under conditions suitable for RNA replication;
b) isolating the total cellular RNA from the cells; and
c) analyzing the RNA so as to measure the amount of HCV RNA replicated.

Preferably, the analysis of RNA levels in step c) is carried out by amplifying the RNA by real-time RT-PCR analysis using HCV specific primers so as to measure the amount of HCV RNA replicated.

Alternatively in this fifth embodiment, the construct comprises a reporter gene, and the analysis of RNA levels in step c) is carried out by assessing the level of reporter expressed.

According to a preferred aspect of the sixth embodiment, the invention is directed to a method for testing a compound for inhibiting HCV replication, including the steps of:
a) carrying step a) as described in the above assay, in the presence or absence of the compound;
b) isolating the total cellular RNA from the cells; and
c) analyzing the RNA so as to measure the amount of HCV RNA replicated.
d) comparing the levels of HCV RNA in cells in the absence and presence of the inhibitor, wherein reduced RNA levels is indicative of the ability of the compound to inhibit replication.

Preferably, the cell line is incubated with the test compound for about 3-4 days at a temperature of about 37° C.

EXAMPLES

Example 1

Replicon Constructs (APGK-12; FIG. 1)

pET9a-EMCV was obtained by ligating an oligonucleotide linker 5' gaattccagatggcgcgcccagatgt-taaccagatccatggcacactctagagtactgtcgac 3' (SEQ ID NO.9) to pET-9a (Novagen) that was cut with EcoRI and SalI to form the vector pET-9a-mod. This linker contains the following restriction sites: EcoRI, AscI, HpaI, NcoI, XbaI, ScaI, SalI. The EMCV IRES was amplified by PCR from the vector pTM1 with primers 5' cggaatcgttaacagaccacaacggtttccctc 3' (SEQ ID NO.10) and 5' ggcgtacccatggtattatcgtgttttca 3' (SEQ ID ggcgtacccatggtattatcgtgtgttttca 3' (SEQ ID Mo. 11) and ligated into pET-9a-mod via EcoRI and NcoI to form pET-9a-EMCV.

The sequence of HCV NS2 to NS5B followed by the 3'UTR of HCV was obtained from the replicon construct 1377/NS2-3' (Lohman et al., 1999 Science 285:110-113; accession number: AJ242651) and synthesized by Operon Technologies Inc. with a T to C change at the NcoI site in NS5B at nucleotide 8032. This sequence was released from an GenOp® vector (Operon Technologies) with NcoI and ScaI and transferred into pET-9a-EMCV to form pET-9a-EMCV-NS2-5B-3'UTR. pET-9a-HCV-neo was obtained by amplification of the HCV IRES from a HCV cDNA isolated from patient serum with primers 5' gcatatgaattctaatacgact-cactataggccagccccgattg 3' (SEQ ID NO.12) containing a T7 promoter and primer 5' ggcgcgcccctttggttttctttgag-gtttaggaftcgtgctcat 3' (SEQ ID NO.13) and amplification of the neomycin phosphotransferase gene from the vector pcDNA 3.1 (Invitrogen) with primers 5' aaagggcgcatgat-tgaacaagatggaftgcacgca 3' (SEQ ID NO.14) and 5' gcatat-gttaactcagaagaactcgtcaagaaggcgata fragments were mixed and amplified with primers 5' gcatatgaattctaatacgactcactat-aggccagccccgattg 3' (SEQ ID NO.16) and 5' gcatatgttaact-cagaagaactcgtcaagaaggcgata 3' (SEQ ID NO.15), cut with Eco RI and HpaI and transferred into pET-9a-mod to form pet-9a-HCV-neo. The EMCV-NS2-5B-3'UTR was released from pET-9a-EMCV-NS2-5B-3'UTR with HpaI and ScaI and transferred into pet-9a-HCV-neo that was cut with HpaI to form pET-9a-APGK12. This insert was sequenced with specific successive primers using a ABI Prism® BigDye™ Terminator Cycle sequencing kit and analyzed on ABI Prism® 377 DNA Sequencer and is shown in SEQ ID NO 1.

RNA in vitro Transcription pET-9a-APGK12 DNA was cut with ScaI for expression of the full-length replicon or with BglII for expression of a truncated negative control RNA. DNA was analyzed on a 1% agarose gel and purified by Phenol/Chloroform extraction. RNA was produced using a T7 Ribomax® kit (Promega) followed by extraction with phenol/chloroform and precipitation with 7.5 M LiCl$_2$. RNA was treated with DNAse I for 15 min to remove the DNA template and further purified with an RNeasy® column (Qiagen). RNA integrity was verified on a denaturing formaldehyde 1% agarose gel.

Example 2

Primary transfection of Huh7 cells and selection of replicon cell lines Human hepatoma Huh7 cells (Health Science Research Resources Bank, Osaka, Japan) were grown in 10% FBS/DMEM. Cells were grown to 70% confluency, trypsinized, washed with phosphate buffered saline (PBS)

and adjusted to 1×10$^7$ cells/ml of PBS. 800 µl of cells were transferred into 0.4 cm cuvettes and mixed with 15 µg of replicon RNA. Cells were electroporated using 960 µF, 300 volts for ~18 msec and evenly distributed into two 15 cm tissue culture plates and incubated in a tissue culture incubator for 24 hours. The selection of first and second generation replicon cell lines was with 10% FBS/DMEM medium supplemented with 1 mg/ml of G418. Cells were selected for 3-5 weeks until colonies were observed that were isolated and expanded.

Following the G418 selection and propagation of Huh-7 cells transfected with APGK12 (SEQ ID NO.1) RNA, cells that formed a distinct colony were treated with trypsin and serially passed into larger culture flasks to establish cell lines. Approximately 10×10$^6$ cells were harvested from each cell line. The cells were lysed and the total cellular RNA extracted and purified as outlined in Qiagen RNAeasy® preparatory procedures. FIG. 2 shows the analysis of 12 µg of total cellular RNA from various cell lines as analyzed on a Northern blot of a denaturing agarose-formaldehyde gel.

FIG. 2A is a Northern blot (radioactively probed with HCV specific minus-strand RNA) that detects the presence of plus-strand replicon RNA. Lanes 1 and 2 are positive controls that contain 10$^9$ copies of in vitro transcribed APGK12 RNA. Lane 2 contains the in vitro transcribed RNA mixed with 12 µg of total cellular from naïve Huh-7 cells. Lane 3 is a negative control of total cellular RNA from untreated Huh-7 cells. Lanes 4 and 5 contain cellular RNA from the B1 and B3 G418 resistant cell lines that have DNA integrated copies of the neomycin phosphotransferase gene. Lane 6 contains total cellular RNA from a Huh-7 cell line, designated S22.3, that harbors high copy number of HCV sub-genomic replicon RNA as detected by the positive signal in the 8 kilo-base range. Other cell lines have no detectable replicon RNA. FIG. 2B is a Northern blot of a duplicate of the gel presented in 2A with the exception that the blot was radioactively probed with HCV specific plus-strand RNA to detect the presence of HCV minus-strand RNA (lanes 1 and 2 are positive control lanes that contain 10$^9$ copies of full length genomic HCV minus strand RNA); only lane 6, which contains 12 µg of total cellular RNA from cell line S22.3, harbors detectable minus-strand replicon RNA at the expected size of 8-9 kilobases. An quantitative estimation of RNA copy number, based on phosphorimager scanning of the Northern blots, is approximately 6×10$^7$ copies of plus-strand/lig of total RNA, and 6×10$^6$ copies of minus strand/µg of total RNA. The presence of the plus-strand and minus-strand intermediate confirms that the HCV sub-genomic RNA is actively replicating in the S22.3 cell line.

Example 3

S22.3 Cell Line Constitutively Expresses HCV Non-Structural Proteins

HCV non-structural protein expression was examined in the S22.3 cell line. FIG. 3 displays the result of indirect immunofluorescence that detects the HCV NS4A protein in the S22.3 cell line and not in the replicon negative B1 cell line (a G418 resistant Huh-7 cell line). Indirect immunofluorescence was performed on cells that were cultured and fixed (with 4% paraformaldehyde) onto Lab-tek chamber slides. Cells were permeabilized with 0.2% Triton X-100 for 10 minutes followed by a 1 hour treatment with 5% milk powder dissolved in phosphate-buffered saline (PBS). A rabbit serum containing polyclonal antibody raised against a peptide spanning the HCV NS4A region was the primary antibody used in detection. Following a 2 hour incubation with the primary antibody, cells were washed with PBS and a secondary goat anti-rabbit antibody conjugated with red-fluor Alexa® 594 (Molecular Probes) was added to cells for 3 hours. Unbound secondary antibody was removed with PBS washes and cells were sealed with a cover slip. FIG. 3 (top panels) shows the results of immunofluorescence as detected by a microscope with specific fluorescent filtering; the bottom panels represent the identical field of cells viewed by diffractive interference contrast (DIC) microscopy. The majority of S22.3 (FIG. 3A) cells within the field stain positively for HCV NS4A protein that localizes in the cytoplasm, whereas the B1 cells (FIG. 3B) that fail to express any HCV proteins, only have background level of staining. A small proportion of S22.3 cells express high levels of intensely stained HCV NS4A.

Expression of the proteins encoded by the bi-cistronic replicon RNA was also examined on Western-blots following SDS-PAGE separation of total proteins extracted from: (i) naïve Huh-7 cell line, (ii) neomycin resistant Huh-7 cell line B1, and (iii) the S22.3 cell line. FIG. 4 panels A, B, and C, demonstrate the results of western blots probed with rabbit polyclonal antisera specific for neomycin phosphotransferase (NPT), HCV NS3, and HCV NS5B, respectively. Visualization was achieved through autoradiographic detection of a chemiluminescent reactive secondary HRP-conjugated goat anti-rabbit antibody. FIG. 4 panel A shows that the S22.3 RNA replicon cell line, expresses the NPT protein at levels higher than B1 cells (which contain an integrated DNA copy of the npt gene) and that the naïve Huh-7 cell line does not produce the NPT protein. FIG. 4 panels B and C show that only the S22.3 cell line produces the mature HCV NS3 and NS5B proteins, respectively. The western blots demonstrate that the S22.3 cell line, which harbors actively replicating HCV sub-genomic replicon RNA, maintains replication of the RNA through the high level expression of the HCV non-structural proteins.

Example 4

Sequence Determination of Adapted Replicons

Total RNA was extracted from replicon containing Huh7 cells using a RNeasy Kit (Qiagen). Replicon RNA was reverse transcribed and amplified by PCR using a OneStep RT-PCR kit (Qiagen) and HCV specific primers (as selected from the full-length sequence disclosed in WO 00/66623). Ten distinct RT-PCR products, that covered the entire bi-cistronic replicon in a staggered fashion, were amplified using oligonucleotide primers. The PCR fragments were sequenced directly with ABI Prism® BigDye™ Terminator Cycle PCR Sequencing and analyzed on ABI Prism® 377 DNA Sequencer. To analyze the sequence of the HCV replicon 3' and 5' ends a RNA ligation/RT-PCR procedure described in Kolykhalov et al. 1996 J. of Virology, 7, p. 3363-3371 was followed. The nucleotide sequence of S22.3 is presented as SEQ ID NO.2.

Example 5

Serial Passage of HCV Replicon RNA

The total cellular RNA from the S22.3 cell line was prepared as described above. HCV Replicon RNA copy number was determined by Taqman® RT-PCR analysis and 20 jg of total S22.3 cellular RNA (containing 1×10$^9$ copies of HCV RNA) was transfected by electroporation into 8×10⁶ naïve Huh-7 cells. Transfected cells were subsequently cultured in 10 cm tissue culture plates containing DMEM supplemented with 10% fetal calf serum (10% FCS). Media was changed to DMEM (10% FCS) supplemented with 1 mg/ml G418 24 hours after transfection and then changed every three days. Twenty-three visible colonies formed three to four weeks post-transfection and G418 selection. G418 resistant colonies were expanded into second generation cell lines that represent the first cell lines harboring serially passaged HCV Replicon RNA. Three of these cell lines: R3, R7, and R16 were the subject of further analyses. First, the efficiency of transduction by each of the adapted replicons was determined by electroporation of the total cellular RNA (extracted from the R3, R7 and R16) into naive Huh-7 cells; following electroporation, the transduction efficiency was determined as described above, by counting the visible G418 resistant colonies that arose following 3 to 5 weeks of G418 selection (Table 1). Second, the sequence of the serially passed adapted replicons was determined from the total cellular RNA that was extracted from each of the R3, R7 and R16 replicon cell lines as described in example 4 (SEQ ID NO.4, 5, 6). Using the pAPGK12 as a reference sequence (SEQ ID NO.1), the nucleotide changes that were selected in HCV segment of the adapted replicons are presented in FIG. 5A. Some of these nucleotide changes are silent and do not change the encoded amino acid whereas others result in an amino acid substitution. FIG. 5B summarizes the amino acid changes encoded by the adapted replicons with the amino acid sequence of pAPGK12 as the reference. It is important to note that the reference sequence APGK-12 (SEQ ID NO.1) contains an extra G at the 5'-terminal (5'-GG) that is not maintained in the replicating RNA of the established cell lines. Also noteworthy is that, in addition to G->A at nucleotide 1, there is also an adapted mutation G->C/R at amino acid 2042 (shown as amino acid 1233 in the sequence listing since a.a. 810 of NS2 is numbered as a.a. 1 in SEQ ID) that can be found in all clones analyzed.

TABLE 1

Transfection of Huh-7 cells

| RNA | Copies of Replicon | # Colonies | SEQ ID |
|---|---|---|---|
| 5 ng APKG12 replicon in 20 µg total Huh-7 RNA | 1.2 × 10⁹ | 0 | |
| 15 µg APKG12 replicon RNA 20 µg total: | 3 × 10¹² | 1 (S22.3) | 1 |
| S22.3 cellular RNA | 3 × 10⁹ | 23 (3 clones analyzed) | 2 |
| R3 cellular RNA | 1 × 10⁹ | 200 | 4 |
| R7 cellular RNA | 1 × 10⁹ | 20 | 5 |
| R16 cellular RNA | 3 × 10⁸ | 100 | 6 |
| cloned R3rep RNA | 2.3 × 10⁸ | 2000 | 7 |

Example 6

Construction of APGK12 with 5' G->A Substitution (APGK12-5' A, SEQ ID NO.24)

The pAPGK12 DNA was modified to change the first nucleotide in the sequence to replace the 5'GG with a 5'A. The change in the pAPGK12 was introduced by replacing an EcoRI/AgeI portion of the sequence with a PCR-generated EcoRI/AgeI fragment that includes the mutation. The oligonucleotides used for the amplification were (SEQ ID. NO.20): 5'-GTG GAC GM TTC TM TAC GAC TCA CTA TM CCA GCC CCC GAT TGG-3' and (SEQ ID. NO.21): 5'-GGA ACG CCC GTC GTG GCC AGC CAC GAT-3' and generated a 195 bp DNA fragment that was then digested with EcoRI and AgeI. The resulting 178 bp restriction fragment was used to replace the EcoRI/AgeI fragment in pAPGK12 to generate the pAPGK12-5'A plasmid.

Example 7 cDNA Cloning of the R3-Replicon (R3REP)

The cDNA clone of the R3 replicon was produced by RT-PCR of RNA extracted from the R3 cell line. The following two oligonucleotides were used: (SEQ ID. NO.22): 5'-GTC GTC TTC TCT GAC ATG GAG AC-3 (SEQ ID. NO.23): 5'-GAG TTG CTC AGT GGA TTG ATG GGC AGC-3'. The ~4400 nt PCR fragment, starting within the NS2 coding region and extending to the 5'-end of the NS5B coding region, was cloned into the plasmid pCR3.1 by TA cloning (Invitrogen). The SacII/XhoI portion of this R3 sequence was then used to replace the SacII/XhoI fragment present in the pAPGK12 and the pAPGK12-5'A described above. Consequently, two R3 cDNA sequences were generated: (I) R3-Rep-5'G with an initiating 5'G (SEQ ID NO.7), and R3-Rep-5'A (SEQ ID NO.25) with an initiating 5'A. Sequencing of the R3 rep cDNA identified unique nucleotide changes that differ from the original pAPGK12 sequence (see FIG. 5A); some of these changes are silent and do not change the encoded amino acid, whereas others do result in an amino acid change (see FIG. 5B). The differences between R3 and the R3-rep reflect the isolation of a unique R3-rep cDNA clone encoding nucleotide changes that were not observed from the sequencing of the total RNA extracted from the R3 cell line.

Example 8

Efficiency of Colony Formation with Modified Constructs

RNA from pAPGK12, pAPGK12-5'A, pR3-Rep and pR3-Rep-5'A was generated by in vitro transcription using the T7 Ribomax® kit (Promega) as described in example 1 above. The reactions containing the pAPGK12-5'A and pR3-Rep-5'A templates were scaled-up 10-fold due to the limitation of commercial RNA polymerase in initiating transcripts with 5'-A. The full length RNAs and control truncated RNA for each clone were introduced into 8×10⁶ naive Huh-7 cells by electroporation as described in example 2. Replicon RNA was supplemented with total cellular Huh-7 carrier RNA to achieve a final 15-20 µg quantity. The cells were then cultured in DMEM medium supplemented with 10% fetal calf serum and 0.25 mg/ml G418 in two 150 mm plates. The lower concentration of G418 was sufficient to isolate and select replicon containing cell lines as none of the transfectants with the control truncated RNA produced any resistant colonies. In contrast, in vitro transcribed APGK-12 RNAs that harbor either a 5'G or 5'A form colonies with the same efficiency (ca. 80 cfu/µg in FIG. 6 panels A and B) following selection with G418. Various quantities (ranging from 0.1 ng to 1 µg) of the R3-rep-5'A RNA, were transfected into naive Huh-7 cells to determine a colony formation efficiency of 1.2×10⁶ cfu/µg of RNA (FIG. 6 panel C depicts transfection with 1 µg of RNA). Various quantities (ranging from 0.1 ng to 1 μg) of R3-rep [5'G] were similarly transfected resulting in a colony formation efficiency of 2×10⁶ cfu/μg of RNA (FIG. 6 panel D depicts colony formation with 1 μg of RNA). Note that, shown for the first time, HCV subgenomic replicons replicate as efficiently with a 5'A nucleotide in place of the 5'G. APGK12 with a 5'A or 5'G RNA have similar transduction efficiencies. Similarly, R3-Rep RNAs with either the 5'A or 5'G both display the markedly increased transduction efficiency. Notably, the adaptive mutants within the HCV non-structural segment encoded by the R3-Rep provides for a substantial increase in transduction efficiency as depicted by the dramatic increase in colony forming units per μg of transfected RNA.

Example 9

Quantification of HCV Replicon RNA Levels in Cell Lines

S22.3 cells, or cell lines harboring other adapted replicons, were seeded in DMEM supplemented with 10% FBS, PenStrep and 1 μg/mL Geneticin. At the end of the incubation period the replicon copy number is evaluated by real-time RT-PCR with the ABI Prism 7700 Sequence Detection System. The TAQMAN® EZ RT-PCR kit provides a system for the detection and analysis of HCV RNA (as first demonstrated by Martell et al. 1999 J. Clin. Microbiol. 37:327-332). Direct detection of the reverse transcription polymerase chain reaction (RT-PCR) product with no downstream processing is accomplished by monitoring the increase in fluorescence of a dye-labeled DNA probe (FIG. 6). The nucleotide sequence of both primers (adapted from Ruster, B. Zeuzem, S. and Roth, W. K., 1995. Analytical Biochemistry 224:597-600) and probe (adapted from Hohne, M., Roeske, H. and Schreier, E. 1998, Poster Presentation: P297 at the Fifth International Meeting on Hepatitis C Virus and Related Viruses Molecular Virology and Pathogenesis, Venezia-Lido Italy, June 25-28,1998) located in the 5'-region of the HCV genome are the following:

HCV Forward primer:
5' ACG CAG AAA GCG TCT AGC CAT GGC (SEQ ID NO. 17) GTT AGT 3'

HCV Reverse primer:
5' TCC CGG GGC ACT CGC AAG CAC CCT (SEQ ID NO. 18) ATC AGG 3'

HCV Probe:
5' FAM-TGG TCT GCG GAA CGG GTG AGT (SEQ ID NO. 19) ACA CC-TAMRA 3'

FAM: Fluorescence reporter dye.

TAMRA: Quencher dye.

Using The TAQMAN® EZ RT-PCR kit, the following reaction was set up:

| Component | Volume per sample (μL) | Final Concentration |
|---|---|---|
| RNase-Free Water | 16 | — |
| 5× Taqman EZ Buffer | 10 | 1× |
| Manganese Acetate 25 mM | 6 | 3 mM |

-continued

| Component | Volume per sample (μL) | Final Concentration |
|---|---|---|
| dATP 10 mM | 1.5 | 300 μM |
| dCTP 10 mM | 1.5 | 300 μM |
| dGTP 10 mM | 1.5 | 300 μM |
| dUTP 20 mM | 1.5 | 300 μM |
| HCV Forward Primer 10 μM | 1 | 200 nM |
| HCV Reverse Primer 10 μM | 1 | 200 nM |
| HCV Probe 5 uM | 2 | 200 nM |
| rTth DNA Polymerase 2.5 U/μL | 2 | 0.1 U/μL |
| AmpErase UNG 1 U/μL | 0.5 | 0.01 U/μL |
| Total Mix | 45 | — |

To this reaction mix, 5 μL of total RNA extracted from S22.3 cells diluted at 10 ng/μL was added, for a total of 50 ng of RNA per reaction. The replicon copy number was evaluated with a standard curve made from known amounts of replicon copies (supplemented with 50 ng of wild type Huh-7 RNA) and assayed in an identical reaction mix (FIG. 7).

Thermal cycler parameters used for the RT-PCR reaction on the ABI Prism 7700 Sequence Detection System were optimized for HCV detection:

| Cycle | Temperature (° C.) | Time (Minutes) | Repeat | Reaction |
|---|---|---|---|---|
| Hold | 50 | 2 | | Initial Step |
| Hold | 60 | 30 | | Reverse Transcription |
| Hold | 95 | 5 | | UNG Deactivation |
| Cycle | 95 | 0:15 | 2 | Melt |
| | 60 | 1 | | Anneal/Extend |
| Cycle | 90 | 0:15 | 40 | Melt |
| | 60 | 1 | | Anneal/Extend |

Quantification is based on the threshold cycle, where the amplification plot crosses a defined fluorescence threshold. Comparison of the threshold cycles provides a highly sensitive measure of relative template concentration in different samples. Monitoring during early cycles, when PCR fidelity is at its highest, provides precise data for accurate quantification. The relative template concentration can be converted to RNA copy numbers by employing a standard curve of HCV RNA with known copy number (FIG. 7).

Example 10

A Specific HCV NS3 Protease Anti-Viral Compound Inhibits Replication of the HCV Replicon in S22.3 Cell Lines In order to determine the effect of a specific HCV NS3 protease anti-viral compound on replicon levels in S22.3 cells, the cells were seeded in 24 Well Cell Culture Cluster at 5×10⁴ cells per well in 500 μL of DMEM complemented with 10% FBS, PenStrep and 1 μg/mL Geneticin. Cells were incubated until compound addition in a 5% CO₂ incubator at 37° C. The dose-response curve of the inhibitor displayed 11 concentrations resulting from serial two-fold dilutions (1:1). The starting concentration of compound A was 100 nM. One control well (without any compound) was also included in the course of the experiment. The 24 well plates were incubated for 4 days in a 5% CO₂ incubator at 37° C.

Following a 4 day incubation period, the cells were washed once with PBS and RNA was extracted with the RNeasy® Mini Kit and Qiashredder® from Qiagen. RNA from each well was eluted in 50 µL of $H_2O$. The RNA was quantified by optical density at 260 nm on a Cary 1E UV-Visible Spectrophotometer. 50 ng of RNA from each well was used to quantify the HCV replicon RNA copy number as detailed in Example 6. The level of inhibition (% inhibition) of each well containing inhibitor was calculated with the following equation (CN=HCV Replicon copy number):

$$\% \cdot \text{inhibition} = \left( \frac{CN \cdot \text{control} - Cn \cdot \text{well}}{CN \cdot \text{control}} \right) * 100$$

The calculated % inhibition values were then used to determine $IC_{50}$, slope factor (n) and maximum inhibition ($I_{max}$) by the non-linear regression routine NLIN procedure of SAS using the following equation:

$$\% \cdot \text{inhibition} = \frac{I_{max} \times [\text{inhibitor}]^n}{[\text{inhibitor}]^n + IC_{50}^n}$$

Compound A was tested in the assay at least 4 times. The $IC_{50}$ curves were analyzed individually by the SAS nonlinear regression analysis. FIG. 8 shows a typical curve and Table 2 shows the individual and average $IC_{50}$ values of compound A. The average $IC_{50}$ of compound A in the replication assay was 1.1 nM.

TABLE 2

$IC_{50}$ of compound A in the S22.3 Cell line Replicon Assay.

| Compound | $IC_{50}$ (nM) | Average $IC_{50}$ (nM) |
|---|---|---|
| A | 1.2 | |
| | 1.2 | |
| | 1.0 | |
| | 0.9 | |
| | | 1.1 ± 0.2 |

DISCUSSION

The reproducible and robust ex vivo propagation of hepatitis C virus, to levels required for the accurate testing of potential anti-viral compounds, has not been achieved with any system. As an alternative approach to studying the molecular mechanisms of hepatitis C virus RNA replication, selectable self-replicating bi-cistronic RNAs were developed (Lohman et al., 1999, Science 285,110-113; Bartenschlager, R. et al., 1993, J. Virol., 67, 3835-3844 CA 2,303,526). Minimally, these replicons encode for some or all of the non-structural proteins and also carry a selectable marker such as the neomycin phosphotransferase. Though intracellular steady-state levels of these sub-genomic replicon RNAs among the selected clones is moderate to high, the frequency of generating G418-resistant colonies upon transfection of the consensus RNA described by Lohman et al. or Bartenschlager, R. et al., 1993, J. Virol., 67, 3835-3844 is very low. Less than 100 colonies are generated when 8 million cells are transfected with 1 µg of in vitro transcribed bi-cistronic replicon RNA. A low efficiency of colony formation was first noted by Lohmann et al (1999 et al, Science 285,110-113). Since then, Lohmann et al. (2001) J. Virol. 1437-1449, Blight et al. 2000, Science 290, 1972-1974, and Guo et al., (2001) J. Virol. 8516-8523, have isolated sub-genomic RNAs with markedly improved efficiencies in the colony formation assay. Lohmann et al., 1999 Science 285,110-113 originally reported that selection of sub genomic replicons may not involve the selection of adaptive mutants as serially passaged RNA did not demonstrate an improved transfection efficiency. Nevertheless, in an effort to characterize the function and fitness of replicating HCV RNA, we serially passaged the replicon RNA that was isolated from the first selected cell-line. Notably, a significant increase in colony forming efficiency was obtained from this experiment, even though the quantity of replicon RNA was orders of magnitude lower than originally used to transfect the in vitro transcribed RNA. Furthermore, a second round serial passage of replicon RNA from this first generation clone into naive Huh-7 cells provided for yet another increase in colony formation efficiency (Table 1).

Our analysis of replicating HCV RNAs identified several adaptive mutations that enhance the efficiency of colony formation by up to 4 orders of magnitude. Adaptive mutations were found in many non-structural proteins, as well as in the 5' non-translated region. The substitution of the 5'-GG doublet for a 5'-A as the inaugurating nucleotide of the HCV 5'-UTR is a variant of the HCV genome that has not been previously described, despite the sequencing of innumerable genotypes and subtypes from across the world. Our original replicon that carried a 5'-GG evolved to variants with either a single 5'-A or 5'-G, both of which showed equal transduction efficiency. We describe here the first report of a HCV genome that can tolerate and stably maintain a 5'A extremity. Moreover, we were successful in re-introducing this defined single nucleotide substitution into our cDNA clone and generate in vitro transcribed RNA harboring such an extremity to confirm that a 5'A functions as efficiently as a 5'G.

We have identified adaptive amino acid substitutions in the HCV non-structural proteins NS3, NS4A and NS5A in the R3 replicon, and a substitution in NS5B in the R7 clone (see FIG. 5B). These mutations, particularly the combination defined by the R3-rep (SEQ ID NO.7), when reconstituted into a cDNA clone and transcribed onto a RNA replicon, result in a significantly enhanced transduction efficiency of up to 20,000 fold from the original wild type APGK12 replicon RNA. However, the steady state levels of intracellular replicon RNA were comparable from each of the different isolated clones. This result suggests that the increase in replication efficiency by the adaptive mutations does not result in higher stable intracellular RNA levels due to higher RNA replication, but rather confers increased permissivity for establishing the replicon in a greater number of Huh7 cells. Such a phenotype may be manifested transiently, through an initial increase of the amount of de novo replication, that is required to surpass a defined threshold to establish persistently replicating RNAs within a population of dividing cells.

Recently three other groups also identified other distinct adaptive mutants. Lohmann et al. (2000) reported enhanced transduction efficiencies of up to 10,000 fold with mutations in NS3, NS4B, NS5A and NS5B. Blight et al. 2000, Science 290:1972-1974 reported an augmentation of transduction efficiencies up to 20,000 fold with a single mutation in NS5A whereas Guo et al., (2001) J. Virol. 8516-8523 reported increases in transduction efficiencies of 5,000-10,000 fold with a deletion of a single amino acid in NS5A. The amino acid substitutions that we describe here have not previously been identified as adaptive mutants that enhance the efficiency of RNA transfection and/or replication. One exception is the mutation of E1202G in NS3 that we found in both the R7 and R16 replicons. This adaptation was previously described by Guo et al., (2001) J. Virol. 8516-8523 and Krieger et al (2001) J. Virol. 4614-4624. All other adaptive mutations, without exception, described herein are unpublished.

The development of selectable subgenomic HCV replicons has provided for potential avenues of exploration on HCV RNA replication, persistence, and pathogenesis in cultured cells. However, the low transduction efficiency with the HCV RNA-containing replicons as originally described (Lohmann et al., 1999 Science 285: 110-113) showed that it was not a practical system for reverse genetics studies. The adaptive mutants described herein overcome the low transduction efficiency. In light of the recent descriptions of adaptive mutants by other groups, we note that adaptation can be achieved by distinct mutations in different HCV NS proteins, although the level of adaptation can vary drastically. The replicons encoding adaptive mutants that are described herein are ideally suited for reverse genetic studies to identify novel HCV targets or host cell targets that may modulate HCV RNA replication or HCV replicon RNA colony formation. The adapted and highly efficient replicons are suitable tools for characterizing subtle genotypic or phenotypic changes that affect an easily quantifiable transduction efficiency.

Lastly, we have used our adapted HCV sub genomic replicon cell-line to demonstrate the proficient inhibition of HCV RNA replication by a specific small molecule inhibitor of the HCV NS3 protease. This is the first demonstration that an antiviral, designed to specifically inhibit one of the HCV non-structural proteins, inhibits HCV RNA replication in cell culture. Moreover, this compound and our S22.3 cell line validate the proposal that RNA replication is directed by the HCV non-structural proteins NS3 to NS5B. The assay that we will be extremely useful in characterizing other inhibitors of HCV non-structural protein function in cell culture in a high throughput fashion.

All references found throughout the present disclosure are herein incorporated by reference.

The invention claimed is:

1. An isolated HCV self-replicating potynucleotide comprising:
   (a) a 5'-Non Translated Region;
   (b) a HCV polynucleotide encoding for an HCV polyprotein that comprises: HCV NS3, NS4A, NS4B, NS5A, and NS5B polypeptides, which contains an amino acid substitution commonly designated as: G(2042)C, wherein the amino acid is numerated from the beginning of the coding region of 1377/NS2-3' construct (EMBL genebank accession number No. AJ242651); and
   (c) a 3'-Non Translated Region.

2. The HCV polynucleotide according to claim 1, further comprising one or more amino acid substitutions selected from the group consisting of:
   I(1984)V and M(2992)T.

3. The HCV polynucleotide according to claim 2, further comprising an amino acid substitution commonly designated as: E(1202)G.

4. The HCV polynucleotide according to claim 3, wherein said substitution is selected from the group consisting of: E(1202)G, I(1984)V, G(2042)C, and M(2992)T.

5. The HCV polynucleotide according to claim 1, wherein said polynucleotide is a DNA molecule selected from the group consisting of: SEQ ID NO, 2, 4, 5, 6, 7 and 25.

6. The HCV polynucleotide according to claim 1, wherein said polynucleotide is an RNA molecule encoded by a DNA selected from the group consisting of: SEQ ID NO, 2, 4, 5, 7 and 25.

* * * * *

UNITED STATES PATENT AND TRADEMARK OFFICE
CERTIFICATE OF CORRECTION

| | | |
|---|---|---|
| PATENT NO. | : 7,344,723 B2 | Page 1 of 1 |
| APPLICATION NO. | : 10/789355 | |
| DATED | : March 18, 2008 | |
| INVENTOR(S) | : George Kukolj and Arnim Pause | |

It is certified that error appears in the above-identified patent and that said Letters Patent is hereby corrected as shown below:

Column 165, line 8 after "G(2042)C" insert -- or G(2042)R --

Column 165, lines 10-11 "the coding region of 1377/NS2-3' construct (EMBL genebank accession number No. AJ242651)" should be changed to -- SEQ ID NO 30 --

Column 165, line 16 after "consisting of:" insert -- R(1135)K, S(1148)G, S(1560)G, K(1691)R, L(1701)F, --

Column 165, line 17 after "I(1984)V" insert -- , T(1993)A, S(2404)P, L(2155)P, P(2166)L, --

Column 166, line 12 after "5," insert -- 6, --

Signed and Sealed this

Sixteenth Day of September, 2008

JON W. DUDAS
*Director of the United States Patent and Trademark Office*

SEQUENCE LISTING

```
<160> NUMBER OF SEQ ID NOS: 25

<210> SEQ ID NO 1
<211> LENGTH: 8639
<212> TYPE: DNA
<213> ORGANISM: HCV
<220> FEATURE:
<221> NAME/KEY: CDS
<222> LOCATION: (1803)...(8408)

<400> SEQUENCE: 1
ggccagcccc cgattggggg cgacactcca ccatagatca ctcccctgtg aggaactact      60
gtcttcacgc agaaagcgtc tagccatggc gttagtatga gtgtcgtgca gcctccagga     120 cccccctcc cgggagagcc atagtggtct gcggaaccgg tgagtacacc ggaattgcca     180
ggacgaccgg gtcctttctt ggatcaaccc gctcaatgcc tggagatttg ggcgtgcccc     240
cgcgagactg ctagccgagt agtgttgggt cgcgaaaggc cttgtggtac tgcctgatag     300
ggtgcttgcg agtgccccgg gaggtctcgt agaccgtgca ccatgagcac gaatcctaaa     360
cctcaaagaa aaaccaaagg gcgcgccatg attgaacaag atggattgca cgcaggttct     420
ccggccgctt gggtggagag gctattcggc tatgactggg cacaacagac aatcggctgc     480
tctgatgccg ccgtgttccg gctgtcagcg caggggcgcc cggttctttt tgtcaagacc     540
gacctgtccg gtgccctgaa tgaactgcag gacgaggcag cgcggctatc gtggctggcc     600
acgacgggcg ttccttgcgc agctgtgctc gacgttgtca ctgaagcggg aagggactgg     660
ctgctattgg gcgaagtgcc ggggcaggat ctcctgtcat ctcaccttgc tcctgccgag     720
aaagtatcca tcatggctga tgcaatgcgg cggctgcata cgcttgatcc ggctacctgc     780
ccattcgacc accaagcgaa acatcgcatc gagcgagcac gtactcggat ggaagccggt     840
cttgtcgatc aggatgatct ggacgaagag catcaggggc tcgcgccagc cgaactgttc     900
gccaggctca aggcgcgcat gcccgacggc gaggatctcg tcgtgaccca tggcgatgcc     960
tgcttgccga atatcatggt ggaaaatggc cgcttttctg gattcatcga ctgtggccgg    1020
ctgggtgtgg cggaccgcta tcaggacata gcgttggcta cccgtgatat tgctgaagag    1080
cttggcggcg aatgggctga ccgcttcctc gtgctttacg gtatcgccgc tcccgattcg    1140
```

```
cagcgcatcg ccttctatcg ccttcttgac gagttcttct gagttcgcgc ccagatgtta   1200
acagaccaca acggtttccc tctagcggga tcaattccgc ccccccccct aacgttactg   1260
gccgaagccg cttggaataa ggccggtgtg cgtttgtcta tatgttattt tccaccatat   1320
tgccgtcttt tggcaatgtg agggcccgga aacctggccc tgtcttcttg acgagcattc   1380
ctaggggtct ttcccctctc gccaaaggaa tgcaaggtct gttgaatgtc gtgaaggaag   1440
cagttcctct ggaagcttct tgaagacaaa caacgtctgt agcgacccTt tgcaggcagc   1500 ggaaccccc acctggcgac aggtgcctct gcggccaaaa gccacgtgta taagatacac    1560
ctgcaaaggc ggcacaaccc cagtgccacg ttgtgagttg atagttgtg gaaagagtca    1620 aatggctctc ctcaagcgta ttcaacaagg ggctgaagga tgcccagaag gtaccccatt   1680
gtatgggatc tgatctgggg cctcggtgca catgctttac atgtgtttag tcgaggttaa   1740
aaaacgtcta ggccccccga accacgggga cgtggttttc ctttgaaaaa cacgataata   1800 cc atg gac cgg gag atg gca gca tcg tgc gga ggc gcg gtt ttc gta       1847
   Met Asp Arg Glu Met Ala Ala Ser Cys Gly Gly Ala Val Phe Val
   1               5                  10                 15 ggt ctg ata ctc ttg acc ttg tca ccg cac tat aag ctg ttc ctc gct       1895
Gly Leu Ile Leu Leu Thr Leu Ser Pro His Tyr Lys Leu Phe Leu Ala
            20                  25                  30 agg ctc ata tgg tgg tta caa tat ttt atc acc agg gcc gag gca cac       1943
Arg Leu Ile Trp Trp Leu Gln Tyr Phe Ile Thr Arg Ala Glu Ala His
        35                  40                  45 ttg caa gtg tgg atc ccc ccc ctc aac gtt cgg ggg ggc cgc gat gcc       1991
Leu Gln Val Trp Ile Pro Pro Leu Asn Val Arg Gly Gly Arg Asp Ala
    50                  55                  60 gtc atc ctc ctc acg tgc gcg atc cac cca gag cta atc ttt acc atc       2039
Val Ile Leu Leu Thr Cys Ala Ile His Pro Glu Leu Ile Phe Thr Ile
65                  70                  75 acc aaa atc ttg ctc gcc ata ctc ggt cca ctc atg gtg ctc cag gct       2087
Thr Lys Ile Leu Leu Ala Ile Leu Gly Pro Leu Met Val Leu Gln Ala
 80                  85                  90                  95 ggt ata acc aaa gtg ccg tac ttc gtg cgc gca cac ggg ctc att cgt       2135
Gly Ile Thr Lys Val Pro Tyr Phe Val Arg Ala His Gly Leu Ile Arg
                100                 105                 110 gca tgc atg ctg gtg cgg aag gtt gct ggg ggt cat tat gtc caa atg       2183
Ala Cys Met Leu Val Arg Lys Val Ala Gly Gly His Tyr Val Gln Met
            115                 120                 125 gct ctc atg aag ttg gcc gca ctg aca ggt acg tac gtt tat gac cat       2231
Ala Leu Met Lys Leu Ala Ala Leu Thr Gly Thr Tyr Val Tyr Asp His
        130                 135                 140 ctc acc cca ctg cgg gac tgg gcc cac gcg ggc cta cga gac ctt gcg       2279
Leu Thr Pro Leu Arg Asp Trp Ala His Ala Gly Leu Arg Asp Leu Ala
    145                 150                 155 gtg gca gtt gag ccc gtc gtc ttc tct gat atg gag acc aag gtt atc       2327
Val Ala Val Glu Pro Val Val Phe Ser Asp Met Glu Thr Lys Val Ile
160                 165                 170                 175 acc tgg ggg gca gac acc gcg gcg tgt ggg gac atc atc ttg ggc ctg       2375
Thr Trp Gly Ala Asp Thr Ala Ala Cys Gly Asp Ile Ile Leu Gly Leu
                180                 185                 190 ccc gtc tcc gcc cgc agg ggg agg gag ata cat ctg gga ccg gca gac       2423
Pro Val Ser Ala Arg Arg Gly Arg Glu Ile His Leu Gly Pro Ala Asp
            195                 200                 205 agc ctt gaa ggg cag ggg tgg cga ctc ctc gcg cct att acg gcc tac       2471
Ser Leu Glu Gly Gln Gly Trp Arg Leu Leu Ala Pro Ile Thr Ala Tyr
        210                 215                 220
```

```
                                                -continued tcc caa cag acg cga ggc cta ctt ggc tgc atc atc act agc ctc aca         2519
Ser Gln Gln Thr Arg Gly Leu Leu Gly Cys Ile Ile Thr Ser Leu Thr
225                 230                 235 ggc cgg gac agg aac cag gtc gag ggg gag gtc caa gtg gtc tcc acc         2567
Gly Arg Asp Arg Asn Gln Val Glu Gly Glu Val Gln Val Val Ser Thr
240                 245                 250                 255 gca aca caa tct ttc ctg gcg acc tgc gtc aat ggc gtg tgt tgg act         2615
Ala Thr Gln Ser Phe Leu Ala Thr Cys Val Asn Gly Val Cys Trp Thr
            260                 265                 270 gtc tat cat ggt gcc ggc tca aag acc ctt gcc ggc cca aag ggc cca         2663
Val Tyr His Gly Ala Gly Ser Lys Thr Leu Ala Gly Pro Lys Gly Pro
        275                 280                 285 atc acc caa atg tac acc aat gtg gac cag gac ctc gtc ggc tgg caa         2711
Ile Thr Gln Met Tyr Thr Asn Val Asp Gln Asp Leu Val Gly Trp Gln
    290                 295                 300 gcg ccc ccc ggg gcg cgt tcc ttg aca cca tgc acc tgc ggc agc tcg         2759
Ala Pro Pro Gly Ala Arg Ser Leu Thr Pro Cys Thr Cys Gly Ser Ser
305                 310                 315 gac ctt tac ttg gtc acg agg cat gcc gat gtc att ccg gtg cgc cgg         2807
Asp Leu Tyr Leu Val Thr Arg His Ala Asp Val Ile Pro Val Arg Arg
320                 325                 330                 335 cgg ggc gac agc agg ggg agc cta ctc tcc ccc agg ccc gtc tcc tac         2855
Arg Gly Asp Ser Arg Gly Ser Leu Leu Ser Pro Arg Pro Val Ser Tyr
            340                 345                 350 ttg aag ggc tct tcg ggc ggt cca ctg ctc tgc ccc tcg ggg cac gct         2903
Leu Lys Gly Ser Ser Gly Gly Pro Leu Leu Cys Pro Ser Gly His Ala
        355                 360                 365 gtg ggc atc ttt cgg gct gcc gtg tgc acc cga ggg gtt gcg aag gcg         2951
Val Gly Ile Phe Arg Ala Ala Val Cys Thr Arg Gly Val Ala Lys Ala
    370                 375                 380 gtg gac ttt gta ccc gtc gag tct atg gaa acc act atg cgg tcc ccg         2999
Val Asp Phe Val Pro Val Glu Ser Met Glu Thr Thr Met Arg Ser Pro
385                 390                 395 gtc ttc acg gac aac tcg tcc cct ccg gcc gta ccg cag aca ttc cag         3047
Val Phe Thr Asp Asn Ser Ser Pro Pro Ala Val Pro Gln Thr Phe Gln
400                 405                 410                 415 gtg gcc cat cta cac gcc cct act ggt agc ggc aag agc act aag gtg         3095
Val Ala His Leu His Ala Pro Thr Gly Ser Gly Lys Ser Thr Lys Val
            420                 425                 430 ccg gct gcg tat gca gcc caa ggg tat aag gtg ctt gtc ctg aac ccg         3143
Pro Ala Ala Tyr Ala Ala Gln Gly Tyr Lys Val Leu Val Leu Asn Pro
        435                 440                 445 tcc gtc gcc gcc acc cta ggt ttc ggg gcg tat atg tct aag gca cat         3191
Ser Val Ala Ala Thr Leu Gly Phe Gly Ala Tyr Met Ser Lys Ala His
    450                 455                 460 ggt atc gac cct aac atc aga acc ggg gta agg acc atc acg acg ggt         3239
Gly Ile Asp Pro Asn Ile Arg Thr Gly Val Arg Thr Ile Thr Thr Gly
465                 470                 475 gcc ccc atc acg tac tcc acc tat ggc aag ttt ctt gcc gac ggt ggt         3287
Ala Pro Ile Thr Tyr Ser Thr Tyr Gly Lys Phe Leu Ala Asp Gly Gly
480                 485                 490                 495 tgc tct ggg ggc gcc tat gac atc ata ata tgt gat gag tgc cac tca         3335
Cys Ser Gly Gly Ala Tyr Asp Ile Ile Ile Cys Asp Glu Cys His Ser
            500                 505                 510 act gac tcg acc act atc ctg ggc atc ggc aca gtc ctg gac caa gcg         3383
Thr Asp Ser Thr Thr Ile Leu Gly Ile Gly Thr Val Leu Asp Gln Ala
        515                 520                 525 gag acg gct gga gcg cga ctc gtc gtg ctc gcc acc gct acg cct ccg         3431
Glu Thr Ala Gly Ala Arg Leu Val Val Leu Ala Thr Ala Thr Pro Pro
530                 535                 540
```

-continued

```
gga tcg gtc acc gtg cca cat cca aac atc gag gag gtg gct ctg tcc      3479
Gly Ser Val Thr Val Pro His Pro Asn Ile Glu Glu Val Ala Leu Ser
545                 550                 555 agc act gga gaa atc ccc ttt tat ggc aaa gcc atc ccc atc gag acc      3527
Ser Thr Gly Glu Ile Pro Phe Tyr Gly Lys Ala Ile Pro Ile Glu Thr
560                 565                 570                 575 atc aag ggg ggg agg cac ctc att ttc tgc cat tcc aag aag aaa tgt      3575
Ile Lys Gly Gly Arg His Leu Ile Phe Cys His Ser Lys Lys Lys Cys
                580                 585                 590 gat gag ctc gcc gcg aag ctg tcc ggc ctc gga ctc aat gct gta gca      3623
Asp Glu Leu Ala Ala Lys Leu Ser Gly Leu Gly Leu Asn Ala Val Ala
            595                 600                 605 tat tac cgg ggc ctt gat gta tcc gtc ata cca act agc gga gac gtc      3671
Tyr Tyr Arg Gly Leu Asp Val Ser Val Ile Pro Thr Ser Gly Asp Val
        610                 615                 620 att gtc gta gca acg gac gct cta atg acg ggc ttt acc ggc gat ttc      3719
Ile Val Val Ala Thr Asp Ala Leu Met Thr Gly Phe Thr Gly Asp Phe
625                 630                 635 gac tca gtg atc gac tgc aat aca tgt gtc acc cag aca gtc gac ttc      3767
Asp Ser Val Ile Asp Cys Asn Thr Cys Val Thr Gln Thr Val Asp Phe
640                 645                 650                 655 agc ctg gac ccg acc ttc acc att gag acg acg acc gtg cca caa gac      3815
Ser Leu Asp Pro Thr Phe Thr Ile Glu Thr Thr Thr Val Pro Gln Asp
                660                 665                 670 gcg gtg tca cgc tcg cag cgg cga ggc agg act ggt agg ggc agg atg      3863
Ala Val Ser Arg Ser Gln Arg Arg Gly Arg Thr Gly Arg Gly Arg Met
            675                 680                 685 ggc att tac agg ttt gtg act cca gga gaa cgg ccc tcg ggc atg ttc      3911
Gly Ile Tyr Arg Phe Val Thr Pro Gly Glu Arg Pro Ser Gly Met Phe
        690                 695                 700 gat tcc tcg gtt ctg tgc gag tgc tat gac gcg ggc tgt gct tgg tac      3959
Asp Ser Ser Val Leu Cys Glu Cys Tyr Asp Ala Gly Cys Ala Trp Tyr
705                 710                 715 gag ctc acg ccc gcc gag acc tca gtt agg ttg cgg gct tac cta aac      4007
Glu Leu Thr Pro Ala Glu Thr Ser Val Arg Leu Arg Ala Tyr Leu Asn
720                 725                 730                 735 aca cca ggg ttg ccc gtc tgc cag gac cat ctg gag ttc tgg gag agc      4055
Thr Pro Gly Leu Pro Val Cys Gln Asp His Leu Glu Phe Trp Glu Ser
                740                 745                 750 gtc ttt aca ggc ctc acc cac ata gac gcc cat ttc ttg tcc cag act      4103
Val Phe Thr Gly Leu Thr His Ile Asp Ala His Phe Leu Ser Gln Thr
            755                 760                 765 aag cag gca gga gac aac ttc ccc tac ctg gta gca tac cag gct acg      4151
Lys Gln Ala Gly Asp Asn Phe Pro Tyr Leu Val Ala Tyr Gln Ala Thr
        770                 775                 780 gtg tgc gcc agg gct cag gct cca cct cca tcg tgg gac caa atg tgg      4199
Val Cys Ala Arg Ala Gln Ala Pro Pro Pro Ser Trp Asp Gln Met Trp
785                 790                 795 aag tgt ctc ata cgg cta aag cct acg ctg cac ggg cca acg ccc ctg      4247
Lys Cys Leu Ile Arg Leu Lys Pro Thr Leu His Gly Pro Thr Pro Leu
800                 805                 810                 815 ctg tat agg ctg gga gcc gtt caa aac gag gtt act acc aca cac ccc      4295
Leu Tyr Arg Leu Gly Ala Val Gln Asn Glu Val Thr Thr Thr His Pro
                820                 825                 830 ata acc aaa tac atc atg gca tgc atg tcg gct gac ctg gag gtc gtc      4343
Ile Thr Lys Tyr Ile Met Ala Cys Met Ser Ala Asp Leu Glu Val Val
            835                 840                 845 acg agc acc tgg gtg ctg gta ggc gga gtc cta gca gct ctg gcc gcg      4391
Thr Ser Thr Trp Val Leu Val Gly Gly Val Leu Ala Ala Leu Ala Ala
```

-continued

```
                    850                 855                 860
tat tgc ctg aca aca ggc agc gtg gtc att gtg ggc agg atc atc ttg      4439
Tyr Cys Leu Thr Thr Gly Ser Val Val Ile Val Gly Arg Ile Ile Leu
    865                 870                 875 tcc gga aag ccg gcc atc att ccc gac agg gaa gtc ctt tac cgg gag      4487
Ser Gly Lys Pro Ala Ile Ile Pro Asp Arg Glu Val Leu Tyr Arg Glu
880                 885                 890                 895 ttc gat gag atg gaa gag tgc gcc tca cac ctc cct tac atc gaa cag      4535
Phe Asp Glu Met Glu Glu Cys Ala Ser His Leu Pro Tyr Ile Glu Gln
                900                 905                 910 gga atg cag ctc gcc gaa caa ttc aaa cag aag gca atc ggg ttg ctg      4583
Gly Met Gln Leu Ala Glu Gln Phe Lys Gln Lys Ala Ile Gly Leu Leu
            915                 920                 925 caa aca gcc acc aag caa gcg gag gct gct gct ccc gtg gtg gaa tcc      4631
Gln Thr Ala Thr Lys Gln Ala Glu Ala Ala Ala Pro Val Val Glu Ser
        930                 935                 940 aag tgg cgg acc ctc gaa gcc ttc tgg gcg aag cat atg tgg aat ttc      4679
Lys Trp Arg Thr Leu Glu Ala Phe Trp Ala Lys His Met Trp Asn Phe
945                 950                 955 atc agc ggg ata caa tat tta gca ggc ttg tcc act ctg cct ggc aac      4727
Ile Ser Gly Ile Gln Tyr Leu Ala Gly Leu Ser Thr Leu Pro Gly Asn
960                 965                 970                 975 ccc gcg ata gca tca ctg atg gca ttc aca gcc tct atc acc agc ccg      4775
Pro Ala Ile Ala Ser Leu Met Ala Phe Thr Ala Ser Ile Thr Ser Pro
                980                 985                 990 ctc acc acc caa cat acc ctc ctg ttt aac atc ctg ggg gga tgg gtg      4823
Leu Thr Thr Gln His Thr Leu Leu Phe Asn Ile Leu Gly Gly Trp Val
            995                 1000                1005 gcc gcc caa ctt gct cct ccc agc gct gct tct gct ttc gta ggc gcc      4871
Ala Ala Gln Leu Ala Pro Pro Ser Ala Ala Ser Ala Phe Val Gly Ala
        1010                1015                1020 ggc atc gct gga gcg gct gtt ggc agc ata ggc ctt ggg aag gtg ctt      4919
Gly Ile Ala Gly Ala Ala Val Gly Ser Ile Gly Leu Gly Lys Val Leu
    1025                1030                1035 gtg gat att ttg gca ggt tat gga gca ggg gtg gca ggc gcg ctc gtg      4967
Val Asp Ile Leu Ala Gly Tyr Gly Ala Gly Val Ala Gly Ala Leu Val
1040                1045                1050                1055 gcc ttt aag gtc atg agc ggc gag atg ccc tcc acc gag gac ctg gtt      5015
Ala Phe Lys Val Met Ser Gly Glu Met Pro Ser Thr Glu Asp Leu Val
                1060                1065                1070 aac cta ctc cct gct atc ctc tcc cct ggc gcc cta gtc gtc ggg gtc      5063
Asn Leu Leu Pro Ala Ile Leu Ser Pro Gly Ala Leu Val Val Gly Val
            1075                1080                1085 gtg tgc gca gcg ata ctg cgt cgg cac gtg ggc cca ggg gag ggg gct      5111
Val Cys Ala Ala Ile Leu Arg Arg His Val Gly Pro Gly Glu Gly Ala
        1090                1095                1100 gtg cag tgg atg aac cgg ctg ata gcg ttc gct tcg cgg ggt aac cac      5159
Val Gln Trp Met Asn Arg Leu Ile Ala Phe Ala Ser Arg Gly Asn His
    1105                1110                1115 gtc tcc ccc acg cac tat gtg cct gag agc gac gct gca gca cgt gtc      5207
Val Ser Pro Thr His Tyr Val Pro Glu Ser Asp Ala Ala Ala Arg Val
1120                1125                1130                1135 act cag atc ctc tct agt ctt acc atc act cag ctg ctg aag agg ctt      5255
Thr Gln Ile Leu Ser Ser Leu Thr Ile Thr Gln Leu Leu Lys Arg Leu
                1140                1145                1150 cac cag tgg atc aac gag gac tgc tcc acg cca tgc tcc ggc tcg tgg      5303
His Gln Trp Ile Asn Glu Asp Cys Ser Thr Pro Cys Ser Gly Ser Trp
            1155                1160                1165 cta aga gat gtt tgg gat tgg ata tgc acg gtg ttg act gat ttc aag      5351
```

-continued

```
Leu Arg Asp Val Trp Asp Trp Ile Cys Thr Val Leu Thr Asp Phe Lys
        1170            1175                1180 acc tgg ctc cag tcc aag ctc ctg ccg cga ttg ccg gga gtc ccc ttc    5399
Thr Trp Leu Gln Ser Lys Leu Leu Pro Arg Leu Pro Gly Val Pro Phe
    1185                1190                1195 ttc tca tgt caa cgt ggg tac aag gga gtc tgg cgg ggc gac ggc atc    5447
Phe Ser Cys Gln Arg Gly Tyr Lys Gly Val Trp Arg Gly Asp Gly Ile
1200                1205                1210                1215 atg caa acc acc tgc cca tgt gga gca cag atc acc gga cat gtg aaa    5495
Met Gln Thr Thr Cys Pro Cys Gly Ala Gln Ile Thr Gly His Val Lys
            1220                1225                1230 aac ggt tcc atg agg atc gtg ggg cct agg acc tgt agt aac acg tgg    5543
Asn Gly Ser Met Arg Ile Val Gly Pro Arg Thr Cys Ser Asn Thr Trp
                1235                1240                1245 cat gga aca ttc ccc att aac gcg tac acc acg ggc ccc tgc acg ccc    5591
His Gly Thr Phe Pro Ile Asn Ala Tyr Thr Thr Gly Pro Cys Thr Pro
                    1250                1255                1260 tcc ccg gcg cca aat tat tct agg gcg ctg tgg cgg gtg gct gct gag    5639
Ser Pro Ala Pro Asn Tyr Ser Arg Ala Leu Trp Arg Val Ala Ala Glu
    1265                1270                1275 gag tac gtg gag gtt acg cgg gtg ggg gat ttc cac tac gtg acg ggc    5687
Glu Tyr Val Glu Val Thr Arg Val Gly Asp Phe His Tyr Val Thr Gly
1280                1285                1290                1295 atg acc act gac aac gta aag tgc ccg tgt cag gtt ccg gcc ccc gaa    5735
Met Thr Thr Asp Asn Val Lys Cys Pro Cys Gln Val Pro Ala Pro Glu
            1300                1305                1310 ttc ttc aca gaa gtg gat ggg gtc cgg ttg cac agg tac gct cca gcg    5783
Phe Phe Thr Glu Val Asp Gly Val Arg Leu His Arg Tyr Ala Pro Ala
                1315                1320                1325 tgc aaa ccc ctc cta cgg gag gag gtc aca ttc ctg gtc ggg ctc aat    5831
Cys Lys Pro Leu Leu Arg Glu Glu Val Thr Phe Leu Val Gly Leu Asn
                    1330                1335                1340 caa tac ctg gtt ggg tca cag ctc cca tgc gag ccc gaa ccg gac gta    5879
Gln Tyr Leu Val Gly Ser Gln Leu Pro Cys Glu Pro Glu Pro Asp Val
    1345                1350                1355 gca gtg ctc act tcc atg ctc acc gac ccc tcc cac att acg gcg gag    5927
Ala Val Leu Thr Ser Met Leu Thr Asp Pro Ser His Ile Thr Ala Glu
1360                1365                1370                1375 acg gct aag cgt agg ctg gcc agg gga tct ccc ccc tcc ttg gcc agc    5975
Thr Ala Lys Arg Arg Leu Ala Arg Gly Ser Pro Pro Ser Leu Ala Ser
            1380                1385                1390 tca tca gct agc cag ctg tct gcg cct tcc ttg aag gca aca tgc act    6023
Ser Ser Ala Ser Gln Leu Ser Ala Pro Ser Leu Lys Ala Thr Cys Thr
                1395                1400                1405 acc cgt cat gac tcc ccg gac gct gac ctc atc gag gcc aac ctc ctg    6071
Thr Arg His Asp Ser Pro Asp Ala Asp Leu Ile Glu Ala Asn Leu Leu
                    1410                1415                1420 tgg cgg cag gag atg ggc ggg aac atc acc cgc gtg gag tca gaa aat    6119
Trp Arg Gln Glu Met Gly Gly Asn Ile Thr Arg Val Glu Ser Glu Asn
    1425                1430                1435 aag gta gta att ttg gac tct ttc gag ccg ctc caa gcg gag gag gat    6167
Lys Val Val Ile Leu Asp Ser Phe Glu Pro Leu Gln Ala Glu Glu Asp
1440                1445                1450                1455 gag agg gaa gta tcc gtt ccg gcg gag atc ctg cgg agg tcc agg aaa    6215
Glu Arg Glu Val Ser Val Pro Ala Glu Ile Leu Arg Arg Ser Arg Lys
            1460                1465                1470 ttc cct cga gcg atg ccc ata tgg gca cgc ccg gat tac aac cct cca    6263
Phe Pro Arg Ala Met Pro Ile Trp Ala Arg Pro Asp Tyr Asn Pro Pro
                1475                1480                1485
```

```
ctg tta gag tcc tgg aag gac ccg gac tac gtc cct cca gtg gta cac      6311
Leu Leu Glu Ser Trp Lys Asp Pro Asp Tyr Val Pro Pro Val Val His
        1490                1495                1500 ggg tgt cca ttg ccg cct gcc aag gcc cct ccg ata cca cct cca cgg      6359
Gly Cys Pro Leu Pro Pro Ala Lys Ala Pro Pro Ile Pro Pro Pro Arg
1505                1510                1515 agg aag agg acg gtt gtc ctg tca gaa tct acc gtg tct tct gcc ttg      6407
Arg Lys Arg Thr Val Val Leu Ser Glu Ser Thr Val Ser Ser Ala Leu
1520                1525                1530                1535 gcg gag ctc gcc aca aag acc ttc ggc agc tcc gaa tcg tcg gcc gtc      6455
Ala Glu Leu Ala Thr Lys Thr Phe Gly Ser Ser Glu Ser Ser Ala Val
                1540                1545                1550 gac agc ggc acg gca acg gcc tct cct gac cag ccc tcc gac gac ggc      6503
Asp Ser Gly Thr Ala Thr Ala Ser Pro Asp Gln Pro Ser Asp Asp Gly
        1555                1560                1565 gac gcg gga tcc gac gtt gag tcg tac tcc tcc atg ccc ccc ctt gag      6551
Asp Ala Gly Ser Asp Val Glu Ser Tyr Ser Ser Met Pro Pro Leu Glu
1570                1575                1580 ggg gag ccg ggg gat ccc gat ctc agc gac ggg tct tgg tct acc gta      6599
Gly Glu Pro Gly Asp Pro Asp Leu Ser Asp Gly Ser Trp Ser Thr Val
        1585                1590                1595 agc gag gag gct agt gag gac gtc gtc tgc tgc tcg atg tcc tac aca      6647
Ser Glu Glu Ala Ser Glu Asp Val Val Cys Cys Ser Met Ser Tyr Thr
1600                1605                1610                1615 tgg aca ggc gcc ctg atc acg cca tgc gct gcg gag gaa acc aag ctg      6695
Trp Thr Gly Ala Leu Ile Thr Pro Cys Ala Ala Glu Glu Thr Lys Leu
                1620                1625                1630 ccc atc aat gca ctg agc aac tct ttg ctc cgt cac cac aac ttg gtc      6743
Pro Ile Asn Ala Leu Ser Asn Ser Leu Leu Arg His His Asn Leu Val
        1635                1640                1645 tat gct aca aca tct cgc agc gca agc ctg cgg cag aag aag gtc acc      6791
Tyr Ala Thr Thr Ser Arg Ser Ala Ser Leu Arg Gln Lys Lys Val Thr
1650                1655                1660 ttt gac aga ctg cag gtc ctg gac gac cac tac cgg gac gtg ctc aag      6839
Phe Asp Arg Leu Gln Val Leu Asp Asp His Tyr Arg Asp Val Leu Lys
        1665                1670                1675 gag atg aag gcg aag gcg tcc aca gtt aag gct aaa ctt cta tcc gtg      6887
Glu Met Lys Ala Lys Ala Ser Thr Val Lys Ala Lys Leu Leu Ser Val
1680                1685                1690                1695 gag gaa gcc tgt aag ctg acg ccc cca cat tcg gcc aga tct aaa ttt      6935
Glu Glu Ala Cys Lys Leu Thr Pro Pro His Ser Ala Arg Ser Lys Phe
                1700                1705                1710 ggc tat ggg gca aag gac gtc cgg aac cta tcc agc aag gcc gtt aac      6983
Gly Tyr Gly Ala Lys Asp Val Arg Asn Leu Ser Ser Lys Ala Val Asn
        1715                1720                1725 cac atc cgc tcc gtg tgg aag gac ttg ctg gaa gac act gag aca cca      7031
His Ile Arg Ser Val Trp Lys Asp Leu Leu Glu Asp Thr Glu Thr Pro
1730                1735                1740 att gac acc acc atc atg gca aaa aat gag gtt ttc tgc gtc caa cca      7079
Ile Asp Thr Thr Ile Met Ala Lys Asn Glu Val Phe Cys Val Gln Pro
        1745                1750                1755 gag aag ggg ggc cgc aag cca gct cgc ctt atc gta ttc cca gat ttg      7127
Glu Lys Gly Gly Arg Lys Pro Ala Arg Leu Ile Val Phe Pro Asp Leu
1760                1765                1770                1775 ggg gtt cgt gtg tgc gag aaa atg gcc ctt tac gat gtg gtc tcc acc      7175
Gly Val Arg Val Cys Glu Lys Met Ala Leu Tyr Asp Val Val Ser Thr
                1780                1785                1790 ctc cct cag gcc gtg atg ggc tct tca tac gga ttc caa tac tct cct      7223
Leu Pro Gln Ala Val Met Gly Ser Ser Tyr Gly Phe Gln Tyr Ser Pro
        1795                1800                1805
```

-continued

| | |
|---|---|
| gga cag cgg gtc gag ttc ctg gtg aat gcc tgg aaa gcg aag aaa tgc<br>Gly Gln Arg Val Glu Phe Leu Val Asn Ala Trp Lys Ala Lys Lys Cys<br>1810                       1815                    1820 | 7271 |
| cct atg ggc ttc gca tat gac acc cgc tgt ttt gac tca acg gtc act<br>Pro Met Gly Phe Ala Tyr Asp Thr Arg Cys Phe Asp Ser Thr Val Thr<br>    1825                   1830                   1835 | 7319 |
| gag aat gac atc cgt gtt gag gag tca atc tac caa tgt tgt gac ttg<br>Glu Asn Asp Ile Arg Val Glu Glu Ser Ile Tyr Gln Cys Cys Asp Leu<br>1840                       1845                    1850                   1855 | 7367 |
| gcc ccc gaa gcc aga cag gcc ata agg tcg ctc aca gag cgg ctt tac<br>Ala Pro Glu Ala Arg Gln Ala Ile Arg Ser Leu Thr Glu Arg Leu Tyr<br>                 1860                   1865                  1870 | 7415 |
| atc ggg ggc ccc ctg act aat tct aaa ggg cag aac tgc ggc tat cgc<br>Ile Gly Gly Pro Leu Thr Asn Ser Lys Gly Gln Asn Cys Gly Tyr Arg<br>    1875                   1880                   1885 | 7463 |
| cgg tgc cgc gcg agc ggt gta ctg acg acc agc tgc ggt aat acc ctc<br>Arg Cys Arg Ala Ser Gly Val Leu Thr Thr Ser Cys Gly Asn Thr Leu<br>1890                       1895                    1900 | 7511 |
| aca tgt tac ttg aag gcc gct gcg gcc tgt cga gct gcg aag ctc cag<br>Thr Cys Tyr Leu Lys Ala Ala Ala Ala Cys Arg Ala Ala Lys Leu Gln<br>    1905                   1910                   1915 | 7559 |
| gac tgc acg atg ctc gta tgc gga gac gac ctt gtc gtt atc tgt gaa<br>Asp Cys Thr Met Leu Val Cys Gly Asp Asp Leu Val Val Ile Cys Glu<br>1920                       1925                    1930                   1935 | 7607 |
| agc gcg ggg acc caa gag gac gag gcg agc cta cgg gcc ttc acg gag<br>Ser Ala Gly Thr Gln Glu Asp Glu Ala Ser Leu Arg Ala Phe Thr Glu<br>                 1940                   1945                  1950 | 7655 |
| gct atg act aga tac tct gcc ccc cct ggg gac ccg ccc aaa cca gaa<br>Ala Met Thr Arg Tyr Ser Ala Pro Pro Gly Asp Pro Pro Lys Pro Glu<br>    1955                   1960                   1965 | 7703 |
| tac gac ttg gag ttg ata aca tca tgc tcc tcc aat gtg tca gtc gcg<br>Tyr Asp Leu Glu Leu Ile Thr Ser Cys Ser Ser Asn Val Ser Val Ala<br>1970                       1975                    1980 | 7751 |
| cac gat gca tct ggc aaa agg gtg tac tat ctc acc cgt gac ccc acc<br>His Asp Ala Ser Gly Lys Arg Val Tyr Tyr Leu Thr Arg Asp Pro Thr<br>    1985                   1990                   1995 | 7799 |
| acc ccc ctt gcg cgg gct gcg tgg gag aca gct aga cac act cca gtc<br>Thr Pro Leu Ala Arg Ala Ala Trp Glu Thr Ala Arg His Thr Pro Val<br>2000                       2005                    2010                   2015 | 7847 |
| aat tcc tgg cta ggc aac atc atc atg tat gcg ccc acc ttg tgg gca<br>Asn Ser Trp Leu Gly Asn Ile Ile Met Tyr Ala Pro Thr Leu Trp Ala<br>                 2020                   2025                  2030 | 7895 |
| agg atg atc ctg atg act cat ttc ttc tcc atc ctt cta gct cag gaa<br>Arg Met Ile Leu Met Thr His Phe Phe Ser Ile Leu Leu Ala Gln Glu<br>    2035                   2040                   2045 | 7943 |
| caa ctt gaa aaa gcc cta gat tgt cag atc tac ggg gcc tgt tac tcc<br>Gln Leu Glu Lys Ala Leu Asp Cys Gln Ile Tyr Gly Ala Cys Tyr Ser<br>2050                       2055                    2060 | 7991 |
| att gag cca ctt gac cta cct cag atc att caa cga ctc cac ggc ctt<br>Ile Glu Pro Leu Asp Leu Pro Gln Ile Ile Gln Arg Leu His Gly Leu<br>    2065                   2070                   2075 | 8039 |
| agc gca ttt tca ctc cat agt tac tct cca ggt gag atc aat agg gtg<br>Ser Ala Phe Ser Leu His Ser Tyr Ser Pro Gly Glu Ile Asn Arg Val<br>2080                       2085                    2090                   2095 | 8087 |
| gct tca tgc ctc agg aaa ctt ggg gta ccg ccc ttg cga gtc tgg aga<br>Ala Ser Cys Leu Arg Lys Leu Gly Val Pro Pro Leu Arg Val Trp Arg<br>                 2100                   2105                  2110 | 8135 |
| cat cgg gcc aga agt gtc cgc gct agg cta ctg tcc cag ggg ggg agg<br>His Arg Ala Arg Ser Val Arg Ala Arg Leu Leu Ser Gln Gly Gly Arg | 8183 |

-continued

```
                   2115                2120                2125
gct gcc act tgt ggc aag tac ctc ttc aac tgg gca gta agg acc aag    8231
Ala Ala Thr Cys Gly Lys Tyr Leu Phe Asn Trp Ala Val Arg Thr Lys
            2130                2135                2140 ctc aaa ctc act cca atc ccg gct gcg tcc cag ttg gat tta tcc agc    8279
Leu Lys Leu Thr Pro Ile Pro Ala Ala Ser Gln Leu Asp Leu Ser Ser
        2145                2150                2155 tgg ttc gtt gct ggt tac agc ggg gga gac ata tat cac agc ctg tct    8327
Trp Phe Val Ala Gly Tyr Ser Gly Gly Asp Ile Tyr His Ser Leu Ser
2160                2165                2170                2175 cgt gcc cga ccc cgc tgg ttc atg tgg tgc cta ctc cta ctt tct gta    8375
Arg Ala Arg Pro Arg Trp Phe Met Trp Cys Leu Leu Leu Leu Ser Val
            2180                2185                2190 ggg gta ggc atc tat cta ctc ccc aac cga tga acggggagct aaacactcca  8428
Gly Val Gly Ile Tyr Leu Leu Pro Asn Arg  *
        2195                2200 ggccaatagg ccatcctgtt tttttccctt tttttttttc tttttttttt tttttttttt  8488
tttttttttt ttttctcctt ttttttttcct cttttttttcc ttttctttcc tttggtggct 8548 ccatcttagc cctagtcacg gctagctgtg aaaggtccgt gagccgcttg actgcagaga  8608
gtgctgatac tggcctctct gcagatcaag t                                 8639
```

<210> SEQ ID NO 2
<211> LENGTH: 8642
<212> TYPE: DNA
<213> ORGANISM: HCV
<220> FEATURE:
<221> NAME/KEY: CDS
<222> LOCATION: (1802)...(8407)
<220> FEATURE:
<221> NAME/KEY: variation
<222> LOCATION: 6268
<223> OTHER INFORMATION: r = a or g
<220> FEATURE:
<221> NAME/KEY: variation
<222> LOCATION: 4446
<223> OTHER INFORMATION: r = a or g

<400> SEQUENCE: 2

```
accagccccc gattgggggc gacactccac catagatcac tccctgtga ggaactactg    60 tcttcacgca gaaagcgtct agccatggcg ttagtatgag tgtcgtgcag cctccaggac  120
cccccctccc gggagagcca tagtggtctg cggaaccggt gagtacaccg gaattgccag  180
gacgaccggg tcctttcttg gatcaacccg ctcaatgcct ggagatttgg gcgtgccccc  240
gcgagactgc tagccgagta gtgttgggtc gcgaaaggcc ttgtggtact gcctgatagg  300
gtgcttgcga gtgccccggg aggtctcgta gaccgtgcac catgagcacg aatcctaaac  360
ctcaaagaaa aaccaaaggg cgcgccatga ttgaacaaga tggattgcac gcaggttctc  420
cggccgcttg ggtggagagg ctattcggct atgactgggc acaacagaca atcgctgct   480 ctgatgccgc cgtgttccgg ctgtcagcgc agggcgcc  ggttctttt gtcaagaccg   540 acctgtccgg tgccctgaat gaactgcagg acgaggcagc gcggctatcg tggctggcca   600
cgacgggcgt tccttgcgca gctgtgctcg acgttgtcac tgaagcggga agggactggc   660
tgctattggg cgaagtgccg ggcaggatc tcctgtcatc tcaccttgct cctgccgaga   720 agtatccat catggctgat gcaatgcggc ggctgcatac gcttgatccg gctacctgcc   780
cattcgacca ccaagcgaaa catcgcatcg agcgagcacg tactcggatg aagccggtc   840 ttgtcgatca ggatgatctg gacgaagagc atcagggct cgcgccagcc gaactgttcg   900
```

```
ccaggctcaa ggcgcgcatg cccgacggcg aggatctcgt cgtgacccat ggcgatgcct    960
gcttgccgaa tatcatggtg gaaaatggcc gcttttctgg attcatcgac tgtggccggc   1020
tgggtgtggc ggaccgctat caggacatag cgttggctac ccgtgatatt gctgaagagc   1080
ttggcggcga atgggctgac cgcttcctcg tgctttacgg tatcgccgct cccgattcgc   1140
agcgcatcgc cttctatcgc cttcttgacg agttcttctg agttcgcgcc cagatgttaa   1200
cagaccacaa cggtttccct ctagcggat caattccgcc cccccccta acgttactgg    1260
ccgaagccgc ttggaataag gccggtgtgc gtttgtctat atgttatttt ccaccatatt   1320
gccgtctttt ggcaatgtga gggcccggaa acctggccct gtcttcttga cgagcattcc   1380
tagggggtctt tccctctcg ccaaaggaat gcaaggtctg ttgaatgtcg tgaaggaagc   1440
agttcctctg gaagcttctt gaagacaaac aacgtctgta cgacccttt gcaggcagcg    1500
gaacccccca cctggcgaca ggtgcctctg cggccaaaag ccacgtgtat aagatacacc   1560
tgcaaaggcg gcacaacccc agtgccacgt tgtgagttgg atagttgtgg aaagagtcaa   1620
atggctctcc tcaagcgtat tcaacaaggg gctgaaggat gcccagaagg taccccattg   1680
tatgggatct gatctggggc ctcggtgcac atgctttaca tgtgtttagt cgaggttaaa   1740
aaacgtctag gccccccgaa ccacggggac gtggttttcc tttgaaaaac acgataatac   1800
```

```
c atg gac cgg gag atg gca gca tcg tgc gga ggc gcg gtt ttc gta ggt     1849
  Met Asp Arg Glu Met Ala Ala Ser Cys Gly Gly Ala Val Phe Val Gly
  1               5                   10                  15 ctg ata ctc ttg acc ttg tca ccg cac tat aag ctg ttc ctc gct agg       1897
Leu Ile Leu Leu Thr Leu Ser Pro His Tyr Lys Leu Phe Leu Ala Arg
             20                  25                  30 ctc ata tgg tgg tta caa tat ttt atc acc agg gcc gag gca cac ttg       1945
Leu Ile Trp Trp Leu Gln Tyr Phe Ile Thr Arg Ala Glu Ala His Leu
         35                  40                  45 caa gtg tgg atc ccc ccc ctc aac gtt cgg ggg ggc cgc gat gcc gtc       1993
Gln Val Trp Ile Pro Pro Leu Asn Val Arg Gly Gly Arg Asp Ala Val
     50                  55                  60 atc ctc ctc acg tgc gcg atc cac cca gag cta atc ttt acc atc acc       2041
Ile Leu Leu Thr Cys Ala Ile His Pro Glu Leu Ile Phe Thr Ile Thr
 65                  70                  75                  80 aaa atc ttg ctc gcc ata ctc ggt cca ctc atg gtg ctc cag gct ggt       2089
Lys Ile Leu Leu Ala Ile Leu Gly Pro Leu Met Val Leu Gln Ala Gly
                 85                  90                  95 ata acc aaa gtg ccg tac ttc gtg cgc gca cac ggg ctc att cgt gca       2137
Ile Thr Lys Val Pro Tyr Phe Val Arg Ala His Gly Leu Ile Arg Ala
            100                 105                 110 tgc atg ctg gtg cgg aag gtt gct ggg ggt cat tat gtc caa atg gct       2185
Cys Met Leu Val Arg Lys Val Ala Gly Gly His Tyr Val Gln Met Ala
        115                 120                 125 ctc atg aag ttg gcc gca ctg aca ggt acg tac gtt tat gac cat ctc       2233
Leu Met Lys Leu Ala Ala Leu Thr Gly Thr Tyr Val Tyr Asp His Leu
    130                 135                 140 acc cca ctg cgg gac tgg gcc cac gcg ggc cta cga gac ctt gcg gtg       2281
Thr Pro Leu Arg Asp Trp Ala His Ala Gly Leu Arg Asp Leu Ala Val
145                 150                 155                 160 gca gtt gag ccc gtc gtc ttc tct gat atg gag acc aag gtt atc acc       2329
Ala Val Glu Pro Val Val Phe Ser Asp Met Glu Thr Lys Val Ile Thr
                165                 170                 175 tgg ggg gca gac acc gcg gcg tgt ggg gac atc atc ttg ggc ctg ccc       2377
Trp Gly Ala Asp Thr Ala Ala Cys Gly Asp Ile Ile Leu Gly Leu Pro
            180                 185                 190 gtc tcc gcc cgc agg ggg agg gag ata cat ctg gga ccg gca gac agc       2425
```

-continued

| | | |
|---|---|---|
| Val Ser Ala Arg Arg Gly Arg Glu Ile His Leu Gly Pro Ala Asp Ser<br>195 200 205 | | |
| ctt gaa ggg cag ggg tgg cga ctc ctc gcg cct att acg gcc tac tcc<br>Leu Glu Gly Gln Gly Trp Arg Leu Leu Ala Pro Ile Thr Ala Tyr Ser<br>210 215 220 | 2473 | |
| caa cag acg cga ggc cta ctt ggc tgc atc atc act agc ctc aca ggc<br>Gln Gln Thr Arg Gly Leu Leu Gly Cys Ile Ile Thr Ser Leu Thr Gly<br>225 230 235 240 | 2521 | |
| cgg gac agg aac cag gtc gag ggg gag gtc caa gtg gtc tcc acc gca<br>Arg Asp Arg Asn Gln Val Glu Gly Glu Val Gln Val Val Ser Thr Ala<br>245 250 255 | 2569 | |
| aca caa tct ttc ctg gcg acc tgc gtc aat ggc gtg tgt tgg act gtc<br>Thr Gln Ser Phe Leu Ala Thr Cys Val Asn Gly Val Cys Trp Thr Val<br>260 265 270 | 2617 | |
| tat cat ggt gcc ggc tca aag acc ctt gcc ggc cca aag ggc cca atc<br>Tyr His Gly Ala Gly Ser Lys Thr Leu Ala Gly Pro Lys Gly Pro Ile<br>275 280 285 | 2665 | |
| acc caa atg tac acc aat gtg gac cag gac ctc gtc ggc tgg caa gcg<br>Thr Gln Met Tyr Thr Asn Val Asp Gln Asp Leu Val Gly Trp Gln Ala<br>290 295 300 | 2713 | |
| ccc ccc ggg gcg cgt tcc ttg aca cca tgc acc tgc ggc agc tcg gac<br>Pro Pro Gly Ala Arg Ser Leu Thr Pro Cys Thr Cys Gly Ser Ser Asp<br>305 310 315 320 | 2761 | |
| ctt tac ttg gtc acg agg cat gcc gat gtc att ccg gtg cgc cgg cgg<br>Leu Tyr Leu Val Thr Arg His Ala Asp Val Ile Pro Val Arg Arg Arg<br>325 330 335 | 2809 | |
| ggc gac agc agg ggg agc cta ctc tcc ccc agg ccc gtc tcc tac ttg<br>Gly Asp Ser Arg Gly Ser Leu Leu Ser Pro Arg Pro Val Ser Tyr Leu<br>340 345 350 | 2857 | |
| aag ggc tct tcg ggc ggt cca ctg ctc tgc ccc tcg ggg cac gct gtg<br>Lys Gly Ser Ser Gly Gly Pro Leu Leu Cys Pro Ser Gly His Ala Val<br>355 360 365 | 2905 | |
| ggc atc ttt cgg gct gcc gtg tgc acc cga ggg gtt gcg aag gcg gtg<br>Gly Ile Phe Arg Ala Ala Val Cys Thr Arg Gly Val Ala Lys Ala Val<br>370 375 380 | 2953 | |
| gac ttt gta ccc gtc gag tct atg gaa acc act atg cgg tcc ccg gtc<br>Asp Phe Val Pro Val Glu Ser Met Glu Thr Thr Met Arg Ser Pro Val<br>385 390 395 400 | 3001 | |
| ttc acg gac aac tcg tcc cct ccg gcc gta ccg cag aca ttc cag gtg<br>Phe Thr Asp Asn Ser Ser Pro Pro Ala Val Pro Gln Thr Phe Gln Val<br>405 410 415 | 3049 | |
| gcc cat cta cac gcc cct act ggt agc ggc aag agc act aag gtg ccg<br>Ala His Leu His Ala Pro Thr Gly Ser Gly Lys Ser Thr Lys Val Pro<br>420 425 430 | 3097 | |
| gct gcg tat gca gcc caa ggg tat aag gtg ctt gtc ctg aac ccg tcc<br>Ala Ala Tyr Ala Ala Gln Gly Tyr Lys Val Leu Val Leu Asn Pro Ser<br>435 440 445 | 3145 | |
| gtc gcc gcc acc cta ggt ttc ggg gcg tat atg tct aag gca cat ggt<br>Val Ala Ala Thr Leu Gly Phe Gly Ala Tyr Met Ser Lys Ala His Gly<br>450 455 460 | 3193 | |
| atc gac cct aac atc aga acc ggg gta agg acc atc acc acg ggt gcc<br>Ile Asp Pro Asn Ile Arg Thr Gly Val Arg Thr Ile Thr Thr Gly Ala<br>465 470 475 480 | 3241 | |
| ccc atc acg tac tcc acc tat ggc aag ttt ctt gcc gac ggt ggt tgc<br>Pro Ile Thr Tyr Ser Thr Tyr Gly Lys Phe Leu Ala Asp Gly Gly Cys<br>485 490 495 | 3289 | |
| tct ggg ggc gcc tat gac atc ata ata tgt gat gag tgc cac tca act<br>Ser Gly Gly Ala Tyr Asp Ile Ile Ile Cys Asp Glu Cys His Ser Thr<br>500 505 510 | 3337 | |

```
gac tcg acc act atc ctg ggc atc ggc aca gtc ctg gac caa gcg gag    3385
Asp Ser Thr Thr Ile Leu Gly Ile Gly Thr Val Leu Asp Gln Ala Glu
            515                 520                 525 acg gct gga gcg cga ctc gtc gtg ctc gcc acc gct acg cct ccg gga    3433
Thr Ala Gly Ala Arg Leu Val Val Leu Ala Thr Ala Thr Pro Pro Gly
530                 535                 540 tcg gtc acc gtg cca cat cca aac atc gag gag gtg gct ctg tcc agc    3481
Ser Val Thr Val Pro His Pro Asn Ile Glu Glu Val Ala Leu Ser Ser
545                 550                 555                 560 act gga gaa atc ccc ttt tat ggc aaa gcc atc ccc atc gag acc atc    3529
Thr Gly Glu Ile Pro Phe Tyr Gly Lys Ala Ile Pro Ile Glu Thr Ile
                565                 570                 575 aag ggg ggg agg cac ctc att ttc tgc cat tcc aag aag aaa tgt gat    3577
Lys Gly Gly Arg His Leu Ile Phe Cys His Ser Lys Lys Lys Cys Asp
            580                 585                 590 gag ctc gcc gcg aag ctg tcc ggc ctc gga ctc aat gct gta gca tat    3625
Glu Leu Ala Ala Lys Leu Ser Gly Leu Gly Leu Asn Ala Val Ala Tyr
            595                 600                 605 tac cgg ggc ctt gat gta tcc gtc ata cca act agc gga gac gtc att    3673
Tyr Arg Gly Leu Asp Val Ser Val Ile Pro Thr Ser Gly Asp Val Ile
610                 615                 620 gtc gta gca acg gac gct cta atg acg ggc ttt acc ggc gat ttc gac    3721
Val Val Ala Thr Asp Ala Leu Met Thr Gly Phe Thr Gly Asp Phe Asp
625                 630                 635                 640 tca gtg atc gac tgc aat aca tgt gtc acc cag aca gtc gac ttc agc    3769
Ser Val Ile Asp Cys Asn Thr Cys Val Thr Gln Thr Val Asp Phe Ser
                645                 650                 655 ctg gac ccg acc ttc acc att gag acg acg acc gtg cca caa gac gcg    3817
Leu Asp Pro Thr Phe Thr Ile Glu Thr Thr Thr Val Pro Gln Asp Ala
            660                 665                 670 gtg tca cgc tcg cag cgg cga ggc agg act ggt agg ggc agg atg ggc    3865
Val Ser Arg Ser Gln Arg Arg Gly Arg Thr Gly Arg Gly Arg Met Gly
            675                 680                 685 att tac agg ttt gtg act cca gga gaa cgg ccc tcg ggc atg ttc gat    3913
Ile Tyr Arg Phe Val Thr Pro Gly Glu Arg Pro Ser Gly Met Phe Asp
690                 695                 700 tcc tcg gtt ctg tgc gag tgc tat gac gcg ggc tgt gct tgg tac gag    3961
Ser Ser Val Leu Cys Glu Cys Tyr Asp Ala Gly Cys Ala Trp Tyr Glu
705                 710                 715                 720 ctc acg ccc gcc gag acc tca gtt agg ttg cgg gct tac cta aac aca    4009
Leu Thr Pro Ala Glu Thr Ser Val Arg Leu Arg Ala Tyr Leu Asn Thr
                725                 730                 735 cca ggg ttg ccc gtc tgc cag gac cat ctg gag ttc tgg gag agc gtc    4057
Pro Gly Leu Pro Val Cys Gln Asp His Leu Glu Phe Trp Glu Ser Val
            740                 745                 750 ttt aca ggc ctc acc cac ata gac gcc cat ttc ttg tcc cag act aag    4105
Phe Thr Gly Leu Thr His Ile Asp Ala His Phe Leu Ser Gln Thr Lys
            755                 760                 765 cag gca gga gac aac ttc ccc tac ctg gta gca tac cag gct acg gtg    4153
Gln Ala Gly Asp Asn Phe Pro Tyr Leu Val Ala Tyr Gln Ala Thr Val
770                 775                 780 tgc gcc agg gct cag gct cca cct cca tcg tgg gac caa atg tgg aag    4201
Cys Ala Arg Ala Gln Ala Pro Pro Pro Ser Trp Asp Gln Met Trp Lys
785                 790                 795                 800 tgt ctc ata cgg cta aag cct acg ctg cac ggg cca acg ccc ctg ctg    4249
Cys Leu Ile Arg Leu Lys Pro Thr Leu His Gly Pro Thr Pro Leu Leu
                805                 810                 815 tat agg ctg gga gcc gtt caa aac gag gtt act acc aca cac ccc ata    4297
Tyr Arg Leu Gly Ala Val Gln Asn Glu Val Thr Thr Thr His Pro Ile
            820                 825                 830
```

-continued

| | |
|---|---|
| acc aaa tac atc atg gca tgc atg tcg gct gac ctg gag gtc gtc acg<br>Thr Lys Tyr Ile Met Ala Cys Met Ser Ala Asp Leu Glu Val Val Thr<br>835                   840                   845 | 4345 |
| agc acc tgg gtg ctg gta ggc gga gtc cta gca gct ctg gcc gcg tat<br>Ser Thr Trp Val Leu Val Gly Gly Val Leu Ala Ala Leu Ala Ala Tyr<br>850                   855                   860 | 4393 |
| tgc ctg aca aca ggc agc gtg gtc att gtg ggc agg atc atc ttg tcc<br>Cys Leu Thr Thr Gly Ser Val Val Ile Val Gly Arg Ile Ile Leu Ser<br>865                   870                 875            880 | 4441 |
| gga arg ccg gcc atc att ccc gac agg gaa gtc ctt tac cgg gag ttc<br>Gly Xaa Pro Ala Ile Ile Pro Asp Arg Glu Val Leu Tyr Arg Glu Phe<br>                   885                   890                   895 | 4489 |
| gat gag atg gaa gag tgc gcc tca cac ctc cct tac atc gaa cag gga<br>Asp Glu Met Glu Glu Cys Ala Ser His Leu Pro Tyr Ile Glu Gln Gly<br>900                   905                   910 | 4537 |
| atg cag ctc gcc gaa caa ttc aaa cag aag gca atc ggg ttg ctg caa<br>Met Gln Leu Ala Glu Gln Phe Lys Gln Lys Ala Ile Gly Leu Leu Gln<br>               915                   920                   925 | 4585 |
| aca gcc acc aag caa gcg gag gct gct gct ccc gtg gtg gaa tcc aag<br>Thr Ala Thr Lys Gln Ala Glu Ala Ala Ala Pro Val Val Glu Ser Lys<br>930                   935                   940 | 4633 |
| tgg cgg acc ctc gaa gcc ttc tgg gcg aag cat atg tgg aat ttc atc<br>Trp Arg Thr Leu Glu Ala Phe Trp Ala Lys His Met Trp Asn Phe Ile<br>945                   950                   955            960 | 4681 |
| agc ggg ata caa tat tta gca ggc ttg tcc act ctg cct ggc aac ccc<br>Ser Gly Ile Gln Tyr Leu Ala Gly Leu Ser Thr Leu Pro Gly Asn Pro<br>                   965                   970                   975 | 4729 |
| gcg ata gca tca ctg atg gca ttc aca gcc tct atc acc agc ccg ctc<br>Ala Ile Ala Ser Leu Met Ala Phe Thr Ala Ser Ile Thr Ser Pro Leu<br>980                   985                   990 | 4777 |
| acc acc caa cat acc ctc ctg ttt aac atc ctg ggg gga tgg gtg gcc<br>Thr Thr Gln His Thr Leu Leu Phe Asn Ile Leu Gly Gly Trp Val Ala<br>               995                  1000             1005 | 4825 |
| gcc caa ctt gct cct ccc agc gct gct tct gct ttc gta ggc gcc ggc<br>Ala Gln Leu Ala Pro Pro Ser Ala Ala Ser Ala Phe Val Gly Ala Gly<br>1010                  1015                  1020 | 4873 |
| atc gct gga gcg gct gtt ggc agc ata ggc ctt ggg aag gtg ctt gtg<br>Ile Ala Gly Ala Ala Val Gly Ser Ile Gly Leu Gly Lys Val Leu Val<br>1025                1030                  1035              1040 | 4921 |
| gat att ttg gca ggt tat gga gca ggg gtg gca ggc gcg ctc gtg gcc<br>Asp Ile Leu Ala Gly Tyr Gly Ala Gly Val Ala Gly Ala Leu Val Ala<br>                  1045                  1050              1055 | 4969 |
| ttt aag gtc atg agc ggc gag atg ccc tcc acc gag gac ctg gtt aac<br>Phe Lys Val Met Ser Gly Glu Met Pro Ser Thr Glu Asp Leu Val Asn<br>1060                  1065                  1070 | 5017 |
| cta ctc cct gct atc ctc tcc cct ggc gcc cta gtc gtc ggg gtc gtg<br>Leu Leu Pro Ala Ile Leu Ser Pro Gly Ala Leu Val Val Gly Val Val<br>                  1075                  1080              1085 | 5065 |
| tgc gca gcg ata ctg cgt cgg cac gtg ggc cca ggg gag ggg gct gtg<br>Cys Ala Ala Ile Leu Arg Arg His Val Gly Pro Gly Glu Gly Ala Val<br>1090                1095                  1100 | 5113 |
| cag tgg atg aac cgg ctg ata gcg ttc gct tcg cgg ggt aac cac gtc<br>Gln Trp Met Asn Arg Leu Ile Ala Phe Ala Ser Arg Gly Asn His Val<br>1105                1110                  1115              1120 | 5161 |
| tcc ccc acg cac tat gtg cct gag agc gac gct gca gca cgt gtc act<br>Ser Pro Thr His Tyr Val Pro Glu Ser Asp Ala Ala Ala Arg Val Thr<br>                  1125                  1130              1135 | 5209 |
| cag atc ctc tct agt ctt acc atc act cag ctg ctg aag agg ctt cac<br>Gln Ile Leu Ser Ser Leu Thr Ile Thr Gln Leu Leu Lys Arg Leu His | 5257 |

-continued

```
                  1140                 1145                 1150
cag tgg atc aac gag gac tgc tcc acg cca tgc tcc ggc tcg tgg cta        5305
Gln Trp Ile Asn Glu Asp Cys Ser Thr Pro Cys Ser Gly Ser Trp Leu
        1155                1160                1165 aga gat gtt tgg gat tgg ata tgc acg gtg ttg act gat ttc aag acc        5353
Arg Asp Val Trp Asp Trp Ile Cys Thr Val Leu Thr Asp Phe Lys Thr
    1170                1175                1180 tgg ctc cag tcc aag ctc ctg ccg cga ttg ccg gga gtc ccc ttc ttc        5401
Trp Leu Gln Ser Lys Leu Leu Pro Arg Leu Pro Gly Val Pro Phe Phe
1185                1190                1195                1200 tca tgt caa cgt ggg tac aag gga gtc tgg cgg ggc gac ggc atc atg        5449
Ser Cys Gln Arg Gly Tyr Lys Gly Val Trp Arg Gly Asp Gly Ile Met
            1205                1210                1215 caa acc acc tgc cca tgt gga gca cag atc acc gga cat gtg aaa aac        5497
Gln Thr Thr Cys Pro Cys Gly Ala Gln Ile Thr Gly His Val Lys Asn
        1220                1225                1230 tgt tcc atg agg atc gtg ggg cct agg acc tgt agt aac acg tgg cat        5545
Cys Ser Met Arg Ile Val Gly Pro Arg Thr Cys Ser Asn Thr Trp His
    1235                1240                1245 gga aca ttc ccc att aac gcg tac acc acg ggc ccc tgc acg ccc tcc        5593
Gly Thr Phe Pro Ile Asn Ala Tyr Thr Thr Gly Pro Cys Thr Pro Ser
1250                1255                1260 ccg gcg cca aat tat tct agg gcg ctg tgg cgg gtg gct gct gag gag        5641
Pro Ala Pro Asn Tyr Ser Arg Ala Leu Trp Arg Val Ala Ala Glu Glu
1265                1270                1275                1280 tac gtg gag gtt acg cgg gtg ggg gat ttc cac tac gtg acg ggc atg        5689
Tyr Val Glu Val Thr Arg Val Gly Asp Phe His Tyr Val Thr Gly Met
            1285                1290                1295 acc act gac aac gta aag tgc ccg tgt cag gtt ccg gcc ccc gaa ttc        5737
Thr Thr Asp Asn Val Lys Cys Pro Cys Gln Val Pro Ala Pro Glu Phe
        1300                1305                1310 ttc aca gaa gtg gat ggg gtg cgg ttg cac agg tac gct cca gcg tgc        5785
Phe Thr Glu Val Asp Gly Val Arg Leu His Arg Tyr Ala Pro Ala Cys
    1315                1320                1325 aaa ccc ctc cta cgg gag gag gtc aca ttc ctg gtc ggg ctc aat caa        5833
Lys Pro Leu Leu Arg Glu Glu Val Thr Phe Leu Val Gly Leu Asn Gln
1330                1335                1340 tac ctg gtt ggg tca cag ctc cca tgc gag ccc gaa ccg gac gta gca        5881
Tyr Leu Val Gly Ser Gln Leu Pro Cys Glu Pro Glu Pro Asp Val Ala
1345                1350                1355                1360 gtg ctc act tcc atg ctc acc gac ccc tcc cac att acg gcg gag acg        5929
Val Leu Thr Ser Met Leu Thr Asp Pro Ser His Ile Thr Ala Glu Thr
            1365                1370                1375 gct aag cgt agg ctg gcc agg gga tct ccc ccc tcc ttg gcc agc tca        5977
Ala Lys Arg Arg Leu Ala Arg Gly Ser Pro Pro Ser Leu Ala Ser Ser
        1380                1385                1390 tca gct agc cag ctg tct gcg cct tcc ttg aag gca aca tgc act acc        6025
Ser Ala Ser Gln Leu Ser Ala Pro Ser Leu Lys Ala Thr Cys Thr Thr
    1395                1400                1405 cgt cat gac tcc ccg gac gct gac ctc atc gag gcc aac ctc ctg tgg        6073
Arg His Asp Ser Pro Asp Ala Asp Leu Ile Glu Ala Asn Leu Leu Trp
1410                1415                1420 cgg cag gag atg ggc ggg aac atc acc cgc gtg gag tca gaa aat aag        6121
Arg Gln Glu Met Gly Gly Asn Ile Thr Arg Val Glu Ser Glu Asn Lys
1425                1430                1435                1440 gta gta att ttg gac tct ttc gag ccg ctc caa gcg gag gag gat gag        6169
Val Val Ile Leu Asp Ser Phe Glu Pro Leu Gln Ala Glu Glu Asp Glu
            1445                1450                1455 agg gaa gta tcc gtt ccg gcg gag atc ctg cgg agg tcc agg aaa ttc        6217
```

```
                    Arg Glu Val Ser Val Pro Ala Glu Ile Leu Arg Arg Ser Arg Lys Phe
                                    1460                1465                1470 cct cga gcg atg ccc ata tgg gca cgc ccg gat tac aac cct cca ctg           6265
Pro Arg Ala Met Pro Ile Trp Ala Arg Pro Asp Tyr Asn Pro Pro Leu
            1475                1480                1485 ttr gag tcc tgg aag gac ccg gac tac gtc cct cca gtg gta cac ggg           6313
Xaa Glu Ser Trp Lys Asp Pro Asp Tyr Val Pro Pro Val Val His Gly
    1490                1495                1500 tgt cca ttg ccg cct gcc aag gcc cct ccg ata cca cct cca cgg agg           6361
Cys Pro Leu Pro Pro Ala Lys Ala Pro Pro Ile Pro Pro Pro Arg Arg
1505                1510                1515                1520 aag agg acg gtt gtc ctg tca gaa tct acc gtg tct tct gcc ttg gcg           6409
Lys Arg Thr Val Val Leu Ser Glu Ser Thr Val Ser Ser Ala Leu Ala
                1525                1530                1535 gag ctc gcc aca aag acc ttc ggc agc tcc gaa tcg tcg gcc gtc gac           6457
Glu Leu Ala Thr Lys Thr Phe Gly Ser Ser Glu Ser Ser Ala Val Asp
            1540                1545                1550 agc ggc acg gca acg gcc tct cct gac cag ccc tcc gac gac ggc gac           6505
Ser Gly Thr Ala Thr Ala Ser Pro Asp Gln Pro Ser Asp Asp Gly Asp
        1555                1560                1565 gcg gga tcc gac gtt gag tcg tac tcc tcc atg ccc ccc ctt gag ggg           6553
Ala Gly Ser Asp Val Glu Ser Tyr Ser Ser Met Pro Pro Leu Glu Gly
1570                1575                1580 gag ccg ggg gat ccc gat ctc agc gac ggg tct tgg tct acc gta agc           6601
Glu Pro Gly Asp Pro Asp Leu Ser Asp Gly Ser Trp Ser Thr Val Ser
1585                1590                1595                1600 gag gag gct agt gag gac gtc gtc tgc tgc tcg atg tcc tac aca tgg           6649
Glu Glu Ala Ser Glu Asp Val Val Cys Cys Ser Met Ser Tyr Thr Trp
                1605                1610                1615 aca ggc gcc ctg atc acg cca tgc gct gcg gag gaa acc aag ctg ccc           6697
Thr Gly Ala Leu Ile Thr Pro Cys Ala Ala Glu Glu Thr Lys Leu Pro
            1620                1625                1630 atc aat gca ctg agc aac tct ttg ctc cgt cac cac aac ttg gtc tat           6745
Ile Asn Ala Leu Ser Asn Ser Leu Leu Arg His His Asn Leu Val Tyr
        1635                1640                1645 gct aca aca tct cgc agc gca agc ctg cgg cag aag aag gtc acc ttt           6793
Ala Thr Thr Ser Arg Ser Ala Ser Leu Arg Gln Lys Lys Val Thr Phe
    1650                1655                1660 gac aga ctg cag gtc ctg gac gac cac tac cgg gac gtg ctc aag gag           6841
Asp Arg Leu Gln Val Leu Asp Asp His Tyr Arg Asp Val Leu Lys Glu
1665                1670                1675                1680 atg aag gcg aag gcg tcc aca gtt aag gct aaa ctt cta tcc gtg gag           6889
Met Lys Ala Lys Ala Ser Thr Val Lys Ala Lys Leu Leu Ser Val Glu
                1685                1690                1695 gaa gcc tgt aag ctg acg ccc cca cat tcg gcc aga tct aaa ttt ggc           6937
Glu Ala Cys Lys Leu Thr Pro Pro His Ser Ala Arg Ser Lys Phe Gly
            1700                1705                1710 tat ggg gca aag gac gtc cgg aac cta tcc agc aag gcc gtt aac cac           6985
Tyr Gly Ala Lys Asp Val Arg Asn Leu Ser Ser Lys Ala Val Asn His
        1715                1720                1725 atc cgc tcc gtg tgg aag gac ttg ctg gaa gac act gag aca cca att           7033
Ile Arg Ser Val Trp Lys Asp Leu Leu Glu Asp Thr Glu Thr Pro Ile
    1730                1735                1740 gac acc acc atc atg gca aaa aat gag gtt ttc tgc gtc caa cca gag           7081
Asp Thr Thr Ile Met Ala Lys Asn Glu Val Phe Cys Val Gln Pro Glu
1745                1750                1755                1760 aag ggg ggc cgc aag cca gct cgc ctt atc gta ttc cca gat ttg ggg           7129
Lys Gly Gly Arg Lys Pro Ala Arg Leu Ile Val Phe Pro Asp Leu Gly
                1765                1770                1775
```

-continued

| | |
|---|---|
| gtt cgt gtg tgc gag aaa atg gcc ctt tac gat gtg gtc tcc acc ctc<br>Val Arg Val Cys Glu Lys Met Ala Leu Tyr Asp Val Val Ser Thr Leu<br>                1780                          1785                          1790 | 7177 |
| cct cag gcc gtg atg ggc tct tca tac gga ttc caa tac tct cct gga<br>Pro Gln Ala Val Met Gly Ser Ser Tyr Gly Phe Gln Tyr Ser Pro Gly<br>                1795                          1800                          1805 | 7225 |
| cag cgg gtc gag ttc ctg gtg aat gcc tgg aaa gcg aag aaa tgc cct<br>Gln Arg Val Glu Phe Leu Val Asn Ala Trp Lys Ala Lys Lys Cys Pro<br>                1810                          1815                          1820 | 7273 |
| atg ggc ttc gca tat gac acc cgc tgt ttt gac tca acg gtc act gag<br>Met Gly Phe Ala Tyr Asp Thr Arg Cys Phe Asp Ser Thr Val Thr Glu<br>1825                          1830                          1835                          1840 | 7321 |
| aat gac atc cgt gtt gag gag tca atc tac caa tgt tgt gac ttg gcc<br>Asn Asp Ile Arg Val Glu Glu Ser Ile Tyr Gln Cys Cys Asp Leu Ala<br>                1845                          1850                          1855 | 7369 |
| ccc gaa gcc aga cag gcc ata agg tcg ctc aca gag cgg ctt tac atc<br>Pro Glu Ala Arg Gln Ala Ile Arg Ser Leu Thr Glu Arg Leu Tyr Ile<br>                1860                          1865                          1870 | 7417 |
| ggg ggc ccc ctg act aat tct aaa ggg cag aac tgc ggc tat cgc cgg<br>Gly Gly Pro Leu Thr Asn Ser Lys Gly Gln Asn Cys Gly Tyr Arg Arg<br>                1875                          1880                          1885 | 7465 |
| tgc cgc gcg agc ggt gta ctg acg acc agc tgc ggt aat acc ctc aca<br>Cys Arg Ala Ser Gly Val Leu Thr Thr Ser Cys Gly Asn Thr Leu Thr<br>                1890                          1895                          1900 | 7513 |
| tgt tac ttg aag gcc gct gcg gcc tgt cga gct gcg aag ctc cag gac<br>Cys Tyr Leu Lys Ala Ala Ala Ala Cys Arg Ala Ala Lys Leu Gln Asp<br>1905                          1910                          1915                          1920 | 7561 |
| tgc acg atg ctc gta tgc gga gac gac ctt gtc gtt atc tgt gaa agc<br>Cys Thr Met Leu Val Cys Gly Asp Asp Leu Val Val Ile Cys Glu Ser<br>                        1925                          1930                          1935 | 7609 |
| gcg ggg acc caa gag gac gag gcg agc cta cgg gcc ttc acg gag gct<br>Ala Gly Thr Gln Glu Asp Glu Ala Ser Leu Arg Ala Phe Thr Glu Ala<br>                    1940                          1945                          1950 | 7657 |
| atg act aga tac tct gcc ccc cct ggg gac ccg ccc aaa cca gaa tac<br>Met Thr Arg Tyr Ser Ala Pro Pro Gly Asp Pro Pro Lys Pro Glu Tyr<br>                1955                          1960                          1965 | 7705 |
| gac ttg gag ttg ata aca tca tgc tcc tcc aat gtg tca gtc gcg cac<br>Asp Leu Glu Leu Ile Thr Ser Cys Ser Ser Asn Val Ser Val Ala His<br>                1970                          1975                          1980 | 7753 |
| gat gca tct ggc aaa agg gtg tac tat ctc acc cgt gac ccc acc acc<br>Asp Ala Ser Gly Lys Arg Val Tyr Tyr Leu Thr Arg Asp Pro Thr Thr<br>1985                          1990                          1995                          2000 | 7801 |
| ccc ctt gcg cgg gct gcg tgg gag aca gct aga cac act cca gtc aat<br>Pro Leu Ala Arg Ala Ala Trp Glu Thr Ala Arg His Thr Pro Val Asn<br>                    2005                          2010                          2015 | 7849 |
| tcc tgg cta ggc aac atc atc atg tat gcg ccc acc ttg tgg gca agg<br>Ser Trp Leu Gly Asn Ile Ile Met Tyr Ala Pro Thr Leu Trp Ala Arg<br>                2020                          2025                          2030 | 7897 |
| atg atc ctg atg act cat ttc ttc tcc atc ctt cta gct cag gaa caa<br>Met Ile Leu Met Thr His Phe Phe Ser Ile Leu Leu Ala Gln Glu Gln<br>                2035                          2040                          2045 | 7945 |
| ctt gaa aaa gcc cta gat tgt cag atc tac ggg gcc tgt tac tcc att<br>Leu Glu Lys Ala Leu Asp Cys Gln Ile Tyr Gly Ala Cys Tyr Ser Ile<br>                2050                          2055                          2060 | 7993 |
| gag cca ctt gac cta cct cag atc att caa cga ctc cac ggc ctt agc<br>Glu Pro Leu Asp Leu Pro Gln Ile Ile Gln Arg Leu His Gly Leu Ser<br>2065                          2070                          2075                          2080 | 8041 |
| gca ttt tca ctc cat agt tac tct cca ggt gag atc aat agg gtg gct<br>Ala Phe Ser Leu His Ser Tyr Ser Pro Gly Glu Ile Asn Arg Val Ala<br>                2085                          2090                          2095 | 8089 |

-continued

```
tca tgc ctc agg aaa ctt ggg gta ccg ccc ttg cga gtc tgg aga cat        8137
Ser Cys Leu Arg Lys Leu Gly Val Pro Pro Leu Arg Val Trp Arg His
        2100                2105                2110 cgg gcc aga agt gtc cgc gct agg cta ctg tcc cag ggg ggg agg gct        8185
Arg Ala Arg Ser Val Arg Ala Arg Leu Leu Ser Gln Gly Gly Arg Ala
        2115                2120                2125 gcc act tgt ggc aag tac ctc ttc aac tgg gca gta agg acc aag ctc        8233
Ala Thr Cys Gly Lys Tyr Leu Phe Asn Trp Ala Val Arg Thr Lys Leu
        2130                2135                2140 aaa ctc act cca atc ccg gct gcg tcc cag ttg gat tta tcc agc tgg        8281
Lys Leu Thr Pro Ile Pro Ala Ala Ser Gln Leu Asp Leu Ser Ser Trp
2145                2150                2155                2160 ttc gtt gct ggt tac agc ggg gga gac ata tat cac agc ctg tct cgt        8329
Phe Val Ala Gly Tyr Ser Gly Gly Asp Ile Tyr His Ser Leu Ser Arg
                2165                2170                2175 gcc cga ccc cgc tgg ttc atg tgg tgc cta ctc cta ctt tct gta ggg        8377
Ala Arg Pro Arg Trp Phe Met Trp Cys Leu Leu Leu Leu Ser Val Gly
        2180                2185                2190 gta ggc atc tat cta ctc ccc aac cga tga acggggagct aaacactcca         8427
Val Gly Ile Tyr Leu Leu Pro Asn Arg *
        2195                2200 ggccaatagg ccatcctgtt tttttcccct tttttttttt tttttttttc tttttttttt      8487
tttttttttt tttttttttc tcctttttt tcctcttttt ttccttttct ttcctttggt       8547
ggctccatct tagccctagt cacggctagc tgtgaaaggt ccgtgagccg cttgactgca      8607
gagagtgctg atactggcct ctctgcagat caagt                                 8642

<210> SEQ ID NO 3
<211> LENGTH: 2201
<212> TYPE: PRT
<213> ORGANISM: HCV
<220> FEATURE:
<221> NAME/KEY: VARIANT
<222> LOCATION: 882
<223> OTHER INFORMATION: Xaa is Lys or Arg
<220> FEATURE:
<221> NAME/KEY: VARIANT
<222> LOCATION: 1489
<223> OTHER INFORMATION: Xaa is Leu

<400> SEQUENCE: 3

Met Asp Arg Glu Met Ala Ala Ser Cys Gly Gly Ala Val Phe Val Gly
1               5                   10                  15

Leu Ile Leu Leu Thr Leu Ser Pro His Tyr Lys Leu Phe Leu Ala Arg
            20                  25                  30

Leu Ile Trp Trp Leu Gln Tyr Phe Ile Thr Arg Ala Glu Ala His Leu
        35                  40                  45

Gln Val Trp Ile Pro Pro Leu Asn Val Arg Gly Gly Arg Asp Ala Val
    50                  55                  60

Ile Leu Leu Thr Cys Ala Ile His Pro Glu Leu Ile Phe Thr Ile Thr
65                  70                  75                  80

Lys Ile Leu Leu Ala Ile Leu Gly Pro Leu Met Val Leu Gln Ala Gly
                85                  90                  95

Ile Thr Lys Val Pro Tyr Phe Val Arg Ala His Gly Leu Ile Arg Ala
            100                 105                 110

Cys Met Leu Val Arg Lys Val Ala Gly Gly His Tyr Val Gln Met Ala
        115                 120                 125

Leu Met Lys Leu Ala Ala Leu Thr Gly Thr Tyr Val Tyr Asp His Leu
    130                 135                 140
```

```
Thr Pro Leu Arg Asp Trp Ala His Ala Gly Leu Arg Asp Leu Ala Val
145                 150                 155                 160

Ala Val Glu Pro Val Val Phe Ser Asp Met Glu Thr Lys Val Ile Thr
            165                 170                 175

Trp Gly Ala Asp Thr Ala Ala Cys Gly Asp Ile Ile Leu Gly Leu Pro
        180                 185                 190

Val Ser Ala Arg Arg Gly Arg Glu Ile His Leu Gly Pro Ala Asp Ser
    195                 200                 205

Leu Glu Gly Gln Gly Trp Arg Leu Leu Ala Pro Ile Thr Ala Tyr Ser
210                 215                 220

Gln Gln Thr Arg Gly Leu Leu Gly Cys Ile Ile Thr Ser Leu Thr Gly
225                 230                 235                 240

Arg Asp Arg Asn Gln Val Glu Gly Glu Val Gln Val Ser Thr Ala
                245                 250                 255

Thr Gln Ser Phe Leu Ala Thr Cys Val Asn Gly Val Cys Trp Thr Val
            260                 265                 270

Tyr His Gly Ala Gly Ser Lys Thr Leu Ala Gly Pro Lys Gly Pro Ile
        275                 280                 285

Thr Gln Met Tyr Thr Asn Val Asp Gln Asp Leu Val Gly Trp Gln Ala
    290                 295                 300

Pro Pro Gly Ala Arg Ser Leu Thr Pro Cys Thr Cys Gly Ser Ser Asp
305                 310                 315                 320

Leu Tyr Leu Val Thr Arg His Ala Asp Val Ile Pro Val Arg Arg Arg
                325                 330                 335

Gly Asp Ser Arg Gly Ser Leu Leu Ser Pro Arg Pro Val Ser Tyr Leu
            340                 345                 350

Lys Gly Ser Ser Gly Gly Pro Leu Leu Cys Pro Ser Gly His Ala Val
        355                 360                 365

Gly Ile Phe Arg Ala Ala Val Cys Thr Arg Gly Val Ala Lys Ala Val
    370                 375                 380

Asp Phe Val Pro Val Glu Ser Met Glu Thr Thr Met Arg Ser Pro Val
385                 390                 395                 400

Phe Thr Asp Asn Ser Ser Pro Pro Ala Val Pro Gln Thr Phe Gln Val
                405                 410                 415

Ala His Leu His Ala Pro Thr Gly Ser Gly Lys Ser Thr Lys Val Pro
            420                 425                 430

Ala Ala Tyr Ala Ala Gln Gly Tyr Lys Val Leu Val Leu Asn Pro Ser
        435                 440                 445

Val Ala Ala Thr Leu Gly Phe Gly Ala Tyr Met Ser Lys Ala His Gly
    450                 455                 460

Ile Asp Pro Asn Ile Arg Thr Gly Val Arg Thr Ile Thr Thr Gly Ala
465                 470                 475                 480

Pro Ile Thr Tyr Ser Thr Tyr Gly Lys Phe Leu Ala Asp Gly Gly Cys
                485                 490                 495

Ser Gly Gly Ala Tyr Asp Ile Ile Ile Cys Asp Glu Cys His Ser Thr
            500                 505                 510

Asp Ser Thr Thr Ile Leu Gly Ile Gly Thr Val Leu Asp Gln Ala Glu
        515                 520                 525

Thr Ala Gly Ala Arg Leu Val Val Leu Ala Thr Ala Thr Pro Pro Gly
    530                 535                 540

Ser Val Thr Val Pro His Pro Asn Ile Glu Glu Val Ala Leu Ser Ser
545                 550                 555                 560
```

-continued

Thr Gly Glu Ile Pro Phe Tyr Gly Lys Ala Ile Pro Ile Glu Thr Ile
            565                 570                 575

Lys Gly Gly Arg His Leu Ile Phe Cys His Ser Lys Lys Cys Asp
        580                 585                 590

Glu Leu Ala Ala Lys Leu Ser Gly Leu Gly Leu Asn Ala Val Ala Tyr
            595                 600                 605

Tyr Arg Gly Leu Asp Val Ser Val Ile Pro Thr Ser Gly Asp Val Ile
610                 615                 620

Val Val Ala Thr Asp Ala Leu Met Thr Gly Phe Thr Gly Asp Phe Asp
625                 630                 635                 640

Ser Val Ile Asp Cys Asn Thr Cys Val Thr Gln Thr Val Asp Phe Ser
            645                 650                 655

Leu Asp Pro Thr Phe Thr Ile Glu Thr Thr Val Pro Gln Asp Ala
            660                 665                 670

Val Ser Arg Ser Gln Arg Arg Gly Arg Thr Gly Arg Gly Arg Met Gly
            675                 680                 685

Ile Tyr Arg Phe Val Thr Pro Gly Glu Arg Pro Ser Gly Met Phe Asp
            690                 695                 700

Ser Ser Val Leu Cys Glu Cys Tyr Asp Ala Gly Cys Ala Trp Tyr Glu
705                 710                 715                 720

Leu Thr Pro Ala Glu Thr Ser Val Arg Leu Arg Ala Tyr Leu Asn Thr
                725                 730                 735

Pro Gly Leu Pro Val Cys Gln Asp His Leu Glu Phe Trp Glu Ser Val
            740                 745                 750

Phe Thr Gly Leu Thr His Ile Asp Ala His Phe Leu Ser Gln Thr Lys
            755                 760                 765

Gln Ala Gly Asp Asn Phe Pro Tyr Leu Val Ala Tyr Gln Ala Thr Val
            770                 775                 780

Cys Ala Arg Ala Gln Ala Pro Pro Ser Trp Asp Gln Met Trp Lys
785                 790                 795                 800

Cys Leu Ile Arg Leu Lys Pro Thr Leu His Gly Pro Thr Pro Leu Leu
                805                 810                 815

Tyr Arg Leu Gly Ala Val Gln Asn Glu Val Thr Thr His Pro Ile
            820                 825                 830

Thr Lys Tyr Ile Met Ala Cys Met Ser Ala Asp Leu Glu Val Val Thr
            835                 840                 845

Ser Thr Trp Val Leu Val Gly Gly Val Leu Ala Ala Leu Ala Ala Tyr
850                 855                 860

Cys Leu Thr Thr Gly Ser Val Val Ile Val Gly Arg Ile Ile Leu Ser
865                 870                 875                 880

Gly Xaa Pro Ala Ile Ile Pro Asp Arg Glu Val Leu Tyr Arg Glu Phe
                885                 890                 895

Asp Glu Met Glu Glu Cys Ala Ser His Leu Pro Tyr Ile Glu Gln Gly
            900                 905                 910

Met Gln Leu Ala Glu Gln Phe Lys Gln Lys Ala Ile Gly Leu Leu Gln
            915                 920                 925

Thr Ala Thr Lys Gln Ala Glu Ala Ala Pro Val Val Glu Ser Lys
            930                 935                 940

Trp Arg Thr Leu Glu Ala Phe Trp Ala Lys His Met Trp Asn Phe Ile
945                 950                 955                 960

Ser Gly Ile Gln Tyr Leu Ala Gly Leu Ser Thr Leu Pro Gly Asn Pro
                965                 970                 975

Ala Ile Ala Ser Leu Met Ala Phe Thr Ala Ser Ile Thr Ser Pro Leu

-continued

```
                980             985             990
Thr Thr Gln His Thr Leu Leu Phe Asn Ile Leu Gly Gly Trp Val Ala
        995             1000            1005
Ala Gln Leu Ala Pro Pro Ser Ala Ala Ser Ala Phe Val Gly Ala Gly
    1010            1015            1020
Ile Ala Gly Ala Ala Val Gly Ser Ile Gly Leu Gly Lys Val Leu Val
1025            1030            1035            1040
Asp Ile Leu Ala Gly Tyr Gly Ala Gly Val Ala Gly Ala Leu Val Ala
            1045            1050            1055
Phe Lys Val Met Ser Gly Glu Met Pro Ser Thr Glu Asp Leu Val Asn
        1060            1065            1070
Leu Leu Pro Ala Ile Leu Ser Pro Gly Ala Leu Val Val Gly Val Val
    1075            1080            1085
Cys Ala Ala Ile Leu Arg Arg His Val Gly Pro Gly Glu Gly Ala Val
    1090            1095            1100
Gln Trp Met Asn Arg Leu Ile Ala Phe Ala Ser Arg Gly Asn His Val
1105            1110            1115            1120
Ser Pro Thr His Tyr Val Pro Glu Ser Asp Ala Ala Ala Arg Val Thr
            1125            1130            1135
Gln Ile Leu Ser Ser Leu Thr Ile Thr Gln Leu Leu Lys Arg Leu His
        1140            1145            1150
Gln Trp Ile Asn Glu Asp Cys Ser Thr Pro Cys Ser Gly Ser Trp Leu
    1155            1160            1165
Arg Asp Val Trp Asp Trp Ile Cys Thr Val Leu Thr Asp Phe Lys Thr
    1170            1175            1180
Trp Leu Gln Ser Lys Leu Leu Pro Arg Leu Pro Gly Val Pro Phe Phe
1185            1190            1195            1200
Ser Cys Gln Arg Gly Tyr Lys Gly Val Trp Arg Gly Asp Gly Ile Met
            1205            1210            1215
Gln Thr Thr Cys Pro Cys Gly Ala Gln Ile Thr Gly His Val Lys Asn
        1220            1225            1230
Cys Ser Met Arg Ile Val Gly Pro Arg Thr Cys Ser Asn Thr Trp His
    1235            1240            1245
Gly Thr Phe Pro Ile Asn Ala Tyr Thr Thr Gly Pro Cys Thr Pro Ser
    1250            1255            1260
Pro Ala Pro Asn Tyr Ser Arg Ala Leu Trp Arg Val Ala Ala Glu Glu
1265            1270            1275            1280
Tyr Val Glu Val Thr Arg Val Gly Asp Phe His Tyr Val Thr Gly Met
            1285            1290            1295
Thr Thr Asp Asn Val Lys Cys Pro Cys Gln Val Pro Ala Pro Glu Phe
        1300            1305            1310
Phe Thr Glu Val Asp Gly Val Arg Leu His Arg Tyr Ala Pro Ala Cys
    1315            1320            1325
Lys Pro Leu Leu Arg Glu Glu Val Thr Phe Leu Val Gly Leu Asn Gln
    1330            1335            1340
Tyr Leu Val Gly Ser Gln Leu Pro Cys Glu Pro Glu Pro Asp Val Ala
1345            1350            1355            1360
Val Leu Thr Ser Met Leu Thr Asp Pro Ser His Ile Thr Ala Glu Thr
            1365            1370            1375
Ala Lys Arg Arg Leu Ala Arg Gly Ser Pro Pro Ser Leu Ala Ser Ser
        1380            1385            1390
Ser Ala Ser Gln Leu Ser Ala Pro Ser Leu Lys Ala Thr Cys Thr Thr
    1395            1400            1405
```

-continued

```
Arg His Asp Ser Pro Asp Ala Asp Leu Ile Glu Ala Asn Leu Leu Trp
    1410                1415                1420
Arg Gln Glu Met Gly Gly Asn Ile Thr Arg Val Glu Ser Glu Asn Lys
1425                1430                1435                1440
Val Val Ile Leu Asp Ser Phe Glu Pro Leu Gln Ala Glu Glu Asp Glu
                1445                1450                1455
Arg Glu Val Ser Val Pro Ala Glu Ile Leu Arg Arg Ser Arg Lys Phe
            1460                1465                1470
Pro Arg Ala Met Pro Ile Trp Ala Arg Pro Asp Tyr Asn Pro Pro Leu
        1475                1480                1485
Xaa Glu Ser Trp Lys Asp Pro Asp Tyr Val Pro Pro Val Val His Gly
    1490                1495                1500
Cys Pro Leu Pro Pro Ala Lys Ala Pro Pro Ile Pro Pro Pro Arg Arg
1505                1510                1515                1520
Lys Arg Thr Val Val Leu Ser Glu Ser Thr Val Ser Ser Ala Leu Ala
                1525                1530                1535
Glu Leu Ala Thr Lys Thr Phe Gly Ser Ser Glu Ser Ser Ala Val Asp
            1540                1545                1550
Ser Gly Thr Ala Thr Ala Ser Pro Asp Gln Pro Ser Asp Asp Gly Asp
        1555                1560                1565
Ala Gly Ser Asp Val Glu Ser Tyr Ser Ser Met Pro Pro Leu Glu Gly
    1570                1575                1580
Glu Pro Gly Asp Pro Asp Leu Ser Asp Gly Ser Trp Ser Thr Val Ser
1585                1590                1595                1600
Glu Glu Ala Ser Glu Asp Val Val Cys Cys Ser Met Ser Tyr Thr Trp
                1605                1610                1615
Thr Gly Ala Leu Ile Thr Pro Cys Ala Ala Glu Glu Thr Lys Leu Pro
            1620                1625                1630
Ile Asn Ala Leu Ser Asn Ser Leu Leu Arg His His Asn Leu Val Tyr
        1635                1640                1645
Ala Thr Thr Ser Arg Ser Ala Ser Leu Arg Gln Lys Lys Val Thr Phe
    1650                1655                1660
Asp Arg Leu Gln Val Leu Asp Asp His Tyr Arg Asp Val Leu Lys Glu
1665                1670                1675                1680
Met Lys Ala Lys Ala Ser Thr Val Lys Ala Lys Leu Leu Ser Val Glu
                1685                1690                1695
Glu Ala Cys Lys Leu Thr Pro Pro His Ser Ala Arg Ser Lys Phe Gly
            1700                1705                1710
Tyr Gly Ala Lys Asp Val Arg Asn Leu Ser Ser Lys Ala Val Asn His
        1715                1720                1725
Ile Arg Ser Val Trp Lys Asp Leu Leu Glu Asp Thr Glu Thr Pro Ile
    1730                1735                1740
Asp Thr Thr Ile Met Ala Lys Asn Glu Val Phe Cys Val Gln Pro Glu
1745                1750                1755                1760
Lys Gly Gly Arg Lys Pro Ala Arg Leu Ile Val Phe Pro Asp Leu Gly
                1765                1770                1775
Val Arg Val Cys Glu Lys Met Ala Leu Tyr Asp Val Val Ser Thr Leu
            1780                1785                1790
Pro Gln Ala Val Met Gly Ser Ser Tyr Gly Phe Gln Tyr Ser Pro Gly
        1795                1800                1805
Gln Arg Val Glu Phe Leu Val Asn Ala Trp Lys Ala Lys Lys Cys Pro
    1810                1815                1820
```

-continued

```
Met Gly Phe Ala Tyr Asp Thr Arg Cys Phe Asp Ser Thr Val Thr Glu
1825                1830                1835                1840

Asn Asp Ile Arg Val Glu Glu Ser Ile Tyr Gln Cys Cys Asp Leu Ala
            1845                1850                1855

Pro Glu Ala Arg Gln Ala Ile Arg Ser Leu Thr Glu Arg Leu Tyr Ile
        1860                1865                1870

Gly Gly Pro Leu Thr Asn Ser Lys Gly Gln Asn Cys Gly Tyr Arg Arg
    1875                1880                1885

Cys Arg Ala Ser Gly Val Leu Thr Thr Ser Cys Gly Asn Thr Leu Thr
1890                1895                1900

Cys Tyr Leu Lys Ala Ala Ala Cys Arg Ala Ala Lys Leu Gln Asp
1905                1910                1915                1920

Cys Thr Met Leu Val Cys Gly Asp Asp Leu Val Val Ile Cys Glu Ser
            1925                1930                1935

Ala Gly Thr Gln Glu Asp Glu Ala Ser Leu Arg Ala Phe Thr Glu Ala
        1940                1945                1950

Met Thr Arg Tyr Ser Ala Pro Pro Gly Asp Pro Pro Lys Pro Glu Tyr
    1955                1960                1965

Asp Leu Glu Leu Ile Thr Ser Cys Ser Ser Asn Val Ser Val Ala His
    1970                1975                1980

Asp Ala Ser Gly Lys Arg Val Tyr Tyr Leu Thr Arg Asp Pro Thr Thr
1985                1990                1995                2000

Pro Leu Ala Arg Ala Ala Trp Glu Thr Ala Arg His Thr Pro Val Asn
        2005                2010                2015

Ser Trp Leu Gly Asn Ile Ile Met Tyr Ala Pro Thr Leu Trp Ala Arg
    2020                2025                2030

Met Ile Leu Met Thr His Phe Phe Ser Ile Leu Leu Ala Gln Glu Gln
    2035                2040                2045

Leu Glu Lys Ala Leu Asp Cys Gln Ile Tyr Gly Ala Cys Tyr Ser Ile
2050                2055                2060

Glu Pro Leu Asp Leu Pro Gln Ile Ile Gln Arg Leu His Gly Leu Ser
2065                2070                2075                2080

Ala Phe Ser Leu His Ser Tyr Ser Pro Gly Glu Ile Asn Arg Val Ala
            2085                2090                2095

Ser Cys Leu Arg Lys Leu Gly Val Pro Pro Leu Arg Val Trp Arg His
        2100                2105                2110

Arg Ala Arg Ser Val Arg Ala Arg Leu Leu Ser Gln Gly Gly Arg Ala
    2115                2120                2125

Ala Thr Cys Gly Lys Tyr Leu Phe Asn Trp Ala Val Arg Thr Lys Leu
    2130                2135                2140

Lys Leu Thr Pro Ile Pro Ala Ala Ser Gln Leu Asp Leu Ser Ser Trp
2145                2150                2155                2160

Phe Val Ala Gly Tyr Ser Gly Gly Asp Ile Tyr His Ser Leu Ser Arg
        2165                2170                2175

Ala Arg Pro Arg Trp Phe Met Trp Cys Leu Leu Leu Leu Ser Val Gly
    2180                2185                2190

Val Gly Ile Tyr Leu Leu Pro Asn Arg
    2195                2200

<210> SEQ ID NO 4
<211> LENGTH: 8643
<212> TYPE: DNA
<213> ORGANISM: HCV
<220> FEATURE:
<221> NAME/KEY: CDS
```

<222> LOCATION: (1802)...(8407)

<400> SEQUENCE: 4

```
accagccccc gattgggggc gacactccac catagatcac tccctgtga ggaactactg      60
tcttcacgca gaaagcgtct agccatggcg ttagtatgag tgtcgtgcag cctccaggac     120
ccccctccc gggagagcca tagtggtctg cggaaccggt gagtacaccg gaattgccag      180
gacgaccggg tcctttcttg gatcaacccg ctcaatgcct ggagatttgg gcgtgccccc     240
gcgagactgc tagccgagta gtgttgggtc gcgaaaggcc ttgtggtact gcctgatagg     300
gtgcttgcga gtgccccggg aggtctcgta gaccgtgcac catgagcacg aatcctaaac     360
ctcaaagaaa aaccaaaggg cgcgccatga ttgaacaaga tggattgcac gcaggttctc     420
cggccgcttg ggtggagagg ctattcggct atgactgggc gcaacagaca atcggctgct     480
ctgatgccgc cgtgttccgg ctgtcagcgc aggggcgccc ggttcttttt gtcaagaccg     540
acctgtccgg tgccctgaat gaactgcagg acgaggcagc gcggctatcg tggctggcca     600
cgacgggcgt tccttgcgca gctgtgctcg acgttgtcac tgaagcggga agggactggc     660
tgctattggg cgaagtgccg gggcaggatc tcctgtcatc tcaccttgct cctgccgaga     720
aagtatccat catggctgat gcaatgcggc ggctgcatac gcttgatccg gctacctgcc     780
cattcgacca ccaagcgaaa catcgcatcg agcgagcacg tactcggatg aagccggtc      840
ttgtcgatca ggatgatctg gacgaagagc atcagggct cgcgccagcc gaactgttcg      900
ccaggctcaa ggcgcgcatg cccgacgcg aggatctcgt cgtgacccat ggcgatgcct     960
gcttgccgaa tatcatggtg gaaaatggcc gcttttctgg attcatcgac tgtggccggc    1020
tgggtgtggc ggaccgctat caggacatag cgttggctac ccgtgatatt gctgaagagc    1080
ttggcggcga atgggctgac cgcttcctcg tgctttacgg tatcgccgct cccgattcgc    1140
agcgcatcgc cttctatcgc cttcttgacg agttcttctg agttgcgcc agatgttaa     1200
cagaccacaa cggtttccct ctagcgggat caattccgcc ccccccccta acgttactgg    1260
ccgaagccgc ttggaataag gccggtgtgc gtttgtctat atgttatttt ccaccatatt    1320
gccgtctttt ggcaatgtga gggcccggaa acctggccct gtcttcttga cgagcattcc    1380
tagggtctt tcccctctcg ccaaaggaat gcaaggtctg ttgaatgtcg tgaaggaagc    1440
agttcctctg gaagcttctt gaagacaaac aacgtctgta gcgaccctt gcaggcagcg    1500
gaaccccca cctggcgaca ggtgcctctg cggccaaaag ccacgtgtat aagatacacc    1560
tgcaaaggcg gcacaacccc agtgccacgt tgtgagttgg atagttgtgg aaagagtcaa    1620
atggctctcc tcaagcgtat tcaacaaggg gctgaaggat gcccagaagg tacccccattg    1680
tatgggatct gatctggggc ctcggtgcac atgctttaca tgtgtttagt cgaggttaga    1740
aaacgtctag gccccccgaa ccacggggac gtggttttcc tttgaaaaac acgataatac    1800
c atg gac cgg gag atg gca gca tcg tgc gga ggc gcg gtt ttc gta ggt   1849
  Met Asp Arg Glu Met Ala Ala Ser Cys Gly Gly Ala Val Phe Val Gly
    1               5                  10                  15 ctg ata ctc ttg acc ttg tca ccg cac tat aag ctg ttc ctc gct agg      1897
Leu Ile Leu Leu Thr Leu Ser Pro His Tyr Lys Leu Phe Leu Ala Arg
         20                  25                  30 ctc ata tgg tgg tta caa tat ttt atc acc agg gcc gag gca cac ttg      1945
Leu Ile Trp Trp Leu Gln Tyr Phe Ile Thr Arg Ala Glu Ala His Leu
 35                  40                  45 caa gtg tgg atc ccc ccc ctc aac gtt cgg ggg ggc cgc gat gcc gtc      1993
Gln Val Trp Ile Pro Pro Leu Asn Val Arg Gly Gly Arg Asp Ala Val
     50                  55                  60
```

```
atc ctc ctc acg tgc gcg atc cac cca gag cta atc ttt acc atc acc      2041
Ile Leu Leu Thr Cys Ala Ile His Pro Glu Leu Ile Phe Thr Ile Thr
 65                  70                  75                  80 aaa atc ttg ctc gcc ata ctc ggt cca ctc atg gtg ctc cag gct ggt      2089
Lys Ile Leu Leu Ala Ile Leu Gly Pro Leu Met Val Leu Gln Ala Gly
                 85                  90                  95 ata acc aaa gtg ccg tac ttc gtg cgc gca cac ggg ctc att cgt gca      2137
Ile Thr Lys Val Pro Tyr Phe Val Arg Ala His Gly Leu Ile Arg Ala
            100                 105                 110 tgc atg ctg gtg cgg aag gtt gct ggg ggt cat tat gtc caa atg gct      2185
Cys Met Leu Val Arg Lys Val Ala Gly Gly His Tyr Val Gln Met Ala
        115                 120                 125 ctc atg aag ttg gcc gca ctg aca ggt acg tac gtt tat gac cat ctc      2233
Leu Met Lys Leu Ala Ala Leu Thr Gly Thr Tyr Val Tyr Asp His Leu
    130                 135                 140 acc cca ctg cgg gac tgg gcc cac gcg ggc cta cga gac ctt gcg gtg      2281
Thr Pro Leu Arg Asp Trp Ala His Ala Gly Leu Arg Asp Leu Ala Val
145                 150                 155                 160 gca gtt gag ccc gtc gtc ttc tct gat atg gag acc aag gtt atc acc      2329
Ala Val Glu Pro Val Val Phe Ser Asp Met Glu Thr Lys Val Ile Thr
                165                 170                 175 tgg ggg gca gac acc gcg gcg tgt ggg gac atc atc ttg ggc ctg ccc      2377
Trp Gly Ala Asp Thr Ala Ala Cys Gly Asp Ile Ile Leu Gly Leu Pro
            180                 185                 190 gtc tcc gcc cgc agg ggg agg gag ata cat ctg gga ccg gca gac agc      2425
Val Ser Ala Arg Arg Gly Arg Glu Ile His Leu Gly Pro Ala Asp Ser
        195                 200                 205 ctt gaa ggg cag ggg tgg cga ctc ctc gcg cct att acg gcc tac tcc      2473
Leu Glu Gly Gln Gly Trp Arg Leu Leu Ala Pro Ile Thr Ala Tyr Ser
    210                 215                 220 caa cag acg cga ggc cta ctt ggc tgc atc atc act agc ctc aca ggc      2521
Gln Gln Thr Arg Gly Leu Leu Gly Cys Ile Ile Thr Ser Leu Thr Gly
225                 230                 235                 240 cgg gac agg aac cag gtc gag ggg gag gtc caa gtg gtc tcc acc gca      2569
Arg Asp Arg Asn Gln Val Glu Gly Glu Val Gln Val Val Ser Thr Ala
                245                 250                 255 aca caa tct ttc ctg gcg acc tgc gtc aat ggc gtg tgt tgg act gtc      2617
Thr Gln Ser Phe Leu Ala Thr Cys Val Asn Gly Val Cys Trp Thr Val
            260                 265                 270 tat cat ggt gcc ggc tca aag acc ctt gcc ggc cca aag ggc cca atc      2665
Tyr His Gly Ala Gly Ser Lys Thr Leu Ala Gly Pro Lys Gly Pro Ile
        275                 280                 285 acc caa atg tac acc aat gtg gac cag gac ctc gtc ggc tgg caa gcg      2713
Thr Gln Met Tyr Thr Asn Val Asp Gln Asp Leu Val Gly Trp Gln Ala
    290                 295                 300 ccc ccc ggg gcg cgt tcc ttg aca cca tgc acc tgc ggc agc tcg gac      2761
Pro Pro Gly Ala Arg Ser Leu Thr Pro Cys Thr Cys Gly Ser Ser Asp
305                 310                 315                 320 ctt tac ttg gtc acg aag cat gcc gat gtc att ccg gtg cgc cgg cgg      2809
Leu Tyr Leu Val Thr Lys His Ala Asp Val Ile Pro Val Arg Arg Arg
                325                 330                 335 ggc gac agc agg ggg agc cta ctc tcc ccc cgg ccc gtc tcc tac ttg      2857
Gly Asp Ser Arg Gly Ser Leu Leu Ser Pro Arg Pro Val Ser Tyr Leu
            340                 345                 350 aag ggc tct tcg ggc ggt cca ctg ctc tgc ccc tcg ggg cac gct gtg      2905
Lys Gly Ser Ser Gly Gly Pro Leu Leu Cys Pro Ser Gly His Ala Val
        355                 360                 365 ggc atc ttt cgg gct gcc gtg tgc acc cga ggg gtt gcg aag gcg gtg      2953
Gly Ile Phe Arg Ala Ala Val Cys Thr Arg Gly Val Ala Lys Ala Val
```

-continued

```
                370                     375                     380
gac ttt gta ccc gtc gag tct atg gaa acc act atg cgg tcc ccg gtc      3001
Asp Phe Val Pro Val Glu Ser Met Glu Thr Thr Met Arg Ser Pro Val
385                     390                     395                     400 ttc acg gac aac tcg tcc cct ccg gcc gta ccg cag aca ttc cag gtg      3049
Phe Thr Asp Asn Ser Ser Pro Pro Ala Val Pro Gln Thr Phe Gln Val
                    405                     410                     415 gcc cat cta cac gcc cct act ggt agc ggc aag agc act aag gtg ccg      3097
Ala His Leu His Ala Pro Thr Gly Ser Gly Lys Ser Thr Lys Val Pro
                420                     425                     430 gct gcg tat gca gcc caa ggg tat aag gtg ctt gtc ctg aac ccg tcc      3145
Ala Ala Tyr Ala Ala Gln Gly Tyr Lys Val Leu Val Leu Asn Pro Ser
            435                     440                     445 gtc gcc gcc acc cta ggt ttc ggg gcg tat atg tct aag gca cat ggt      3193
Val Ala Ala Thr Leu Gly Phe Gly Ala Tyr Met Ser Lys Ala His Gly
        450                     455                     460 atc gac cct aac atc aga acc ggg gta agg acc atc acc acg ggt gcc      3241
Ile Asp Pro Asn Ile Arg Thr Gly Val Arg Thr Ile Thr Thr Gly Ala
465                     470                     475                     480 ccc atc acg tac tcc acc tat ggc aag ttt ctt gcc gac ggt ggt tgc      3289
Pro Ile Thr Tyr Ser Thr Tyr Gly Lys Phe Leu Ala Asp Gly Gly Cys
                    485                     490                     495 tct ggg ggc gcc tat gac atc ata ata tgt gat gag tgc cac tca act      3337
Ser Gly Gly Ala Tyr Asp Ile Ile Ile Cys Asp Glu Cys His Ser Thr
                500                     505                     510 gac tcg acc act atc ctg ggc atc ggc aca gtc ctg gac caa gcg gag      3385
Asp Ser Thr Thr Ile Leu Gly Ile Gly Thr Val Leu Asp Gln Ala Glu
            515                     520                     525 acg gct gga gcg cga ctc gtc gtg ctc gcc acc gct acg cct ccg gga      3433
Thr Ala Gly Ala Arg Leu Val Val Leu Ala Thr Ala Thr Pro Pro Gly
        530                     535                     540 tcg gtc acc gtg cca cat cca aac atc gag gag gtg gct ctg tcc agc      3481
Ser Val Thr Val Pro His Pro Asn Ile Glu Glu Val Ala Leu Ser Ser
545                     550                     555                     560 act gga gaa atc ccc ttt tat ggc aaa gcc atc ccc atc gag acc atc      3529
Thr Gly Glu Ile Pro Phe Tyr Gly Lys Ala Ile Pro Ile Glu Thr Ile
                    565                     570                     575 aag ggg ggg agg cac ctc att ttc tgc cat tcc aag aag aaa tgt gat      3577
Lys Gly Gly Arg His Leu Ile Phe Cys His Ser Lys Lys Lys Cys Asp
                580                     585                     590 gag ctc gcc gcg aag ctg tcc ggc ctc gga ctc aat gct gta gca tat      3625
Glu Leu Ala Ala Lys Leu Ser Gly Leu Gly Leu Asn Ala Val Ala Tyr
            595                     600                     605 tac cgg ggc ctt gat gta tcc gtc ata cca act agc gga gac gtc att      3673
Tyr Arg Gly Leu Asp Val Ser Val Ile Pro Thr Ser Gly Asp Val Ile
        610                     615                     620 gtc gta gca acg gac gct cta atg acg ggc ttt acc ggc gat ttc gac      3721
Val Val Ala Thr Asp Ala Leu Met Thr Gly Phe Thr Gly Asp Phe Asp
625                     630                     635                     640 tca gtg atc gac tgc aat aca tgt gtc acc cag aca gtc gac ttc agc      3769
Ser Val Ile Asp Cys Asn Thr Cys Val Thr Gln Thr Val Asp Phe Ser
                    645                     650                     655 ctg gac ccg acc ttc acc att gag acg acg acc gtg cca caa gac gcg      3817
Leu Asp Pro Thr Phe Thr Ile Glu Thr Thr Thr Val Pro Gln Asp Ala
                660                     665                     670 gtg tca cgc tcg cag cgg cga ggc agg act ggt agg ggc agg atg ggc      3865
Val Ser Arg Ser Gln Arg Arg Gly Arg Thr Gly Arg Gly Arg Met Gly
            675                     680                     685 att tac agg ttt gtg act cca gga gaa cgg ccc tcg ggc atg ttc gat      3913
```

```
Ile Tyr Arg Phe Val Thr Pro Gly Glu Arg Pro Ser Gly Met Phe Asp
    690                 695                 700 tcc tcg gtt ctg tgc gag tgc tat gac gcg ggc tgt gct tgg tac gag      3961
Ser Ser Val Leu Cys Glu Cys Tyr Asp Ala Gly Cys Ala Trp Tyr Glu
705                 710                 715                 720 ctc acg ccc gcc gag acc tca gtt agg ttg cgg gct tac cta aac aca      4009
Leu Thr Pro Ala Glu Thr Ser Val Arg Leu Arg Ala Tyr Leu Asn Thr
                725                 730                 735 cca ggg ttg ccc gtc tgc cag gac cat ctg gag ttc tgg gag ggc gtc      4057
Pro Gly Leu Pro Val Cys Gln Asp His Leu Glu Phe Trp Glu Gly Val
            740                 745                 750 ttt aca ggc ctc acc cac ata gac gcc cat ttc ttg tcc cag act aag      4105
Phe Thr Gly Leu Thr His Ile Asp Ala His Phe Leu Ser Gln Thr Lys
        755                 760                 765 cag gca gga gac aac ttc ccc tac ctg gta gca tac cag gct acg gtg      4153
Gln Ala Gly Asp Asn Phe Pro Tyr Leu Val Ala Tyr Gln Ala Thr Val
    770                 775                 780 tgc gcc agg gct cag gct cca cct cca tcg tgg gac caa atg tgg aag      4201
Cys Ala Arg Ala Gln Ala Pro Pro Pro Ser Trp Asp Gln Met Trp Lys
785                 790                 795                 800 tgt ctc ata cgg cta aag cct acg ctg cac ggg cca acg ccc ctg ctg      4249
Cys Leu Ile Arg Leu Lys Pro Thr Leu His Gly Pro Thr Pro Leu Leu
                805                 810                 815 tat agg ctg gga gcc gtt caa aac gag gtt act acc aca cac ccc ata      4297
Tyr Arg Leu Gly Ala Val Gln Asn Glu Val Thr Thr Thr His Pro Ile
            820                 825                 830 acc aaa tac atc atg gca tgc atg tcg gct gac ctg gag gtc gtc acg      4345
Thr Lys Tyr Ile Met Ala Cys Met Ser Ala Asp Leu Glu Val Val Thr
        835                 840                 845 agc acc tgg gtg ctg gta ggc gga gtc cta gca gct ctg gcc gcg tat      4393
Ser Thr Trp Val Leu Val Gly Gly Val Leu Ala Ala Leu Ala Ala Tyr
    850                 855                 860 tgc ctg aca aca ggc agc gtg gtc att gtg ggc agg atc atc ttg tcc      4441
Cys Leu Thr Thr Gly Ser Val Val Ile Val Gly Arg Ile Ile Leu Ser
865                 870                 875                 880 gga agg ccg gcc atc att ccc gac agg gaa gtc ctt tac cgg gag ttc      4489
Gly Arg Pro Ala Ile Ile Pro Asp Arg Glu Val Leu Tyr Arg Glu Phe
                885                 890                 895 gat gag atg gaa gag tgc gcc tca cac ctc cct tac atc gaa cag gga      4537
Asp Glu Met Glu Glu Cys Ala Ser His Leu Pro Tyr Ile Glu Gln Gly
            900                 905                 910 atg cag ctc gcc gaa caa ttc aaa cag aag gca atc ggg ttg ctg caa      4585
Met Gln Leu Ala Glu Gln Phe Lys Gln Lys Ala Ile Gly Leu Leu Gln
        915                 920                 925 aca gcc acc aag caa gcg gag gct gct gct ccc gtg gtg gaa tcc aag      4633
Thr Ala Thr Lys Gln Ala Glu Ala Ala Ala Pro Val Val Glu Ser Lys
    930                 935                 940 tgg cgg acc ctc gaa gcc ttc tgg gcg aag cat atg tgg aat ttc atc      4681
Trp Arg Thr Leu Glu Ala Phe Trp Ala Lys His Met Trp Asn Phe Ile
945                 950                 955                 960 agc ggg ata caa tat tta gca ggc ttg tcc act ctg cct ggc aac ccc      4729
Ser Gly Ile Gln Tyr Leu Ala Gly Leu Ser Thr Leu Pro Gly Asn Pro
                965                 970                 975 gcg ata gca tca ctg atg gca ttc aca gcc tct atc acc agc ccg ctc      4777
Ala Ile Ala Ser Leu Met Ala Phe Thr Ala Ser Ile Thr Ser Pro Leu
            980                 985                 990 acc acc caa cat acc ctc ctg ttt aac atc ctg ggg gga tgg gtg gcc      4825
Thr Thr Gln His Thr Leu Leu Phe Asn Ile Leu Gly Gly Trp Val Ala
        995                 1000                1005
```

```
gcc caa ctt gct cct ccc agc gct gct tcc gct ttc gta ggc gcc ggc         4873
Ala Gln Leu Ala Pro Pro Ser Ala Ala Ser Ala Phe Val Gly Ala Gly
    1010                1015                1020 atc gct gga gcg gct gtt ggc agc ata ggc ctt ggg aag gtg ctt gtg         4921
Ile Ala Gly Ala Ala Val Gly Ser Ile Gly Leu Gly Lys Val Leu Val
1025                1030                1035                1040 gat att ttg gca ggt tat gga gca ggg gtg gca ggc gcg ctc gtg gcc         4969
Asp Ile Leu Ala Gly Tyr Gly Ala Gly Val Ala Gly Ala Leu Val Ala
                1045                1050                1055 ttt aag gtc atg agc ggc gag atg ccc tcc acc gag gac ctg gtt aac         5017
Phe Lys Val Met Ser Gly Glu Met Pro Ser Thr Glu Asp Leu Val Asn
            1060                1065                1070 cta ctc cct gct atc ctc tcc cct ggc gcc cta gtc gtc ggg gtc gtg         5065
Leu Leu Pro Ala Ile Leu Ser Pro Gly Ala Leu Val Val Gly Val Val
        1075                1080                1085 tgc gca gcg ata ctg cgt cgg cac gtg ggc cca ggg gag ggg gct gtg         5113
Cys Ala Ala Ile Leu Arg Arg His Val Gly Pro Gly Glu Gly Ala Val
    1090                1095                1100 cag tgg atg aac cgg ctg ata gcg ttc gct tcg cgg ggt aac cac gtc         5161
Gln Trp Met Asn Arg Leu Ile Ala Phe Ala Ser Arg Gly Asn His Val
1105                1110                1115                1120 tcc ccc acg cac tat gtg cct gag agc gac gct gca gca cgt gtc act         5209
Ser Pro Thr His Tyr Val Pro Glu Ser Asp Ala Ala Ala Arg Val Thr
                1125                1130                1135 cag atc ctc tct agt ctt acc atc act cag ctg ctg aag agg ctt cac         5257
Gln Ile Leu Ser Ser Leu Thr Ile Thr Gln Leu Leu Lys Arg Leu His
            1140                1145                1150 cag tgg atc aac gag gac tgc tcc acg cca tgc tcc ggc tcg tgg cta         5305
Gln Trp Ile Asn Glu Asp Cys Ser Thr Pro Cys Ser Gly Ser Trp Leu
        1155                1160                1165 aga gat gtt tgg gat tgg ata tgc acg gtg ttg act gat ttc aag gcc         5353
Arg Asp Val Trp Asp Trp Ile Cys Thr Val Leu Thr Asp Phe Lys Ala
    1170                1175                1180 tgg ctc cag tcc aag ctc ctg ccg cga ttg ccg gga gtc ccc ttc ttc         5401
Trp Leu Gln Ser Lys Leu Leu Pro Arg Leu Pro Gly Val Pro Phe Phe
1185                1190                1195                1200 tca tgt caa cgt ggg tac aag gga gtc tgg cgg ggc gac ggc atc atg         5449
Ser Cys Gln Arg Gly Tyr Lys Gly Val Trp Arg Gly Asp Gly Ile Met
                1205                1210                1215 caa acc acc tgc cca tgt gga gca cag atc acc gga cat gtg aaa aac         5497
Gln Thr Thr Cys Pro Cys Gly Ala Gln Ile Thr Gly His Val Lys Asn
            1220                1225                1230 tgt tcc atg agg atc gtg ggg cct agg acc tgt agt aac acg tgg cat         5545
Cys Ser Met Arg Ile Val Gly Pro Arg Thr Cys Ser Asn Thr Trp His
        1235                1240                1245 gga aca ttc ccc att aac gcg tac acc acg ggc ccc tgc acg ccc tcc         5593
Gly Thr Phe Pro Ile Asn Ala Tyr Thr Thr Gly Pro Cys Thr Pro Ser
    1250                1255                1260 ccg gcg cca aat tat tct agg gcg ctg tgg cgg gtg gct gct gag gag         5641
Pro Ala Pro Asn Tyr Ser Arg Ala Leu Trp Arg Val Ala Ala Glu Glu
1265                1270                1275                1280 tac gtg gag gtt acg cga gtg ggg gat ttc cac tac gtg acg ggc atg         5689
Tyr Val Glu Val Thr Arg Val Gly Asp Phe His Tyr Val Thr Gly Met
                1285                1290                1295 acc act gac aac gta aag tgc ccg tgt cag gtt ccg gcc ccc gaa ttc         5737
Thr Thr Asp Asn Val Lys Cys Pro Cys Gln Val Pro Ala Pro Glu Phe
            1300                1305                1310 ttc aca gaa gtg gat ggg gtg cgg ttg cac agg tac gct cca gcg tgc         5785
Phe Thr Glu Val Asp Gly Val Arg Leu His Arg Tyr Ala Pro Ala Cys
        1315                1320                1325
```

-continued

```
aaa ccc ctc cta cgg gag gag gtc aca ttc ctg gtc ggg ctc aat caa      5833
Lys Pro Leu Leu Arg Glu Glu Val Thr Phe Leu Val Gly Leu Asn Gln
    1330                1335                1340 tac ctg gtt ggg tca cag ctc cca tgc gag ccc gaa ctg gac gta gca      5881
Tyr Leu Val Gly Ser Gln Leu Pro Cys Glu Pro Glu Leu Asp Val Ala
1345                1350                1355                1360 gtg ctc act tcc atg ctc acc gac ccc tcc cac att acg gcg gag acg      5929
Val Leu Thr Ser Met Leu Thr Asp Pro Ser His Ile Thr Ala Glu Thr
                1365                1370                1375 gct aag cgt agg ctg gcc agg gga tct ccc ccc tcc ttg gcc agc tca      5977
Ala Lys Arg Arg Leu Ala Arg Gly Ser Pro Pro Ser Leu Ala Ser Ser
        1380                1385                1390 tca gct agc cag ctg tct gcg cct tcc ttg aag gca aca tgc act acc      6025
Ser Ala Ser Gln Leu Ser Ala Pro Ser Leu Lys Ala Thr Cys Thr Thr
    1395                1400                1405 cgt cat gac tcc ccg gac gct gac ctc atc gag gcc aac ctc ctg tgg      6073
Arg His Asp Ser Pro Asp Ala Asp Leu Ile Glu Ala Asn Leu Leu Trp
1410                1415                1420 cgg cag gag atg ggc ggg aac atc acc cgc gtg gag tca gaa aat aag      6121
Arg Gln Glu Met Gly Gly Asn Ile Thr Arg Val Glu Ser Glu Asn Lys
1425                1430                1435                1440 gta gta att ttg gac tct ttc gag ccg ctc caa gcg gag gag gat gag      6169
Val Val Ile Leu Asp Ser Phe Glu Pro Leu Gln Ala Glu Glu Asp Glu
                1445                1450                1455 agg gaa gta tcc gtt ccg gcg gag atc ctg cgg agg tcc agg aaa ttc      6217
Arg Glu Val Ser Val Pro Ala Glu Ile Leu Arg Arg Ser Arg Lys Phe
        1460                1465                1470 cct cga gcg atg ccc ata tgg gca cgc ccg gat tac aac cct cca ctg      6265
Pro Arg Ala Met Pro Ile Trp Ala Arg Pro Asp Tyr Asn Pro Pro Leu
    1475                1480                1485 ttg gag tcc tgg aag gac ccg gac tac gtc cct cca gtg gta cac ggg      6313
Leu Glu Ser Trp Lys Asp Pro Asp Tyr Val Pro Pro Val Val His Gly
1490                1495                1500 tgt cca ttg ccg cct gcc aag gcc cct ccg ata cca cct cca cgg agg      6361
Cys Pro Leu Pro Pro Ala Lys Ala Pro Pro Ile Pro Pro Pro Arg Arg
1505                1510                1515                1520 aag agg acg gtt gtc ctg tca gaa tct acc gtg tct tct gcc ttg gcg      6409
Lys Arg Thr Val Val Leu Ser Glu Ser Thr Val Ser Ser Ala Leu Ala
                1525                1530                1535 gag ctc gcc aca aag acc ttc ggc agc tcc gaa tcg tcg gcc gtc gac      6457
Glu Leu Ala Thr Lys Thr Phe Gly Ser Ser Glu Ser Ser Ala Val Asp
        1540                1545                1550 agc ggc acg gca acg gcc tct cct gac cag ccc tcc gac gac ggc gac      6505
Ser Gly Thr Ala Thr Ala Ser Pro Asp Gln Pro Ser Asp Asp Gly Asp
    1555                1560                1565 gcg gga tcc gac gtt gag tcg tac tcc tcc atg ccc ccc ctt gag ggg      6553
Ala Gly Ser Asp Val Glu Ser Tyr Ser Ser Met Pro Pro Leu Glu Gly
1570                1575                1580 gag ccg ggg gat ccc gat ctc agc gac ggg tct tgg tct acc gta agc      6601
Glu Pro Gly Asp Pro Asp Leu Ser Asp Gly Ser Trp Ser Thr Val Ser
1585                1590                1595                1600 gag gag gct agt gag gac gtc gtc tgc tgc tcg atg tcc tac aca tgg      6649
Glu Glu Ala Ser Glu Asp Val Val Cys Cys Ser Met Ser Tyr Thr Trp
                1605                1610                1615 acg ggc gcc ctg atc acg cca tgc gct gcg gag gaa acc aag ctg ccc      6697
Thr Gly Ala Leu Ile Thr Pro Cys Ala Ala Glu Glu Thr Lys Leu Pro
        1620                1625                1630 atc aat gca ctg agc aac tct ttg ctc cgt cac cac aac ttg gtc tat      6745
Ile Asn Ala Leu Ser Asn Ser Leu Leu Arg His His Asn Leu Val Tyr
```

-continued

```
           1635                1640                1645
gct aca aca tct cgc agc gca agc ctg cgg cag aag aag gtc acc ttt    6793
Ala Thr Thr Ser Arg Ser Ala Ser Leu Arg Gln Lys Lys Val Thr Phe
    1650                1655                1660 gac aga ctg cag gtc ctg gac gac cac tac cgg gac gtg ctc aag gag    6841
Asp Arg Leu Gln Val Leu Asp Asp His Tyr Arg Asp Val Leu Lys Glu
1665                1670                1675                1680 atg aag gcg aag gcg tcc aca gtt aag gct aaa ctt cta tcc gtg gag    6889
Met Lys Ala Lys Ala Ser Thr Val Lys Ala Lys Leu Leu Ser Val Glu
                1685                1690                1695 gaa gcc tgt aag ctg acg ccc cca cat tcg gcc aga tct aaa ttt ggc    6937
Glu Ala Cys Lys Leu Thr Pro Pro His Ser Ala Arg Ser Lys Phe Gly
        1700                1705                1710 tat ggg gca aag gac gtc cgg aac cta tcc agc aag gcc gtt aac cac    6985
Tyr Gly Ala Lys Asp Val Arg Asn Leu Ser Ser Lys Ala Val Asn His
            1715                1720                1725 atc cgc tcc gtg tgg aag gac ttg ctg gaa gac act gag aca cca att    7033
Ile Arg Ser Val Trp Lys Asp Leu Leu Glu Asp Thr Glu Thr Pro Ile
    1730                1735                1740 gac acc acc atc atg gca aaa aat gag gtt ttc tgc gtc caa cca gag    7081
Asp Thr Thr Ile Met Ala Lys Asn Glu Val Phe Cys Val Gln Pro Glu
1745                1750                1755                1760 aag ggg ggc cgc aag cca gct cgc ctt atc gta ttc cca gat ttg ggg    7129
Lys Gly Gly Arg Lys Pro Ala Arg Leu Ile Val Phe Pro Asp Leu Gly
                1765                1770                1775 gtt cgt gtg tgc gag aaa atg gcc ctt tac gat gtg gtc tcc acc ctc    7177
Val Arg Val Cys Glu Lys Met Ala Leu Tyr Asp Val Val Ser Thr Leu
        1780                1785                1790 cct cag gcc gtg atg ggc tct tca tac gga ttc caa tac tct cct gga    7225
Pro Gln Ala Val Met Gly Ser Ser Tyr Gly Phe Gln Tyr Ser Pro Gly
            1795                1800                1805 cag cgg gtc gag ttc ctg gtg aat gcc tgg aaa gcg aag aaa tgc cct    7273
Gln Arg Val Glu Phe Leu Val Asn Ala Trp Lys Ala Lys Lys Cys Pro
    1810                1815                1820 atg ggc ttc gca tat gac acc cgc tgt ttt gac tca acg gtc act gag    7321
Met Gly Phe Ala Tyr Asp Thr Arg Cys Phe Asp Ser Thr Val Thr Glu
1825                1830                1835                1840 aat gac atc cgt gtt gag gag tca atc tac caa tgt tgt gac ttg gcc    7369
Asn Asp Ile Arg Val Glu Glu Ser Ile Tyr Gln Cys Cys Asp Leu Ala
                1845                1850                1855 ccc gaa gcc aga cag gcc ata agg tcg ctc aca gag cgg ctt tac atc    7417
Pro Glu Ala Arg Gln Ala Ile Arg Ser Leu Thr Glu Arg Leu Tyr Ile
        1860                1865                1870 ggg ggc ccc ctg act aat tct aaa ggg cag aac tgc ggc tat cgc cgg    7465
Gly Gly Pro Leu Thr Asn Ser Lys Gly Gln Asn Cys Gly Tyr Arg Arg
            1875                1880                1885 tgc cgc gcg agc ggt gta ctg acg acc agc tgc ggt aat acc ctc aca    7513
Cys Arg Ala Ser Gly Val Leu Thr Thr Ser Cys Gly Asn Thr Leu Thr
    1890                1895                1900 tgt tac ttg aag gcc gct gcg gcc tgt cga gct gcg aag ctc cag gac    7561
Cys Tyr Leu Lys Ala Ala Ala Ala Cys Arg Ala Ala Lys Leu Gln Asp
1905                1910                1915                1920 tgc acg atg ctc gta tgc gga gac gac ctt gtc gtt atc tgt gaa agc    7609
Cys Thr Met Leu Val Cys Gly Asp Asp Leu Val Val Ile Cys Glu Ser
                1925                1930                1935 gcg ggg acc caa gag gac gag gcg agc cta cgg gcc ttc acg gag gct    7657
Ala Gly Thr Gln Glu Asp Glu Ala Ser Leu Arg Ala Phe Thr Glu Ala
        1940                1945                1950 atg act aga tac tct gcc ccc cct ggg gac ccg ccc aaa cca gaa tac    7705
```

-continued

```
                Met Thr Arg Tyr Ser Ala Pro Pro Gly Asp Pro Pro Lys Pro Glu Tyr
                        1955                1960                1965 gac ttg gag ttg ata aca tca tgc tcc tcc aat gtg tca gtc gcg cac         7753
Asp Leu Glu Leu Ile Thr Ser Cys Ser Ser Asn Val Ser Val Ala His
        1970                1975                1980 gat gca tct ggc aaa agg gtg tac tat ctc acc cgt gac ccc acc acc         7801
Asp Ala Ser Gly Lys Arg Val Tyr Tyr Leu Thr Arg Asp Pro Thr Thr
1985                1990                1995                2000 ccc ctt gcg cgg gct gcg tgg gag aca gct aga cac act cca gtc aat         7849
Pro Leu Ala Arg Ala Ala Trp Glu Thr Ala Arg His Thr Pro Val Asn
            2005                2010                2015 tcc tgg cta ggc aac atc atc atg tat gcg ccc acc ttg tgg gca agg         7897
Ser Trp Leu Gly Asn Ile Ile Met Tyr Ala Pro Thr Leu Trp Ala Arg
                2020                2025                2030 atg atc ctg atg act cat ttc ttc tcc atc ctt cta gct cag gaa caa         7945
Met Ile Leu Met Thr His Phe Phe Ser Ile Leu Leu Ala Gln Glu Gln
                    2035                2040                2045 ctt gaa aaa gcc cta gat tgt cag atc tac ggg gcc tgt tac tcc att         7993
Leu Glu Lys Ala Leu Asp Cys Gln Ile Tyr Gly Ala Cys Tyr Ser Ile
        2050                2055                2060 gag cca ctt gac cta cct cag atc att caa cga ctc cac ggc ctt agc         8041
Glu Pro Leu Asp Leu Pro Gln Ile Ile Gln Arg Leu His Gly Leu Ser
2065                2070                2075                2080 gca ttt tca ctc cat agt tac tct cca ggt gag atc aat agg gtg gct         8089
Ala Phe Ser Leu His Ser Tyr Ser Pro Gly Glu Ile Asn Arg Val Ala
            2085                2090                2095 tca tgc ctc agg aaa ctt ggg gta ccg ccc ttg cga gtc tgg aga cat         8137
Ser Cys Leu Arg Lys Leu Gly Val Pro Pro Leu Arg Val Trp Arg His
                2100                2105                2110 cgg gcc aga agt gtc cgc gct agg cta ctg tcc cag ggg ggg agg gct         8185
Arg Ala Arg Ser Val Arg Ala Arg Leu Leu Ser Gln Gly Gly Arg Ala
                    2115                2120                2125 gcc act tgt ggc aag tac ctc ttc aac tgg gca gta agg acc aag ctc         8233
Ala Thr Cys Gly Lys Tyr Leu Phe Asn Trp Ala Val Arg Thr Lys Leu
        2130                2135                2140 aaa ctc act cca atc ccg gct gcg tcc cag ttg gat tta tcc agc tgg         8281
Lys Leu Thr Pro Ile Pro Ala Ala Ser Gln Leu Asp Leu Ser Ser Trp
2145                2150                2155                2160 ttc gtt gct ggt tac agc ggg gga gac ata tat cac agc ctg tct cgt         8329
Phe Val Ala Gly Tyr Ser Gly Gly Asp Ile Tyr His Ser Leu Ser Arg
            2165                2170                2175 gcc cga ccc cgc tgg ttc atg tgg tgc cta ctc cta ctt tct gta ggg         8377
Ala Arg Pro Arg Trp Phe Met Trp Cys Leu Leu Leu Leu Ser Val Gly
                2180                2185                2190 gta ggc atc tat cta ctc ccc aac cga tga acggggagct aaacactcca           8427
Val Gly Ile Tyr Leu Leu Pro Asn Arg  *
                    2195                2200 ggccaatagg ccatcctgtt ttttcccttt tttttttttt tttttttttt tttttttttt      8487
tttttttttt tttttttttt ttttctttt tcccaatttt tttcctttc tttcctttgg         8547 tggctccatc ttagccctag tcacggctag ctgtgaaagg tccgtgagcc gcttgactgc       8607
agagagtgct gatactggcc tctctgcaga tcaagt                                 8643

<210> SEQ ID NO 5
<211> LENGTH: 8648
<212> TYPE: DNA
<213> ORGANISM: HCV
<220> FEATURE:
<221> NAME/KEY: CDS
<222> LOCATION: (1802)...(8407)
```

```
<400> SEQUENCE: 5
gccagccccc gattgggggc gacactccac catagatcac tcccctgtga ggaactactg    60
tcttcacgca gaaagcgtct agccatggcg ttagtatgag tgtcgtgcag cctccaggac   120
cccccctccc gggagagcca tagtggtctg cggaaccggt gagtacaccg gaattgccag   180
gacgaccggg tcctttcttg gatcaacccg ctcaatgcct ggagatttgg gcgtgccccc   240
gcgagactgc tagccgagta gtgttgggtc gcgaaaggcc ttgtggtact gcctgatagg   300
gtgcttgcga gtgccccggg aggtctcgta gaccgtgcac catgagcacg aatcctaaac   360
ctcaaagaaa aaccaaaggg cgcgccatga ttgaacaaga tggattgcac gcaggttctc   420
cggccgcttg ggtggagagg ctattcggct atgactgggc acaacagaca atcggctgct   480
ctgatgccgc cgtgttccgg ctgtcagcgc agggggcgccc ggttcttttt gtcaagaccg   540
acctgtccgg tgccctgaat gaactgcagg acgaggcagc gcggctatcg tggctggcca   600
cgacgggcgt tccttgcgca gctgtgctcg acgttgtcac tgaagcggga agggactggc   660
tgctattggg cgaagtgccg gggcaggatc tcctgtcatc tcaccttgct cctgccgaga   720
aagtatccat catggctgat gcaatgcggc ggctgcatac gcttgatccg gctacctgcc   780
cattcgacca ccaagcgaaa catcgcatcg agcgagcacg tactcggatg aagccggtc    840 ttgtcgatca ggatgatctg gacgaagagc atcagggggct cgcgccagcc gaactgttcg   900
ccaggctcaa ggcgcgcatg cccgacggcg aggatctcgt cgtgacccat ggcgatgcct   960
gcttgccgaa tatcatggtg gaaaatggcc gcttttctgg attcatcgac tgtggccggc  1020
tgggtgtggc ggaccgctat caggacatag cgttggctac ccgtgatatt gctgaagagc  1080
ttggcggcga atgggctgac cgcttcctcg tgctttacgg tatcgccgct cccgattcgc  1140
agcgcatcgc cttctatcgc cttcttgacg agttcttctg agttcgcgcc cagatgttaa  1200
cagaccacaa cggtttccct ctagcgggat caattccgcc ccccccccta acgttactgg  1260
ccgaagccgc ttggaataag gccggtgtgc gtttgtctat atgttatttt ccaccatatt  1320
gccgtctttt ggcaatgtga gggcccggaa acctggccct gtcttcttga cgagcattcc  1380
taggggtctt tcccctctcg ccaaaggaat gcaaggtctg ttgaatgtcg tgaaggaagc  1440
agttcctctg gaagcttctt gaagacaaac aacgtctgta gcgacccttt gcaggcagcg  1500
gaacccccca cctggcgaca ggtgcctctg cggccaaaag ccacgtgtat aagatacacc  1560
tgcaaaggcg gcacaacccc agtgccacgt tgtgagttgg atagttgtgg aaagagtcaa  1620
atggctctcc tcaagcgtat tcaacaaggg gctgaaggat gcccagaagg taccccattg  1680
tatgggatct gatctgggc ctcggtgcac atgctttaca tgtgtttagt cgaggttaaa   1740
aaacgtctag gccccccgaa ccacggggac gtggttttcc tttgaaaaac acgataatac  1800 c atg gac cgg gag atg gca gca tcg tgc gga ggc gcg gtt ttc gta ggt  1849
  Met Asp Arg Glu Met Ala Ala Ser Cys Gly Gly Ala Val Phe Val Gly
  1               5                  10                  15 ctg ata ctc ttg acc ttg tca ccg cac tat aag ctg ttc ctc gct agg    1897
Leu Ile Leu Leu Thr Leu Ser Pro His Tyr Lys Leu Phe Leu Ala Arg
                20                  25                  30 ctc ata tgg tgg tta caa tat ttt atc acc agg gcc gag gca cac ttg    1945
Leu Ile Trp Trp Leu Gln Tyr Phe Ile Thr Arg Ala Glu Ala His Leu
            35                  40                  45 caa gtg tgg atc ccc ccc ctc aac gtt cgg ggg ggc cgc gat gcc gtc    1993
Gln Val Trp Ile Pro Pro Leu Asn Val Arg Gly Gly Arg Asp Ala Val
        50                  55                  60
```

```
atc ctc ctc acg tgc gcg atc cac cca gag cta atc ttt acc atc acc    2041
Ile Leu Leu Thr Cys Ala Ile His Pro Glu Leu Ile Phe Thr Ile Thr
 65              70                  75                  80 aaa atc ttg ctc gcc ata ctc ggt cca ctc atg gtg ctc cag gct ggt    2089
Lys Ile Leu Leu Ala Ile Leu Gly Pro Leu Met Val Leu Gln Ala Gly
                 85                  90                  95 ata acc aaa gtg ccg tac ttc gtg cgc gca cac ggg ctc att cgt gca    2137
Ile Thr Lys Val Pro Tyr Phe Val Arg Ala His Gly Leu Ile Arg Ala
            100                 105                 110 tgc atg ctg gtg cgg aag gtt gct ggg ggt cat tat gtc caa atg gct    2185
Cys Met Leu Val Arg Lys Val Ala Gly Gly His Tyr Val Gln Met Ala
        115                 120                 125 ctc atg aag ttg gcc gca ctg aca ggt acg tac gtt tat gac cat ctc    2233
Leu Met Lys Leu Ala Ala Leu Thr Gly Thr Tyr Val Tyr Asp His Leu
130                 135                 140 acc cca ctg cgg gac tgg gcc cac gcg ggc cta cga gac ctt gcg gtg    2281
Thr Pro Leu Arg Asp Trp Ala His Ala Gly Leu Arg Asp Leu Ala Val
145                 150                 155                 160 gca gtt gag ccc gtc gtc ttc tct gat atg gag acc aag gtt atc acc    2329
Ala Val Glu Pro Val Val Phe Ser Asp Met Glu Thr Lys Val Ile Thr
                165                 170                 175 tgg ggg gca gac acc gcg gcg tgt ggg gac atc atc ttg ggc ctg ccc    2377
Trp Gly Ala Asp Thr Ala Ala Cys Gly Asp Ile Ile Leu Gly Leu Pro
            180                 185                 190 gtc tcc gcc cgc agg ggg agg gag ata cat ctg gga ccg gca gac agc    2425
Val Ser Ala Arg Arg Gly Arg Glu Ile His Leu Gly Pro Ala Asp Ser
        195                 200                 205 ctt gaa ggg cag ggg tgg cga ctc ctc gcg cct att acg gcc tac tcc    2473
Leu Glu Gly Gln Gly Trp Arg Leu Leu Ala Pro Ile Thr Ala Tyr Ser
    210                 215                 220 caa cag acg cga ggc cta ctt ggc tgc atc atc act agc ctc aca ggc    2521
Gln Gln Thr Arg Gly Leu Leu Gly Cys Ile Ile Thr Ser Leu Thr Gly
225                 230                 235                 240 cgg gac agg aac cag gtc gag ggg gag gtc caa gtg gtc tcc acc gca    2569
Arg Asp Arg Asn Gln Val Glu Gly Glu Val Gln Val Val Ser Thr Ala
                245                 250                 255 aca caa tct ttc ctg gcg acc tgc gtc aat ggc gtg tgt tgg act gtc    2617
Thr Gln Ser Phe Leu Ala Thr Cys Val Asn Gly Val Cys Trp Thr Val
            260                 265                 270 tat cat ggt gcc ggc tca aag acc ctt gcc ggc cca aag ggc cca atc    2665
Tyr His Gly Ala Gly Ser Lys Thr Leu Ala Gly Pro Lys Gly Pro Ile
        275                 280                 285 acc caa atg tac acc aat gtg gac cag gac ctc gtc ggc tgg caa gcg    2713
Thr Gln Met Tyr Thr Asn Val Asp Gln Asp Leu Val Gly Trp Gln Ala
    290                 295                 300 ccc ccc ggg gcg cgt tcc ttg aca cca tgc acc tgc ggc agc tcg gac    2761
Pro Pro Gly Ala Arg Ser Leu Thr Pro Cys Thr Cys Gly Ser Ser Asp
305                 310                 315                 320 ctt tac ttg gtc acg agg cat gcc gat gtc att ccg gtg cgc cgg cgg    2809
Leu Tyr Leu Val Thr Arg His Ala Asp Val Ile Pro Val Arg Arg Arg
                325                 330                 335 ggc gac agc agg ggg agc cta ctc tcc ccc agg ccc gtc tcc tac ttg    2857
Gly Asp Ser Arg Gly Ser Leu Leu Ser Pro Arg Pro Val Ser Tyr Leu
            340                 345                 350 aag ggc tct tcg ggc ggt cca ctg ctc tgc ccc tcg ggg cac gct gtg    2905
Lys Gly Ser Ser Gly Gly Pro Leu Leu Cys Pro Ser Gly His Ala Val
        355                 360                 365 ggc atc ttt cgg gct gcc gtg tgc acc cgg ggg gtt gcg aag gcg gtg    2953
Gly Ile Phe Arg Ala Ala Val Cys Thr Arg Gly Val Ala Lys Ala Val
    370                 375                 380
```

-continued

| | |
|---|---|
| gac ttt gta ccc gtc gag tct atg gga acc act atg cgg tcc ccg gtc<br>Asp Phe Val Pro Val Glu Ser Met Gly Thr Thr Met Arg Ser Pro Val<br>385                      390                      395                      400 | 3001 |
| ttc acg gac aac tcg tcc cct ccg gcc gta ccg cag aca ttc cag gtg<br>Phe Thr Asp Asn Ser Ser Pro Pro Ala Val Pro Gln Thr Phe Gln Val<br>                    405                      410                      415 | 3049 |
| gcc cat cta cac gcc cct act ggt agc ggc aag agc act aag gtg ccg<br>Ala His Leu His Ala Pro Thr Gly Ser Gly Lys Ser Thr Lys Val Pro<br>        420                      425                      430 | 3097 |
| gct gcg tat gca gcc caa ggg tat aag gtg ctt gtc ctg aac ccg tcc<br>Ala Ala Tyr Ala Ala Gln Gly Tyr Lys Val Leu Val Leu Asn Pro Ser<br>            435                      440                      445 | 3145 |
| gtc gcc gcc acc cta ggt ttc ggg gcg tat atg tct aag gca cat ggt<br>Val Ala Ala Thr Leu Gly Phe Gly Ala Tyr Met Ser Lys Ala His Gly<br>450                      455                      460 | 3193 |
| atc gac cct aac atc aga acc ggg gta agg acc atc acg acg ggt gcc<br>Ile Asp Pro Asn Ile Arg Thr Gly Val Arg Thr Ile Thr Thr Gly Ala<br>465                      470                      475                      480 | 3241 |
| ccc atc acg tac tcc acc tat ggc aag ttt ctt gcc gac ggt ggt tgc<br>Pro Ile Thr Tyr Ser Thr Tyr Gly Lys Phe Leu Ala Asp Gly Gly Cys<br>                    485                      490                      495 | 3289 |
| tct ggg ggc gcc tat gac atc ata ata tgt gat gag tgc cac tca act<br>Ser Gly Gly Ala Tyr Asp Ile Ile Ile Cys Asp Glu Cys His Ser Thr<br>        500                      505                      510 | 3337 |
| gac tcg acc act atc ctg ggc atc ggc aca gtc ctg gac caa gcg gag<br>Asp Ser Thr Thr Ile Leu Gly Ile Gly Thr Val Leu Asp Gln Ala Glu<br>            515                      520                      525 | 3385 |
| acg gct gga gcg cga ctc gtc gtg ctc gcc acc gct acg cct ccg gga<br>Thr Ala Gly Ala Arg Leu Val Val Leu Ala Thr Ala Thr Pro Pro Gly<br>530                      535                      540 | 3433 |
| tcg gtc acc gtg cca cat cca aac atc gag gag gtg gct ctg tcc agc<br>Ser Val Thr Val Pro His Pro Asn Ile Glu Glu Val Ala Leu Ser Ser<br>545                      550                      555                      560 | 3481 |
| act gga gaa atc ccc ttt tat ggc aaa gcc atc ccc atc gag acc atc<br>Thr Gly Glu Ile Pro Phe Tyr Gly Lys Ala Ile Pro Ile Glu Thr Ile<br>                    565                      570                      575 | 3529 |
| aag ggg ggg agg cac ctc att ttc tgc cat tcc aag aag aaa tgt gat<br>Lys Gly Gly Arg His Leu Ile Phe Cys His Ser Lys Lys Lys Cys Asp<br>        580                      585                      590 | 3577 |
| gag ctc gcc gcg aag ctg tcc ggc ctc gga ctc aat gct gta gca tat<br>Glu Leu Ala Ala Lys Leu Ser Gly Leu Gly Leu Asn Ala Val Ala Tyr<br>            595                      600                      605 | 3625 |
| tac cgg ggc ctt gat gta tcc gtc ata cca act agc gga gac gtc att<br>Tyr Arg Gly Leu Asp Val Ser Val Ile Pro Thr Ser Gly Asp Val Ile<br>610                      615                      620 | 3673 |
| gtc gta gca acg gac gct cta atg acg ggc ttt acc ggc gat ttc gac<br>Val Val Ala Thr Asp Ala Leu Met Thr Gly Phe Thr Gly Asp Phe Asp<br>625                      630                      635                      640 | 3721 |
| tca gtg atc gac tgc aat aca tgt gtc acc cag aca gtc gac ttc agc<br>Ser Val Ile Asp Cys Asn Thr Cys Val Thr Gln Thr Val Asp Phe Ser<br>                    645                      650                      655 | 3769 |
| ctg gac ccg acc ttc acc att gag acg acg acc gtg cca caa gac gcg<br>Leu Asp Pro Thr Phe Thr Ile Glu Thr Thr Thr Val Pro Gln Asp Ala<br>        660                      665                      670 | 3817 |
| gtg tca cgc tcg cag cgg cga ggc agg act ggt agg ggc agg atg ggc<br>Val Ser Arg Ser Gln Arg Arg Gly Arg Thr Gly Arg Gly Arg Met Gly<br>            675                      680                      685 | 3865 |
| att tac agg ttt gtg act cca gga gaa cgg ccc tcg ggc atg ttc gat<br>Ile Tyr Arg Phe Val Thr Pro Gly Glu Arg Pro Ser Gly Met Phe Asp | 3913 |

```
                690              695              700
tcc tcg gtt ctg tgc gag tgc tat gac gcg ggc tgt gct tgg tac gag    3961
Ser Ser Val Leu Cys Glu Cys Tyr Asp Ala Gly Cys Ala Trp Tyr Glu
705              710              715              720 ctc acg ccc gcc gag acc tca gtt agg ttg cgg gct tac cta aac aca    4009
Leu Thr Pro Ala Glu Thr Ser Val Arg Leu Arg Ala Tyr Leu Asn Thr
            725              730              735 cca ggg ttg ccc gtc tgc cag gac cat ctg gag ttc tgg gag agc gtc    4057
Pro Gly Leu Pro Val Cys Gln Asp His Leu Glu Phe Trp Glu Ser Val
        740              745              750 ttt aca ggc ctc acc cac ata gac gcc cat ttc ttg tcc cag act aag    4105
Phe Thr Gly Leu Thr His Ile Asp Ala His Phe Leu Ser Gln Thr Lys
    755              760              765 cag gca gga gac aac ttc ccc tac ctg gta gca tac cag gct acg gtg    4153
Gln Ala Gly Asp Asn Phe Pro Tyr Leu Val Ala Tyr Gln Ala Thr Val
770              775              780 tgc gcc agg gct cag gct cca cct cca tcg tgg gac caa atg tgg aag    4201
Cys Ala Arg Ala Gln Ala Pro Pro Pro Ser Trp Asp Gln Met Trp Lys
785              790              795              800 tgt ctc ata cgg cta aag cct acg ctg cac ggg cca acg ccc ctg ctg    4249
Cys Leu Ile Arg Leu Lys Pro Thr Leu His Gly Pro Thr Pro Leu Leu
            805              810              815 tat agg ctg gga gcc gtt caa aac gag gtt act acc aca cac ccc ata    4297
Tyr Arg Leu Gly Ala Val Gln Asn Glu Val Thr Thr Thr His Pro Ile
        820              825              830 acc aaa tac atc atg gca tgc atg tcg gct gac ctg gag gtc gtc acg    4345
Thr Lys Tyr Ile Met Ala Cys Met Ser Ala Asp Leu Glu Val Val Thr
    835              840              845 agc acc tgg gtg ctg gta ggc gga gtc cta gca gct ctg gcc gcg tat    4393
Ser Thr Trp Val Leu Val Gly Gly Val Leu Ala Ala Leu Ala Ala Tyr
850              855              860 tgc ctg aca aca ggc agc gtg gtc att gtg ggc agg atc atc ttg tcc    4441
Cys Leu Thr Thr Gly Ser Val Val Ile Val Gly Arg Ile Ile Leu Ser
865              870              875              880 gga aag ccg gcc atc att ccc gac agg gaa gtc ctt tac cgg gag ttc    4489
Gly Lys Pro Ala Ile Ile Pro Asp Arg Glu Val Leu Tyr Arg Glu Phe
            885              890              895 gat gag atg gaa gag tgc gcc tca cac ctc cct tac atc gaa cag gga    4537
Asp Glu Met Glu Glu Cys Ala Ser His Leu Pro Tyr Ile Glu Gln Gly
        900              905              910 atg cag ctc gcc gaa caa ttc aaa cag aag gca atc ggg ttg ctg caa    4585
Met Gln Leu Ala Glu Gln Phe Lys Gln Lys Ala Ile Gly Leu Leu Gln
    915              920              925 aca gcc acc aag caa gcg gag gct gct gct ccc gtg gtg gaa tcc aag    4633
Thr Ala Thr Lys Gln Ala Glu Ala Ala Ala Pro Val Val Glu Ser Lys
930              935              940 tgg cgg acc ctc gaa gcc ttc tgg gcg aag cat atg tgg aat ttc atc    4681
Trp Arg Thr Leu Glu Ala Phe Trp Ala Lys His Met Trp Asn Phe Ile
945              950              955              960 agc ggg ata caa tat tta gca ggc ttg tcc act ctg cct ggc aac ccc    4729
Ser Gly Ile Gln Tyr Leu Ala Gly Leu Ser Thr Leu Pro Gly Asn Pro
            965              970              975 gcg ata gca tca ctg atg gca ttc aca gcc tct atc acc agc ccg ctc    4777
Ala Ile Ala Ser Leu Met Ala Phe Thr Ala Ser Ile Thr Ser Pro Leu
        980              985              990 acc acc caa cat acc ctc ctg ttt aac atc ctg ggg gga tgg gtg gcc    4825
Thr Thr Gln His Thr Leu Leu Phe Asn Ile Leu Gly Gly Trp Val Ala
    995              1000             1005 gcc caa ctt gct cct ccc agc gct gct tct gct ttc gta ggc gcc ggc    4873
```

```
Ala Gln Leu Ala Pro Pro Ser Ala Ala Ser Ala Phe Val Gly Ala Gly
    1010                1015                1020 atc gct gga gcg gct gtt ggc agc ata ggc ctt ggg aag gtg ctt gtg      4921
Ile Ala Gly Ala Ala Val Gly Ser Ile Gly Leu Gly Lys Val Leu Val
1025                1030                1035                1040 gat att ttg gca ggt tat gga gca ggg gtg gca ggc gcg ctc gtg gcc      4969
Asp Ile Leu Ala Gly Tyr Gly Ala Gly Val Ala Gly Ala Leu Val Ala
                1045                1050                1055 ttt aag gtc atg agc ggc gag atg ccc tcc acc gag gac ctg gtt aac      5017
Phe Lys Val Met Ser Gly Glu Met Pro Ser Thr Glu Asp Leu Val Asn
            1060                1065                1070 cta ctc cct gct atc ctc tcc cct ggc gcc cta gtc gtc ggg gtc gtg      5065
Leu Leu Pro Ala Ile Leu Ser Pro Gly Ala Leu Val Val Gly Val Val
        1075                1080                1085 tgc gca gcg ata ctg cgt cgg cac gtg ggc cca ggg gag ggg gct gtg      5113
Cys Ala Ala Ile Leu Arg Arg His Val Gly Pro Gly Glu Gly Ala Val
    1090                1095                1100 cag tgg atg aac cgg ctg ata gcg ttc gct tcg cgg ggt aac cac gtc      5161
Gln Trp Met Asn Arg Leu Ile Ala Phe Ala Ser Arg Gly Asn His Val
1105                1110                1115                1120 tcc ccc acg cac tat gtg cct gag agc gac gct gca gca cgt gtc act      5209
Ser Pro Thr His Tyr Val Pro Glu Ser Asp Ala Ala Ala Arg Val Thr
                1125                1130                1135 cag atc ctc tct agt ctt acc atc act cag ctg ctg aag agg ctt cac      5257
Gln Ile Leu Ser Ser Leu Thr Ile Thr Gln Leu Leu Lys Arg Leu His
            1140                1145                1150 cag tgg atc aac gag gac tgc tcc acg cca tgc tcc ggc tcg tgg cta      5305
Gln Trp Ile Asn Glu Asp Cys Ser Thr Pro Cys Ser Gly Ser Trp Leu
        1155                1160                1165 aga gat gtt tgg gat tgg gta tgc acg gtg ttg act gat ttc aag acc      5353
Arg Asp Val Trp Asp Trp Val Cys Thr Val Leu Thr Asp Phe Lys Thr
    1170                1175                1180 tgg ctc cag tcc aag ctc ctg ccg cga ttg ccg gga gtc ccc ttc ttc      5401
Trp Leu Gln Ser Lys Leu Leu Pro Arg Leu Pro Gly Val Pro Phe Phe
1185                1190                1195                1200 tca tgt caa cgt ggg tac aag gga gtc tgg cgg ggc gac ggc atc atg      5449
Ser Cys Gln Arg Gly Tyr Lys Gly Val Trp Arg Gly Asp Gly Ile Met
                1205                1210                1215 caa acc acc tgc cca tgt gga gca cag atc acc gga cat gtg aaa aac      5497
Gln Thr Thr Cys Pro Cys Gly Ala Gln Ile Thr Gly His Val Lys Asn
            1220                1225                1230 tgt tcc atg agg atc gtg ggg cct agg acc tgt agt aac acg tgg cat      5545
Cys Ser Met Arg Ile Val Gly Pro Arg Thr Cys Ser Asn Thr Trp His
        1235                1240                1245 gga aca ttc ccc att aac gcg tac acc acg ggc ccc tgc acg ccc tcc      5593
Gly Thr Phe Pro Ile Asn Ala Tyr Thr Thr Gly Pro Cys Thr Pro Ser
    1250                1255                1260 ccg gcg cca aat tat tct agg gcg ctg tgg cgg gtg gct gct gag gag      5641
Pro Ala Pro Asn Tyr Ser Arg Ala Leu Trp Arg Val Ala Ala Glu Glu
1265                1270                1275                1280 tac gtg gag gtt acg cgg gtg ggg gat ttc cac tac gtg acg ggc atg      5689
Tyr Val Glu Val Thr Arg Val Gly Asp Phe His Tyr Val Thr Gly Met
                1285                1290                1295 acc act gac aac gta aag tgc ccg tgt cag gtt ccg gcc ccc gaa ttc      5737
Thr Thr Asp Asn Val Lys Cys Pro Cys Gln Val Pro Ala Pro Glu Phe
            1300                1305                1310 ttc aca gaa gtg gat ggg gtg cgg ttg cac agg tac gct cca gcg tgc      5785
Phe Thr Glu Val Asp Gly Val Arg Leu His Arg Tyr Ala Pro Ala Cys
        1315                1320                1325
```

-continued

| | |
|---|---|
| aaa ccc ctc cta cgg gag gag gtc aca ttc ctg gtc ggg ctc aat caa<br>Lys Pro Leu Leu Arg Glu Glu Val Thr Phe Leu Val Gly Leu Asn Gln<br>1330                              1335                       1340 | 5833 |
| tac ctg gtt ggg tca cag ctc cca tgc gag ccc gaa ccg gac gta gca<br>Tyr Leu Val Gly Ser Gln Leu Pro Cys Glu Pro Glu Pro Asp Val Ala<br>1345                              1350                       1355                     1360 | 5881 |
| gtg ctc act tcc atg ctc acc gac ccc tcc cac att acg gcg gag acg<br>Val Leu Thr Ser Met Leu Thr Asp Pro Ser His Ile Thr Ala Glu Thr<br>                        1365                       1370                     1375 | 5929 |
| gct aag cgt agg ctg gcc agg gga tct ccc ccc tcc ttg gcc agc tca<br>Ala Lys Arg Arg Leu Ala Arg Gly Ser Pro Pro Ser Leu Ala Ser Ser<br>            1380                       1385                     1390 | 5977 |
| tca gct agc cag ctg tct gcg ccc tcc ttg aag gca aca tgc act acc<br>Ser Ala Ser Gln Leu Ser Ala Pro Ser Leu Lys Ala Thr Cys Thr Thr<br>1395                              1400                       1405 | 6025 |
| cgt cat gac tcc ccg gac gct gac ctc atc gag gcc aac ctc ctg tgg<br>Arg His Asp Ser Pro Asp Ala Asp Leu Ile Glu Ala Asn Leu Leu Trp<br>            1410                       1415                     1420 | 6073 |
| cgg cag gag atg ggc ggg aac atc acc cgc gtg gag tca gaa aat aag<br>Arg Gln Glu Met Gly Gly Asn Ile Thr Arg Val Glu Ser Glu Asn Lys<br>1425                              1430                       1435                     1440 | 6121 |
| gta gta att ttg gac tct ttc gag ccg ctc caa gcg gag gag gat gag<br>Val Val Ile Leu Asp Ser Phe Glu Pro Leu Gln Ala Glu Glu Asp Glu<br>                        1445                       1450                     1455 | 6169 |
| agg gaa gta tcc gtt ccg gcg gag atc ctg cgg agg tcc agg aaa ttc<br>Arg Glu Val Ser Val Pro Ala Glu Ile Leu Arg Arg Ser Arg Lys Phe<br>            1460                       1465                     1470 | 6217 |
| cct cga gcg atg ccc ata tgg gca cgc ccg gat tac aac cct cca ctg<br>Pro Arg Ala Met Pro Ile Trp Ala Arg Pro Asp Tyr Asn Pro Pro Leu<br>1475                              1480                       1485 | 6265 |
| tta gag tcc tgg aag gac ccg gac tac gtc cct cca gtg gta cac ggg<br>Leu Glu Ser Trp Lys Asp Pro Asp Tyr Val Pro Pro Val Val His Gly<br>            1490                       1495                     1500 | 6313 |
| tgt cca ttg ccg cct gcc aag gcc cct ccg ata cca cct cca cgg agg<br>Cys Pro Leu Pro Pro Ala Lys Ala Pro Pro Ile Pro Pro Pro Arg Arg<br>1505                              1510                       1515                     1520 | 6361 |
| aag agg acg gtt gtc ctg tca gaa tct acc gtg tct tct gcc ttg gcg<br>Lys Arg Thr Val Val Leu Ser Glu Ser Thr Val Ser Ser Ala Leu Ala<br>                        1525                       1530                     1535 | 6409 |
| gag ctc gcc aca aag acc ttc ggc agc tcc gaa tcg tcg gcc gtc gac<br>Glu Leu Ala Thr Lys Thr Phe Gly Ser Ser Glu Ser Ser Ala Val Asp<br>            1540                       1545                     1550 | 6457 |
| agc ggc acg gca acg gcc tct cct gac cag ccc tcc gac gac ggc gac<br>Ser Gly Thr Ala Thr Ala Ser Pro Asp Gln Pro Ser Asp Asp Gly Asp<br>                        1555                       1560                     1565 | 6505 |
| gcg gga tcc gac gtt gag tcg tac tcc tcc atg ccc ccc ctt gag ggg<br>Ala Gly Ser Asp Val Glu Ser Tyr Ser Ser Met Pro Pro Leu Glu Gly<br>1570                              1575                       1580 | 6553 |
| gag ccg ggg gat ccc gat ctc agc gac ggg tct tgg tct acc gta agc<br>Glu Pro Gly Asp Pro Asp Leu Ser Asp Gly Ser Trp Ser Thr Val Ser<br>1585                              1590                       1595                     1600 | 6601 |
| gag gag gct agt gag gac gtc gtc tgc tgc tcg atg tcc tac aca tgg<br>Glu Glu Ala Ser Glu Asp Val Val Cys Cys Ser Met Ser Tyr Thr Trp<br>                        1605                       1610                     1615 | 6649 |
| aca ggc gcc ctg atc acg cca tgc gct gcg gag gaa acc aag ctg ccc<br>Thr Gly Ala Leu Ile Thr Pro Cys Ala Ala Glu Glu Thr Lys Leu Pro<br>            1620                       1625                     1630 | 6697 |
| atc aat gca ctg agc aac tct ttg ctc cgt cac cac aac ttg gtc tat<br>Ile Asn Ala Leu Ser Asn Ser Leu Leu Arg His His Asn Leu Val Tyr<br>1635                              1640                       1645 | 6745 |

-continued

| | |
|---|---|
| gct aca aca tct cgc agc gca agc ctg cgg cag aag aag gtc acc ttt<br>Ala Thr Thr Ser Arg Ser Ala Ser Leu Arg Gln Lys Lys Val Thr Phe<br>   1650                    1655                    1660 | 6793 |
| gac aga ctg cag gtc ctg gac gac cac tac cgg gac gtg ctc aag gag<br>Asp Arg Leu Gln Val Leu Asp Asp His Tyr Arg Asp Val Leu Lys Glu<br>1665                    1670                    1675                    1680 | 6841 |
| atg aag gcg aag gcg tcc aca gtt aag gct aaa ctt cta tcc gtg gag<br>Met Lys Ala Lys Ala Ser Thr Val Lys Ala Lys Leu Leu Ser Val Glu<br>                   1685                    1690                    1695 | 6889 |
| gaa gcc tgt aag ctg acg ccc cca cat tcg gcc aga tct aaa ttt ggc<br>Glu Ala Cys Lys Leu Thr Pro Pro His Ser Ala Arg Ser Lys Phe Gly<br>           1700                    1705                    1710 | 6937 |
| tat ggg gca aag gac gtc cgg aac cta tcc agc aag gcc gtt aac cac<br>Tyr Gly Ala Lys Asp Val Arg Asn Leu Ser Ser Lys Ala Val Asn His<br>                 1715                    1720                    1725 | 6985 |
| atc cgc tcc gtg tgg aag gac ttg ctg gaa gac act gag aca cca att<br>Ile Arg Ser Val Trp Lys Asp Leu Leu Glu Asp Thr Glu Thr Pro Ile<br>   1730                    1735                    1740 | 7033 |
| gac acc acc atc atg gca aaa aat gag gtt ttc tgc gtc caa cca gag<br>Asp Thr Thr Ile Met Ala Lys Asn Glu Val Phe Cys Val Gln Pro Glu<br>1745                    1750                    1755                    1760 | 7081 |
| aag ggg ggc cgc aag cca gct cgc ctt atc gta ttc cca gat ttg ggg<br>Lys Gly Gly Arg Lys Pro Ala Arg Leu Ile Val Phe Pro Asp Leu Gly<br>                 1765                    1770                    1775 | 7129 |
| gtt cgt gtg tgc gag aaa atg gcc ctt tac gat gtg gtc tcc acc ctc<br>Val Arg Val Cys Glu Lys Met Ala Leu Tyr Asp Val Val Ser Thr Leu<br>                   1780                    1785                    1790 | 7177 |
| cct cag gcc gtg atg ggc tct tca tac gga ttc caa tac tct cct gga<br>Pro Gln Ala Val Met Gly Ser Ser Tyr Gly Phe Gln Tyr Ser Pro Gly<br>           1795                    1800                    1805 | 7225 |
| cag cgg gtc gag ttc ctg gtg aat gct tgg aaa gcg aag aaa tgc cct<br>Gln Arg Val Glu Phe Leu Val Asn Ala Trp Lys Ala Lys Lys Cys Pro<br>   1810                    1815                    1820 | 7273 |
| atg ggc ttc gca tat gac acc cgc tgt ttt gac tca acg gtc act gag<br>Met Gly Phe Ala Tyr Asp Thr Arg Cys Phe Asp Ser Thr Val Thr Glu<br>1825                    1830                    1835                    1840 | 7321 |
| aat gac atc cgt gtt gag gag tca atc tac caa tgt tgt gac ttg gcc<br>Asn Asp Ile Arg Val Glu Glu Ser Ile Tyr Gln Cys Cys Asp Leu Ala<br>                 1845                    1850                    1855 | 7369 |
| ccc gaa gcc aga cag gcc ata agg tcg ctc aca gag cgg ctt tac atc<br>Pro Glu Ala Arg Gln Ala Ile Arg Ser Leu Thr Glu Arg Leu Tyr Ile<br>           1860                    1865                    1870 | 7417 |
| ggg ggc ccc ctg act aat tct aaa ggg cag aac tgc ggc tat cgc cgg<br>Gly Gly Pro Leu Thr Asn Ser Lys Gly Gln Asn Cys Gly Tyr Arg Arg<br>                 1875                    1880                    1885 | 7465 |
| tgc cgc gcg agc ggt gta ctg acg acc agc tgc ggt aat acc ctc aca<br>Cys Arg Ala Ser Gly Val Leu Thr Thr Ser Cys Gly Asn Thr Leu Thr<br>   1890                    1895                    1900 | 7513 |
| tgt tac ttg aag gcc gct gcg gcc tgt cga gct gcg aag ctc cag gac<br>Cys Tyr Leu Lys Ala Ala Ala Ala Cys Arg Ala Ala Lys Leu Gln Asp<br>1905                    1910                    1915                    1920 | 7561 |
| tgc acg atg ctc gta tgc gga gac gac ctt gtc gtt atc tgt gaa agc<br>Cys Thr Met Leu Val Cys Gly Asp Asp Leu Val Val Ile Cys Glu Ser<br>                 1925                    1930                    1935 | 7609 |
| gcg ggg acc caa gag gac gag gcg agc cta cgg gcc ttc acg gag gct<br>Ala Gly Thr Gln Glu Asp Glu Ala Ser Leu Arg Ala Phe Thr Glu Ala<br>           1940                    1945                    1950 | 7657 |
| atg act aga tac tct gcc ccc cct ggg gac ccg ccc aaa cca gaa tac<br>Met Thr Arg Tyr Ser Ala Pro Pro Gly Asp Pro Pro Lys Pro Glu Tyr | 7705 |

```
                     1955                1960                1965
gac ttg gag ttg ata aca tca tgc tcc tcc aat gtg tca gtc gcg cac    7753
Asp Leu Glu Leu Ile Thr Ser Cys Ser Ser Asn Val Ser Val Ala His
         1970                1975                1980 gat gca tct ggc aaa agg gtg tac tat ctc acc cgt gac ccc acc acc    7801
Asp Ala Ser Gly Lys Arg Val Tyr Tyr Leu Thr Arg Asp Pro Thr Thr
1985                1990                1995                2000 ccc ctt gcg cgg gct gcg tgg gag aca gct aga cac act cca gtc aat    7849
Pro Leu Ala Arg Ala Ala Trp Glu Thr Ala Arg His Thr Pro Val Asn
                 2005                2010                2015 tcc tgg cta ggc aac atc atc atg tat gcg ccc acc ttg tgg gca agg    7897
Ser Trp Leu Gly Asn Ile Ile Met Tyr Ala Pro Thr Leu Trp Ala Arg
         2020                2025                2030 atg atc ctg atg act cat ttc ttc tcc atc ctt cta gct cag gaa caa    7945
Met Ile Leu Met Thr His Phe Phe Ser Ile Leu Leu Ala Gln Glu Gln
2035                2040                2045 ctt gaa aaa gcc cta gat tgt cag atc tac ggg gcc tgt tac tcc att    7993
Leu Glu Lys Ala Leu Asp Cys Gln Ile Tyr Gly Ala Cys Tyr Ser Ile
         2050                2055                2060 gag cca ctt gac cta cct cag atc att caa cga ctc cac ggc ctt agc    8041
Glu Pro Leu Asp Leu Pro Gln Ile Ile Gln Arg Leu His Gly Leu Ser
2065                2070                2075                2080 gca ttt tca ctc cat agt tac tct cca ggt gag atc aat agg gtg gct    8089
Ala Phe Ser Leu His Ser Tyr Ser Pro Gly Glu Ile Asn Arg Val Ala
                 2085                2090                2095 tca tgc ctc agg aaa ctt ggg gta ccg ccc ttg cga gtc tgg aga cat    8137
Ser Cys Leu Arg Lys Leu Gly Val Pro Pro Leu Arg Val Trp Arg His
         2100                2105                2110 cgg gcc aga agt gtc cgc gct agg cta ctg tcc cag ggg ggg agg gct    8185
Arg Ala Arg Ser Val Arg Ala Arg Leu Leu Ser Gln Gly Gly Arg Ala
2115                2120                2125 gcc act tgt ggc aag tac ctc ttc aac tgg gca gta agg acc aag ctc    8233
Ala Thr Cys Gly Lys Tyr Leu Phe Asn Trp Ala Val Arg Thr Lys Leu
         2130                2135                2140 aaa ctc act cca atc ccg gct gcg tcc cag ttg gat tta tcc agc tgg    8281
Lys Leu Thr Pro Ile Pro Ala Ala Ser Gln Leu Asp Leu Ser Ser Trp
2145                2150                2155                2160 ttc gtt gct ggt tac agc ggg gga gac ata tat cac agc ctg tct cgt    8329
Phe Val Ala Gly Tyr Ser Gly Gly Asp Ile Tyr His Ser Leu Ser Arg
                 2165                2170                2175 gcc cga ccc cgc tgg ttc acg tgg tgc cta ctc cta ctt tct gta ggg    8377
Ala Arg Pro Arg Trp Phe Thr Trp Cys Leu Leu Leu Leu Ser Val Gly
         2180                2185                2190 gta ggc atc tat cta ctc ccc aac cga tga acgggagct aaacactcca       8427
Val Gly Ile Tyr Leu Leu Pro Asn Arg *
         2195                2200 ggccaatagg ccatcctgtt ttttccctt ttttccttt ttttttttt ttttttttt      8487 tttttttttt tttttttttt ttcccccct tttttccct tttttttcc tttttcttcc     8547 tttggtggct ccatcttagc cctagtcacg gctagctgtg aaaggtccgt gagccgcttg  8607
actgcagaga gtgctgatac tggcctctct gcagatcaag t                      8648

<210> SEQ ID NO 6
<211> LENGTH: 8638
<212> TYPE: DNA
<213> ORGANISM: HCV
<220> FEATURE:
<221> NAME/KEY: CDS
<222> LOCATION: (1802)...(8407)
```

<400> SEQUENCE: 6

```
accagccccc gattgggggc gacactccac catagatcac tccctgtga ggaactactg    60
tcttcacgca gaaagcgtct agccatggcg ttagtatgag tgtcgtgcag cctccaggac   120
cccccctccc gggagagcca tagtggtctg cggaaccggt gagtacaccg gaattgccag   180
gacgaccggg tcctttcttg gatcaacccg ctcaatgcct ggagatttgg gcgtgccccc   240
gcgagactgc tagccgagta gtgttgggtc gcgaaaggcc ttgtggtact gcctgatagg   300
gtgcttgcga gtgccccggg aggtctcgta gaccgtgcac catgagcacg aatcctaaac   360
ctcaaagaaa aaccaaaggg cgcgccatga ttgaacaaga tggattgcac gcaggttctc   420
cggccgcttg ggtggagagg ctattcggct atgactgggc acaacagaca atcggctgct   480
ctgatgccgc cgtgttccgg ctgtcagcgc aggggcgccc ggttctttt gtcaagaccg   540
acctgtccgg tgccctgaat gaactgcagg acgaggcagc gcggctatcg tggctggcca   600
cgacgggcgt tccttgcgca gctgtgctcg acgttgtcac tgaagcggga agggactggc   660
tgctattggg cgaagtgccg gggcaggatc tcctgtcatc tcaccttgct cctgccgaga   720
aagtatccat catggctgat gcaatgcggc ggctgcatac gcttgatccg gctacctgcc   780
cattcgacca ccaagcgaaa catcgcatcg agcgagcacg tactcggatg aagccggtc    840
ttgtcgatca ggatgatctg gacgaagagc atcaggggct cgcgccagcc gaactgttcg   900
ccaggctcaa ggcgcgcatg cccgacggcg aggatctcgt cgtgacccat ggcgatgcct   960
gcttgccgaa tatcatggtg gaaaatggcc gcttttctgg attcatcgac tgtggccggc  1020
tgggtgtggc ggaccgctat caggacatag cgttggctac ccgtgatatt gctgaagagc  1080
ttggcggcga atgggctgac cgcttcctcg tgctttacgg tatcgccgct cccgattcgc  1140
agcgcatcgc cttctatcgc cttcttgacg agttcttctg agttcgcgcc cagatgttaa  1200
cagaccacaa cggtttccct ctagcgggat caattccgcc ccccccccta acgttactgg  1260
ccgaagccgc ttggaataag gccggtgtgc gtttgtctat atgttatttt ccaccatatt  1320
gccgtctttt ggcaatgtga gggcccggaa acctggccct gtcttcttga cgagcattcc  1380
taggggtctt tcccctctcg ccaaaggaat gcaaggtctg ttgaatgtcg tgaaggaagc  1440
agttcctctg gaagcttctt gaagacaaac aacgtctgta gcgaccctt gcaggcagcg  1500
gaacccccca cctggcgaca ggtgcctctg cggccaaaag ccacgtgtat aagatacacc  1560
tgcaaaggcg gcacaacccc agtgccacgt tgtgagttgg atagttgtgg aaagagtcaa  1620
atggctctcc tcaagcgtat tcaacaaggg gctgaaggat gcccagaagg taccccattg  1680
tatgggatct gatctgggc ctcggtgcac atgctttaca tgtgtttagt cgaggttaaa   1740
aaacgtctag gccccccgaa ccacggggac gtggttttcc tttgaaaaac acgataatac  1800
```

|       |       |       |       |       |       |       |       |       |       |       |       |       |       |       |       |       |
|---|---|---|---|---|---|---|---|---|---|---|---|---|---|---|---|---|
| c atg | gac | cgg | gag | atg | gca | gca | tcg | tgc | gga | ggc | gcg | gtt | ttc | gta | ggt | 1849 |
| Met | Asp | Arg | Glu | Met | Ala | Ala | Ser | Cys | Gly | Gly | Ala | Val | Phe | Val | Gly |  |
| 1 |  |  |  | 5 |  |  |  |  | 10 |  |  |  |  | 15 |  |  |

| ctg | ata | ctc | ttg | acc | ttg | tca | ccg | cac | tat | aag | ctg | ttc | ctc | gct | agg | 1897 |
|---|---|---|---|---|---|---|---|---|---|---|---|---|---|---|---|---|
| Leu | Ile | Leu | Leu | Thr | Leu | Ser | Pro | His | Tyr | Lys | Leu | Phe | Leu | Ala | Arg |  |
|  |  |  | 20 |  |  |  |  | 25 |  |  |  |  | 30 |  |  |  |

| ctc | ata | tgg | tgg | tta | caa | tat | ttt | atc | acc | agg | gcc | gag | gca | cac | ttg | 1945 |
|---|---|---|---|---|---|---|---|---|---|---|---|---|---|---|---|---|
| Leu | Ile | Trp | Trp | Leu | Gln | Tyr | Phe | Ile | Thr | Arg | Ala | Glu | Ala | His | Leu |  |
|  | 35 |  |  |  |  | 40 |  |  |  |  | 45 |  |  |  |  |  |

| caa | gtg | tgg | atc | ccc | ccc | ctc | aac | gtt | cgg | ggg | ggc | cgc | gat | gcc | gtc | 1993 |
|---|---|---|---|---|---|---|---|---|---|---|---|---|---|---|---|---|
| Gln | Val | Trp | Ile | Pro | Pro | Leu | Asn | Val | Arg | Gly | Gly | Arg | Asp | Ala | Val |  |
| 50 |  |  |  |  | 55 |  |  |  |  | 60 |  |  |  |  |  |  |

| atc | ctc | ctc | acg | tgc | gcg | atc | cac | cca | gag | cta | atc | ttt | acc | atc | acc | 2041 |

```
Ile Leu Leu Thr Cys Ala Ile His Pro Glu Leu Ile Phe Thr Ile Thr
 65                  70                  75                  80 aaa atc ttg ctc gcc ata ctc ggt cca ctc atg gtg ctc cag gct ggt        2089
Lys Ile Leu Leu Ala Ile Leu Gly Pro Leu Met Val Leu Gln Ala Gly
                 85                  90                  95 ata acc aaa gtg ccg tac ttc gtg cgc gca cac ggg ctc att cgt gca        2137
Ile Thr Lys Val Pro Tyr Phe Val Arg Ala His Gly Leu Ile Arg Ala
            100                 105                 110 tgc atg ctg gtg cgg aag gtt gct ggg ggt cat tat gtc caa atg gct        2185
Cys Met Leu Val Arg Lys Val Ala Gly Gly His Tyr Val Gln Met Ala
        115                 120                 125 ctc atg aag ttg gcc gca ctg aca ggt acg tac gtt tat gac cat ctc        2233
Leu Met Lys Leu Ala Ala Leu Thr Gly Thr Tyr Val Tyr Asp His Leu
    130                 135                 140 acc cca ctg cgg gac tgg gcc cac gcg ggc cta cga gac ctt gcg gtg        2281
Thr Pro Leu Arg Asp Trp Ala His Ala Gly Leu Arg Asp Leu Ala Val
145                 150                 155                 160 gca gtt gag ccc gtc gtc ttc tct gat atg gag acc aag gtt atc acc        2329
Ala Val Glu Pro Val Val Phe Ser Asp Met Glu Thr Lys Val Ile Thr
                165                 170                 175 tgg ggg gca gac acc gcg gcg tgt ggg gac atc atc ttg ggc ctg ccc        2377
Trp Gly Ala Asp Thr Ala Ala Cys Gly Asp Ile Ile Leu Gly Leu Pro
            180                 185                 190 gtc tcc gcc cgc agg ggg agg gag ata cat ctg gga ccg gca gac agc        2425
Val Ser Ala Arg Arg Gly Arg Glu Ile His Leu Gly Pro Ala Asp Ser
        195                 200                 205 ctt gaa ggg cag ggg tgg cga ctc ctc gcg cct att acg gcc tac tcc        2473
Leu Glu Gly Gln Gly Trp Arg Leu Leu Ala Pro Ile Thr Ala Tyr Ser
    210                 215                 220 caa cag acg cga ggc cta ctt ggc tgc atc atc act agc ctc aca ggc        2521
Gln Gln Thr Arg Gly Leu Leu Gly Cys Ile Ile Thr Ser Leu Thr Gly
225                 230                 235                 240 cgg gac agg aac cag gtc gag ggg gag gtc caa gtg gtc tcc acc gca        2569
Arg Asp Arg Asn Gln Val Glu Gly Glu Val Gln Val Val Ser Thr Ala
                245                 250                 255 aca caa tct ttc ctg gcg acc tgc gtc aat ggc gtg tgt tgg act gtc        2617
Thr Gln Ser Phe Leu Ala Thr Cys Val Asn Gly Val Cys Trp Thr Val
            260                 265                 270 tat cat ggt gcc ggc tca aag acc ctt gcc ggc cca aag ggc cca atc        2665
Tyr His Gly Ala Gly Ser Lys Thr Leu Ala Gly Pro Lys Gly Pro Ile
        275                 280                 285 acc caa atg tac acc aat gtg gac cag gac ctc gtc ggc tgg caa gcg        2713
Thr Gln Met Tyr Thr Asn Val Asp Gln Asp Leu Val Gly Trp Gln Ala
    290                 295                 300 ccc ccc ggg gcg cgt tcc ttg aca cca tgc acc tgc ggc agc tcg gac        2761
Pro Pro Gly Ala Arg Ser Leu Thr Pro Cys Thr Cys Gly Ser Ser Asp
305                 310                 315                 320 ctt tac ttg gtc acg agg cat gcc gat gtc att ccg gtg cgc cgg cgg        2809
Leu Tyr Leu Val Thr Arg His Ala Asp Val Ile Pro Val Arg Arg Arg
                325                 330                 335 ggc gac ggc agg ggg agc cta ctc tcc ccc agg ccc gtc tcc tac ttg        2857
Gly Asp Gly Arg Gly Ser Leu Leu Ser Pro Arg Pro Val Ser Tyr Leu
            340                 345                 350 aag ggc tct tcg ggc ggt cca ctg ctc tgc ccc tcg ggg cac gct gtg        2905
Lys Gly Ser Ser Gly Gly Pro Leu Leu Cys Pro Ser Gly His Ala Val
        355                 360                 365 ggc atc ttt cgg gct gcc gtg tgc acc cga ggg gtt gcg aag gcg gtg        2953
Gly Ile Phe Arg Ala Ala Val Cys Thr Arg Gly Val Ala Lys Ala Val
    370                 375                 380
```

```
gac ttt gta ccc gtc gag tct atg gga acc act atg cgg tcc ccg gtc      3001
Asp Phe Val Pro Val Glu Ser Met Gly Thr Thr Met Arg Ser Pro Val
385                 390                 395                 400 ttc acg gac aac tcg tcc cct ccg gcc gta ccg cag aca ttc cag gtg      3049
Phe Thr Asp Asn Ser Ser Pro Pro Ala Val Pro Gln Thr Phe Gln Val
            405                 410                 415 gcc cat cta cac gcc cct act ggt agc ggc aag agc act aag gtg ccg      3097
Ala His Leu His Ala Pro Thr Gly Ser Gly Lys Ser Thr Lys Val Pro
        420                 425                 430 gct gcg tat gca gcc caa ggg tat aag gtg ctt gtc ctg aac ccg tcc      3145
Ala Ala Tyr Ala Ala Gln Gly Tyr Lys Val Leu Val Leu Asn Pro Ser
    435                 440                 445 gtc gcc gcc acc cta ggt ttc ggg gcg tat atg tct aag gca cat ggt      3193
Val Ala Ala Thr Leu Gly Phe Gly Ala Tyr Met Ser Lys Ala His Gly
450                 455                 460 atc gac cct aac atc aga acc ggg gta agg acc atc acc acg ggt gcc      3241
Ile Asp Pro Asn Ile Arg Thr Gly Val Arg Thr Ile Thr Thr Gly Ala
465                 470                 475                 480 ccc atc acg tac tcc acc tat ggc aag ttt ctt gcc gac ggt ggt tgc      3289
Pro Ile Thr Tyr Ser Thr Tyr Gly Lys Phe Leu Ala Asp Gly Gly Cys
            485                 490                 495 tct ggg ggc gcc tat gac atc ata ata tgt gat gag tgc cac tca act      3337
Ser Gly Gly Ala Tyr Asp Ile Ile Ile Cys Asp Glu Cys His Ser Thr
        500                 505                 510 gac tcg acc act atc ctg ggc atc ggc aca gtc ctg gac caa gcg gag      3385
Asp Ser Thr Thr Ile Leu Gly Ile Gly Thr Val Leu Asp Gln Ala Glu
    515                 520                 525 acg gct gga gcg cga ctc gtc gtg ctc gcc acc gct acg cct ccg gga      3433
Thr Ala Gly Ala Arg Leu Val Val Leu Ala Thr Ala Thr Pro Pro Gly
530                 535                 540 tcg gtc acc gtg cca cat cca aac atc gag gag gtg gct ctg tcc agc      3481
Ser Val Thr Val Pro His Pro Asn Ile Glu Glu Val Ala Leu Ser Ser
545                 550                 555                 560 act gga gaa atc ccc ttt tat ggc aaa gcc atc ccc atc gag acc atc      3529
Thr Gly Glu Ile Pro Phe Tyr Gly Lys Ala Ile Pro Ile Glu Thr Ile
            565                 570                 575 aag ggg ggg agg cac ctc att ttc tgc cat tcc aag aag aaa tgt gat      3577
Lys Gly Gly Arg His Leu Ile Phe Cys His Ser Lys Lys Lys Cys Asp
        580                 585                 590 gag ctc gcc gcg aag ctg tcc ggc ctc gga ctc aat gct gta gca tat      3625
Glu Leu Ala Ala Lys Leu Ser Gly Leu Gly Leu Asn Ala Val Ala Tyr
    595                 600                 605 tac cgg ggc ctt gat gta tcc gtc ata cca act agc gga gac gtc att      3673
Tyr Arg Gly Leu Asp Val Ser Val Ile Pro Thr Ser Gly Asp Val Ile
610                 615                 620 gtc gta gca acg gac gct cta atg acg ggc ttt acc ggc gat ttc gac      3721
Val Val Ala Thr Asp Ala Leu Met Thr Gly Phe Thr Gly Asp Phe Asp
625                 630                 635                 640 tca gtg atc gac tgc aat aca tgt gtc acc cag aca gtc gac ttc agc      3769
Ser Val Ile Asp Cys Asn Thr Cys Val Thr Gln Thr Val Asp Phe Ser
            645                 650                 655 ctg gac ccg acc ttc acc att gag acg acg acc gtg cca caa gac gcg      3817
Leu Asp Pro Thr Phe Thr Ile Glu Thr Thr Thr Val Pro Gln Asp Ala
        660                 665                 670 gtg tca cgc tcg cag cgg cga ggc agg act ggt agg ggc agg atg ggc      3865
Val Ser Arg Ser Gln Arg Arg Gly Arg Thr Gly Arg Gly Arg Met Gly
    675                 680                 685 att tac agg ttt gtg act cca gga gaa cgg ccc tcg ggc atg ttc gat      3913
Ile Tyr Arg Phe Val Thr Pro Gly Glu Arg Pro Ser Gly Met Phe Asp
690                 695                 700
```

-continued

| | | |
|---|---|---|
| tcc tcg gtt ctg tgc gag tgc tat gac gcg ggc tgt gct tgg tac gag<br>Ser Ser Val Leu Cys Glu Cys Tyr Asp Ala Gly Cys Ala Trp Tyr Glu<br>705                                710                             715                      720 | 3961 |
| ctc acg ccc gcc gag acc tca gtt agg ttg cgg gct tac cta aac aca<br>Leu Thr Pro Ala Glu Thr Ser Val Arg Leu Arg Ala Tyr Leu Asn Thr<br>                        725                        730                        735 | 4009 |
| cca ggg ttg ccc gtc tgc cag gac cat ctg gag ttc tgg gag agc gtc<br>Pro Gly Leu Pro Val Cys Gln Asp His Leu Glu Phe Trp Glu Ser Val<br>               740                        745                             750 | 4057 |
| ttt aca ggc ctc acc cac ata gac gcc cat ttc ttg tcc cag act aag<br>Phe Thr Gly Leu Thr His Ile Asp Ala His Phe Leu Ser Gln Thr Lys<br>               755                        760                        765 | 4105 |
| cag gca gga gac aac ttc ccc tac ctg gta gca tac cag gct acg gtg<br>Gln Ala Gly Asp Asn Phe Pro Tyr Leu Val Ala Tyr Gln Ala Thr Val<br>770                                775                             780 | 4153 |
| tgc gcc agg gct cag gct cca cct cca tcg tgg gac caa atg tgg aag<br>Cys Ala Arg Ala Gln Ala Pro Pro Pro Ser Trp Asp Gln Met Trp Lys<br>785                                790                             800 | 4201 |
| tgt ctc ata cgg cta aag cct acg ctg cac ggg cca acg ccc ctg ctg<br>Cys Leu Ile Arg Leu Lys Pro Thr Leu His Gly Pro Thr Pro Leu Leu<br>                        805                        810                        815 | 4249 |
| tat agg ctg gga gcc gtt caa aac gag gtt act acc aca cac ccc ata<br>Tyr Arg Leu Gly Ala Val Gln Asn Glu Val Thr Thr Thr His Pro Ile<br>               820                        825                        830 | 4297 |
| acc aaa tac atc atg gca tgc atg tcg gct gac ctg gag gtc gtc acg<br>Thr Lys Tyr Ile Met Ala Cys Met Ser Ala Asp Leu Glu Val Val Thr<br>                        835                        840                        845 | 4345 |
| agc acc tgg gtg ctg gta ggc gga gtc cta gca gct ctg gcc gcg tat<br>Ser Thr Trp Val Leu Val Gly Gly Val Leu Ala Ala Leu Ala Ala Tyr<br>850                                855                             860 | 4393 |
| tgc ctg aca aca ggc agc gtg gtc att gtg ggc agg atc atc ttg tcc<br>Cys Leu Thr Thr Gly Ser Val Val Ile Val Gly Arg Ile Ile Leu Ser<br>865                                870                             880 | 4441 |
| gga aag ccg gcc atc att ccc gac agg gaa gtc ttt tac cgg gag ttc<br>Gly Lys Pro Ala Ile Ile Pro Asp Arg Glu Val Phe Tyr Arg Glu Phe<br>                        885                        890                        895 | 4489 |
| gat gag atg gaa gag tgc gcc tca cac ctc cct tac atc gaa cag gga<br>Asp Glu Met Glu Glu Cys Ala Ser His Leu Pro Tyr Ile Glu Gln Gly<br>               900                        905                        910 | 4537 |
| atg cag ctc gcc gaa caa ttc aaa cag aag gca atc ggg ttg ctg caa<br>Met Gln Leu Ala Glu Gln Phe Lys Gln Lys Ala Ile Gly Leu Leu Gln<br>               915                        920                        925 | 4585 |
| aca gcc acc aag caa gcg gag gct gct gct ccc gtg gtg gaa tcc aag<br>Thr Ala Thr Lys Gln Ala Glu Ala Ala Ala Pro Val Val Glu Ser Lys<br>930                                935                             940 | 4633 |
| tgg cgg acc ctc gaa gcc ttc tgg gcg aag cat atg tgg aat ttc atc<br>Trp Arg Thr Leu Glu Ala Phe Trp Ala Lys His Met Trp Asn Phe Ile<br>945                                950                        955                        960 | 4681 |
| agc ggg ata caa tat tta gca ggc ttg tcc act ctg cct ggc aac ccc<br>Ser Gly Ile Gln Tyr Leu Ala Gly Leu Ser Thr Leu Pro Gly Asn Pro<br>                        965                        970                        975 | 4729 |
| gcg ata gca tca ctg atg gca ttc aca gcc tct atc acc agc ccg ctc<br>Ala Ile Ala Ser Leu Met Ala Phe Thr Ala Ser Ile Thr Ser Pro Leu<br>               980                        985                        990 | 4777 |
| acc acc caa cat acc ctc ctg ttt aac atc ctg ggg gga tgg gtg gcc<br>Thr Thr Gln His Thr Leu Leu Phe Asn Ile Leu Gly Gly Trp Val Ala<br>               995                      1000                        1005 | 4825 |
| gcc caa ctt gct cct ccc agc gct gct tct gct ttc gta ggc gcc ggc<br>Ala Gln Leu Ala Pro Pro Ser Ala Ala Ser Ala Phe Val Gly Ala Gly | 4873 |

-continued

```
            1010                1015                1020
    atc gct gga gcg gct gtt ggc agc ata ggc ctt ggg aag gtg ctt gtg       4921
    Ile Ala Gly Ala Ala Val Gly Ser Ile Gly Leu Gly Lys Val Leu Val
    1025                1030                1035                1040 gat att ttg gca ggt tat gga gca ggg gtg gca ggc gcg ctc gtg gcc       4969
    Asp Ile Leu Ala Gly Tyr Gly Ala Gly Val Ala Gly Ala Leu Val Ala
                    1045                1050                1055 ttt aag gtc atg agc ggc gag atg ccc tcc acc gag gac ctg gtt aac       5017
    Phe Lys Val Met Ser Gly Glu Met Pro Ser Thr Glu Asp Leu Val Asn
            1060                1065                1070 cta ctc cct gct atc ctc tcc cct ggc gcc cta gtc gtc ggg gtc gtg       5065
    Leu Leu Pro Ala Ile Leu Ser Pro Gly Ala Leu Val Val Gly Val Val
                1075                1080                1085 tgc gca gcg ata ctg cgt cgg cac gtg ggc cca ggg gag ggg gct gtg       5113
    Cys Ala Ala Ile Leu Arg Arg His Val Gly Pro Gly Glu Gly Ala Val
            1090                1095                1100 cag tgg atg aac cgg ctg ata gcg ttc gct tcg cgg ggt aac cac gtc       5161
    Gln Trp Met Asn Arg Leu Ile Ala Phe Ala Ser Arg Gly Asn His Val
    1105                1110                1115                1120 tcc ccc acg cac tat gtg cct gag agc gac gct gca gca cgt gtc act       5209
    Ser Pro Thr His Tyr Val Pro Glu Ser Asp Ala Ala Ala Arg Val Thr
                    1125                1130                1135 cag atc ctc tct agt ctt acc atc act cag ctg ctg aag agg ctt cac       5257
    Gln Ile Leu Ser Ser Leu Thr Ile Thr Gln Leu Leu Lys Arg Leu His
            1140                1145                1150 cag tgg atc aac gag gac tgc tcc acg cca tgc tcc ggc tcg tgg cta       5305
    Gln Trp Ile Asn Glu Asp Cys Ser Thr Pro Cys Ser Gly Ser Trp Leu
                1155                1160                1165 aga gat gtt tgg gat tgg ata tgc acg gtg ttg act gat ttc aag acc       5353
    Arg Asp Val Trp Asp Trp Ile Cys Thr Val Leu Thr Asp Phe Lys Thr
            1170                1175                1180 tgg ctc cag tcc aag ctc ctg ccg cga ttg ccg gga gtc ccc ttc ttc       5401
    Trp Leu Gln Ser Lys Leu Leu Pro Arg Leu Pro Gly Val Pro Phe Phe
    1185                1190                1195                1200 tca tgt caa cgt ggg tac aag gga gtc tgg cgg ggc gac ggc atc atg       5449
    Ser Cys Gln Arg Gly Tyr Lys Gly Val Trp Arg Gly Asp Gly Ile Met
                    1205                1210                1215 caa acc acc tgc cca tgt gga gca cag atc acc gga cat gtg aaa aac       5497
    Gln Thr Thr Cys Pro Cys Gly Ala Gln Ile Thr Gly His Val Lys Asn
            1220                1225                1230 cgt tcc atg agg atc gtg ggg cct agg acc tgt agt aac acg tgg cat       5545
    Arg Ser Met Arg Ile Val Gly Pro Arg Thr Cys Ser Asn Thr Trp His
                1235                1240                1245 gga aca ttc ccc att aac gcg tac acc acg ggc ccc tgc acg ccc tcc       5593
    Gly Thr Phe Pro Ile Asn Ala Tyr Thr Thr Gly Pro Cys Thr Pro Ser
            1250                1255                1260 ccg gcg cca aat tat tct agg gcg ctg tgg cgg gtg gct gct gag gag       5641
    Pro Ala Pro Asn Tyr Ser Arg Ala Leu Trp Arg Val Ala Ala Glu Glu
    1265                1270                1275                1280 tac gtg gag gtt acg cgg gtg ggg gat ttc cac tac gtg acg ggc atg       5689
    Tyr Val Glu Val Thr Arg Val Gly Asp Phe His Tyr Val Thr Gly Met
                    1285                1290                1295 acc act gac aac gta aag tgc ccg tgt cag gtt ccg gcc ccc gaa ttc       5737
    Thr Thr Asp Asn Val Lys Cys Pro Cys Gln Val Pro Ala Pro Glu Phe
            1300                1305                1310 ttc aca gaa gtg gat ggg gtg cgg ttg cac agg tac gct cca gcg tgc       5785
    Phe Thr Glu Val Asp Gly Val Arg Leu His Arg Tyr Ala Pro Ala Cys
                1315                1320                1325 aaa ccc ctc cta cgg gag gag gtc aca ttc ctg gtc ggg ctc aat caa       5833
```

```
Lys Pro Leu Leu Arg Glu Glu Val Thr Phe Leu Val Gly Leu Asn Gln
        1330                1335                1340 tac ctg gtt ggg tca cag ctc cca tgc gag ccc gaa ccg gac gta gca      5881
Tyr Leu Val Gly Ser Gln Leu Pro Cys Glu Pro Glu Pro Asp Val Ala
1345                1350                1355                1360 gtg ctc act tcc atg ctc acc gac ccc tcc cac att acg gcg gag acg      5929
Val Leu Thr Ser Met Leu Thr Asp Pro Ser His Ile Thr Ala Glu Thr
                1365                1370                1375 gct aag cgt agg ctg gcc agg gga tct ccc ccc tcc ttg gcc agc tca      5977
Ala Lys Arg Arg Leu Ala Arg Gly Ser Pro Pro Ser Leu Ala Ser Ser
        1380                1385                1390 tca gct agc cag ctg tct gcg cct tcc ttg aag gca aca tgc act acc      6025
Ser Ala Ser Gln Leu Ser Ala Pro Ser Leu Lys Ala Thr Cys Thr Thr
        1395                1400                1405 cgt cat gac tcc ccg gac gct gac ctc atc gag gcc aac ctc ctg tgg      6073
Arg His Asp Ser Pro Asp Ala Asp Leu Ile Glu Ala Asn Leu Leu Trp
        1410                1415                1420 cgg cag gag atg ggc ggg aac atc acc cgc gtg gag tca gaa aat aag      6121
Arg Gln Glu Met Gly Gly Asn Ile Thr Arg Val Glu Ser Glu Asn Lys
1425                1430                1435                1440 gta gta att ttg gac tct ttc gag ccg ctc caa gcg gag gag gat gag      6169
Val Val Ile Leu Asp Ser Phe Glu Pro Leu Gln Ala Glu Glu Asp Glu
                1445                1450                1455 agg gaa gta tcc gtt ccg gcg gag atc ctg cgg agg tcc agg aaa ttc      6217
Arg Glu Val Ser Val Pro Ala Glu Ile Leu Arg Arg Ser Arg Lys Phe
        1460                1465                1470 cct cga gcg atg ccc ata tgg gca cgc ccg gat tac aac cct cca ctg      6265
Pro Arg Ala Met Pro Ile Trp Ala Arg Pro Asp Tyr Asn Pro Pro Leu
        1475                1480                1485 tta gag tcc tgg aag gac ccg gac tac gtc cct cca gtg gta cac ggg      6313
Leu Glu Ser Trp Lys Asp Pro Asp Tyr Val Pro Pro Val Val His Gly
        1490                1495                1500 tgt cca ctg ccg cct gcc aag gcc cct ccg ata cca cct cca cgg agg      6361
Cys Pro Leu Pro Pro Ala Lys Ala Pro Pro Ile Pro Pro Pro Arg Arg
1505                1510                1515                1520 aag agg acg gtt gtc ctg tca gaa tct acc gtg tct tct gcc ttg gcg      6409
Lys Arg Thr Val Val Leu Ser Glu Ser Thr Val Ser Ser Ala Leu Ala
                1525                1530                1535 gag ctc gcc aca aag acc ttc ggc agc tcc gaa tcg tcg gcc gtc gac      6457
Glu Leu Ala Thr Lys Thr Phe Gly Ser Ser Glu Ser Ser Ala Val Asp
        1540                1545                1550 agc ggc acg gca acg gcc tct cct gac cag ccc tcc gac gac ggc gac      6505
Ser Gly Thr Ala Thr Ala Ser Pro Asp Gln Pro Ser Asp Asp Gly Asp
        1555                1560                1565 gcg gga tcc gac gtt gag tcg tac tcc tcc atg ccc ccc ctt gag ggg      6553
Ala Gly Ser Asp Val Glu Ser Tyr Ser Ser Met Pro Pro Leu Glu Gly
        1570                1575                1580 gag ccg ggg gat ccc gat ctc agc gac ggg cct tgg tct acc gta agc      6601
Glu Pro Gly Asp Pro Asp Leu Ser Asp Gly Pro Trp Ser Thr Val Ser
1585                1590                1595                1600 gag gag gct agt gag gac gtc gtc tgc tgc tcg atg tcc tac aca tgg      6649
Glu Glu Ala Ser Glu Asp Val Val Cys Cys Ser Met Ser Tyr Thr Trp
                1605                1610                1615 aca ggc gcc ctg atc acg cca tgc gct gcg gag gaa acc aag ctg ccc      6697
Thr Gly Ala Leu Ile Thr Pro Cys Ala Ala Glu Glu Thr Lys Leu Pro
        1620                1625                1630 atc aat gca ctg agc aac tct ttg ctc cgt cac cac aac ttg gtc tat      6745
Ile Asn Ala Leu Ser Asn Ser Leu Leu Arg His His Asn Leu Val Tyr
        1635                1640                1645
```

-continued

```
gct aca aca tct cgc agc gca agc ctg cgg cag aag aag gtc acc ttt      6793
Ala Thr Thr Ser Arg Ser Ala Ser Leu Arg Gln Lys Lys Val Thr Phe
        1650            1655                1660 gac aga ctg cag gtc ctg gac gac cac tac cgg gac gtg ctc aag gag      6841
Asp Arg Leu Gln Val Leu Asp Asp His Tyr Arg Asp Val Leu Lys Glu
1665            1670                1675                1680 atg aag gcg aag gcg tcc aca gtt aag gct aaa ctt cta tcc gtg gag      6889
Met Lys Ala Lys Ala Ser Thr Val Lys Ala Lys Leu Leu Ser Val Glu
                1685                1690                1695 gaa gcc tgt aag ctg acg ccc cca cat tcg gcc aga tct aaa ttt ggc      6937
Glu Ala Cys Lys Leu Thr Pro Pro His Ser Ala Arg Ser Lys Phe Gly
            1700                1705                1710 tat ggg gca aag gac gtc cgg aac cta tcc agc aag gcc gtt aac cac      6985
Tyr Gly Ala Lys Asp Val Arg Asn Leu Ser Ser Lys Ala Val Asn His
        1715                1720                1725 atc cgc tcc gtg tgg aag gac ttg ctg gaa gac act gag aca cca att      7033
Ile Arg Ser Val Trp Lys Asp Leu Leu Glu Asp Thr Glu Thr Pro Ile
    1730                1735                1740 gac acc acc atc atg gca aaa aat gag gtt ttc tgc gtc caa cca gag      7081
Asp Thr Thr Ile Met Ala Lys Asn Glu Val Phe Cys Val Gln Pro Glu
1745                1750                1755                1760 aag ggg ggc cgc aag cca gct cgc ctt atc gta ttc cca gat ttg ggg      7129
Lys Gly Gly Arg Lys Pro Ala Arg Leu Ile Val Phe Pro Asp Leu Gly
                1765                1770                1775 gtt cgt gtg tgc gag aaa atg gcc ctt tac gat gtg gtc tcc acc ctc      7177
Val Arg Val Cys Glu Lys Met Ala Leu Tyr Asp Val Val Ser Thr Leu
            1780                1785                1790 cct cag gcc gtg atg ggc tct tca tac gga ttc caa tac tct cct gga      7225
Pro Gln Ala Val Met Gly Ser Ser Tyr Gly Phe Gln Tyr Ser Pro Gly
        1795                1800                1805 cag cgg gtc gag ttc ctg gtg aat gcc tgg aaa gcg aag aaa tgc cct      7273
Gln Arg Val Glu Phe Leu Val Asn Ala Trp Lys Ala Lys Lys Cys Pro
    1810                1815                1820 atg ggc ttc gca tat gac acc cgc tgt ttt gac tca acg gtc act gag      7321
Met Gly Phe Ala Tyr Asp Thr Arg Cys Phe Asp Ser Thr Val Thr Glu
1825                1830                1835                1840 aat gac atc cgt gtt gag gag tca atc tac caa tgt tgt gac ttg gcc      7369
Asn Asp Ile Arg Val Glu Glu Ser Ile Tyr Gln Cys Cys Asp Leu Ala
                1845                1850                1855 ccc gaa gcc aga cag gcc ata agg tcg ctc aca gag cgg ctt tac atc      7417
Pro Glu Ala Arg Gln Ala Ile Arg Ser Leu Thr Glu Arg Leu Tyr Ile
            1860                1865                1870 ggg ggc ccc ctg act aat tct aaa ggg cag aac tgc ggc tat cgc cgg      7465
Gly Gly Pro Leu Thr Asn Ser Lys Gly Gln Asn Cys Gly Tyr Arg Arg
        1875                1880                1885 tgc cgc gcg agc ggt gta ctg acg acc agc tgc ggt aat acc ctc aca      7513
Cys Arg Ala Ser Gly Val Leu Thr Thr Ser Cys Gly Asn Thr Leu Thr
    1890                1895                1900 tgt tac ttg aag gcc gct gcg gcc tgt cga gct gcg aag ctc cag gac      7561
Cys Tyr Leu Lys Ala Ala Ala Ala Cys Arg Ala Ala Lys Leu Gln Asp
1905                1910                1915                1920 tgc acg atg ctc gta tgc gga gac gac ctt gtc gtt atc tgt gaa agc      7609
Cys Thr Met Leu Val Cys Gly Asp Asp Leu Val Val Ile Cys Glu Ser
                1925                1930                1935 gcg ggg acc caa gag gac gag gcg agc cta cgg gcc ttc acg gag gct      7657
Ala Gly Thr Gln Glu Asp Glu Ala Ser Leu Arg Ala Phe Thr Glu Ala
            1940                1945                1950 atg act aga tac tct gcc ccc cct ggg gac ccg ccc aaa cca gaa tac      7705
Met Thr Arg Tyr Ser Ala Pro Pro Gly Asp Pro Pro Lys Pro Glu Tyr
        1955                1960                1965
```

```
gac ttg gag ttg ata aca tca tgc tcc tcc aat gtg tca gtc gcg cac      7753
Asp Leu Glu Leu Ile Thr Ser Cys Ser Ser Asn Val Ser Val Ala His
    1970            1975                1980 gat gca tct ggc aaa agg gtg tac tat ctc acc cgt gac ccc acc acc      7801
Asp Ala Ser Gly Lys Arg Val Tyr Tyr Leu Thr Arg Asp Pro Thr Thr
1985            1990                1995                2000 ccc ctt gcg cgg gct gcg tgg gag aca gct aga cac act cca gtc aat      7849
Pro Leu Ala Arg Ala Ala Trp Glu Thr Ala Arg His Thr Pro Val Asn
                2005                2010                2015 tcc tgg cta ggc aac atc atc atg tat gcg ccc acc ttg tgg gca agg      7897
Ser Trp Leu Gly Asn Ile Ile Met Tyr Ala Pro Thr Leu Trp Ala Arg
        2020                2025                2030 atg atc ctg atg act cat ttc ttc tcc atc ctt cta gct cag gaa caa      7945
Met Ile Leu Met Thr His Phe Phe Ser Ile Leu Leu Ala Gln Glu Gln
            2035                2040                2045 ctt gaa aaa gcc cta gat tgt cag atc tac ggg gcc tgt tac tcc att      7993
Leu Glu Lys Ala Leu Asp Cys Gln Ile Tyr Gly Ala Cys Tyr Ser Ile
                2050                2055                2060 gag cca ctt gac cta cct cag atc att caa cga ctc cac ggc ctt agc      8041
Glu Pro Leu Asp Leu Pro Gln Ile Ile Gln Arg Leu His Gly Leu Ser
2065                2070                2075                2080 gca ttt tca ctc cat agt tac tct cca ggt gag atc aat agg gtg gct      8089
Ala Phe Ser Leu His Ser Tyr Ser Pro Gly Glu Ile Asn Arg Val Ala
                    2085                2090                2095 tca tgc ctc agg aaa ctt ggg gta ccg ccc ttg cga gtc tgg aga cat      8137
Ser Cys Leu Arg Lys Leu Gly Val Pro Pro Leu Arg Val Trp Arg His
                2100                2105                2110 cgg gcc aga agt gtc cgc gct agg cta ctg tcc cag ggg ggg agg gct      8185
Arg Ala Arg Ser Val Arg Ala Arg Leu Leu Ser Gln Gly Gly Arg Ala
            2115                2120                2125 gcc act tgt ggc aag tac ctc ttc aac tgg gca gta agg acc aag ctc      8233
Ala Thr Cys Gly Lys Tyr Leu Phe Asn Trp Ala Val Arg Thr Lys Leu
        2130                2135                2140 aaa ctc act cca atc ccg gct gcg tcc cag ttg gat tta tcc agc tgg      8281
Lys Leu Thr Pro Ile Pro Ala Ala Ser Gln Leu Asp Leu Ser Ser Trp
2145                2150                2155                2160 ttc gtt gct ggt tac agc ggg gga gac ata tat cac agc ctg tct cgt      8329
Phe Val Ala Gly Tyr Ser Gly Gly Asp Ile Tyr His Ser Leu Ser Arg
                2165                2170                2175 gcc cga ccc cgc tgg ttc atg tgg tgc cta ctc cta ctt tct gta ggg      8377
Ala Arg Pro Arg Trp Phe Met Trp Cys Leu Leu Leu Leu Ser Val Gly
                2180                2185                2190 gta ggc atc tat cta ctc ccc aac cga tga acggggagct aaacactcca        8427
Val Gly Ile Tyr Leu Leu Pro Asn Arg  *
        2195                2200 ggccaatagg ccatcctgtt tttttttttt tttttttttt tttttttttt tttttttttt    8487
tttttttttt tttttttttt ttttttcctc tttttttcc tttctttcc tttggtggct      8547 ccatcttagc cctagtcacg gctagctgtg aaaggtccgt gagccgcttg actgcagaga    8607
gtgctgatac tggcctctct gcagatcaag t                                   8638

<210> SEQ ID NO 7
<211> LENGTH: 8638
<212> TYPE: DNA
<213> ORGANISM: HCV
<220> FEATURE:
<221> NAME/KEY: CDS
<222> LOCATION: (1802)...(8407)

<400> SEQUENCE: 7
```

```
gccagccccc gattgggggc gacactccac catagatcac tccctgtga ggaactactg    60
tcttcacgca gaaagcgtct agccatggcg ttagtatgag tgtcgtgcag cctccaggac   120
ccccctccc gggagagcca tagtggtctg cggaaccggt gagtacaccg gaattgccag   180
gacgaccggg tcctttcttg atcaacccg ctcaatgcct ggagatttgg gcgtgccccc   240
gcgagactgc tagccgagta gtgttgggtc gcgaaaggcc ttgtggtact gcctgatagg   300
gtgcttgcga gtgccccggg aggtctcgta gaccgtgcac catgagcacg aatcctaaac   360
ctcaaagaaa aaccaaaggg cgcgccatga ttgaacaaga tggattgcac gcaggttctc   420
cggccgcttg ggtggagagg ctattcggct atgactgggc acaacagaca atcggctgct   480
ctgatgccgc cgtgttccgg ctgtcagcgc aggggcgccc ggttcttttt gtcaagaccg   540
acctgtccgg tgccctgaat gaactgcagg acgaggcagc gcggctatcg tggctggcca   600
cgacgggcgt tccttgcgca gctgtgctcg acgttgtcac tgaagcggga agggactggc   660
tgctattggg cgaagtgccg gggcaggatc tcctgtcatc tcaccttgct cctgccgaga   720
aagtatccat catggctgat gcaatgcggc ggctgcatac gcttgatccg gctacctgcc   780
cattcgacca ccaagcgaaa catcgcatcg agcgagcacg tactcggatg aagccggtc    840
ttgtcgatca ggatgatctg gacgaagagc atcaggggct cgcgccagcc gaactgttcg   900
ccaggctcaa ggcgcgcatg cccgacgcg aggatctcgt cgtgacccat ggcgatgcct   960
gcttgccgaa tatcatggtg gaaaatggcc gcttttctgg attcatcgac tgtggccggc  1020
tgggtgtggc ggaccgctat caggacatag cgttggctac ccgtgatatt gctgaagagc  1080
ttggcggcga atgggctgac cgcttcctcg tgctttacgg tatcgccgct cccgattcgc  1140
agcgcatcgc cttctatcgc cttcttgacg agttcttctg agttcgcgcc cagatgttaa  1200
cagaccacaa cggtttccct ctagcgggat caattccgcc ccccccccta acgttactgg  1260
ccgaagccgc ttggaataag gccggtgtgc gtttgtctat atgttatttt ccaccatatt  1320
gccgtctttt ggcaatgtga gggcccggaa acctggccct gtcttcttga cgagcattcc  1380
taggggtctt tcccctctcg ccaaaggaat gcaaggtctg ttgaatgtcg tgaaggaagc  1440
agttcctctg gaagcttctt gaagacaaac aacgtctgta gcgaccctt gcaggcagcg  1500
gaaccccca cctggcgaca ggtgcctctg cggccaaaag ccacgtgtat aagatacacc  1560
tgcaaaggcg gcacaacccc agtgccacgt tgtgagttgg atagttgtgg aaagagtcaa  1620
atggctctcc tcaagcgtat tcaacaaggg gctgaaggat gcccagaagg taccccattg  1680
tatgggatct gatctggggc ctcggtgcac atgctttaca tgtgtttagt cgaggttaaa  1740
aaacgtctag gccccccgaa ccacggggac gtggttttcc tttgaaaaac acgataatac  1800
c atg gac cgg gag atg gca gca tcg tgc gga ggc gcg gtt ttc gta ggt  1849
  Met Asp Arg Glu Met Ala Ala Ser Cys Gly Gly Ala Val Phe Val Gly
   1               5                  10                  15 ctg ata ctc ttg acc ttg tca ccg cac tat aag ctg ttc ctc gct agg    1897
Leu Ile Leu Leu Thr Leu Ser Pro His Tyr Lys Leu Phe Leu Ala Arg
             20                  25                  30 ctc ata tgg tgg tta caa tat ttt atc acc agg gcc gag gca cac ttg    1945
Leu Ile Trp Trp Leu Gln Tyr Phe Ile Thr Arg Ala Glu Ala His Leu
         35                  40                  45 caa gtg tgg atc ccc ccc ctc aac gtt cgg ggg ggc cgc gat gcc gtc    1993
Gln Val Trp Ile Pro Pro Leu Asn Val Arg Gly Gly Arg Asp Ala Val
     50                  55                  60 atc ctc ctc acg tgc gcg atc cac cca gag cta atc ttt acc atc acc    2041
Ile Leu Leu Thr Cys Ala Ile His Pro Glu Leu Ile Phe Thr Ile Thr
```

```
                65                   70                   75                   80
aaa atc ttg ctc gcc ata ctc ggt cca ctc atg gtg ctc cag gct ggt          2089
Lys Ile Leu Leu Ala Ile Leu Gly Pro Leu Met Val Leu Gln Ala Gly
                    85                   90                   95 ata acc aaa gtg ccg tac ttc gtg cgc gca cac ggg ctc att cgt gca          2137
Ile Thr Lys Val Pro Tyr Phe Val Arg Ala His Gly Leu Ile Arg Ala
               100                  105                  110 tgc atg ctg gtg cgg aag gtt gct ggg ggt cat tat gtc caa atg gct          2185
Cys Met Leu Val Arg Lys Val Ala Gly Gly His Tyr Val Gln Met Ala
           115                  120                  125 ctc atg aag ttg gcc gca ctg aca ggt acg tac gtt tat gac cat ctc          2233
Leu Met Lys Leu Ala Ala Leu Thr Gly Thr Tyr Val Tyr Asp His Leu
       130                  135                  140 acc cca ctg cgg gac tgg gcc cac gcg ggc cta cga gac ctt gcg gtg          2281
Thr Pro Leu Arg Asp Trp Ala His Ala Gly Leu Arg Asp Leu Ala Val
145                  150                  155                  160 gca gtt gag ccc gtc gtc ttc tct gat atg gag acc aag gtt atc acc          2329
Ala Val Glu Pro Val Val Phe Ser Asp Met Glu Thr Lys Val Ile Thr
                165                  170                  175 tgg ggg gca gac acc gcg gcg tgt ggg gac atc atc ttg ggc ctg ccc          2377
Trp Gly Ala Asp Thr Ala Ala Cys Gly Asp Ile Ile Leu Gly Leu Pro
            180                  185                  190 gtc tcc gcc cgc agg ggg agg gag ata cat ctg gga ccg gca gac agc          2425
Val Ser Ala Arg Arg Gly Arg Glu Ile His Leu Gly Pro Ala Asp Ser
        195                  200                  205 ctt gaa ggg cag ggg tgg cga ctc ctc gcg cct att acg gcc tac tcc          2473
Leu Glu Gly Gln Gly Trp Arg Leu Leu Ala Pro Ile Thr Ala Tyr Ser
    210                  215                  220 caa cag acg cga ggc cta ctt ggc tgc atc atc acc agc ctc aca ggc          2521
Gln Gln Thr Arg Gly Leu Leu Gly Cys Ile Ile Thr Ser Leu Thr Gly
225                  230                  235                  240 cgg gac agg aac cag gtc gag ggg gag gtc caa gtg gtc tcc acc gca          2569
Arg Asp Arg Asn Gln Val Glu Gly Glu Val Gln Val Val Ser Thr Ala
                245                  250                  255 aca caa tct ttc ctg gcg acc tgc gtc aat ggc gtg tgt tgg act gtc          2617
Thr Gln Ser Phe Leu Ala Thr Cys Val Asn Gly Val Cys Trp Thr Val
            260                  265                  270 tat cat ggt gcc ggc tca aag acc ctt gcc ggc cca aag ggc cca atc          2665
Tyr His Gly Ala Gly Ser Lys Thr Leu Ala Gly Pro Lys Gly Pro Ile
        275                  280                  285 acc caa atg tac acc aat gtg gac cag gac ctc gtc ggc tgg caa gcg          2713
Thr Gln Met Tyr Thr Asn Val Asp Gln Asp Leu Val Gly Trp Gln Ala
    290                  295                  300 ccc ccc ggg gcg cgt tcc ttg aca cca tgc acc tgc ggc agc tcg gac          2761
Pro Pro Gly Ala Arg Ser Leu Thr Pro Cys Thr Cys Gly Ser Ser Asp
305                  310                  315                  320 ctt tac ttg gtc acg aag cat gcc gat gtc att ccg gtg cgc cgg cgg          2809
Leu Tyr Leu Val Thr Lys His Ala Asp Val Ile Pro Val Arg Arg Arg
                325                  330                  335 ggc gac agc agg ggg agc cta ctc tcc ccc cgg ccc gtc tcc tac ttg          2857
Gly Asp Ser Arg Gly Ser Leu Leu Ser Pro Arg Pro Val Ser Tyr Leu
            340                  345                  350 aag ggc tct tcg ggc ggt cca ctg ctc tgc ccc tcg ggg cac gct gtg          2905
Lys Gly Ser Ser Gly Gly Pro Leu Leu Cys Pro Ser Gly His Ala Val
        355                  360                  365 ggc atc ttt cgg gct gcc gtg tgc acc cga ggg gtt gcg aag gcg gtg          2953
Gly Ile Phe Arg Ala Ala Val Cys Thr Arg Gly Val Ala Lys Ala Val
    370                  375                  380 gac ttt gta ccc gtc gag tct atg gaa acc act atg cgg tcc ccg gtc          3001
```

```
                Asp Phe Val Pro Val Glu Ser Met Glu Thr Thr Met Arg Ser Pro Val
                385                 390                 395                 400 ttc acg gac aac tcg tcc cct ccg gcc gta ccg cag aca ttc cag gtg           3049
Phe Thr Asp Asn Ser Ser Pro Pro Ala Val Pro Gln Thr Phe Gln Val
                405                 410                 415 gcc cat cta cac gcc cct act ggt agc ggc aag agc act aag gtg ccg           3097
Ala His Leu His Ala Pro Thr Gly Ser Gly Lys Ser Thr Lys Val Pro
                    420                 425                 430 gct gcg tat gca gcc caa ggg tat aag gtg ctt gtc ctg aac ccg tcc           3145
Ala Ala Tyr Ala Ala Gln Gly Tyr Lys Val Leu Val Leu Asn Pro Ser
                435                 440                 445 gtc gcc gcc acc cta ggt ttc ggg gcg tat atg tct aag gca cat ggt           3193
Val Ala Ala Thr Leu Gly Phe Gly Ala Tyr Met Ser Lys Ala His Gly
                450                 455                 460 atc gac cct aac atc aga acc ggg gta agg acc atc acc acg ggt gcc           3241
Ile Asp Pro Asn Ile Arg Thr Gly Val Arg Thr Ile Thr Thr Gly Ala
465                 470                 475                 480 ccc atc acg tac tcc acc tat ggc aag ttt ctt gcc gac ggt ggt tgc           3289
Pro Ile Thr Tyr Ser Thr Tyr Gly Lys Phe Leu Ala Asp Gly Gly Cys
                    485                 490                 495 tct ggg ggc gcc tat gac atc ata ata tgt gat gag tgc cac tca act           3337
Ser Gly Gly Ala Tyr Asp Ile Ile Ile Cys Asp Glu Cys His Ser Thr
                500                 505                 510 gac tcg acc act atc ctg ggc atc ggc aca gtc ctg gac caa gcg gag           3385
Asp Ser Thr Thr Ile Leu Gly Ile Gly Thr Val Leu Asp Gln Ala Glu
                    515                 520                 525 acg gct gga gcg cga ctc gtc gtg ctc gcc acc gct acg cct ccg gga           3433
Thr Ala Gly Ala Arg Leu Val Val Leu Ala Thr Ala Thr Pro Pro Gly
530                 535                 540 tcg gtc acc gtg cca cat cca aac atc gag gag gtg gct ctg tcc agc           3481
Ser Val Thr Val Pro His Pro Asn Ile Glu Glu Val Ala Leu Ser Ser
545                 550                 555                 560 act gga gaa atc ccc ttt tat ggc aaa gcc atc ccc atc gag acc atc           3529
Thr Gly Glu Ile Pro Phe Tyr Gly Lys Ala Ile Pro Ile Glu Thr Ile
                    565                 570                 575 aag ggg ggg agg cac ctc att ttc tgc cat tcc aag aag aaa tgc gat           3577
Lys Gly Gly Arg His Leu Ile Phe Cys His Ser Lys Lys Lys Cys Asp
                580                 585                 590 gag ctc gcc gcg aag ctg tcc ggc ctc gga ctc aat gct gta gca tat           3625
Glu Leu Ala Ala Lys Leu Ser Gly Leu Gly Leu Asn Ala Val Ala Tyr
                    595                 600                 605 tac cgg ggc ctt gat gta tcc gtc ata cca act agc gga gac gtc att           3673
Tyr Arg Gly Leu Asp Val Ser Val Ile Pro Thr Ser Gly Asp Val Ile
610                 615                 620 gtc gta gca acg gac gct cta atg acg ggc ttt acc ggc gat ttc gac           3721
Val Val Ala Thr Asp Ala Leu Met Thr Gly Phe Thr Gly Asp Phe Asp
625                 630                 635                 640 tca gtg atc gac tgc aat aca tgt gtc acc cag aca gtc gac ttc agc           3769
Ser Val Ile Asp Cys Asn Thr Cys Val Thr Gln Thr Val Asp Phe Ser
                    645                 650                 655 ctg gac ccg acc ttc acc att gag acg acg acc gtg cca caa gac gcg           3817
Leu Asp Pro Thr Phe Thr Ile Glu Thr Thr Thr Val Pro Gln Asp Ala
                660                 665                 670 gtg tca cgc tcg cag cgg cga ggc agg act ggt agg ggc agg atg ggc           3865
Val Ser Arg Ser Gln Arg Arg Gly Arg Thr Gly Arg Gly Arg Met Gly
                    675                 680                 685 att tac agg ttt gtg act cca gga gaa cgg ccc tcg ggc atg ttc gat           3913
Ile Tyr Arg Phe Val Thr Pro Gly Glu Arg Pro Ser Gly Met Phe Asp
690                 695                 700
```

-continued

| | |
|---|---|
| tcc tcg gtt ctg tgc gag tgc tat gac gcg ggc tgt gct tgg tac gag<br>Ser Ser Val Leu Cys Glu Cys Tyr Asp Ala Gly Cys Ala Trp Tyr Glu<br>705                              710                        715                        720 | 3961 |
| ctc acg ccc gcc gag acc tca gtt agg ttg cgg gct tac cta aac aca<br>Leu Thr Pro Ala Glu Thr Ser Val Arg Leu Arg Ala Tyr Leu Asn Thr<br>                        725                            730                        735 | 4009 |
| cca ggg ttg ccc gtc tgc cag gac cat ctg gag ttc tgg gag ggc gtc<br>Pro Gly Leu Pro Val Cys Gln Asp His Leu Glu Phe Trp Glu Gly Val<br>                    740                            745                        750 | 4057 |
| ttt aca ggc ctc acc cac ata gac gcc cat ttc ttg tcc cag act aag<br>Phe Thr Gly Leu Thr His Ile Asp Ala His Phe Leu Ser Gln Thr Lys<br>                        755                            760                        765 | 4105 |
| cag gca gga gac aac ttc ccc tac ctg gta gca tac cag gct acg gtg<br>Gln Ala Gly Asp Asn Phe Pro Tyr Leu Val Ala Tyr Gln Ala Thr Val<br>770                              775                        780 | 4153 |
| tgc gcc agg gct cag gct cca cct cca tcg tgg gac caa atg tgg aag<br>Cys Ala Arg Ala Gln Ala Pro Pro Pro Ser Trp Asp Gln Met Trp Lys<br>785                              790                        795                        800 | 4201 |
| tgt ctc ata cgg cta aag cct acg ctg cac ggg cca acg ccc ctg ctg<br>Cys Leu Ile Arg Leu Lys Pro Thr Leu His Gly Pro Thr Pro Leu Leu<br>                    805                            810                        815 | 4249 |
| tat agg ctg gga gcc gtt caa aac gag gtt act acc aca cac ccc ata<br>Tyr Arg Leu Gly Ala Val Gln Asn Glu Val Thr Thr Thr His Pro Ile<br>                  820                            825                        830 | 4297 |
| acc aaa tac atc atg gca tgc atg tcg gct gac ctg gag gtc gtc acg<br>Thr Lys Tyr Ile Met Ala Cys Met Ser Ala Asp Leu Glu Val Val Thr<br>                835                            840                        845 | 4345 |
| agc acc tgg gtg ctg gta ggc gga gtc cta gca gct ctg gct gcg tat<br>Ser Thr Trp Val Leu Val Gly Gly Val Leu Ala Ala Leu Ala Ala Tyr<br>            850                            855                        860 | 4393 |
| tgc ctg aca aca ggc agc gtg gtc att gtg ggc agg atc atc ttg tcc<br>Cys Leu Thr Thr Gly Ser Val Val Ile Val Gly Arg Ile Ile Leu Ser<br>865                              870                        875                        880 | 4441 |
| gga agg ccg gcc atc att ccc gac agg gaa gtc ctt tac cgg gag ttc<br>Gly Arg Pro Ala Ile Ile Pro Asp Arg Glu Val Leu Tyr Arg Glu Phe<br>                    885                            890                        895 | 4489 |
| gat gag atg gaa gag tgt gcc tca cac ctc cct tac atc gaa cag gga<br>Asp Glu Met Glu Glu Cys Ala Ser His Leu Pro Tyr Ile Glu Gln Gly<br>                900                            905                        910 | 4537 |
| atg cag ctc gcc gaa caa ttc aaa cag aag gca atc ggg ttg ctg caa<br>Met Gln Leu Ala Glu Gln Phe Lys Gln Lys Ala Ile Gly Leu Leu Gln<br>              915                            920                        925 | 4585 |
| aca gcc acc aag caa gcg gag gct gct gct ccc gtg gtg gaa tcc aag<br>Thr Ala Thr Lys Gln Ala Glu Ala Ala Ala Pro Val Val Glu Ser Lys<br>          930                            935                        940 | 4633 |
| tgg cgg acc ctc gaa gcc ttc tgg gcg aag cat atg tgg aat ttc atc<br>Trp Arg Thr Leu Glu Ala Phe Trp Ala Lys His Met Trp Asn Phe Ile<br>945                              950                        955                        960 | 4681 |
| agc ggg ata caa tat tta gca ggc ttg tcc act ctg cct ggc aac ccc<br>Ser Gly Ile Gln Tyr Leu Ala Gly Leu Ser Thr Leu Pro Gly Asn Pro<br>                    965                            970                        975 | 4729 |
| gcg ata gca tca ctg atg gca ttc aca gcc tct atc acc agc ccg ctc<br>Ala Ile Ala Ser Leu Met Ala Phe Thr Ala Ser Ile Thr Ser Pro Leu<br>                980                            985                        990 | 4777 |
| acc acc caa cat acc ctc ctg ttt aac atc ctg ggg gga tgg gtg gcc<br>Thr Thr Gln His Thr Leu Leu Phe Asn Ile Leu Gly Gly Trp Val Ala<br>              995                            1000                     1005 | 4825 |
| gcc caa ctt gct cct ccc agc gct gct tcc gct ttc gta ggc gcc ggc<br>Ala Gln Leu Ala Pro Pro Ser Ala Ala Ser Ala Phe Val Gly Ala Gly<br>          1010                          1015                     1020 | 4873 |

-continued

| | |
|---|---|
| atc gct gga gcg gct gtt ggc agc ata ggc ctt ggg aag gtg ctt gtg<br>Ile Ala Gly Ala Ala Val Gly Ser Ile Gly Leu Gly Lys Val Leu Val<br>1025                   1030                   1035                   1040 | 4921 |
| gat att ttg gca ggt tat gga gca ggg gtg gca ggc gcg ctc gtg gcc<br>Asp Ile Leu Ala Gly Tyr Gly Ala Gly Val Ala Gly Ala Leu Val Ala<br>                  1045                   1050                   1055 | 4969 |
| ttt aag gtc atg agc ggc gag atg ccc tcc acc gag gac ctg gtt aac<br>Phe Lys Val Met Ser Gly Glu Met Pro Ser Thr Glu Asp Leu Val Asn<br>1060                   1065                   1070 | 5017 |
| cta ctc cct gct atc ctc tcc cct ggc gcc cta gtc gtc ggg gtc gtg<br>Leu Leu Pro Ala Ile Leu Ser Pro Gly Ala Leu Val Val Gly Val Val<br>                  1075                   1080                   1085 | 5065 |
| tgc gca gcg ata ctg cgt cgg cac gtg ggc cca ggg gag ggg gct gtg<br>Cys Ala Ala Ile Leu Arg Arg His Val Gly Pro Gly Glu Gly Ala Val<br>1090                   1095                   1100 | 5113 |
| cag tgg atg aac cgg ctg ata gcg ttc gct tcg cgg ggt aac cac gtc<br>Gln Trp Met Asn Arg Leu Ile Ala Phe Ala Ser Arg Gly Asn His Val<br>1105                   1110                   1115                   1120 | 5161 |
| tcc ccc acg cac tat gtg cct gag agc gac gct gca gca cgt gtc act<br>Ser Pro Thr His Tyr Val Pro Glu Ser Asp Ala Ala Ala Arg Val Thr<br>                  1125                   1130                   1135 | 5209 |
| cag atc ctc tct agt ctt acc atc act cag ctg ctg aag agg ctt cac<br>Gln Ile Leu Ser Ser Leu Thr Ile Thr Gln Leu Leu Lys Arg Leu His<br>                  1140                   1145                   1150 | 5257 |
| cag tgg atc aac gag gac tgc tcc acg cca tgc tcc ggc tcg tgg cta<br>Gln Trp Ile Asn Glu Asp Cys Ser Thr Pro Cys Ser Gly Ser Trp Leu<br>                  1155                   1160                   1165 | 5305 |
| aga gat gtt tgg gat tgg ata tgc acg gtg ttg act gat ttc aag gcc<br>Arg Asp Val Trp Asp Trp Ile Cys Thr Val Leu Thr Asp Phe Lys Ala<br>             1170                   1175                   1180 | 5353 |
| tgg ctc cag tcc aag ctc ctg ccg cga ttg ccg gga gtc ccc ttc ttc<br>Trp Leu Gln Ser Lys Leu Leu Pro Arg Leu Pro Gly Val Pro Phe Phe<br>1185                   1190                   1195                   1200 | 5401 |
| tca tgt caa cgt ggg tac aag gga gtc tgg cgg ggc gac ggc atc atg<br>Ser Cys Gln Arg Gly Tyr Lys Gly Val Trp Arg Gly Asp Gly Ile Met<br>                  1205                   1210                   1215 | 5449 |
| caa acc acc tgc cca tgt gga gca cag atc acc gga cat gtg aaa aac<br>Gln Thr Thr Cys Pro Cys Gly Ala Gln Ile Thr Gly His Val Lys Asn<br>             1220                   1225                   1230 | 5497 |
| tgt tcc atg agg atc gtg ggg cct agg acc tgt agt aac acg tgg cat<br>Cys Ser Met Arg Ile Val Gly Pro Arg Thr Cys Ser Asn Thr Trp His<br>                  1235                   1240                   1245 | 5545 |
| gga aca ttc ccc att aac gcg tac acc acg ggc ccc tgc acg ccc tcc<br>Gly Thr Phe Pro Ile Asn Ala Tyr Thr Thr Gly Pro Cys Thr Pro Ser<br>           1250                   1255                   1260 | 5593 |
| ccg gcg cca aat tat tct agg gcg ctg tgg cgg gtg gct gct gag gag<br>Pro Ala Pro Asn Tyr Ser Arg Ala Leu Trp Arg Val Ala Ala Glu Glu<br>1265                   1270                   1275                   1280 | 5641 |
| tac gtg gag gtt acg cga gtg ggg gat ttc cac tac gtg acg ggc atg<br>Tyr Val Glu Val Thr Arg Val Gly Asp Phe His Tyr Val Thr Gly Met<br>                  1285                   1290                   1295 | 5689 |
| acc act gac aac gta aag tgc ccg tgt cag gtt ccg gcc ccc gaa ttc<br>Thr Thr Asp Asn Val Lys Cys Pro Cys Gln Val Pro Ala Pro Glu Phe<br>             1300                   1305                   1310 | 5737 |
| ttc aca gaa gtg gat ggg gtg cgg ttg cac agg tac gct cca gcg tgc<br>Phe Thr Glu Val Asp Gly Val Arg Leu His Arg Tyr Ala Pro Ala Cys<br>                  1315                   1320                   1325 | 5785 |
| aaa ccc ctc cta cgg gag gag gtc aca ttc ctg gtc ggg ctc aat caa<br>Lys Pro Leu Leu Arg Glu Glu Val Thr Phe Leu Val Gly Leu Asn Gln | 5833 |

-continued

```
        1330                1335                1340
tac ccg gtt ggg tca cag ctc cca tgc gag ccc gaa ctg gac gta gca    5881
Tyr Pro Val Gly Ser Gln Leu Pro Cys Glu Pro Glu Leu Asp Val Ala
1345                1350                1355                1360 gtg ctc act tcc atg ctc acc gac ccc tcc cac att acg gcg gag acg    5929
Val Leu Thr Ser Met Leu Thr Asp Pro Ser His Ile Thr Ala Glu Thr
            1365                1370                1375 gct aag cgt agg ctg gcc agg gga tct ccc ccc tcc ttg gcc agc tca    5977
Ala Lys Arg Arg Leu Ala Arg Gly Ser Pro Pro Ser Leu Ala Ser Ser
        1380                1385                1390 tca gct agc cag ctg tct gcg cct tcc ttg aag gca aca tgc act acc    6025
Ser Ala Ser Gln Leu Ser Ala Pro Ser Leu Lys Ala Thr Cys Thr Thr
    1395                1400                1405 cgt cat gac tcc ccg gac gct gac ctc atc gag gcc aac ctc ctg tgg    6073
Arg His Asp Ser Pro Asp Ala Asp Leu Ile Glu Ala Asn Leu Leu Trp
1410                1415                1420 cgg cag gag atg ggc ggg aac atc acc cgc gtg gag tca gag aat aag    6121
Arg Gln Glu Met Gly Gly Asn Ile Thr Arg Val Glu Ser Glu Asn Lys
1425                1430                1435                1440 gta gta att ttg gac tct ttc gag ccg ctc caa gcg gag gag gat gag    6169
Val Val Ile Leu Asp Ser Phe Glu Pro Leu Gln Ala Glu Glu Asp Glu
            1445                1450                1455 agg gaa gta tcc gtt ccg gcg gag atc ctg cgg agg tcc agg aaa ttc    6217
Arg Glu Val Ser Val Pro Ala Glu Ile Leu Arg Arg Ser Arg Lys Phe
        1460                1465                1470 cct cga gcg atg ccc ata tgg gca cgc ccg gat tac aac cct cca ctg    6265
Pro Arg Ala Met Pro Ile Trp Ala Arg Pro Asp Tyr Asn Pro Pro Leu
    1475                1480                1485 tta gag tcc tgg aag gac ccg gac tac gtc cct cca gtg gta cac ggg    6313
Leu Glu Ser Trp Lys Asp Pro Asp Tyr Val Pro Pro Val Val His Gly
1490                1495                1500 tgt cca ttg ccg cct gcc aag gcc cct ccg ata cca cct cca cgg agg    6361
Cys Pro Leu Pro Pro Ala Lys Ala Pro Pro Ile Pro Pro Pro Arg Arg
1505                1510                1515                1520 aag agg acg gtt gtc ctg tca gaa tct acc gtg tct tct gcc ttg gcg    6409
Lys Arg Thr Val Val Leu Ser Glu Ser Thr Val Ser Ser Ala Leu Ala
            1525                1530                1535 gag ctc gcc aca aag acc ttc ggc agc tcc gaa tcg tcg gcc gtc gac    6457
Glu Leu Ala Thr Lys Thr Phe Gly Ser Ser Glu Ser Ser Ala Val Asp
        1540                1545                1550 agc ggc acg gca acg gcc tct cct gac cag ccc tcc gac gac ggc gac    6505
Ser Gly Thr Ala Thr Ala Ser Pro Asp Gln Pro Ser Asp Asp Gly Asp
    1555                1560                1565 gcg gga tcc gac gtt gag tcg tac tcc tcc atg ccc ccc ctt gag ggg    6553
Ala Gly Ser Asp Val Glu Ser Tyr Ser Ser Met Pro Pro Leu Glu Gly
1570                1575                1580 gag ccg ggg gat ccc gat ctc agc gac ggg tct tgg tct acc gta agc    6601
Glu Pro Gly Asp Pro Asp Leu Ser Asp Gly Ser Trp Ser Thr Val Ser
1585                1590                1595                1600 gag gag gct agt gag gac gtc gtc tgc tgc tcg atg tcc tac aca tgg    6649
Glu Glu Ala Ser Glu Asp Val Val Cys Cys Ser Met Ser Tyr Thr Trp
            1605                1610                1615 aca ggc gcc ctg atc acg cca tgc gct gcg gag gaa acc aag ctg ccc    6697
Thr Gly Ala Leu Ile Thr Pro Cys Ala Ala Glu Glu Thr Lys Leu Pro
        1620                1625                1630 atc aat gca ctg agc aac tct ttg ctc cgt cac cac aac ttg gtc tat    6745
Ile Asn Ala Leu Ser Asn Ser Leu Leu Arg His His Asn Leu Val Tyr
    1635                1640                1645 gct aca aca tct cgc agc gca agc ctg cgg cag aag aag gtc acc ttt    6793
```

```
                                                              -continued

Ala Thr Thr Ser Arg Ser Ala Ser Leu Arg Gln Lys Lys Val Thr Phe
    1650            1655                1660 gac aga ctg cag gtc ctg gac gac cac tac cgg gac gtg ctc aag gag      6841
Asp Arg Leu Gln Val Leu Asp Asp His Tyr Arg Asp Val Leu Lys Glu
1665            1670                1675                1680 atg aag gcg aag gcg tcc aca gtt aag gct aaa ctt cta tcc gtg gag      6889
Met Lys Ala Lys Ala Ser Thr Val Lys Ala Lys Leu Leu Ser Val Glu
                1685                1690                1695 gaa gcc tgt aag ctg acg ccc cca cat tcg gcc aga tct aaa ttt ggc      6937
Glu Ala Cys Lys Leu Thr Pro Pro His Ser Ala Arg Ser Lys Phe Gly
            1700                1705                1710 tat ggg gca aag gac gtc cgg aac cta tcc agc aag gcc gtt aac cac      6985
Tyr Gly Ala Lys Asp Val Arg Asn Leu Ser Ser Lys Ala Val Asn His
        1715                1720                1725 atc cgc tcc gtg tgg aag gac ttg ctg gaa gac act gag aca cca att      7033
Ile Arg Ser Val Trp Lys Asp Leu Leu Glu Asp Thr Glu Thr Pro Ile
    1730                1735                1740 gac acc acc atc atg gca aaa aat gag gtt ttc tgc gtc caa cca gag      7081
Asp Thr Thr Ile Met Ala Lys Asn Glu Val Phe Cys Val Gln Pro Glu
1745                1750                1755                1760 aag ggg ggc cgc aag cca gct cgc ctt atc gta ttc cca gat ttg ggg      7129
Lys Gly Gly Arg Lys Pro Ala Arg Leu Ile Val Phe Pro Asp Leu Gly
                1765                1770                1775 gtt cgt gtg tgc gag aaa atg gcc ctt tac gat gtg gtc tcc acc ctc      7177
Val Arg Val Cys Glu Lys Met Ala Leu Tyr Asp Val Val Ser Thr Leu
            1780                1785                1790 cct cag gcc gtg atg ggc tct tca tac gga ttc caa tac tct cct gga      7225
Pro Gln Ala Val Met Gly Ser Ser Tyr Gly Phe Gln Tyr Ser Pro Gly
        1795                1800                1805 cag cgg gtc gag ttc ctg gtg aat gcc tgg aaa gcg aag aaa tgc cct      7273
Gln Arg Val Glu Phe Leu Val Asn Ala Trp Lys Ala Lys Lys Cys Pro
    1810                1815                1820 atg ggc ttc gca tat gac acc cgc tgt ttt gac tca acg gtc act gag      7321
Met Gly Phe Ala Tyr Asp Thr Arg Cys Phe Asp Ser Thr Val Thr Glu
1825                1830                1835                1840 aat gac atc cgt gtt gag gag tca atc tac caa tgt tgt gac ttg gcc      7369
Asn Asp Ile Arg Val Glu Glu Ser Ile Tyr Gln Cys Cys Asp Leu Ala
                1845                1850                1855 ccc gaa gcc aga cag gcc ata agg tcg ctc aca gag cgg ctt tac atc      7417
Pro Glu Ala Arg Gln Ala Ile Arg Ser Leu Thr Glu Arg Leu Tyr Ile
            1860                1865                1870 ggg ggc ccc ctg act aat tct aaa ggg cag aac tgc ggc tat cgc cgg      7465
Gly Gly Pro Leu Thr Asn Ser Lys Gly Gln Asn Cys Gly Tyr Arg Arg
        1875                1880                1885 tgc cgc gcg agc ggt gta ctg acg acc agc tgc ggt aat acc ctc aca      7513
Cys Arg Ala Ser Gly Val Leu Thr Thr Ser Cys Gly Asn Thr Leu Thr
    1890                1895                1900 tgt tac ttg aag gcc gct gcg gcc tgt cga gct gcg aag ctc cag gac      7561
Cys Tyr Leu Lys Ala Ala Ala Ala Cys Arg Ala Ala Lys Leu Gln Asp
1905                1910                1915                1920 tgc acg atg ctc gta tgc gga gac gac ctt gtc gtt atc tgt gaa agc      7609
Cys Thr Met Leu Val Cys Gly Asp Asp Leu Val Val Ile Cys Glu Ser
                1925                1930                1935 gcg ggg acc caa gag gac gag gcg agc cta cgg gcc ttc acg gag gct      7657
Ala Gly Thr Gln Glu Asp Glu Ala Ser Leu Arg Ala Phe Thr Glu Ala
            1940                1945                1950 atg act aga tac tct gcc ccc cct ggg gac ccg ccc aaa cca gaa tac      7705
Met Thr Arg Tyr Ser Ala Pro Pro Gly Asp Pro Pro Lys Pro Glu Tyr
        1955                1960                1965
```

```
gac ttg gag ttg ata aca tca tgc tcc tcc aat gtg tca gtc gcg cac      7753
Asp Leu Glu Leu Ile Thr Ser Cys Ser Ser Asn Val Ser Val Ala His
    1970            1975                1980 gat gca tct ggc aaa agg gtg tac tat ctc acc cgt gac ccc acc acc      7801
Asp Ala Ser Gly Lys Arg Val Tyr Tyr Leu Thr Arg Asp Pro Thr Thr
1985                1990                1995                2000 ccc ctt gcg cgg gct gcg tgg gag aca gct aga cac act cca gtc aat      7849
Pro Leu Ala Arg Ala Ala Trp Glu Thr Ala Arg His Thr Pro Val Asn
            2005                2010                2015 tcc tgg cta ggc aac atc atc atg tat gcg ccc acc ttg tgg gca agg      7897
Ser Trp Leu Gly Asn Ile Ile Met Tyr Ala Pro Thr Leu Trp Ala Arg
        2020                2025                2030 atg atc ctg atg act cat ttc ttc tcc atc ctt cta gct cag gaa caa      7945
Met Ile Leu Met Thr His Phe Phe Ser Ile Leu Leu Ala Gln Glu Gln
    2035                2040                2045 ctt gaa aaa gcc cta gat tgt cag atc tac ggg gcc tgt tac tcc att      7993
Leu Glu Lys Ala Leu Asp Cys Gln Ile Tyr Gly Ala Cys Tyr Ser Ile
2050                2055                2060 gag cca ctt gac cta cct cag atc att caa cga ctc cac ggc ctt agc      8041
Glu Pro Leu Asp Leu Pro Gln Ile Ile Gln Arg Leu His Gly Leu Ser
2065                2070                2075                2080 gca ttt tca ctc cat agt tac tct cca ggt gag atc aat agg gtg gct      8089
Ala Phe Ser Leu His Ser Tyr Ser Pro Gly Glu Ile Asn Arg Val Ala
            2085                2090                2095 tca tgc ctc agg aaa ctt ggg gta ccg ccc ttg cga gtc tgg aga cat      8137
Ser Cys Leu Arg Lys Leu Gly Val Pro Pro Leu Arg Val Trp Arg His
        2100                2105                2110 cgg gcc aga agt gtc cgc gct agg cta ctg tcc cag ggg ggg agg gct      8185
Arg Ala Arg Ser Val Arg Ala Arg Leu Leu Ser Gln Gly Gly Arg Ala
    2115                2120                2125 gcc act tgt ggc aag tac ctc ttc aac tgg gca gta agg acc aag ctc      8233
Ala Thr Cys Gly Lys Tyr Leu Phe Asn Trp Ala Val Arg Thr Lys Leu
2130                2135                2140 aaa ctc act cca atc ccg gct gcg tcc cag ttg gat tta tcc agc tgg      8281
Lys Leu Thr Pro Ile Pro Ala Ala Ser Gln Leu Asp Leu Ser Ser Trp
2145                2150                2155                2160 ttc gtt gct ggt tac agc ggg gga gac ata tat cac agc ctg tct cgt      8329
Phe Val Ala Gly Tyr Ser Gly Gly Asp Ile Tyr His Ser Leu Ser Arg
            2165                2170                2175 gcc cga ccc cgc tgg ttc atg tgg tgc cta ctc cta ctt tct gta ggg      8377
Ala Arg Pro Arg Trp Phe Met Trp Cys Leu Leu Leu Leu Ser Val Gly
        2180                2185                2190 gta ggc atc tat cta ctc ccc aac cga tga acggggagct aaacactcca        8427
Val Gly Ile Tyr Leu Leu Pro Asn Arg *
    2195                2200 ggccaatagg ccatcctgtt tttttcccct ttttttttc ttttttttt ttttttttt      8487 tttttttttt ttttctcctt ttttttttcct cttttttcc tttttcttcc tttggtggct   8547
ccatcttagc cctagtcacg gctagctgtg aaaggtccgt gagccgcttg actgcagaga   8607
gtgctgatac tggcctctct gcagatcaag t                                  8638

<210> SEQ ID NO 8
<211> LENGTH: 6
<212> TYPE: DNA
<213> ORGANISM: HCV

<400> SEQUENCE: 8 accagc                                                              6
```

<210> SEQ ID NO 9
<211> LENGTH: 63
<212> TYPE: DNA
<213> ORGANISM: HCV

<400> SEQUENCE: 9
gaattccaga tggcgcgccc agatgttaac cagatccatg gcacactcta gagtactgtc    60
gac                                                                  63

<210> SEQ ID NO 10
<211> LENGTH: 33
<212> TYPE: DNA
<213> ORGANISM: HCV

<400> SEQUENCE: 10
cggaatcgtt aacagaccac aacggtttcc ctc                                 33

<210> SEQ ID NO 11
<211> LENGTH: 30
<212> TYPE: DNA
<213> ORGANISM: HCV

<400> SEQUENCE: 11
ggcgtaccca tggtattatc gtgttttttca                                    30

<210> SEQ ID NO 12
<211> LENGTH: 45
<212> TYPE: DNA
<213> ORGANISM: HCV

<400> SEQUENCE: 12
gcatatgaat tctaatacga ctcactatag gccagccccc gattg                    45

<210> SEQ ID NO 13
<211> LENGTH: 45
<212> TYPE: DNA
<213> ORGANISM: HCV

<400> SEQUENCE: 13
ggcgcgccct tggttttttc tttgaggttt aggattcgtg ctcat                    45

<210> SEQ ID NO 14
<211> LENGTH: 36
<212> TYPE: DNA
<213> ORGANISM: HCV

<400> SEQUENCE: 14
aaagggcgca tgattgaaca agatggattg cacgca                              36

<210> SEQ ID NO 15
<211> LENGTH: 39
<212> TYPE: DNA
<213> ORGANISM: HCV

<400> SEQUENCE: 15
gcatatgtta actcagaaga actcgtcaag aaggcgata                           39

<210> SEQ ID NO 16
<211> LENGTH: 45
<212> TYPE: DNA
<213> ORGANISM: HCV

<400> SEQUENCE: 16

-continued

```
gcatatgaat tctaatacga ctcactatag gccagccccc gattg          45

<210> SEQ ID NO 17
<211> LENGTH: 30
<212> TYPE: DNA
<213> ORGANISM: HCV

<400> SEQUENCE: 17
acgcagaaag cgtctagcca tggcgttagt                           30

<210> SEQ ID NO 18
<211> LENGTH: 30
<212> TYPE: DNA
<213> ORGANISM: HCV

<400> SEQUENCE: 18
tcccggggca ctcgcaagca ccctatcagg                           30

<210> SEQ ID NO 19
<211> LENGTH: 26
<212> TYPE: DNA
<213> ORGANISM: HCV
<220> FEATURE:
<223> OTHER INFORMATION: Label with FAM: fluorescence reporter dye
<223> OTHER INFORMATION: Label with TAMRA: Quencher dye

<400> SEQUENCE: 19
tggtctgcgg aacgggtgag tacacc                               26

<210> SEQ ID NO 20
<211> LENGTH: 45
<212> TYPE: DNA
<213> ORGANISM: HCV

<400> SEQUENCE: 20
gtggacgaat tctaatacga ctcactataa ccagccccg attgg           45

<210> SEQ ID NO 21
<211> LENGTH: 27
<212> TYPE: DNA
<213> ORGANISM: HCV

<400> SEQUENCE: 21
ggaacgcccg tcgtggccag ccacgat                              27

<210> SEQ ID NO 22
<211> LENGTH: 23
<212> TYPE: DNA
<213> ORGANISM: HCV

<400> SEQUENCE: 22
gtcgtcttct ctgacatgga gac                                  23

<210> SEQ ID NO 23
<211> LENGTH: 27
<212> TYPE: DNA
<213> ORGANISM: HCV

<400> SEQUENCE: 23
gagttgctca gtggattgat gggcagc                              27

<210> SEQ ID NO 24
<211> LENGTH: 8638
<212> TYPE: DNA
```

<213> ORGANISM: HCV
<220> FEATURE:
<221> NAME/KEY: CDS
<222> LOCATION: (1802)...(8407)

<400> SEQUENCE: 24

```
accagccccc gattggggc gacactccac catagatcac tccctgtga ggaactactg      60
tcttcacgca gaaagcgtct agccatggcg ttagtatgag tgtcgtgcag cctccaggac     120
ccccctccc gggagagcca tagtggtctg cggaaccggt gagtacaccg gaattgccag     180
gacgaccggg tcctttcttg gatcaacccg ctcaatgcct ggagatttgg gcgtgccccc     240
gcgagactgc tagccgagta gtgttgggtc gcgaaaggcc ttgtggtact gcctgatagg     300
gtgcttgcga gtgccccggg aggtctcgta gaccgtgcac catgagcacg aatcctaaac     360
ctcaaagaaa aaccaaaggg cgcgccatga ttgaacaaga tggattgcac gcaggttctc     420
cggccgcttg ggtggagagg ctattcggct atgactgggc acaacagaca atcggctgct     480
ctgatgccgc cgtgttccgg ctgtcagcgc agggcgcccc ggttcttttt gtcaagaccg     540
acctgtccgg tgccctgaat gaactgcagg acgaggcagc gcggctatcg tggctggcca     600
cgacgggcgt tccttgcgca gctgtgctcg acgttgtcac tgaagcggga agggactggc     660
tgctattggg cgaagtgccg gggcaggatc tcctgtcatc tcaccttgct cctgccgaga     720
aagtatccat catggctgat gcaatgcggc ggctgcatac gcttgatccg ctacctgcc     780
cattcgacca ccaagcgaaa catcgcatcg agcgagcacg tactcggatg aagccggtc     840
ttgtcgatca ggatgatctg gacgaagagc atcaggggct cgcgccagcc gaactgttcg     900
ccaggctcaa ggcgcgcatg cccgacggcg aggatctcgt cgtgacccat ggcgatgcct     960
gcttgccgaa tatcatggtg gaaaatggcc gcttttctgg attcatcgac tgtggccggc    1020
tgggtgtggc ggaccgctat caggacatag cgttggctac ccgtgatatt gctgaagagc    1080
ttggcggcga atgggctgac cgcttcctcg tgctttacgg tatcgccgct cccgattcgc    1140
agcgcatcgc cttctatcgc cttcttgacg agttcttctg agttcgcgcc cagatgttaa    1200
cagaccacaa cggtttccct ctagcgggat caattccgcc ccccccccta acgttactgg    1260
ccgaagccgc ttggaataag gccggtgtgc gtttgtctat atgttatttt ccaccatatt    1320
gccgtctttt ggcaatgtga gggcccggaa acctggccct gtcttcttga cgagcattcc    1380
tagggtctt tcccctctcg ccaaaggaat gcaaggtctg ttgaatgtcg tgaaggaagc    1440
agttcctctg gaagcttctt gaagacaaac aacgtctgta gcgacccttt gcaggcagcg    1500
gaaccccca cctggcgaca ggtgcctctg cggccaaaag ccacgtgtat aagatacacc    1560
tgcaaaggcg gcacaacccc agtgccacgt tgtgagttgg atagttgtgg aaagagtcaa    1620
atggctctcc tcaagcgtat tcaacaaggg gctgaaggat gcccagaagg taccccattg    1680
tatgggatct gatctggggc ctcggtgcac atgctttaca tgtgtttagt cgaggttaaa    1740
aaacgtctag gccccccgaa ccacggggac gtggttttcc tttgaaaaac acgataatac    1800
c atg gac cgg gag atg gca gca tcg tgc gga ggc gcg gtt ttc gta ggt    1849
  Met Asp Arg Glu Met Ala Ala Ser Cys Gly Gly Ala Val Phe Val Gly
    1               5                  10                  15
ctg ata ctc ttg acc ttg tca ccg cac tat aag ctg ttc ctc gct agg    1897
Leu Ile Leu Leu Thr Leu Ser Pro His Tyr Lys Leu Phe Leu Ala Arg
             20                  25                  30
ctc ata tgg tgg tta caa tat ttt atc acc agg gcc gag gca cac ttg    1945
Leu Ile Trp Trp Leu Gln Tyr Phe Ile Thr Arg Ala Glu Ala His Leu
         35                  40                  45
```

-continued

| | | |
|---|---|---|
| caa gtg tgg atc ccc ccc ctc aac gtt cgg ggg ggc cgc gat gcc gtc<br>Gln Val Trp Ile Pro Pro Leu Asn Val Arg Gly Gly Arg Asp Ala Val<br>     50                       55                   60 | 1993 |
| atc ctc ctc acg tgc gcg atc cac cca gag cta atc ttt acc atc acc<br>Ile Leu Leu Thr Cys Ala Ile His Pro Glu Leu Ile Phe Thr Ile Thr<br>65                      70                    75                   80 | 2041 |
| aaa atc ttg ctc gcc ata ctc ggt cca ctc atg gtg ctc cag gct ggt<br>Lys Ile Leu Leu Ala Ile Leu Gly Pro Leu Met Val Leu Gln Ala Gly<br>                   85                    90                   95 | 2089 |
| ata acc aaa gtg ccg tac ttc gtg cgc gca cac ggg ctc att cgt gca<br>Ile Thr Lys Val Pro Tyr Phe Val Arg Ala His Gly Leu Ile Arg Ala<br>            100                    105                  110 | 2137 |
| tgc atg ctg gtg cgg aag gtt gct ggg ggt cat tat gtc caa atg gct<br>Cys Met Leu Val Arg Lys Val Ala Gly Gly His Tyr Val Gln Met Ala<br>         115                   120                   125 | 2185 |
| ctc atg aag ttg gcc gca ctg aca ggt acg tac gtt tat gac cat ctc<br>Leu Met Lys Leu Ala Ala Leu Thr Gly Thr Tyr Val Tyr Asp His Leu<br>130                     135                   140 | 2233 |
| acc cca ctg cgg gac tgg gcc cac gcg ggc cta cga gac ctt gcg gtg<br>Thr Pro Leu Arg Asp Trp Ala His Ala Gly Leu Arg Asp Leu Ala Val<br>145                     150                   155                   160 | 2281 |
| gca gtt gag ccc gtc gtc ttc tct gat atg gag acc aag gtt atc acc<br>Ala Val Glu Pro Val Val Phe Ser Asp Met Glu Thr Lys Val Ile Thr<br>                        165                    170                  175 | 2329 |
| tgg ggg gca gac acc gcg gcg tgt ggg gac atc atc ttg ggc ctg ccc<br>Trp Gly Ala Asp Thr Ala Ala Cys Gly Asp Ile Ile Leu Gly Leu Pro<br>                 180                    185                  190 | 2377 |
| gtc tcc gcc cgc agg ggg agg gag ata cat ctg gga ccg gca gac agc<br>Val Ser Ala Arg Arg Gly Arg Glu Ile His Leu Gly Pro Ala Asp Ser<br>             195                    200                  205 | 2425 |
| ctt gaa ggg cag ggg tgg cga ctc ctc gcg cct att acg gcc tac tcc<br>Leu Glu Gly Gln Gly Trp Arg Leu Leu Ala Pro Ile Thr Ala Tyr Ser<br>         210                    215                  220 | 2473 |
| caa cag acg cga ggc cta ctt ggc tgc atc atc act agc ctc aca ggc<br>Gln Gln Thr Arg Gly Leu Leu Gly Cys Ile Ile Thr Ser Leu Thr Gly<br>225                     230                   235                   240 | 2521 |
| cgg gac agg aac cag gtc gag ggg gag gtc caa gtg gtc tcc acc gca<br>Arg Asp Arg Asn Gln Val Glu Gly Glu Val Gln Val Val Ser Thr Ala<br>                        245                    250                  255 | 2569 |
| aca caa tct ttc ctg gcg acc tgc gtc aat ggc gtg tgt tgg act gtc<br>Thr Gln Ser Phe Leu Ala Thr Cys Val Asn Gly Val Cys Trp Thr Val<br>                 260                    265                  270 | 2617 |
| tat cat ggt gcc ggc tca aag acc ctt gcc ggc cca aag ggc cca atc<br>Tyr His Gly Ala Gly Ser Lys Thr Leu Ala Gly Pro Lys Gly Pro Ile<br>             275                    280                  285 | 2665 |
| acc caa atg tac acc aat gtg gac cag gac ctc gtc ggc tgg caa gcg<br>Thr Gln Met Tyr Thr Asn Val Asp Gln Asp Leu Val Gly Trp Gln Ala<br>290                     295                   300 | 2713 |
| ccc ccc ggg gcg cgt tcc ttg aca cca tgc acc tgc ggc agc tcg gac<br>Pro Pro Gly Ala Arg Ser Leu Thr Pro Cys Thr Cys Gly Ser Ser Asp<br>305                     310                   315                   320 | 2761 |
| ctt tac ttg gtc acg agg cat gcc gat gtc att ccg gtg cgc cgg cgg<br>Leu Tyr Leu Val Thr Arg His Ala Asp Val Ile Pro Val Arg Arg Arg<br>                       325                    330                  335 | 2809 |
| ggc gac agc agg ggg agc cta ctc tcc ccc agg ccc gtc tcc tac ttg<br>Gly Asp Ser Arg Gly Ser Leu Leu Ser Pro Arg Pro Val Ser Tyr Leu<br>             340                    345                  350 | 2857 |
| aag ggc tct tcg ggc ggt cca ctg ctc tgc ccc tcg ggg cac gct gtg<br>Lys Gly Ser Ser Gly Gly Pro Leu Leu Cys Pro Ser Gly His Ala Val<br>         355                    360                  365 | 2905 |

```
ggc atc ttt cgg gct gcc gtg tgc acc cga ggg gtt gcg aag gcg gtg    2953
Gly Ile Phe Arg Ala Ala Val Cys Thr Arg Gly Val Ala Lys Ala Val
        370                 375                 380 gac ttt gta ccc gtc gag tct atg gaa acc act atg cgg tcc ccg gtc    3001
Asp Phe Val Pro Val Glu Ser Met Glu Thr Thr Met Arg Ser Pro Val
385                 390                 395                 400 ttc acg gac aac tcg tcc cct ccg gcc gta ccg cag aca ttc cag gtg    3049
Phe Thr Asp Asn Ser Ser Pro Pro Ala Val Pro Gln Thr Phe Gln Val
                405                 410                 415 gcc cat cta cac gcc cct act ggt agc ggc aag agc act aag gtg ccg    3097
Ala His Leu His Ala Pro Thr Gly Ser Gly Lys Ser Thr Lys Val Pro
        420                 425                 430 gct gcg tat gca gcc caa ggg tat aag gtg ctt gtc ctg aac ccg tcc    3145
Ala Ala Tyr Ala Ala Gln Gly Tyr Lys Val Leu Val Leu Asn Pro Ser
        435                 440                 445 gtc gcc gcc acc cta ggt ttc ggg gcg tat atg tct aag gca cat ggt    3193
Val Ala Ala Thr Leu Gly Phe Gly Ala Tyr Met Ser Lys Ala His Gly
450                 455                 460 atc gac cct aac atc aga acc ggg gta agg acc atc acg acg ggt gcc    3241
Ile Asp Pro Asn Ile Arg Thr Gly Val Arg Thr Ile Thr Thr Gly Ala
465                 470                 475                 480 ccc atc acg tac tcc acc tat ggc aag ttt ctt gcc gac ggt ggt tgc    3289
Pro Ile Thr Tyr Ser Thr Tyr Gly Lys Phe Leu Ala Asp Gly Gly Cys
                485                 490                 495 tct ggg ggc gcc tat gac atc ata ata tgt gat gag tgc cac tca act    3337
Ser Gly Gly Ala Tyr Asp Ile Ile Ile Cys Asp Glu Cys His Ser Thr
        500                 505                 510 gac tcg acc act atc ctg ggc atc ggc aca gtc ctg gac caa gcg gag    3385
Asp Ser Thr Thr Ile Leu Gly Ile Gly Thr Val Leu Asp Gln Ala Glu
        515                 520                 525 acg gct gga gcg cga ctc gtc gtg ctc gcc acc gct acg cct ccg gga    3433
Thr Ala Gly Ala Arg Leu Val Val Leu Ala Thr Ala Thr Pro Pro Gly
530                 535                 540 tcg gtc acc gtg cca cat cca aac atc gag gag gtg gct ctg tcc agc    3481
Ser Val Thr Val Pro His Pro Asn Ile Glu Glu Val Ala Leu Ser Ser
545                 550                 555                 560 act gga gaa atc ccc ttt tat ggc aaa gcc atc ccc atc gag acc atc    3529
Thr Gly Glu Ile Pro Phe Tyr Gly Lys Ala Ile Pro Ile Glu Thr Ile
                565                 570                 575 aag ggg ggg agg cac ctc att ttc tgc cat tcc aag aag aaa tgt gat    3577
Lys Gly Gly Arg His Leu Ile Phe Cys His Ser Lys Lys Lys Cys Asp
                580                 585                 590 gag ctc gcc gcg aag ctg tcc ggc ctc gga ctc aat gct gta gca tat    3625
Glu Leu Ala Ala Lys Leu Ser Gly Leu Gly Leu Asn Ala Val Ala Tyr
        595                 600                 605 tac cgg ggc ctt gat gta tcc gtc ata cca act agc gga gac gtc att    3673
Tyr Arg Gly Leu Asp Val Ser Val Ile Pro Thr Ser Gly Asp Val Ile
610                 615                 620 gtc gta gca acg gac gct cta atg acg ggc ttt acc ggc gat ttc gac    3721
Val Val Ala Thr Asp Ala Leu Met Thr Gly Phe Thr Gly Asp Phe Asp
625                 630                 635                 640 tca gtg atc gac tgc aat aca tgt gtc acc cag aca gtc gac ttc agc    3769
Ser Val Ile Asp Cys Asn Thr Cys Val Thr Gln Thr Val Asp Phe Ser
                645                 650                 655 ctg gac ccg acc ttc acc att gag acg acg acc gtg cca caa gac gcg    3817
Leu Asp Pro Thr Phe Thr Ile Glu Thr Thr Thr Val Pro Gln Asp Ala
                660                 665                 670 gtg tca cgc tcg cag cgg cga ggc agg act ggt agg ggc agg atg ggc    3865
Val Ser Arg Ser Gln Arg Arg Gly Arg Thr Gly Arg Gly Arg Met Gly
```

```
                    675                  680                   685
att tac agg ttt gtg act cca gga gaa cgg ccc tcg ggc atg ttc gat    3913
Ile Tyr Arg Phe Val Thr Pro Gly Glu Arg Pro Ser Gly Met Phe Asp
    690                  695                   700 tcc tcg gtt ctg tgc gag tgc tat gac gcg ggc tgt gct tgg tac gag    3961
Ser Ser Val Leu Cys Glu Cys Tyr Asp Ala Gly Cys Ala Trp Tyr Glu
705                  710                   715                  720 ctc acg ccc gcc gag acc tca gtt agg ttg cgg gct tac cta aac aca    4009
Leu Thr Pro Ala Glu Thr Ser Val Arg Leu Arg Ala Tyr Leu Asn Thr
                725                  730                   735 cca ggg ttg ccc gtc tgc cag gac cat ctg gag ttc tgg gag agc gtc    4057
Pro Gly Leu Pro Val Cys Gln Asp His Leu Glu Phe Trp Glu Ser Val
            740                  745                   750 ttt aca ggc ctc acc cac ata gac gcc cat ttc ttg tcc cag act aag    4105
Phe Thr Gly Leu Thr His Ile Asp Ala His Phe Leu Ser Gln Thr Lys
        755                  760                   765 cag gca gga gac aac ttc ccc tac ctg gta gca tac cag gct acg gtg    4153
Gln Ala Gly Asp Asn Phe Pro Tyr Leu Val Ala Tyr Gln Ala Thr Val
    770                  775                   780 tgc gcc agg gct cag gct cca cct cca tcg tgg gac caa atg tgg aag    4201
Cys Ala Arg Ala Gln Ala Pro Pro Pro Ser Trp Asp Gln Met Trp Lys
785                  790                   795                  800 tgt ctc ata cgg cta aag cct acg ctg cac ggg cca acg ccc ctg ctg    4249
Cys Leu Ile Arg Leu Lys Pro Thr Leu His Gly Pro Thr Pro Leu Leu
                805                  810                   815 tat agg ctg gga gcc gtt caa aac gag gtt act acc aca cac ccc ata    4297
Tyr Arg Leu Gly Ala Val Gln Asn Glu Val Thr Thr Thr His Pro Ile
            820                  825                   830 acc aaa tac atc atg gca tgc atg tcg gct gac ctg gag gtc gtc acg    4345
Thr Lys Tyr Ile Met Ala Cys Met Ser Ala Asp Leu Glu Val Val Thr
        835                  840                   845 agc acc tgg gtg ctg gta ggc gga gtc cta gca gct ctg gcc gcg tat    4393
Ser Thr Trp Val Leu Val Gly Gly Val Leu Ala Ala Leu Ala Ala Tyr
    850                  855                   860 tgc ctg aca aca ggc agc gtg gtc att gtg ggc agg atc atc ttg tcc    4441
Cys Leu Thr Thr Gly Ser Val Val Ile Val Gly Arg Ile Ile Leu Ser
865                  870                   875                  880 gga aag ccg gcc atc att ccc gac agg gaa gtc ctt tac cgg gag ttc    4489
Gly Lys Pro Ala Ile Ile Pro Asp Arg Glu Val Leu Tyr Arg Glu Phe
                885                  890                   895 gat gag atg gaa gag tgc gcc tca cac ctc cct tac atc gaa cag gga    4537
Asp Glu Met Glu Glu Cys Ala Ser His Leu Pro Tyr Ile Glu Gln Gly
            900                  905                   910 atg cag ctc gcc gaa caa ttc aaa cag aag gca atc ggg ttg ctg caa    4585
Met Gln Leu Ala Glu Gln Phe Lys Gln Lys Ala Ile Gly Leu Leu Gln
        915                  920                   925 aca gcc acc aag caa gcg gag gct gct gct ccc gtg gtg gaa tcc aag    4633
Thr Ala Thr Lys Gln Ala Glu Ala Ala Ala Pro Val Val Glu Ser Lys
    930                  935                   940 tgg cgg acc ctc gaa gcc ttc tgg gcg aag cat atg tgg aat ttc atc    4681
Trp Arg Thr Leu Glu Ala Phe Trp Ala Lys His Met Trp Asn Phe Ile
945                  950                   955                  960 agc ggg ata caa tat tta gca ggc ttg tcc act ctg cct ggc aac ccc    4729
Ser Gly Ile Gln Tyr Leu Ala Gly Leu Ser Thr Leu Pro Gly Asn Pro
                965                  970                   975 gcg ata gca tca ctg atg gca ttc aca gcc tct atc acc agc ccg ctc    4777
Ala Ile Ala Ser Leu Met Ala Phe Thr Ala Ser Ile Thr Ser Pro Leu
            980                  985                   990 acc acc caa cat acc ctc ctg ttt aac atc ctg ggg gga tgg gtg gcc    4825
```

```
Thr Thr Gln His Thr Leu Leu Phe Asn Ile Leu Gly Gly Trp Val Ala
            995                 1000                1005 gcc caa ctt gct cct ccc agc gct gct tct gct ttc gta ggc gcc ggc        4873
Ala Gln Leu Ala Pro Pro Ser Ala Ala Ser Ala Phe Val Gly Ala Gly
1010                1015                1020 atc gct gga gcg gct gtt ggc agc ata ggc ctt ggg aag gtg ctt gtg        4921
Ile Ala Gly Ala Ala Val Gly Ser Ile Gly Leu Gly Lys Val Leu Val
1025                1030                1035                1040 gat att ttg gca ggt tat gga gca ggg gtg gca ggc gcg ctc gtg gcc        4969
Asp Ile Leu Ala Gly Tyr Gly Ala Gly Val Ala Gly Ala Leu Val Ala
                1045                1050                1055 ttt aag gtc atg agc ggc gag atg ccc tcc acc gag gac ctg gtt aac        5017
Phe Lys Val Met Ser Gly Glu Met Pro Ser Thr Glu Asp Leu Val Asn
                1060                1065                1070 cta ctc cct gct atc ctc tcc cct ggc gcc cta gtc gtc ggg gtc gtg        5065
Leu Leu Pro Ala Ile Leu Ser Pro Gly Ala Leu Val Val Gly Val Val
                1075                1080                1085 tgc gca gcg ata ctg cgt cgg cac gtg ggc cca ggg gag ggg gct gtg        5113
Cys Ala Ala Ile Leu Arg Arg His Val Gly Pro Gly Glu Gly Ala Val
                1090                1095                1100 cag tgg atg aac cgg ctg ata gcg ttc gct tcg cgg ggt aac cac gtc        5161
Gln Trp Met Asn Arg Leu Ile Ala Phe Ala Ser Arg Gly Asn His Val
1105                1110                1115                1120 tcc ccc acg cac tat gtg cct gag agc gac gct gca gca cgt gtc act        5209
Ser Pro Thr His Tyr Val Pro Glu Ser Asp Ala Ala Ala Arg Val Thr
                1125                1130                1135 cag atc ctc tct agt ctt acc atc act cag ctg ctg aag agg ctt cac        5257
Gln Ile Leu Ser Ser Leu Thr Ile Thr Gln Leu Leu Lys Arg Leu His
                1140                1145                1150 cag tgg atc aac gag gac tgc tcc acg cca tgc tcc ggc tcg tgg cta        5305
Gln Trp Ile Asn Glu Asp Cys Ser Thr Pro Cys Ser Gly Ser Trp Leu
                1155                1160                1165 aga gat gtt tgg gat tgg ata tgc acg gtg ttg act gat ttc aag acc        5353
Arg Asp Val Trp Asp Trp Ile Cys Thr Val Leu Thr Asp Phe Lys Thr
1170                1175                1180 tgg ctc cag tcc aag ctc ctg ccg cga ttg ccg gga gtc ccc ttc ttc        5401
Trp Leu Gln Ser Lys Leu Leu Pro Arg Leu Pro Gly Val Pro Phe Phe
1185                1190                1195                1200 tca tgt caa cgt ggg tac aag gga gtc tgg cgg ggc gac ggc atc atg        5449
Ser Cys Gln Arg Gly Tyr Lys Gly Val Trp Arg Gly Asp Gly Ile Met
                1205                1210                1215 caa acc acc tgc cca tgt gga gca cag atc acc gga cat gtg aaa aac        5497
Gln Thr Thr Cys Pro Cys Gly Ala Gln Ile Thr Gly His Val Lys Asn
                1220                1225                1230 ggt tcc atg agg atc gtg ggg cct agg acc tgt agt aac acg tgg cat        5545
Gly Ser Met Arg Ile Val Gly Pro Arg Thr Cys Ser Asn Thr Trp His
                1235                1240                1245 gga aca ttc ccc att aac gcg tac acc acg ggc ccc tgc acg ccc tcc        5593
Gly Thr Phe Pro Ile Asn Ala Tyr Thr Thr Gly Pro Cys Thr Pro Ser
                1250                1255                1260 ccg gcg cca aat tat tct agg gcg ctg tgg cgg gtg gct gct gag gag        5641
Pro Ala Pro Asn Tyr Ser Arg Ala Leu Trp Arg Val Ala Ala Glu Glu
1265                1270                1275                1280 tac gtg gag gtt acg cgg gtg ggg gat ttc cac tac gtg acg ggc atg        5689
Tyr Val Glu Val Thr Arg Val Gly Asp Phe His Tyr Val Thr Gly Met
                1285                1290                1295 acc act gac aac gta aag tgc ccg tgt cag gtt ccg gcc ccc gaa ttc        5737
Thr Thr Asp Asn Val Lys Cys Pro Cys Gln Val Pro Ala Pro Glu Phe
                1300                1305                1310
```

-continued

| | |
|---|---|
| ttc aca gaa gtg gat ggg gtg cgg ttg cac agg tac gct cca gcg tgc<br>Phe Thr Glu Val Asp Gly Val Arg Leu His Arg Tyr Ala Pro Ala Cys<br>    1315                   1320                  1325 | 5785 |
| aaa ccc ctc cta cgg gag gag gtc aca ttc ctg gtc ggg ctc aat caa<br>Lys Pro Leu Leu Arg Glu Glu Val Thr Phe Leu Val Gly Leu Asn Gln<br>1330                   1335                   1340 | 5833 |
| tac ctg gtt ggg tca cag ctc cca tgc gag ccc gaa ccg gac gta gca<br>Tyr Leu Val Gly Ser Gln Leu Pro Cys Glu Pro Glu Pro Asp Val Ala<br>1345                   1350                   1355               1360 | 5881 |
| gtg ctc act tcc atg ctc acc gac ccc tcc cac att acg gcg gag acg<br>Val Leu Thr Ser Met Leu Thr Asp Pro Ser His Ile Thr Ala Glu Thr<br>               1365                   1370                  1375 | 5929 |
| gct aag cgt agg ctg gcc agg gga tct ccc ccc tcc ttg gcc agc tca<br>Ala Lys Arg Arg Leu Ala Arg Gly Ser Pro Pro Ser Leu Ala Ser Ser<br>1380                   1385                   1390 | 5977 |
| tca gct agc cag ctg tct gcg cct tcc ttg aag gca aca tgc act acc<br>Ser Ala Ser Gln Leu Ser Ala Pro Ser Leu Lys Ala Thr Cys Thr Thr<br>    1395                   1400                  1405 | 6025 |
| cgt cat gac tcc ccg gac gct gac ctc atc gag gcc aac ctc ctg tgg<br>Arg His Asp Ser Pro Asp Ala Asp Leu Ile Glu Ala Asn Leu Leu Trp<br>1410                   1415                   1420 | 6073 |
| cgg cag gag atg ggc ggg aac atc acc cgc gtg gag tca gaa aat aag<br>Arg Gln Glu Met Gly Gly Asn Ile Thr Arg Val Glu Ser Glu Asn Lys<br>1425                   1430                   1435               1440 | 6121 |
| gta gta att ttg gac tct ttc gag ccg ctc caa gcg gag gag gat gag<br>Val Val Ile Leu Asp Ser Phe Glu Pro Leu Gln Ala Glu Glu Asp Glu<br>               1445                   1450                  1455 | 6169 |
| agg gaa gta tcc gtt ccg gcg gag atc ctg cgg agg tcc agg aaa ttc<br>Arg Glu Val Ser Val Pro Ala Glu Ile Leu Arg Arg Ser Arg Lys Phe<br>                   1460                   1465                  1470 | 6217 |
| cct cga gcg atg ccc ata tgg gca cgc ccg gat tac aac cct cca ctg<br>Pro Arg Ala Met Pro Ile Trp Ala Arg Pro Asp Tyr Asn Pro Pro Leu<br>1475                   1480                   1485 | 6265 |
| tta gag tcc tgg aag gac ccg gac tac gtc cct cca gtg gta cac ggg<br>Leu Glu Ser Trp Lys Asp Pro Asp Tyr Val Pro Pro Val Val His Gly<br>    1490                   1495                  1500 | 6313 |
| tgt cca ttg ccg cct gcc aag gcc cct ccg ata cca cct cca cgg agg<br>Cys Pro Leu Pro Pro Ala Lys Ala Pro Pro Ile Pro Pro Pro Arg Arg<br>1505                   1510                   1515               1520 | 6361 |
| aag agg acg gtt gtc ctg tca gaa tct acc gtg tct tct gcc ttg gcg<br>Lys Arg Thr Val Val Leu Ser Glu Ser Thr Val Ser Ser Ala Leu Ala<br>               1525                   1530                  1535 | 6409 |
| gag ctc gcc aca aag acc ttc ggc agc tcc gaa tcg tcg gcc gtc gac<br>Glu Leu Ala Thr Lys Thr Phe Gly Ser Ser Glu Ser Ser Ala Val Asp<br>               1540                   1545                  1550 | 6457 |
| agc ggc acg gca acg gcc tct cct gac cag ccc tcc gac gac ggc gac<br>Ser Gly Thr Ala Thr Ala Ser Pro Asp Gln Pro Ser Asp Asp Gly Asp<br>    1555                   1560                  1565 | 6505 |
| gcg gga tcc gac gtt gag tcg tac tcc tcc atg ccc ccc ctt gag ggg<br>Ala Gly Ser Asp Val Glu Ser Tyr Ser Ser Met Pro Pro Leu Glu Gly<br>1570                   1575                   1580 | 6553 |
| gag ccg ggg gat ccc gat ctc agc gac ggg tct tgg tct acc gta agc<br>Glu Pro Gly Asp Pro Asp Leu Ser Asp Gly Ser Trp Ser Thr Val Ser<br>1585                   1590                   1595               1600 | 6601 |
| gag gag gct agt gag gac gtc gtc tgc tgc tcg atg tcc tac aca tgg<br>Glu Glu Ala Ser Glu Asp Val Val Cys Cys Ser Met Ser Tyr Thr Trp<br>               1605                   1610                  1615 | 6649 |
| aca ggc gcc ctg atc acg cca tgc gct gcg gag gaa acc aag ctg ccc<br>Thr Gly Ala Leu Ile Thr Pro Cys Ala Ala Glu Glu Thr Lys Leu Pro<br>                   1620                   1625                  1630 | 6697 |

```
atc aat gca ctg agc aac tct ttg ctc cgt cac cac aac ttg gtc tat      6745
Ile Asn Ala Leu Ser Asn Ser Leu Leu Arg His His Asn Leu Val Tyr
        1635                1640                1645 gct aca aca tct cgc agc gca agc ctg cgg cag aag aag gtc acc ttt      6793
Ala Thr Thr Ser Arg Ser Ala Ser Leu Arg Gln Lys Lys Val Thr Phe
1650                1655                1660 gac aga ctg cag gtc ctg gac gac cac tac cgg gac gtg ctc aag gag      6841
Asp Arg Leu Gln Val Leu Asp Asp His Tyr Arg Asp Val Leu Lys Glu
1665                1670                1675                1680 atg aag gcg aag gcg tcc aca gtt aag gct aaa ctt cta tcc gtg gag      6889
Met Lys Ala Lys Ala Ser Thr Val Lys Ala Lys Leu Leu Ser Val Glu
        1685                1690                1695 gaa gcc tgt aag ctg acg ccc cca cat tcg gcc aga tct aaa ttt ggc      6937
Glu Ala Cys Lys Leu Thr Pro Pro His Ser Ala Arg Ser Lys Phe Gly
    1700                1705                1710 tat ggg gca aag gac gtc cgg aac cta tcc agc aag gcc gtt aac cac      6985
Tyr Gly Ala Lys Asp Val Arg Asn Leu Ser Ser Lys Ala Val Asn His
        1715                1720                1725 atc cgc tcc gtg tgg aag gac ttg ctg gaa gac act gag aca cca att      7033
Ile Arg Ser Val Trp Lys Asp Leu Leu Glu Asp Thr Glu Thr Pro Ile
        1730                1735                1740 gac acc acc atc atg gca aaa aat gag gtt ttc tgc gtc caa cca gag      7081
Asp Thr Thr Ile Met Ala Lys Asn Glu Val Phe Cys Val Gln Pro Glu
1745                1750                1755                1760 aag ggg ggc cgc aag cca gct cgc ctt atc gta ttc cca gat ttg ggg      7129
Lys Gly Gly Arg Lys Pro Ala Arg Leu Ile Val Phe Pro Asp Leu Gly
        1765                1770                1775 gtt cgt gtg tgc gag aaa atg gcc ctt tac gat gtg gtc tcc acc ctc      7177
Val Arg Val Cys Glu Lys Met Ala Leu Tyr Asp Val Val Ser Thr Leu
        1780                1785                1790 cct cag gcc gtg atg ggc tct tca tac gga ttc caa tac tct cct gga      7225
Pro Gln Ala Val Met Gly Ser Ser Tyr Gly Phe Gln Tyr Ser Pro Gly
        1795                1800                1805 cag cgg gtc gag ttc ctg gtg aat gcc tgg aaa gcg aag aaa tgc cct      7273
Gln Arg Val Glu Phe Leu Val Asn Ala Trp Lys Ala Lys Lys Cys Pro
1810                1815                1820 atg ggc ttc gca tat gac acc cgc tgt ttt gac tca acg gtc act gag      7321
Met Gly Phe Ala Tyr Asp Thr Arg Cys Phe Asp Ser Thr Val Thr Glu
1825                1830                1835                1840 aat gac atc cgt gtt gag gag tca atc tac caa tgt tgt gac ttg gcc      7369
Asn Asp Ile Arg Val Glu Glu Ser Ile Tyr Gln Cys Cys Asp Leu Ala
        1845                1850                1855 ccc gaa gcc aga cag gcc ata agg tcg ctc aca gag cgg ctt tac atc      7417
Pro Glu Ala Arg Gln Ala Ile Arg Ser Leu Thr Glu Arg Leu Tyr Ile
1860                1865                1870 ggg ggc ccc ctg act aat tct aaa ggg cag aac tgc ggc tat cgc cgg      7465
Gly Gly Pro Leu Thr Asn Ser Lys Gly Gln Asn Cys Gly Tyr Arg Arg
        1875                1880                1885 tgc cgc gcg agc ggt gta ctg acg acc agc tgc ggt aat acc ctc aca      7513
Cys Arg Ala Ser Gly Val Leu Thr Thr Ser Cys Gly Asn Thr Leu Thr
        1890                1895                1900 tgt tac ttg aag gcc gct gcg gcc tgt cga gct gcg aag ctc cag gac      7561
Cys Tyr Leu Lys Ala Ala Ala Ala Cys Arg Ala Ala Lys Leu Gln Asp
1905                1910                1915                1920 tgc acg atg ctc gta tgc gga gac gac ctt gtc gtt atc tgt gaa agc      7609
Cys Thr Met Leu Val Cys Gly Asp Asp Leu Val Val Ile Cys Glu Ser
        1925                1930                1935 gcg ggg acc caa gag gac gag gcg agc cta cgg gcc ttc acg gag gct      7657
Ala Gly Thr Gln Glu Asp Glu Ala Ser Leu Arg Ala Phe Thr Glu Ala
```

```
atg act aga tac tct gcc ccc cct ggg gac ccg ccc aaa cca gaa tac      7705
Met Thr Arg Tyr Ser Ala Pro Pro Gly Asp Pro Pro Lys Pro Glu Tyr
        1955            1960            1965 gac ttg gag ttg ata aca tca tgc tcc tcc aat gtg tca gtc gcg cac      7753
Asp Leu Glu Leu Ile Thr Ser Cys Ser Ser Asn Val Ser Val Ala His
    1970            1975            1980 gat gca tct ggc aaa agg gtg tac tat ctc acc cgt gac ccc acc acc      7801
Asp Ala Ser Gly Lys Arg Val Tyr Tyr Leu Thr Arg Asp Pro Thr Thr
1985            1990            1995            2000 ccc ctt gcg cgg gct gcg tgg gag aca gct aga cac act cca gtc aat      7849
Pro Leu Ala Arg Ala Ala Trp Glu Thr Ala Arg His Thr Pro Val Asn
            2005            2010            2015 tcc tgg cta ggc aac atc atc atg tat gcg ccc acc ttg tgg gca agg      7897
Ser Trp Leu Gly Asn Ile Ile Met Tyr Ala Pro Thr Leu Trp Ala Arg
        2020            2025            2030 atg atc ctg atg act cat ttc ttc tcc atc ctt cta gct cag gaa caa      7945
Met Ile Leu Met Thr His Phe Phe Ser Ile Leu Leu Ala Gln Glu Gln
    2035            2040            2045 ctt gaa aaa gcc cta gat tgt cag atc tac ggg gcc tgt tac tcc att      7993
Leu Glu Lys Ala Leu Asp Cys Gln Ile Tyr Gly Ala Cys Tyr Ser Ile
2050            2055            2060 gag cca ctt gac cta cct cag atc att caa cga ctc cac ggc ctt agc      8041
Glu Pro Leu Asp Leu Pro Gln Ile Ile Gln Arg Leu His Gly Leu Ser
2065            2070            2075            2080 gca ttt tca ctc cat agt tac tct cca ggt gag atc aat agg gtg gct      8089
Ala Phe Ser Leu His Ser Tyr Ser Pro Gly Glu Ile Asn Arg Val Ala
            2085            2090            2095 tca tgc ctc agg aaa ctt ggg gta ccg ccc ttg cga gtc tgg aga cat      8137
Ser Cys Leu Arg Lys Leu Gly Val Pro Pro Leu Arg Val Trp Arg His
        2100            2105            2110 cgg gcc aga agt gtc cgc gct agg cta ctg tcc cag ggg ggg agg gct      8185
Arg Ala Arg Ser Val Arg Ala Arg Leu Leu Ser Gln Gly Gly Arg Ala
    2115            2120            2125 gcc act tgt ggc aag tac ctc ttc aac tgg gca gta agg acc aag ctc      8233
Ala Thr Cys Gly Lys Tyr Leu Phe Asn Trp Ala Val Arg Thr Lys Leu
2130            2135            2140 aaa ctc act cca atc ccg gct gcg tcc cag ttg gat tta tcc agc tgg      8281
Lys Leu Thr Pro Ile Pro Ala Ala Ser Gln Leu Asp Leu Ser Ser Trp
2145            2150            2155            2160 ttc gtt gct ggt tac agc ggg gga gac ata tat cac agc ctg tct cgt      8329
Phe Val Ala Gly Tyr Ser Gly Gly Asp Ile Tyr His Ser Leu Ser Arg
            2165            2170            2175 gcc cga ccc cgc tgg ttc atg tgg tgc cta ctc cta ctt tct gta ggg      8377
Ala Arg Pro Arg Trp Phe Met Trp Cys Leu Leu Leu Ser Val Gly
        2180            2185            2190 gta ggc atc tat cta ctc ccc aac cga tga acggggagct aaacactcca       8427
Val Gly Ile Tyr Leu Leu Pro Asn Arg *
    2195            2200 ggccaatagg ccatcctgtt ttttcccctt tttttttttc tttttttttt tttttttttt   8487
tttttttttt ttttctcctt tttttttcct ctttttttcc ttttctttcc tttggtggct   8547
ccatcttagc cctagtcacg gctagctgtg aaaggtccgt gagccgcttg actgcagaga   8607
gtgctgatac tggcctctct gcagatcaag t                                  8638

<210> SEQ ID NO 25
<211> LENGTH: 8638
<212> TYPE: DNA
<213> ORGANISM: HCV
```

```
<220> FEATURE:
<221> NAME/KEY: CDS
<222> LOCATION: (1802)...(8407)

<400> SEQUENCE: 25
accagccccc gattgggggc gacactccac catagatcac tccoctgtga ggaactactg      60 tcttcacgca gaaagcgtct agccatggcg ttagtatgag tgtcgtgcag cctccaggac     120 ccccoctccc gggagagcca tagtggtctg cggaaccggt gagtacaccg gaattgccag     180
gacgaccggg tcctttcttg gatcaacccg ctcaatgcct ggagatttgg gcgtgccccc     240
gcgagactgc tagccgagta gtgttgggtc gcgaaaggcc ttgtggtact gcctgatagg     300
gtgcttgcga gtgccccggg aggtctcgta gaccgtgcac catgagcacg aatcctaaac     360
ctcaaagaaa aaccaaaggg cgcgccatga ttgaacaaga tggattgcac gcaggttctc     420
cggccgcttg ggtggagagg ctattcggct atgactgggc acaacagaca atcggctgct     480
ctgatgccgc cgtgttccgg ctgtcagcgc aggggcgccc ggttcttttt gtcaagaccg     540
acctgtccgg tgccctgaat gaactgcagg acgaggcagc gcggctatcg tggctggcca     600
cgacgggcgt tccttgcgca gctgtgctcg acgttgtcac tgaagcggga agggactggc     660
tgctattggg cgaagtgccg gggcaggatc tcctgtcatc tcaccttgct cctgccgaga     720
aagtatccat catggctgat gcaatgcggc ggctgcatac gcttgatccg gctacctgcc     780
cattcgacca ccaagcgaaa catcgcatcg agcgagcacg tactcggatg gaagccggtc     840
ttgtcgatca ggatgatctg gacgaagagc atcaggggct cgcgccagcc gaactgttcg     900
ccaggctcaa ggcgcgcatg cccgacggcg aggatctcgt cgtgacccat ggcgatgcct     960
gcttgccgaa tatcatggtg gaaaatggcc gcttttctgg attcatcgac tgtggccggc    1020
tgggtgtggc ggaccgctat caggacatag cgttggctac ccgtgatatt gctgaagagc    1080
ttggcggcga atgggctgac cgcttcctcg tgctttacgg tatcgccgct cccgattcgc    1140
agcgcatcgc cttctatcgc cttcttgacg agttcttctg agttcgcgcc cagatgttaa    1200
cagaccacaa cggtttccct ctagcgggat caattccgcc cccccccta acgttactgg    1260 ccgaagccgc ttggaataag gccggtgtgc gtttgtctat atgttatttt ccaccatatt    1320
gccgtctttt ggcaatgtga gggcccggaa acctggccct gtcttcttga cgagcattcc    1380 tagggggtctt tcccctctcg ccaaaggaat gcaaggtctg ttgaatgtcg tgaaggaagc    1440
agttcctctg gaagcttctt gaagacaaac aacgtctgta gcgacccttt gcaggcagcg    1500 gaaccccccca cctggcgaca ggtgcctctg cggccaaaag ccacgtgtat aagatacacc    1560
tgcaaaggcg gcacaacccc agtgccacgt tgtgagttgg atagttgtgg aaagagtcaa    1620
atggctctcc tcaagcgtat tcaacaaggg gctgaaggat gcccagaagg taccccattg    1680
tatgggatct gatctggggc ctcggtgcac atgctttaca tgtgtttagt cgaggttaaa    1740
aaacgtctag gccccccgaa ccacggggac gtggttttcc tttgaaaaac acgataatac    1800 c atg gac cgg gag atg gca gca tcg tgc gga ggc gcg gtt ttc gta ggt    1849
  Met Asp Arg Glu Met Ala Ala Ser Cys Gly Gly Ala Val Phe Val Gly
   1               5                  10                  15
ctg ata ctc ttg acc ttg tca ccg cac tat aag ctg ttc ctc gct agg       1897
Leu Ile Leu Leu Thr Leu Ser Pro His Tyr Lys Leu Phe Leu Ala Arg
             20                  25                  30
ctc ata tgg tgg tta caa tat ttt atc acc agg gcc gag gca cac ttg       1945
Leu Ile Trp Trp Leu Gln Tyr Phe Ile Thr Arg Ala Glu Ala His Leu
         35                  40                  45
caa gtg tgg atc ccc ccc ctc aac gtt cgg ggg ggc cgc gat gcc gtc       1993
Gln Val Trp Ile Pro Pro Leu Asn Val Arg Gly Gly Arg Asp Ala Val
```

```
            50                  55                  60
atc ctc ctc acg tgc gcg atc cac cca gag cta atc ttt acc atc acc    2041
Ile Leu Leu Thr Cys Ala Ile His Pro Glu Leu Ile Phe Thr Ile Thr
 65                  70                  75                  80 aaa atc ttg ctc gcc ata ctc ggt cca ctc atg gtg ctc cag gct ggt    2089
Lys Ile Leu Leu Ala Ile Leu Gly Pro Leu Met Val Leu Gln Ala Gly
                 85                  90                  95 ata acc aaa gtg ccg tac ttc gtg cgc gca cac ggg ctc att cgt gca    2137
Ile Thr Lys Val Pro Tyr Phe Val Arg Ala His Gly Leu Ile Arg Ala
            100                 105                 110 tgc atg ctg gtg cgg aag gtt gct ggg ggt cat tat gtc caa atg gct    2185
Cys Met Leu Val Arg Lys Val Ala Gly Gly His Tyr Val Gln Met Ala
        115                 120                 125 ctc atg aag ttg gcc gca ctg aca ggt acg tac gtt tat gac cat ctc    2233
Leu Met Lys Leu Ala Ala Leu Thr Gly Thr Tyr Val Tyr Asp His Leu
    130                 135                 140 acc cca ctg cgg gac tgg gcc cac gcg ggc cta cga gac ctt gcg gtg    2281
Thr Pro Leu Arg Asp Trp Ala His Ala Gly Leu Arg Asp Leu Ala Val
145                 150                 155                 160 gca gtt gag ccc gtc gtc ttc tct gat atg gag acc aag gtt atc acc    2329
Ala Val Glu Pro Val Val Phe Ser Asp Met Glu Thr Lys Val Ile Thr
                165                 170                 175 tgg ggg gca gac acc gcg gcg tgt ggg gac atc atc ttg ggc ctg ccc    2377
Trp Gly Ala Asp Thr Ala Ala Cys Gly Asp Ile Ile Leu Gly Leu Pro
            180                 185                 190 gtc tcc gcc cgc agg ggg agg gag ata cat ctg gga ccg gca gac agc    2425
Val Ser Ala Arg Arg Gly Arg Glu Ile His Leu Gly Pro Ala Asp Ser
        195                 200                 205 ctt gaa ggg cag ggg tgg cga ctc ctc gcg cct att acg gcc tac tcc    2473
Leu Glu Gly Gln Gly Trp Arg Leu Leu Ala Pro Ile Thr Ala Tyr Ser
    210                 215                 220 caa cag acg cga ggc cta ctt ggc tgc atc atc acc agc ctc aca ggc    2521
Gln Gln Thr Arg Gly Leu Leu Gly Cys Ile Ile Thr Ser Leu Thr Gly
225                 230                 235                 240 cgg gac agg aac cag gtc gag ggg gag gtc caa gtg gtc tcc acc gca    2569
Arg Asp Arg Asn Gln Val Glu Gly Glu Val Gln Val Val Ser Thr Ala
                245                 250                 255 aca caa tct ttc ctg gcg acc tgc gtc aat ggc gtg tgt tgg act gtc    2617
Thr Gln Ser Phe Leu Ala Thr Cys Val Asn Gly Val Cys Trp Thr Val
            260                 265                 270 tat cat ggt gcc ggc tca aag acc ctt gcc ggc cca aag ggc cca atc    2665
Tyr His Gly Ala Gly Ser Lys Thr Leu Ala Gly Pro Lys Gly Pro Ile
        275                 280                 285 acc caa atg tac acc aat gtg gac cag gac ctc gtc ggc tgg caa gcg    2713
Thr Gln Met Tyr Thr Asn Val Asp Gln Asp Leu Val Gly Trp Gln Ala
    290                 295                 300 ccc ccc ggg gcg cgt tcc ttg aca cca tgc acc tgc ggc agc tcg gac    2761
Pro Pro Gly Ala Arg Ser Leu Thr Pro Cys Thr Cys Gly Ser Ser Asp
305                 310                 315                 320 ctt tac ttg gtc acg aag cat gcc gat gtc att ccg gtg cgc cgg cgg    2809
Leu Tyr Leu Val Thr Lys His Ala Asp Val Ile Pro Val Arg Arg Arg
                325                 330                 335 ggc gac agc agg ggg agc cta ctc tcc ccc agg ccc gtc tcc tac ttg    2857
Gly Asp Ser Arg Gly Ser Leu Leu Ser Pro Arg Pro Val Ser Tyr Leu
            340                 345                 350 aag ggc tct tcg ggc ggt cca ctg ctc tgc ccc tcg ggg cac gct gtg    2905
Lys Gly Ser Ser Gly Gly Pro Leu Leu Cys Pro Ser Gly His Ala Val
        355                 360                 365 ggc atc ttt cgg gct gcc gtg tgc acc cga ggg gtt gcg aag gcg gtg    2953
```

```
Gly Ile Phe Arg Ala Ala Val Cys Thr Arg Gly Val Ala Lys Ala Val
    370             375             380 gac ttt gta ccc gtc gag tct atg gaa acc act atg cgg tcc ccg gtc      3001
Asp Phe Val Pro Val Glu Ser Met Glu Thr Thr Met Arg Ser Pro Val
385             390             395             400 ttc acg gac aac tcg tcc cct ccg gcc gta ccg cag aca ttc cag gtg      3049
Phe Thr Asp Asn Ser Ser Pro Pro Ala Val Pro Gln Thr Phe Gln Val
                405             410             415 gcc cat cta cac gcc cct act ggt agc ggc aag agc act aag gtg ccg      3097
Ala His Leu His Ala Pro Thr Gly Ser Gly Lys Ser Thr Lys Val Pro
            420             425             430 gct gcg tat gca gcc caa ggg tat aag gtg ctt gtc ctg aac ccg tcc      3145
Ala Ala Tyr Ala Ala Gln Gly Tyr Lys Val Leu Val Leu Asn Pro Ser
        435             440             445 gtc gcc gcc acc cta ggt ttc ggg gcg tat atg tct aag gca cat ggt      3193
Val Ala Ala Thr Leu Gly Phe Gly Ala Tyr Met Ser Lys Ala His Gly
    450             455             460 atc gac cct aac atc aga acc ggg gta agg acc atc acc acg ggt gcc      3241
Ile Asp Pro Asn Ile Arg Thr Gly Val Arg Thr Ile Thr Thr Gly Ala
465             470             475             480 ccc atc acg tac tcc acc tat ggc aag ttt ctt gcc gac ggt ggt tgc      3289
Pro Ile Thr Tyr Ser Thr Tyr Gly Lys Phe Leu Ala Asp Gly Gly Cys
                485             490             495 tct ggg ggc gcc tat gac atc ata ata tgt gat gag tgc cac tca act      3337
Ser Gly Gly Ala Tyr Asp Ile Ile Ile Cys Asp Glu Cys His Ser Thr
            500             505             510 gac tcg acc act atc ctg ggc atc ggc aca gtc ctg gac caa gcg gag      3385
Asp Ser Thr Thr Ile Leu Gly Ile Gly Thr Val Leu Asp Gln Ala Glu
        515             520             525 acg gct gga gcg cga ctc gtc gtg ctc gcc acc gct acg cct ccg gga      3433
Thr Ala Gly Ala Arg Leu Val Val Leu Ala Thr Ala Thr Pro Pro Gly
    530             535             540 tcg gtc acc gtg cca cat cca aac atc gag gag gtg gct ctg tcc agc      3481
Ser Val Thr Val Pro His Pro Asn Ile Glu Glu Val Ala Leu Ser Ser
545             550             555             560 act gga gaa atc ccc ttt tat ggc aaa gcc atc ccc atc gag acc atc      3529
Thr Gly Glu Ile Pro Phe Tyr Gly Lys Ala Ile Pro Ile Glu Thr Ile
                565             570             575 aag ggg ggg agg cac ctc att ttc tgc cat tcc aag aag aaa tgc gat      3577
Lys Gly Gly Arg His Leu Ile Phe Cys His Ser Lys Lys Lys Cys Asp
            580             585             590 gag ctc gcc gcg aag ctg tcc ggc ctc gga ctc aat gct gta gca tat      3625
Glu Leu Ala Ala Lys Leu Ser Gly Leu Gly Leu Asn Ala Val Ala Tyr
        595             600             605 tac cgg ggc ctt gat gta tcc gtc ata cca act agc gga gac gtc att      3673
Tyr Arg Gly Leu Asp Val Ser Val Ile Pro Thr Ser Gly Asp Val Ile
    610             615             620 gtc gta gca acg gac gct cta atg acg ggc ttt acc ggc gat ttc gac      3721
Val Val Ala Thr Asp Ala Leu Met Thr Gly Phe Thr Gly Asp Phe Asp
625             630             635             640 tca gtg atc gac tgc aat aca tgt gtc acc cag aca gtc gac ttc agc      3769
Ser Val Ile Asp Cys Asn Thr Cys Val Thr Gln Thr Val Asp Phe Ser
                645             650             655 ctg gac ccg acc ttc acc att gag acg acg acc gtg cca caa gac gcg      3817
Leu Asp Pro Thr Phe Thr Ile Glu Thr Thr Thr Val Pro Gln Asp Ala
            660             665             670 gtg tca cgc tcg cag cgg cga ggc agg act ggt agg ggc agg atg ggc      3865
Val Ser Arg Ser Gln Arg Arg Gly Arg Thr Gly Arg Gly Arg Met Gly
        675             680             685
```

-continued

| | | |
|---|---|---|
| att tac agg ttt gtg act cca gga gaa cgg ccc tcg ggc atg ttc gat<br>Ile Tyr Arg Phe Val Thr Pro Gly Glu Arg Pro Ser Gly Met Phe Asp<br>690                         695                        700 | 3913 |
| tcc tcg gtt ctg tgc gag tgc tat gac gcg ggc tgt gct tgg tac gag<br>Ser Ser Val Leu Cys Glu Cys Tyr Asp Ala Gly Cys Ala Trp Tyr Glu<br>705                         710                       715                720 | 3961 |
| ctc acg ccc gcc gag acc tca gtt agg ttg cgg gct tac cta aac aca<br>Leu Thr Pro Ala Glu Thr Ser Val Arg Leu Arg Ala Tyr Leu Asn Thr<br>                      725                       730                     735 | 4009 |
| cca ggg ttg ccc gtc tgc cag gac cat ctg gag ttc tgg gag ggc gtc<br>Pro Gly Leu Pro Val Cys Gln Asp His Leu Glu Phe Trp Glu Gly Val<br>               740                       745                     750 | 4057 |
| ttt aca ggc ctc acc cac ata gac gcc cat ttc ttg tcc cag act aag<br>Phe Thr Gly Leu Thr His Ile Asp Ala His Phe Leu Ser Gln Thr Lys<br>               755                       760                     765 | 4105 |
| cag gca gga gac aac ttc ccc tac ctg gta gca tac cag gct acg gtg<br>Gln Ala Gly Asp Asn Phe Pro Tyr Leu Val Ala Tyr Gln Ala Thr Val<br>770                         775                       780 | 4153 |
| tgc gcc agg gct cag gct cca cct cca tcg tgg gac caa atg tgg aag<br>Cys Ala Arg Ala Gln Ala Pro Pro Pro Ser Trp Asp Gln Met Trp Lys<br>785                         790                       795                800 | 4201 |
| tgt ctc ata cgg cta aag cct acg ctg cac ggg cca acg ccc ctg ctg<br>Cys Leu Ile Arg Leu Lys Pro Thr Leu His Gly Pro Thr Pro Leu Leu<br>                      805                       810                     815 | 4249 |
| tat agg ctg gga gcc gtt caa aac gag gtt act acc aca cac ccc ata<br>Tyr Arg Leu Gly Ala Val Gln Asn Glu Val Thr Thr Thr His Pro Ile<br>               820                       825                     830 | 4297 |
| acc aaa tac atc atg gca tgc atg tcg gct gac ctg gag gtc gtc acg<br>Thr Lys Tyr Ile Met Ala Cys Met Ser Ala Asp Leu Glu Val Val Thr<br>               835                       840                     845 | 4345 |
| agc acc tgg gtg ctg gta ggc gga gtc cta gca gct ctg gct gcg tat<br>Ser Thr Trp Val Leu Val Gly Gly Val Leu Ala Ala Leu Ala Ala Tyr<br>850                         855                       860 | 4393 |
| tgc ctg aca aca ggc agc gtg gtc att gtg ggc agg atc atc ttg tcc<br>Cys Leu Thr Thr Gly Ser Val Val Ile Val Gly Arg Ile Ile Leu Ser<br>865                         870                       875                880 | 4441 |
| gga agg ccg gcc atc att ccc gac agg gaa gtc ctt tac cgg gag ttc<br>Gly Arg Pro Ala Ile Ile Pro Asp Arg Glu Val Leu Tyr Arg Glu Phe<br>                      885                       890                     895 | 4489 |
| gat gag atg gaa gag tgt gcc tca cac ctc cct tac atc gaa cag gga<br>Asp Glu Met Glu Glu Cys Ala Ser His Leu Pro Tyr Ile Glu Gln Gly<br>               900                       905                     910 | 4537 |
| atg cag ctc gcc gaa caa ttc aaa cag aag gca atc ggg ttg ctg caa<br>Met Gln Leu Ala Glu Gln Phe Lys Gln Lys Ala Ile Gly Leu Leu Gln<br>               915                       920                     925 | 4585 |
| aca gcc acc aag caa gcg gag gct gct gct ccc gtg gtg gaa tcc aag<br>Thr Ala Thr Lys Gln Ala Glu Ala Ala Ala Pro Val Val Glu Ser Lys<br>930                         935                       940 | 4633 |
| tgg cgg acc ctc gaa gcc ttc tgg gcg aag cat atg tgg aat ttc atc<br>Trp Arg Thr Leu Glu Ala Phe Trp Ala Lys His Met Trp Asn Phe Ile<br>945                         950                       955                960 | 4681 |
| agc ggg ata caa tat tta gca ggc ttg tcc act ctg cct ggc aac ccc<br>Ser Gly Ile Gln Tyr Leu Ala Gly Leu Ser Thr Leu Pro Gly Asn Pro<br>                      965                       970                     975 | 4729 |
| gcg ata gca tca ctg atg gca ttc aca gcc tct atc acc agc ccg ctc<br>Ala Ile Ala Ser Leu Met Ala Phe Thr Ala Ser Ile Thr Ser Pro Leu<br>               980                       985                     990 | 4777 |
| acc acc caa cat acc ctc ctg ttt aac atc ctg ggg gga tgg gtg gcc<br>Thr Thr Gln His Thr Leu Leu Phe Asn Ile Leu Gly Gly Trp Val Ala<br>               995                     1000                   1005 | 4825 |

```
gcc caa ctt gct cct ccc agc gct gct tcc gct ttc gta ggc gcc ggc     4873
Ala Gln Leu Ala Pro Pro Ser Ala Ala Ser Ala Phe Val Gly Ala Gly
    1010                1015                1020 atc gct gga gcg gct gtt ggc agc ata ggc ctt ggg aag gtg ctt gtg     4921
Ile Ala Gly Ala Ala Val Gly Ser Ile Gly Leu Gly Lys Val Leu Val
1025                1030                1035                1040 gat att ttg gca ggt tat gga gca ggg gtg gca ggc gcg ctc gtg gcc     4969
Asp Ile Leu Ala Gly Tyr Gly Ala Gly Val Ala Gly Ala Leu Val Ala
                1045                1050                1055 ttt aag gtc atg agc ggc gag atg ccc tcc acc gag gac ctg gtt aac     5017
Phe Lys Val Met Ser Gly Glu Met Pro Ser Thr Glu Asp Leu Val Asn
            1060                1065                1070 cta ctc cct gct atc ctc tcc cct ggc gcc cta gtc gtc ggg gtc gtg     5065
Leu Leu Pro Ala Ile Leu Ser Pro Gly Ala Leu Val Val Gly Val Val
        1075                1080                1085 tgc gca gcg ata ctg cgt cgg cac gtg ggc cca ggg gag ggg gct gtg     5113
Cys Ala Ala Ile Leu Arg Arg His Val Gly Pro Gly Glu Gly Ala Val
    1090                1095                1100 cag tgg atg aac cgg ctg ata gcg ttc gct tcg cgg ggt aac cac gtc     5161
Gln Trp Met Asn Arg Leu Ile Ala Phe Ala Ser Arg Gly Asn His Val
1105                1110                1115                1120 tcc ccc acg cac tat gtg cct gag agc gac gct gca gca cgt gtc act     5209
Ser Pro Thr His Tyr Val Pro Glu Ser Asp Ala Ala Ala Arg Val Thr
                1125                1130                1135 cag atc ctc tct agt ctt acc atc act cag ctg ctg aag agg ctt cac     5257
Gln Ile Leu Ser Ser Leu Thr Ile Thr Gln Leu Leu Lys Arg Leu His
            1140                1145                1150 cag tgg atc aac gag gac tgc tcc acg cca tgc tcc ggc tcg tgg cta     5305
Gln Trp Ile Asn Glu Asp Cys Ser Thr Pro Cys Ser Gly Ser Trp Leu
        1155                1160                1165 aga gat gtt tgg gat tgg ata tgc acg gtg ttg act gat ttc aag gcc     5353
Arg Asp Val Trp Asp Trp Ile Cys Thr Val Leu Thr Asp Phe Lys Ala
    1170                1175                1180 tgg ctc cag tcc aag ctc ctg ccg cga ttg ccg gga gtc ccc ttc ttc     5401
Trp Leu Gln Ser Lys Leu Leu Pro Arg Leu Pro Gly Val Pro Phe Phe
1185                1190                1195                1200 tca tgt caa cgt ggg tac aag gga gtc tgg cgg ggc gac ggc atc atg     5449
Ser Cys Gln Arg Gly Tyr Lys Gly Val Trp Arg Gly Asp Gly Ile Met
                1205                1210                1215 caa acc acc tgc cca tgt gga gca cag atc acc gga cat gtg aaa aac     5497
Gln Thr Thr Cys Pro Cys Gly Ala Gln Ile Thr Gly His Val Lys Asn
            1220                1225                1230 tgt tcc atg agg atc gtg ggg cct agg acc tgt agt aac acg tgg cat     5545
Cys Ser Met Arg Ile Val Gly Pro Arg Thr Cys Ser Asn Thr Trp His
        1235                1240                1245 gga aca ttc ccc att aac gcg tac acc acg ggc ccc tgc acg ccc tcc     5593
Gly Thr Phe Pro Ile Asn Ala Tyr Thr Thr Gly Pro Cys Thr Pro Ser
    1250                1255                1260 ccg gcg cca aat tat tct agg gcg ctg tgg cgg gtg gct gct gag gag     5641
Pro Ala Pro Asn Tyr Ser Arg Ala Leu Trp Arg Val Ala Ala Glu Glu
1265                1270                1275                1280 tac gtg gag gtt acg cga gtg ggg gat ttc cac tac gtg acg ggc atg     5689
Tyr Val Glu Val Thr Arg Val Gly Asp Phe His Tyr Val Thr Gly Met
                1285                1290                1295 acc act gac aac gta aag tgc ccg tgt cag gtt ccg gcc ccc gaa ttc     5737
Thr Thr Asp Asn Val Lys Cys Pro Cys Gln Val Pro Ala Pro Glu Phe
            1300                1305                1310 ttc aca gaa gtg gat ggg gtg cgg ttg cac agg tac gct cca gcg tgc     5785
Phe Thr Glu Val Asp Gly Val Arg Leu His Arg Tyr Ala Pro Ala Cys
```

```
                    1315                1320                1325
aaa ccc ctc cta cgg gag gag gtc aca ttc ctg gtc ggg ctc aat caa     5833
Lys Pro Leu Leu Arg Glu Glu Val Thr Phe Leu Val Gly Leu Asn Gln
1330                1335                1340 tac ccg gtt ggg tca cag ctc cca tgc gag ccc gaa ctg gac gta gca     5881
Tyr Pro Val Gly Ser Gln Leu Pro Cys Glu Pro Glu Leu Asp Val Ala
    1345                1350                1355                1360 gtg ctc act tcc atg ctc acc gac ccc tcc cac att acg gcg gag acg     5929
Val Leu Thr Ser Met Leu Thr Asp Pro Ser His Ile Thr Ala Glu Thr
                1365                1370                1375 gct aag cgt agg ctg gcc agg gga tct ccc ccc tcc ttg gcc agc tca     5977
Ala Lys Arg Arg Leu Ala Arg Gly Ser Pro Pro Ser Leu Ala Ser Ser
            1380                1385                1390 tca gct agc cag ctg tct gcg cct tcc ttg aag gca aca tgc act acc     6025
Ser Ala Ser Gln Leu Ser Ala Pro Ser Leu Lys Ala Thr Cys Thr Thr
        1395                1400                1405 cgt cat gac tcc ccg gac gct gac ctc atc gag gcc aac ctc ctg tgg     6073
Arg His Asp Ser Pro Asp Ala Asp Leu Ile Glu Ala Asn Leu Leu Trp
    1410                1415                1420 cgg cag gag atg ggc ggg aac atc acc cgc gtg gag tca gag aat aag     6121
Arg Gln Glu Met Gly Gly Asn Ile Thr Arg Val Glu Ser Glu Asn Lys
1425                1430                1435                1440 gta gta att ttg gac tct ttc gag ccg ctc caa gcg gag gag gat gag     6169
Val Val Ile Leu Asp Ser Phe Glu Pro Leu Gln Ala Glu Glu Asp Glu
                1445                1450                1455 agg gaa gta tcc gtt ccg gcg gag atc ctg cgg agg tcc agg aaa ttc     6217
Arg Glu Val Ser Val Pro Ala Glu Ile Leu Arg Arg Ser Arg Lys Phe
            1460                1465                1470 cct cga gcg atg ccc ata tgg gca cgc ccg gat tac aac cct cca ctg     6265
Pro Arg Ala Met Pro Ile Trp Ala Arg Pro Asp Tyr Asn Pro Pro Leu
        1475                1480                1485 tta gag tcc tgg aag gac ccg gac tac gtc cct cca gtg gta cac ggg     6313
Leu Glu Ser Trp Lys Asp Pro Asp Tyr Val Pro Pro Val Val His Gly
    1490                1495                1500 tgt cca ttg ccg cct gcc aag gcc cct ccg ata cca cct cca cgg agg     6361
Cys Pro Leu Pro Pro Ala Lys Ala Pro Pro Ile Pro Pro Pro Arg Arg
1505                1510                1515                1520 aag agg acg gtt gtc ctg tca gaa tct acc gtg tct tct gcc ttg gcg     6409
Lys Arg Thr Val Val Leu Ser Glu Ser Thr Val Ser Ser Ala Leu Ala
                1525                1530                1535 gag ctc gcc aca aag acc ttc ggc agc tcc gaa tcg tcg gcc gtc gac     6457
Glu Leu Ala Thr Lys Thr Phe Gly Ser Ser Glu Ser Ser Ala Val Asp
            1540                1545                1550 agc ggc acg gca acg gcc tct cct gac cag ccc tcc gac gac ggc gac     6505
Ser Gly Thr Ala Thr Ala Ser Pro Asp Gln Pro Ser Asp Asp Gly Asp
        1555                1560                1565 gcg gga tcc gac gtt gag tcg tac tcc tcc atg ccc ccc ctt gag ggg     6553
Ala Gly Ser Asp Val Glu Ser Tyr Ser Ser Met Pro Pro Leu Glu Gly
    1570                1575                1580 gag ccg ggg gat ccc gat ctc agc gac ggg tct tgg tct acc gta agc     6601
Glu Pro Gly Asp Pro Asp Leu Ser Asp Gly Ser Trp Ser Thr Val Ser
1585                1590                1595                1600 gag gag gct agt gag gac gtc gtc tgc tgc tcg atg tcc tac aca tgg     6649
Glu Glu Ala Ser Glu Asp Val Val Cys Cys Ser Met Ser Tyr Thr Trp
                1605                1610                1615 aca ggc gcc ctg atc acg cca tgc gct gcg gag gaa acc aag ctg ccc     6697
Thr Gly Ala Leu Ile Thr Pro Cys Ala Ala Glu Glu Thr Lys Leu Pro
            1620                1625                1630 atc aat gca ctg agc aac tct ttg ctc cgt cac cac aac ttg gtc tat     6745
```

```
                    -continued

Ile Asn Ala Leu Ser Asn Ser Leu Leu Arg His His Asn Leu Val Tyr
        1635                1640                1645 gct aca aca tct cgc agc gca agc ctg cgg cag aag aag gtc acc ttt        6793
Ala Thr Thr Ser Arg Ser Ala Ser Leu Arg Gln Lys Lys Val Thr Phe
    1650                1655                1660 gac aga ctg cag gtc ctg gac gac cac tac cgg gac gtg ctc aag gag        6841
Asp Arg Leu Gln Val Leu Asp Asp His Tyr Arg Asp Val Leu Lys Glu
1665                1670                1675                1680 atg aag gcg aag gcg tcc aca gtt aag gct aaa ctt cta tcc gtg gag        6889
Met Lys Ala Lys Ala Ser Thr Val Lys Ala Lys Leu Leu Ser Val Glu
                1685                1690                1695 gaa gcc tgt aag ctg acg ccc cca cat tcg gcc aga tct aaa ttt ggc        6937
Glu Ala Cys Lys Leu Thr Pro Pro His Ser Ala Arg Ser Lys Phe Gly
            1700                1705                1710 tat ggg gca aag gac gtc cgg aac cta tcc agc aag gcc gtt aac cac        6985
Tyr Gly Ala Lys Asp Val Arg Asn Leu Ser Ser Lys Ala Val Asn His
        1715                1720                1725 atc cgc tcc gtg tgg aag gac ttg ctg gaa gac act gag aca cca att        7033
Ile Arg Ser Val Trp Lys Asp Leu Leu Glu Asp Thr Glu Thr Pro Ile
    1730                1735                1740 gac acc acc atc atg gca aaa aat gag gtt ttc tgc gtc caa cca gag        7081
Asp Thr Thr Ile Met Ala Lys Asn Glu Val Phe Cys Val Gln Pro Glu
1745                1750                1755                1760 aag ggg ggc cgc aag cca gct cgc ctt atc gta ttc cca gat ttg ggg        7129
Lys Gly Gly Arg Lys Pro Ala Arg Leu Ile Val Phe Pro Asp Leu Gly
                1765                1770                1775 gtt cgt gtg tgc gag aaa atg gcc ctt tac gat gtg gtc tcc acc ctc        7177
Val Arg Val Cys Glu Lys Met Ala Leu Tyr Asp Val Val Ser Thr Leu
            1780                1785                1790 cct cag gcc gtg atg ggc tct tca tac gga ttc caa tac tct cct gga        7225
Pro Gln Ala Val Met Gly Ser Ser Tyr Gly Phe Gln Tyr Ser Pro Gly
        1795                1800                1805 cag cgg gtc gag ttc ctg gtg aat gcc tgg aaa gcg aag aaa tgc cct        7273
Gln Arg Val Glu Phe Leu Val Asn Ala Trp Lys Ala Lys Lys Cys Pro
    1810                1815                1820 atg ggc ttc gca tat gac acc cgc tgt ttt gac tca acg gtc act gag        7321
Met Gly Phe Ala Tyr Asp Thr Arg Cys Phe Asp Ser Thr Val Thr Glu
1825                1830                1835                1840 aat gac atc cgt gtt gag gag tca atc tac caa tgt tgt gac ttg gcc        7369
Asn Asp Ile Arg Val Glu Glu Ser Ile Tyr Gln Cys Cys Asp Leu Ala
                1845                1850                1855 ccc gaa gcc aga cag gcc ata agg tcg ctc aca gag cgg ctt tac atc        7417
Pro Glu Ala Arg Gln Ala Ile Arg Ser Leu Thr Glu Arg Leu Tyr Ile
            1860                1865                1870 ggg ggc ccc ctg act aat tct aaa ggg cag aac tgc ggc tat cgc cgg        7465
Gly Gly Pro Leu Thr Asn Ser Lys Gly Gln Asn Cys Gly Tyr Arg Arg
        1875                1880                1885 tgc cgc gcg agc ggt gta ctg acg acc agc tgc ggt aat acc ctc aca        7513
Cys Arg Ala Ser Gly Val Leu Thr Thr Ser Cys Gly Asn Thr Leu Thr
    1890                1895                1900 tgt tac ttg aag gcc gct gcg gcc tgt cga gct gcg aag ctc cag gac        7561
Cys Tyr Leu Lys Ala Ala Ala Ala Cys Arg Ala Ala Lys Leu Gln Asp
1905                1910                1915                1920 tgc acg atg ctc gta tgc gga gac gac ctt gtc gtt atc tgt gaa agc        7609
Cys Thr Met Leu Val Cys Gly Asp Asp Leu Val Val Ile Cys Glu Ser
                1925                1930                1935 gcg ggg acc caa gag gac gag gcg agc cta cgg gcc ttc acg gag gct        7657
Ala Gly Thr Gln Glu Asp Glu Ala Ser Leu Arg Ala Phe Thr Glu Ala
            1940                1945                1950
```

```
atg act aga tac tct gcc ccc cct ggg gac ccg ccc aaa cca gaa tac     7705
Met Thr Arg Tyr Ser Ala Pro Pro Gly Asp Pro Pro Lys Pro Glu Tyr
        1955                1960                1965 gac ttg gag ttg ata aca tca tgc tcc tcc aat gtg tca gtc gcg cac     7753
Asp Leu Glu Leu Ile Thr Ser Cys Ser Ser Asn Val Ser Val Ala His
1970                1975                1980 gat gca tct ggc aaa agg gtg tac tat ctc acc cgt gac ccc acc acc     7801
Asp Ala Ser Gly Lys Arg Val Tyr Tyr Leu Thr Arg Asp Pro Thr Thr
1985                1990                1995                2000 ccc ctt gcg cgg gct gcg tgg gag aca gct aga cac act cca gtc aat     7849
Pro Leu Ala Arg Ala Ala Trp Glu Thr Ala Arg His Thr Pro Val Asn
        2005                2010                2015 tcc tgg cta ggc aac atc atc atg tat gcg ccc acc ttg tgg gca agg     7897
Ser Trp Leu Gly Asn Ile Ile Met Tyr Ala Pro Thr Leu Trp Ala Arg
        2020                2025                2030 atg atc ctg atg act cat ttc ttc tcc atc ctt cta gct cag gaa caa     7945
Met Ile Leu Met Thr His Phe Phe Ser Ile Leu Leu Ala Gln Glu Gln
        2035                2040                2045 ctt gaa aaa gcc cta gat tgt cag atc tac ggg gcc tgt tac tcc att     7993
Leu Glu Lys Ala Leu Asp Cys Gln Ile Tyr Gly Ala Cys Tyr Ser Ile
2050                2055                2060 gag cca ctt gac cta cct cag atc att caa cga ctc cac ggc ctt agc     8041
Glu Pro Leu Asp Leu Pro Gln Ile Ile Gln Arg Leu His Gly Leu Ser
2065                2070                2075                2080 gca ttt tca ctc cat agt tac tct cca ggt gag atc aat agg gtg gct     8089
Ala Phe Ser Leu His Ser Tyr Ser Pro Gly Glu Ile Asn Arg Val Ala
        2085                2090                2095 tca tgc ctc agg aaa ctt ggg gta ccg ccc ttg cga gtc tgg aga cat     8137
Ser Cys Leu Arg Lys Leu Gly Val Pro Pro Leu Arg Val Trp Arg His
        2100                2105                2110 cgg gcc aga agt gtc cgc gct agg cta ctg tcc cag ggg ggg agg gct     8185
Arg Ala Arg Ser Val Arg Ala Arg Leu Leu Ser Gln Gly Gly Arg Ala
        2115                2120                2125 gcc act tgt ggc aag tac ctc ttc aac tgg gca gta agg acc aag ctc     8233
Ala Thr Cys Gly Lys Tyr Leu Phe Asn Trp Ala Val Arg Thr Lys Leu
        2130                2135                2140 aaa ctc act cca atc ccg gct gcg tcc cag ttg gat tta tcc agc tgg     8281
Lys Leu Thr Pro Ile Pro Ala Ala Ser Gln Leu Asp Leu Ser Ser Trp
2145                2150                2155                2160 ttc gtt gct ggt tac agc ggg gga gac ata tat cac agc ctg tct cgt     8329
Phe Val Ala Gly Tyr Ser Gly Gly Asp Ile Tyr His Ser Leu Ser Arg
        2165                2170                2175 gcc cga ccc cgc tgg ttc atg tgg tgc cta ctc cta ctt tct gta ggg     8377
Ala Arg Pro Arg Trp Phe Met Trp Cys Leu Leu Leu Ser Val Gly
        2180                2185                2190 gta ggc atc tat cta ctc ccc aac cga tga acggggagct aaacactcca      8427
Val Gly Ile Tyr Leu Leu Pro Asn Arg *
        2195                2200 ggccaatagg ccatcctgtt ttttttcctt ttttttttc ttttttttt tttttttttt    8487 tttttttttt tttctcctt ttttttttcct ctttttttcc ttttctttcc tttggtggct  8547
ccatcttagc cctagtcacg gctagctgtg aaaggtccgt gagccgcttg actgcagaga  8607
gtgctgatac tggcctctct gcagatcaag t                                 8638
```